US00RE45323E

(19) United States
(12) Reissued Patent
Grundl et al.

(10) Patent Number: US RE45,323 E
(45) Date of Reissued Patent: Jan. 6, 2015

(54) SUBSTITUTED PIPERIDINES AS CCR3 ANTAGONISTS

(71) Applicants: Marc Grundl, Biberach an der Riss (DE); Horst Dollinger, Schemmerhofen (DE); Riccardo Giovannini, Verona (IT); Christoph Hoenke, Biberach an der Riss (DE); Matthias Hoffmann, Mittelbiberach (DE); Jan Kriegl, Ulm (DE); Domnic Martyres, Biberach an der Riss (DE); Georg Rast, Singen (DE); Peter Seither, Biberach an der Riss (DE)

(72) Inventors: Marc Grundl, Biberach an der Riss (DE); Horst Dollinger, Schemmerhofen (DE); Riccardo Giovannini, Verona (IT); Christoph Hoenke, Biberach an der Riss (DE); Matthias Hoffmann, Mittelbiberach (DE); Jan Kriegl, Ulm (DE); Domnic Martyres, Biberach an der Riss (DE); Georg Rast, Singen (DE); Peter Seither, Biberach an der Riss (DE)

(73) Assignee: Boehringer Ingelheim International GmbH, Ingelheim am Rhein (DE)

(21) Appl. No.: 14/175,082

(22) Filed: Feb. 7, 2014

Related U.S. Patent Documents

Reissue of:
(64) Patent No.: 8,278,302
Issued: Oct. 2, 2012
Appl. No.: 12/727,318
Filed: Mar. 19, 2010

(30) Foreign Application Priority Data

Apr. 8, 2009 (EP) ..... 09157653
Nov. 3, 2009 (EP) ..... 09174917

(51) Int. Cl.
*A61K 31/535* (2006.01)
*A61K 31/445* (2006.01)
*C07D 413/04* (2006.01)
*C07D 413/14* (2006.01)
*C07D 401/04* (2006.01)
*C07D 401/14* (2006.01)

(52) U.S. Cl.
USPC ..... 514/237.2; 514/326; 544/130; 546/208

(58) Field of Classification Search
CPC ..... A61K 31/506; A61K 31/4709; A61K 31/454; A61K 31/56; A61K 31/4523; A61K 31/4725; A61K 31/5355; A61K 31/4545; C07D 413/04; C07D 401/04; C07D 417/14; C07D 413/14; C07D 401/14
USPC ..... 514/237.2, 326; 544/130; 546/208
See application file for complete search history.

(56) References Cited

U.S. PATENT DOCUMENTS

| | | | | |
|---|---|---|---|---|
| 4,289,781 | A * | 9/1981 | Bengtsson et al. | 514/323 |
| 6,433,165 | B1 | 8/2002 | Luly et al. | |
| 6,476,054 | B1 | 11/2002 | Caldwell et al. | |
| 7,176,219 | B2 | 2/2007 | Hayakawa et al. | |
| 8,278,302 | B2 | 10/2012 | Grundl et al. | |
| 2005/0090504 | A1 | 4/2005 | Gong et al. | |
| 2005/0182095 | A1 | 8/2005 | Ting et al. | |
| 2009/0123375 | A1 | 5/2009 | Ambati | |
| 2010/0261687 | A1 | 10/2010 | Grundl et al. | |
| 2012/0264729 | A1 | 10/2012 | Frank et al. | |
| 2013/0023517 | A1 | 1/2013 | Grundl et al. | |
| 2013/0261153 | A1 | 10/2013 | Nivens et al. | |
| 2013/0261307 | A1 | 10/2013 | Duran et al. | |
| 2013/0266646 | A1 | 10/2013 | Fetscher et al. | |
| 2014/0135307 | A1 | 5/2014 | Frank et al. | |

FOREIGN PATENT DOCUMENTS

| | | | |
|---|---|---|---|
| EP | 0468187 | A2 | 1/1992 |
| JP | 2002501052 | A | 1/2002 |
| JP | 2002501898 | A | 1/2002 |
| JP | 2006137718 | A | 6/2006 |
| WO | 2006083390 | A2 | 8/2006 |
| WO | 2006091671 | A1 | 8/2006 |
| WO | 2006095671 | A1 | 9/2006 |
| WO | 2007116313 | A2 | 10/2007 |
| WO | 2008092681 | A1 | 8/2008 |
| WO | 2009145721 | A1 | 12/2009 |
| WO | 2010115836 | A1 | 10/2010 |
| WO | 2012045803 | A1 | 4/2012 |

OTHER PUBLICATIONS

Kozma, David "Resolving Agents"., CRC Handbook of Optical Resolutions Via Diastereomeric Salt Formation, Chapter 4, CRC Press LLC, Boca Raton, 2001, 47 pages.

(Continued)

*Primary Examiner* — Rebecca Anderson
(74) *Attorney, Agent, or Firm* — Michael P. Morris; Mary-Ellen M. Devlin

(57) ABSTRACT

Object of the present invention are novel substituted compounds of the formula 1,

1 wherein A, $R^1$, $R^2$, $R^3$ and $R^4$ are defined as in the description. Another object of the present invention is to provide antagonists of CCR3, more particularly to provide pharmaceutical compositions comprising a pharmaceutically acceptable carrier and a therapeutically effective amount of at least one of the compounds of the present invention or a pharmaceutically acceptable salt thereof.

26 Claims, No Drawings

(56) References Cited

OTHER PUBLICATIONS

London et al., "Update and Review of Central Retinal Vein Occlusion". Current Opinion in Ophthalmology, vol. 22, 2011, pp. 159-165.
Abstract in English of JP2006137718, 2006.
Bachert, C. et al., "Pharmacological Management of Nasal Polyposis." Drugs, 2005, vol. 65, No. 11, pp. 1537-1552.
Blanchard, C. et al., "Eotaxin-3 and a Uniquely Conserved Gene-Expression Profile in Eosinophilic Esophagitis." The Journal of Clinical Investigation, 2006, vol. 116, No. 2, pp. 536-547.
De Lucca et al., "Discovery and Structure-Activity Relationship of N-(Ureidoalkyl)-Benzyl-Piperidines as Potent Small Molecule CC Chemokine Receptor-3 (CCR3) Antagonists". Journal of Medicinal Chemistry, vol. 45, 2002, pp. 3794-3804.
International Search Report and Written Opinion for PCT/ EP2010/ 054396 mailed Sep. 6, 2010.
Sato et al., "Synthesis and structure-activity relations of N-{1-[(6-fluoro-2-naphthyl)methyl]piperidin-4-y1}benzamide derivatives as novel CCR3 antagonists". Bioorganic & Medicinal Chemistry, vol. 16, 2008, pp. 144-156.
Takeda, A. et al., "CCR3 is a Target for Age-Related Macular Degeneration Diagnosis and Therapy." Nature, 2009, vol. 460, No. 7252, pp. 225-230.
Ting et al., "The synthesis of substituted bipiperidine amide compounds as CCR3 antagonists". Bioorganic & Medicinal Chemistry Letters, No. 15, 2005, pp. 1375-1378.
Wuts et al., "Protection for the Carboxyl Group". Greene's Protective Groups in Organic Synthesis, Ch. 5, 4th Edition, NY Wiley, 2007, pp. 553-559 and pp. 582-588.

* cited by examiner

SUBSTITUTED PIPERIDINES AS CCR3 ANTAGONISTS

Matter enclosed in heavy brackets [ ] appears in the original patent but forms no part of this reissue specification; matter printed in italics indicates the additions made by reissue.

Object of the present invention are novel substituted compounds of the formula 1,

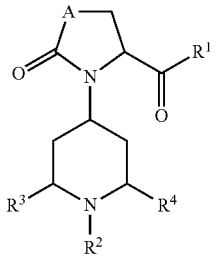

wherein $R^1$, $R^2$, $R^3$ and $R^4$ are defined as in the description. Another object of the present invention is to provide antagonists of CCR3, more particularly to provide pharmaceutical compositions comprising a pharmaceutically acceptable carrier and a therapeutically effective amount of at least one of the compounds of the present invention or a pharmaceutically acceptable salt thereof.

BACKGROUND INFORMATION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998); Rollins, Blood, 90, 909-928 (1997); Lloyd, Curr Opin Pharmacol., 3, 443-448 (2003); Murray, Current Drug Targets., 7, 579-588 (2006); Smit, Eur J. Pharmacol., 533, 277-88 (2006)

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-Ia, MIP-1, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, mast cells, dendritic cells, and basophils. Also in existence are the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994); Murphy, Pharmacol Rev., 54 (2):227-229 (2002); Allen, Annu. Rev. Immunol., 25, 787-820 (2007)) which are termed "chemokine receptors." On binding their cognate ligands, chemokine receptors transduce an intracellular signal through the associated trimeric G proteins, resulting in, among other responses, a rapid increase in intracellular calcium concentration, activation of G-proteins, changes in cell shape, increased expression of cellular adhesion molecules, degranulation, promotion of cell migration, survival and proliferation. There are at least eleven human chemokine receptors that bind or respond to CC chemokines with the following characteristic patterns: CCR-1 (or "CKR-1" or "CC—CKR-1") [MIP-Ia, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC—CKR-2A"/"CC CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR3 (or "CKR-3" or "CC—CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC—CKR-4") [TARC, MIP-Ia, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-Ia, RANTES, MIP-Ip] (Sanson, et al., Biochemistry, 35, 3362-3367 (1996)); CCR-6 (or "CKR-6" or "CC—CKR-6") [LARC] (Baba et al., J. Biol. Chem., 272, 14893-14898 (1997)); CCR-7 (or "CKR-7" or "CC—CKR-7") [ELC] (Yoshie et al., J. Leukoc. Biol. 62, 634-644 (1997)); CCR-8 (or "CKR-8" or "CC—CKR-8") [1-309, TARC, MIP-1p] (Napolitano et al., J. Immunol., 157, 2759-2763 (1996), Bernardini et al., Eur. J. Immunol., 28, 582-588 (1998)); CCR-10 (or "CKR-10" or "CC—CKR-10") [MCP-1, MCP-3] (Bonini et al, DNA and Cell Biol., 16, 1249-1256 (1997)); and CCR31 (or "CKR-11" or "CC—CKR-11") [MCP-1, MCP-2, MCP-4] (Schweickart et al., J Biol Chem, 275 9550-9556 (2000)).

In addition to the mammalian chemokine receptors, the Decoy receptors CCX—CKR, D6 and DARC/Duffy as well proteins expressed by mammalian cytomegaloviruses, herpes viruses and poxviruses, exhibit binding properties of chemokine receptors (reviewed by Wells and Schwartz, Curr. Opin. Biotech., 8, 741-748 (1997); Comerford, Bioessays., 29(3):237-47 (2007)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR2, CCR3, CCR5 and CCR8, can act as co receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease, chronic obstructive pulmonary disease, and atherosclerosis. For example, the chemokine receptor CCR3 is expressed among others on eosinophils, basophils, TH2 cells, alveolar macrophages, mast cells, epithelial cells, microglia cells, astrocytes and fibroblasts. CCR3 plays a pivotal role in attracting eosinophils to sites of allergic inflammation and in subsequently activating these cells. The chemokine ligands for CCR3 induce a rapid increase in intracellular calcium concentration, increased GTP exchange of G-proteins, increased ERK phosphorylation, enhanced receptor internalization, eosinophil shape change, increased expression of cellular adhesion molecules, cellular degranulation, and the promotion of migration. Accordingly, agents that inhibit chemokine receptors would be useful in such disorders and diseases. In addition, agents that inhibit chemokine receptors would also be useful in infectious diseases such as by blocking infection of CCR3 expressing cells by HIV or in preventing the manipulation of immune cellular responses by viruses such as cytomegaloviruses.

Therefore, CCR3 is an important target and antagonism of CCR3 is likely to be effective in the treatment of inflammatory, eosinophilic, immunoregulatory and infectious disorders and diseases (Wegmann, Am J Respir Cell Mol. Biol., 36(1):61-67 (2007); Fryer J Clin Invest., 116(1):228-236 (2006); De Lucca, Curr Opin Drug Discov Devel., 9(4):516-524 (2006)

The compounds of the instant application are useful for manufacturing a medicament for the prevention and/or treatment of diseases wherein the activity of a CCR3-receptor is involved. Preferred is the manufacturing of a medicament for the prevention and/or treatment of a wide variety of inflammatory, infectious, and immunoregulatory disorders and diseases of the respiratory or gastrointestinal complaints as well as inflammatory diseases of the joints and allergic diseases of the nasopharynx, eyes, and skin, including asthma and allergic diseases, eosinophilic diseases, infection by pathogenic microbes (which, by definition, includes viruses), as well as autoimmune pathologies such as the rheumatoid arthritis and atherosclerosis.

The problem underlying the present invention was the provision of novel CCR3 antagonists, preferred with reduced side effects. It has been found surprisingly that substituted piperidines of formula 1 are highly suitable as CCR3 antagonists, having less side effects, e.g. inhibition of norepinephrine (NET), dopamine (DAT) or serotonin reuptake transporters (5-HTT) as described by Watson P S, Bioorg MED Chem Lett., 16(21):5695-5699 (2006), or inhibition of 5HT2A, 5HT2C or Dopamine D2 receptors as described by De Lucca, J Med Chem., 48(6):2194-2211 (2005), or inhibition of the hERG channel as described by De Lucca, Curr Opin Drug Discov Devel., 9(4):516-524 (2006), or inhibition of the alpha1B adrenergic receptor.

DETAILED DESCRIPTION OF THE INVENTION

Embodiment of the present invention are compounds of formula 1, wherein

1

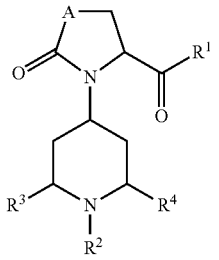

A is $CH_2$, O or N—$C_{1-6}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$alkyl, $NHSO_2$-phenyl, NHCONH-phenyl, halogen, CN, $SO_2$—$C_{1-6}$-alkyl, COO—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, methoxy-phenyl;

a group selected from NHCH(pyridinyl)$CH_2$COO—$C_{1-6}$-alkyl, NHCH($CH_2$O—$C_{1-6}$-alkyl)benzoimidazolyl, optionally substituted with halogen or CN;

or 1-aminocyclopentyl, optionally substituted with methyl-oxadiazole $R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}\text{-alkyl})_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}$-alkyl)($CH_2CON(C_{1-4}\text{-alky})_2$) O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2$CO-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-6}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

a aromatic or non-aromatic $C_{9\ or\ 10}$-bicyclic-ring, whereas one or two carbon atoms are replaced by N, O or S each optionally substituted with one or two residues selected from the group consisting of $N(C_{1-6}\text{-alkyl})_2$, CONH—$C_{1-6}$-alkyl, =O;

a heterocyclic non-aromatic ring, optionally substituted with pyridinyl;

4,5-dihydro-naphtho[2,1-d]thiazole, optionally substituted with NHCO—$C_{1-6}$-alkyl, $R^{1.2.1}$ H, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-haloalkyl, phenyl, heteroaryl;

$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-6}$-alkyl;

$R^4$ is H, $C_{1-6}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}\text{-alkyl})_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}\text{-alkyl})(CH_2CON(C_{1-4}\text{-alky})_2)$ O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-4}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

$R^{1.2.1}$ $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-haloalkyl, phenyl, heteroaryl; preferably $R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$alkyl, O—$C_{1-6}$-haloalkyl, phenyl, pyrrolidinyl;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$. O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from $NHR^{1.1}$, $NMeR^{1.1}$;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}\text{-alkyl})_2$, $CH_2NHCONH$—$C_{3-6}$-cycloalkyl, CN, CO-pyridinyl, $CONR^{1.1.1}R^{1.1.2}$, COO—$C_{1-6}$-alkyl, $N(SO_2$—$C_{1-6}\text{-alkyl})(CH_2CON(C_{1-4}\text{-alkyl})_2)$ O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2CO$-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^2$ is selected from the group consisting of $C_{1-6}$alkylene-phenyl, $C_{1-6}$-alkylene-naphthyl, and $C_{1-6}$alkylene-thiophenyl; each optionally substituted with one, two or three residues selected from the group consisting of $C_{1-6}$-alkyl, $C_{1-6}$haloalkyl, O—$C_{1-6}$alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from $NHR^{1.2}$, $NMeR^{1.2}$;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-4}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

benzothiazolyl, indazolyl, dihydro-indolyl, indanyl, tetrahydro-quinolinyl, each optionally substituted with one or two residues selected from the group consisting of $N(C_{1-6}\text{-alkyl})_2$, CONH—$C_{1-6}$-alkyl, =O;

piperidinyl, optionally substituted with pyridinyl;

4,5-dihydro-naphtho[2,1-d]thiazole, optionally substituted with NHCO—$C_{1-6}$-alkyl, $R^{1.2.1}$ H, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-4}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

$R^{1.2.1}$ H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl R1.2.2 H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from $NHCH_2$—$R^{1.3}$;

$R^{1.3}$ is selected from phenyl, pyrazolyl, isoxazolyl, pyridinyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, pyrrolidinyl;

$R^2$ is selected from the group consisting of $C_{1-6}$-alkylene-phenyl, $C_{1-6}$-alkylene-naphthyl, and $C_{1-6}$-alkylene-thiophenyl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or N—$C_{1-4}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

NH—$C_{3-6}$-cycloalkyl, whereas optionally one carbon atom is replaced by a nitrogen atom, whereas the ring is optionally substituted with one or two residues selected from the group consisting of $C_{1-6}$alkyl, O—$C_{1-6}$alkyl, $NHSO_2$-phenyl, NHCONH-phenyl, halogen, CN, $SO_2$—$C_{1-6}$-alkyl, COO—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$alkyl, $NO_2$, halogen, CN, $NHSO_2$—$C_{1-6}$-alkyl, m-methoxyphenyl;

a group selected from NHCH(pyridinyl)$CH_2$COO—$C_{1-6}$-alkyl, NHCH($CH_2$O—$C_{1-6}$-alkyl)benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-6}$-alkyl, $C_{1-6}$-haloalkyl, $CH_2CON(C_{1-6}\text{-alkyl})_2$, $CH_2NHCONH$—$C_{3-6}$-cycloalkyl, CN, $CONR^{1.1.1}R^{1.1.2}$, COO—$C_{1-6}$-alkyl, O—$C_{1-6}$-alkyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2$CO-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from heteroaryl, optionally substituted with one or two residues selected from the group consisting of $C_{1-6}$-alkyl, $C_{3-6}$-cycloalkyl, $CH_2COO$—$C_{1-6}$-alkyl, $CONR^{1.2.1}R^{1.2.2}$, COO—$C_{1-6}$-alkyl, $CONH_2$, O—$C_{1-6}$-alkyl, halogen, CN, CO-pyrrolidinyl, CO-morpholinyl or heteroaryl optionally substituted with one or two residues selected from the group consisting of $C_{1-6}$-alkyl;

benzothiazolyl, indazolyl, dihydro-indolyl, indanyl, tetrahydro-quinolinyl, each optionally substituted with one or two residues selected from the group consisting of $N(C_{1-6}\text{-alkyl})_2$, CONH—$C_{1-6}$-alkyl, =O;

piperidinyl, optionally substituted with pyridinyl;

4,5-dihydro-naphtho[2,1-d]thiazole, optionally substituted with NHCO—$C_{1-6}$-alkyl, $R^{1.2.1}$ H, $C_{1-6}$-alkyl;

$R^{1.2.2}$ H, $C_{1-6}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl;

$R^2$ is selected from $C_{1-6}$-alkylene-phenyl or $C_{1-6}$-alkylene-naphthyl, both optionally substituted with one or two residues selected from the group consisting of $C_{1-6}$-alkyl, $C_{1-6}$-haloalkyl, O—$C_{1-6}$-alkyl, O—$C_{1-6}$-haloalkyl, halogen; or $CH_2$-thiophenyl, optionally substituted with one or two residues selected from the group consisting of halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

Another embodiment of the present invention are compounds of formula 1, wherein

A is $CH_2$, O or NMe;

$R^1$ is selected from $NHR^{1.1}$, $NMeR^{1.1}$;

$NHR^{1.2}$, $NMeR^{1.2}$;

$NHCH_2$—$R^{1.3}$;

NH-cyclohexyl, optionally substituted with one or two residues selected from the group consisting of $C_{1-4}$-alkyl, $NHSO_2$-phenyl, NHCONH-phenyl, halogen;

NH-pyrrolidinyl, optionally substituted with one or two residues selected from the group consisting of $SO_2$—$C_{1-4}$-alkyl, COO—$C_{1-4}$-alkyl;

piperidinyl, optionally substituted with one or two residues selected from the group consisting of $NHSO_2$—$C_{1-4}$-alkyl, m-methoxyphenyl;

dihydro-indolyl, dihydro-isoindolyl, tetrahydro-quinolinyl or tetrahydro-isoquinolinyl, optionally substituted with one or two residues selected from the group consisting of $C_{1-4}$-alkyl, COO—$C_{1-4}$-alkyl, $C_{1-4}$-haloalkyl, $NO_2$, halogen;

a group selected from NHCH(pyridinyl)$CH_2$COO—$C_{1-4}$-alkyl, NHCH($CH_2$O—$C_{1-4}$-alkyl)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-4}$-alkyl, $C_{1-4}$-haloalkyl, $CH_2CON(C_{1-4}\text{-alkyl})_2$, $CH_2NHCONH$—$C_{3-6}$-cycloalkyl, CN, $CONR^{1.1.1}R^{1.1.2}$, COO—$C_{1-4}$-alkyl, O—$C_{1-4}$-alkyl, $SO_2$—$C_{1-4}$-alkyl, $SO_2$—$C_{1-4}$-alkylen-OH, $SO_2$—$C_{3-6}$-cycloalkyl, $SO_2$-piperidinyl, $SO_2NH$—$C_{1-4}$-alkyl, $SO_2N(C_{1-4}\text{-alkyl})_2$, halogen, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of $C_{1-4}$-alkyl, $NHC_{1-4}$-alkyl, =O;

$R^{1.1.1}$ H, $C_{1-6}$-alkyl, $C_{3-6}$-cycloalkyl, $C_{1-4}$-haloalkyl, $CH_2CON(C_{1-4}\text{-alkyl})_2$, $CH_2$CO-azetindinyl, $C_{1-4}$-alkylen-$C_{3-6}$-cycloalkyl, $CH_2$-pyranyl, $CH_2$-tetrahydrofuranyl, $CH_2$-furanyl, $C_{1-4}$-alkylen-OH or thiadiazolyl, optionally substituted with $C_{1-4}$-alkyl;

$R^{1.1.2}$ H, $C_{1-4}$-alkyl, $SO_2C_{1-4}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyridazinyl, pyrrolyl, pyrazolyl, isoxazolyl, thiazolyl, thiadiazolyl, optionally substituted with one or two residues selected from the group consisting of $C_{1-4}$-alkyl, $C_{3-6}$-cycloalkyl, $CH_2COO—C_{1-4}$-alkyl, $CONR^{1.2.1}R^{1.2.2}$, $COO—C_{1-4}$-alkyl, $CONH_2$, $O—C_{1-4}$-alkyl, halogen, CO-pyrrolidinyl, CO-morpholinyl or pyrazolyl, triazolyl, tetrazolyl, isoxazolyl, oxadiazolyl, each optionally substituted with one or two residues selected from the group consisting of $C_{1-4}$-alkyl;

benzothiazolyl, indazolyl, dihydro-indolyl, indanyl, tetrahydro-quinolinyl, each optionally substituted with one or two residues selected from the group consisting of $N(C_{1-4}\text{-alkyl})_2$, $CONH—C_{1-4}$-alkyl, =O;

piperidinyl, optionally substituted with pyridinyl;

4,5-dihydro-naphtho[2,1-d]thiazole, optionally substituted with $NHCO—C_{1-4}$-alkyl, $R^{1.2.1}$ H, $C_{1-4}$-alkyl;

$R^{1.2.2}$ H, $C_{1-4}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-4}$-alkyl, $C_{3-6}$cycloalkyl, $O—C_{1-4}$-alkyl, $O—C_{1-4}$-haloalkyl;

$R^2$ is selected from $C_{1-6}$-alkylene-phenyl or $C_{1-6}$alkylene-naphthyl, both optionally substituted with one or two residues selected from the group consisting of $C_{1-4}$-alkyl, $C_{1-4}$-haloalkyl, $O—C_{1-4}$-haloalkyl, halogen; or $CH_2$-thiophenyl, optionally substituted with one or two residues selected from the group consisting of halogen;

$R^3$ is H;

$R^4$ is H;

or $R^3$ and $R^4$ together are forming a $CH_2—CH_2$ group.

Another embodiment of the present invention are compounds of formula 1, wherein

A is $CH_2$, O or NMe;

$R^1$ is selected from $NHR^{1.1}$, $NMeR^{1.1}$;

$NHR^{1.2}$, $NMeR^{1.2}$;

$NHCH_2—R^{1.3}$;

NH-piperidinyl, optionally substituted with pyridinyl;

NH-cyclohexyl, optionally substituted with one or two residues selected from the group consisting of t-Bu, $NHSO_2$-phenyl, NHCONH-phenyl, F;

NH-pyrrolidinyl, optionally substituted with one or two residues selected from the group consisting of $SO_2Me$, COO-t-Bu;

piperidinyl, optionally substituted with one or two residues selected from the group consisting of $NHSO_2$-n-Bu, m-methoxyphenyl;

dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br;

a group selected from $NHCH(pyridinyl)CH_2COOMe$, $NHCH(CH_2OMe)$-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, t-Bu, i-Pr, cyclopropyl, $CH_2$-i-Pr, $CH_2$-t-Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, $R^{1.2.1}$ H, Me;

$R^{1.2.2}$ H, Me;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2—CH_2$ group.

Another embodiment of the present invention are compounds of formula 1, wherein

A is $CH_2$, O or NMe;

$R^1$ is selected from $NHR^{1.1}$ $NHR^{1.2}$, $R^{1.1}$ is phenyl, optionally substituted with one or two residues selected from the group consisting of Me, Et, Pr, Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, t-Bu, i-Pr, cyclopropyl, $CH_2$-t-Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, $R^{1.2.1}$ H, Me;

$R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et $R^3$ is H;

$R^4$ is H.

Another embodiment of the present invention are compounds of formula 1, wherein

A is $CH_2$, O or NMe;

is selected from $NHR^{1.1}$, $NMeR^{1.1}$;

$NHR^{1.2}$, $NMeR^{1.2}$;

$NHCH_2$—$R^{1.3}$;

$R^{1.1}$ is phenyl, optionally substituted with one or two residues selected from the group consisting of Me, Et, Pr, Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, Pr, Bu, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, $R^{1.2.1}$ H, Me;

$R^{1.2.2}$ H, Me;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention are compounds of formula 1, wherein

A is $CH_2$, O or NMe;

$R^1$ is selected from $NHR^{1.1}$, $NMeR^{1.1}$;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention are compounds of formula 1, wherein

A is $CH_2$, O or NMe;

$R^1$ is selected from $NHR^{1.1}$, $NMeR^{1.1}$;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^2$ is defined as in table 1 shown below;

$R^3$ is H;

$R^4$ is H;

Another embodiment of the present invention are compounds of formula 1, wherein

A is $CH_2$, O or NMe;

$R^1$ is selected from $NHR^{1.1}$, $NMeR^{1.1}$;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

and $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$;

$R^2$ is defined as in table 1 shown below;

$R^3$ is H;

$R^4$ is H;

Another embodiment of the present invention are compounds of formula 1, wherein

A is $CH_2$, O or NMe;

$R^1$ is selected from $NHR^{1.1}$, $NMeR^{1.1}$;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, F, Cl;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ $R^2$ is defined as in table 1 shown below;

$R^3$ is H;

$R^4$ is H;

Another embodiment of the present invention are compounds of formula 1, wherein

A is $CH_2$, O or NMe;

$R^1$ is selected from $NHR^{1.1}$, $NMeR^{1.1}$;

$R^{1.1}$ is phenyl, optionally substituted with one or two residues selected from the group consisting of $SO_2Me$, $SO_2CH_2CH_2OH$, $SO_2Et$, $SO_2$-cyclopropyl, $SO_2$-piperidinyl, $SO_2NHEt$, $SO_2NMeEt$;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ $R^2$ is defined as in table 1 shown below;

$R^3$ is H;

$R^4$ is H;

Another embodiment of the present invention are compounds of formula 1, wherein

A is $CH_2$, O or NMe;

$R^{1.1}$ is selected from $NHR^{1.1}$, $NMeR^{1.1}$;

$R^{1.1}$ is phenyl, optionally substituted with one residue selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, and additionally with one residue selected from the group consisting of CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, Bu, Pr, cyclopropyl, $CH_2$—Pr, $CH_2$—Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydrofuranyl, $CH_2$-furanyl, $CH_2CH_2OH$ or thiadiazolyl, optionally substituted with Me;

$R^{1.1.2}$ H, Me, Et, $SO_2Me$, $SO_2Et$ $R^2$ is defined as in table 1 shown below;

$R^3$ is H;

$R^4$ is H;

Another embodiment of the present invention are compounds of formula 1, wherein

A is $CH_2$, O or NMe;

$R^1$ is selected from $NHR^{1.2}$, $NMeR^{1.2}$;

$R^{1.2}$ is selected from pyridinyl, pyridazinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, $R^{1.2.1}$ H, Me;

$R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et;

or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention are compounds of formula 1, wherein

A is $CH_2$, O or NMe;

$R^1$ is selected from $NHR^{1.2}$, $NMeR^{1.2}$;

$R^{1.2}$ is selected from pyridinyl, pyridazinyl, pyrrolyl, pyrazolyl, isoxazolyl, thiazolyl, thiadiazolyl, optionally substituted with one or two residues selected from the group consisting of Me, Et, n-Pr, i-Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

$R^{1.2.1}$ H, Me;

$R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention are compounds of formula 1, wherein

A is $CH_2$, O or NMe;

$R^1$ is selected from $NHCH_2$—$R^{1.3}$;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

Another embodiment of the present invention are compounds of formula 1, wherein

A is $CH_2$, O or NMe;

$R^1$ is selected from

NH-piperidinyl, optionally substituted with pyridinyl;

NH-cyclohexyl, optionally substituted with one or two residues selected from the group consisting of t-Bu, $NHSO_2$-phenyl, NHCONH-phenyl, F;

NH-pyrrolidinyl, optionally substituted with one or two residues selected from the group consisting of $SO_2Me$, COO-t-Bu;

piperidinyl, optionally substituted with one or two residues selected from the group consisting of $NHSO_2$-n-Bu, m-methoxyphenyl;

dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br;

a group selected from NHCH(pyridinyl)$CH_2$COOMe, NHCH($CH_2$OMe)-benzoimidazolyl, optionally substituted with Cl;

or 1-aminocyclopentyl, optionally substituted with Methyl-Oxadiazolyl;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$ $CH_2$ group.

Another embodiment of the present invention are compounds of formula 1, wherein A is $CH_2$, O or NMe, $R^1$ is selected from $NHR^{1.2}$, $NMeR^{1.2}$; $R^2$ is defined as in table 1 shown below; $R^3$ is H; $R^4$ is and $R^{1.2}$ is selected from pyridinyl, optionally substituted with one or two residues selected from the group consisting of Me, Et, i-Pr, n-Bu, cyclopropyl, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

pyrrolyl, optionally substituted with one or two residues selected from the group consisting of Me, Et, COOMe, COOEt;

pyrazolyl, optionally substituted with one or two residues selected from the group consisting of Me, Et, cyclopropyl, COOEt, CO-pyrrolidinyl;

isoxazolyl, optionally substituted with one or two residues selected from the group consisting of t-Bu, COOEt;

thiazolyl, optionally substituted with one or two residues selected from the group consisting of Me, n-Pr, i-Pr, Bu, COOMe, COOEt, $CH_2COOEt$, $CONR^{1.2.1}R^{1.2.2}$;

thiadiazolyl, optionally substituted with one or two residues selected from the group consisting of COOEt;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, and $R^{1.2.1}$ is H or Me;

$R^{1.2.2}$ is H or Me.

Another embodiment of the present invention are compounds of formula 1, wherein A is $CH_2$, O or NMe, $R^1$ is selected from $NHR^{1.2}$, $NMeR^{1.2}$; $R^2$ is defined as in table 1 shown below; $R^3$ is H; $R^4$ is and $R^{1.2}$ is selected from pyridinyl, optionally substituted with one or two residues selected from the group consisting of Me, Et, i-Pr, n-Bu, $CONR^{1.2.1}R^{1.2.2}$, COOMe, COOEt, $CONH_2$, OMe, Cl, Br;

pyrrolyl, optionally substituted with one or two residues selected from the group consisting of Me, Et, COOMe, COOEt;

pyrazolyl, optionally substituted with one or two residues selected from the group consisting of Me, Et, cyclopropyl, COOEt, CO-pyrrolidinyl;

isoxazolyl, optionally substituted with one or two residues selected from the group consisting of t-Bu, COOEt;

thiazolyl, optionally substituted with one or two residues selected from the group consisting of Me, n-Pr, i-Pr, Bu, COOMe, COOEt, $CONR^{1.2.1}R^{1.2.2}$;

thiadiazolyl, optionally substituted with one or two residues selected from the group consisting of COOEt;

benzothiazolyl, indazolyl, dihydro-indolyl, indanyl, tetrahydro-quinolinyl, each optionally substituted with one or two residues selected from the group consisting of $NMe_2$, CONHMe, =O;

and $R^{1.2.1}$ is H or Me;

$R^{1.2.2}$ is H or Me.

Another embodiment of the present invention are compounds of formula 1, wherein

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is pyridinyl, optionally substituted with one or two residues selected from the group consisting of Me, Et, i-Pr, n-Bu, $CONR^{1.2.1}R^{1.2.2}$, COOMe, COOEt, $CONH_2$, OMe, Cl, Br; $R^{1.2}$, is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is pyrrolyl, optionally substituted with one or two residues selected from the group consisting of Me, Et, COOMe, COOEt; $R^{1.2.1}$ is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is pyrazolyl, optionally substituted with one or two residues selected from the group consisting of Me, Et, cyclopropyl, COOEt, CO-pyrrolidinyl; $R^{1.2.1}$ is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is isoxazolyl, optionally substituted with one or two residues selected from the group consisting of t-Bu, COOE; $R^{1.2.1}$ is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is thiazolyl, optionally substituted with one or two residues selected from the group consisting of Me, n-Pr, i-Pr, Bu, COOMe, COOEt, $CONR^{1.2.1}R^{1.2.2}$; $R^{1.2.1}$ is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is thiadiazolyl, optionally substituted with one or two residues selected from the group consisting of COOEt; $R^{1.2.1}$ is H or Me and $R^{1.2.2}$ is H or Me.

A is $CH_2$, O or NMe, $R^1$ is selected from $NHR^{1.2}$, $NMeR^{1.2}$; $R^2$ is defined as in table 1 shown below; $R^3$ is H; $R^4$ is H; $R^{1.2}$ is benzothiazolyl, indazolyl, dihydroindolyl, indanyl, tetrahydro-quinolinyl, each optionally substituted with one or two residues selected from the group consisting of $NMe_2$, CONHMe, =O; $R^{1.2.1}$ is H or Me and $R^{1.2.2}$ is H or Me.

Another embodiment of the present invention are compounds of formula 1, wherein all groups are defined as above except $R^{1.3}$ is selected from phenyl, optionally substituted with $OCHF_2$;

pyrazolyl, optionally substituted with Me or Et;

isoxazolyl, optionally substituted with Pr;

pyrimidinyl, optionally substituted with two OMe;

indolyl;

oxadiazolyl, optionally substituted with cyclopentyl.

Another embodiment of the present invention are compounds of formula 1, wherein all groups are defined as above except A is $CH_2$.

Another embodiment of the present invention are compounds of formula 1, wherein all groups are defined as above except A is O.

Another embodiment of the present invention are compounds of formula 1, wherein all groups are defined as above except A is NMe.

Another embodiment of the present invention are compounds of formula 1, wherein

A is $CH_2$, O or NMe;

$R^1$ is selected from

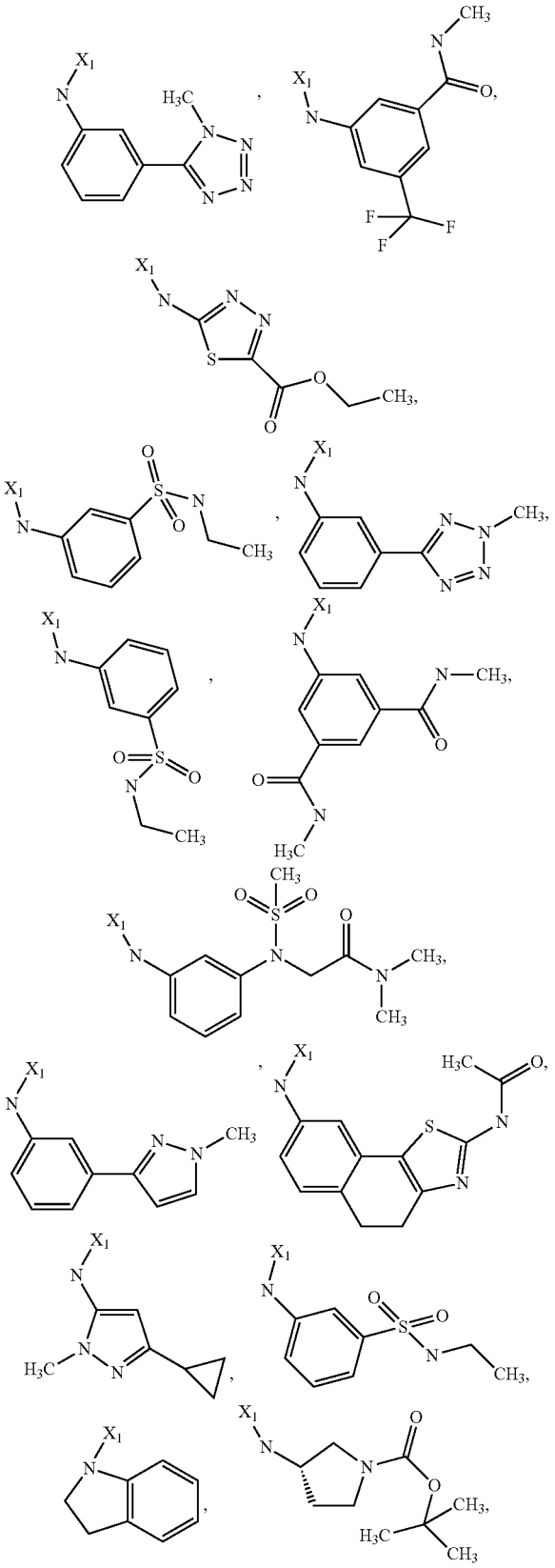

-continued
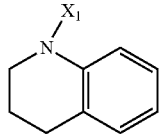
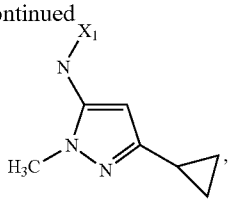
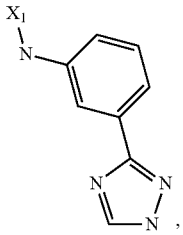
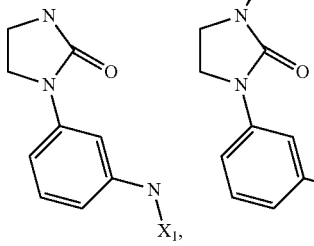
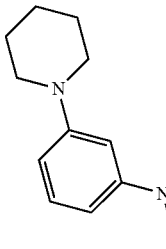
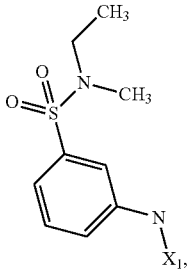
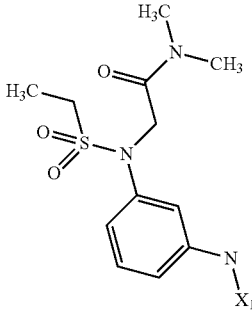
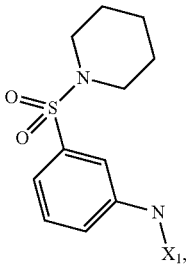
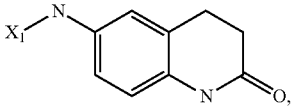
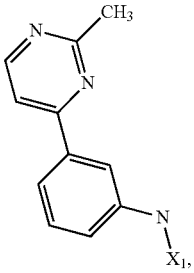
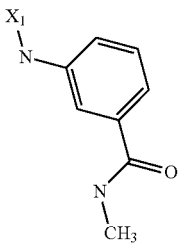
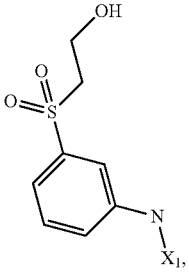
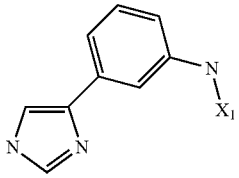
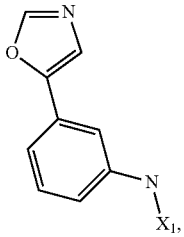
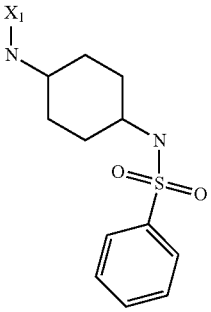
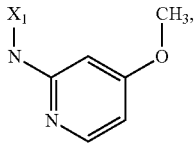
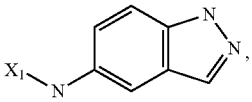
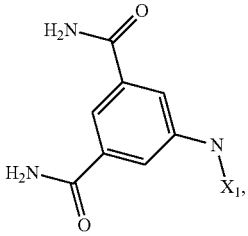
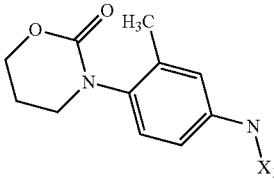
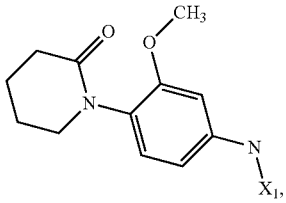
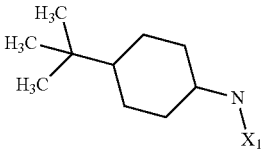
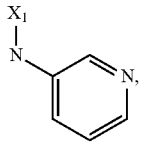
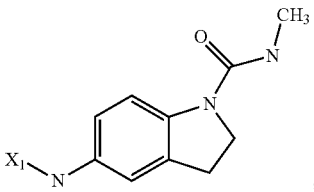
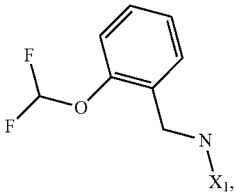
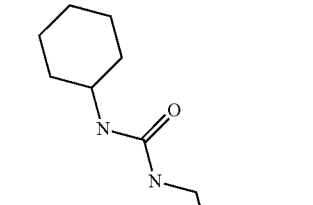
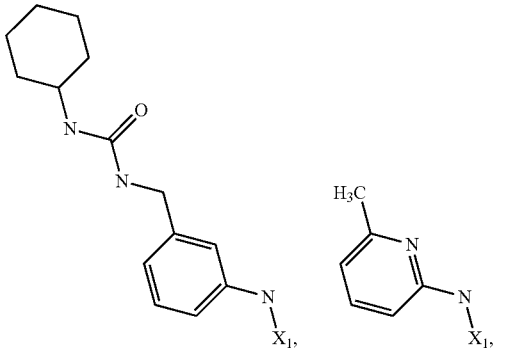

-continued
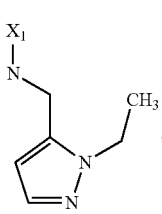
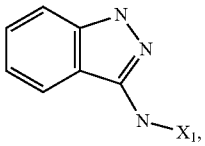
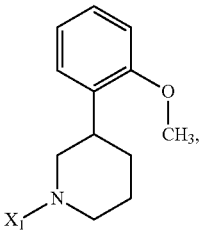
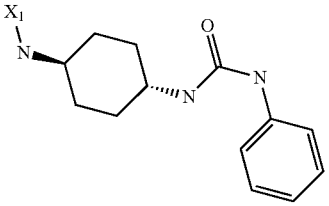
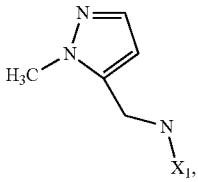
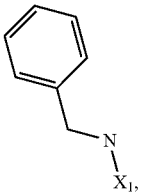
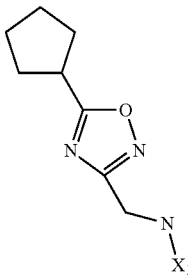
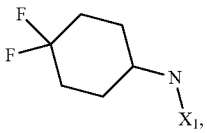
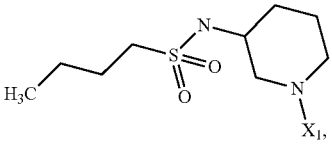
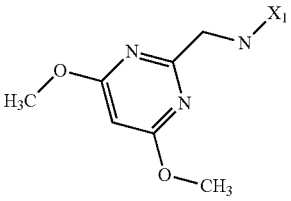
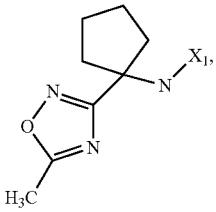
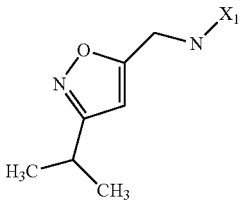
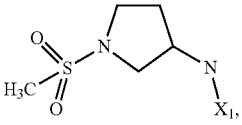
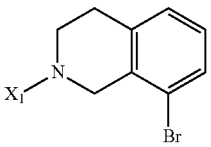
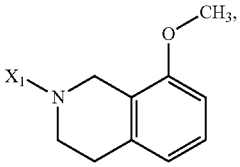
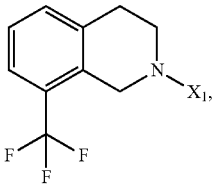
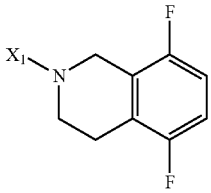
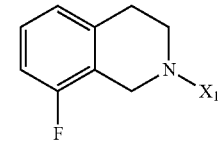
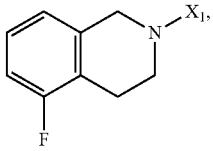
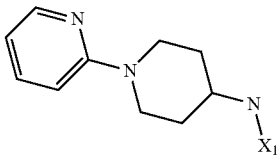
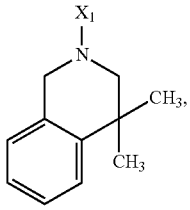
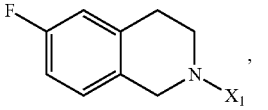
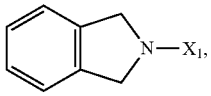
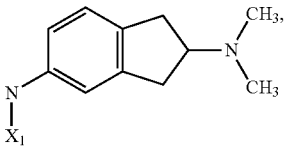
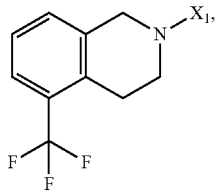
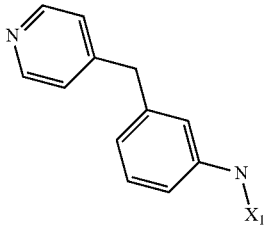
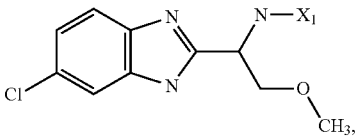
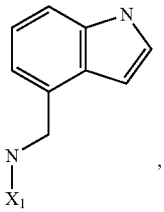
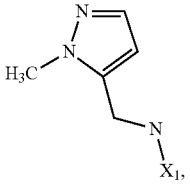
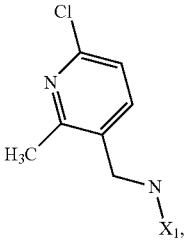
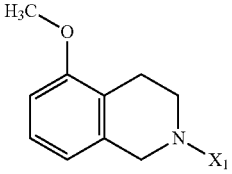
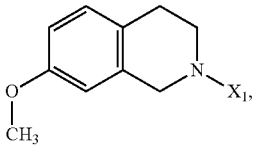
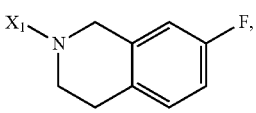
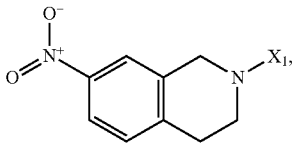

-continued
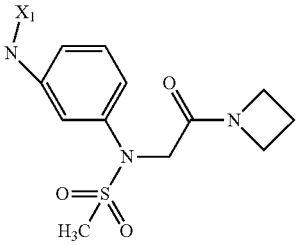
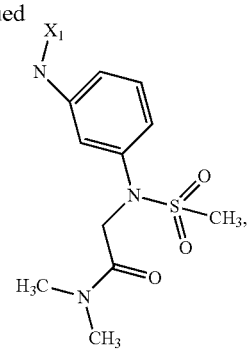
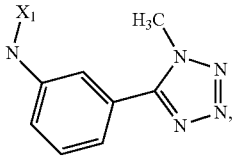
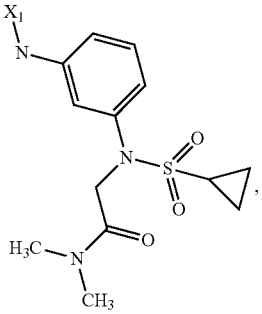
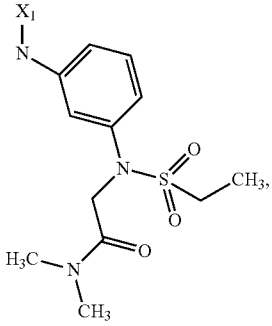
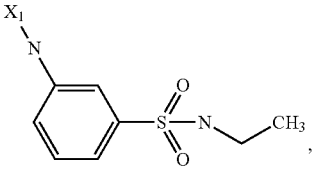
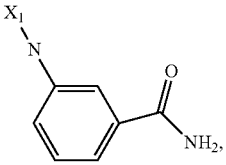
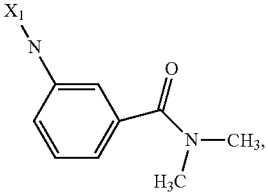
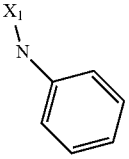
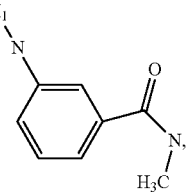
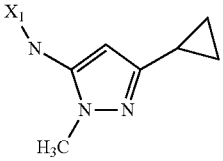
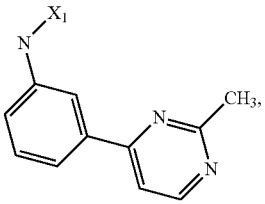
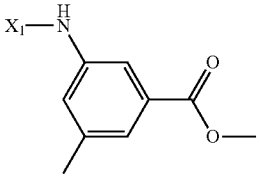
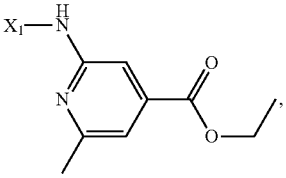
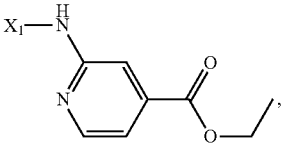
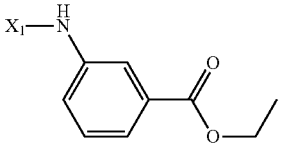
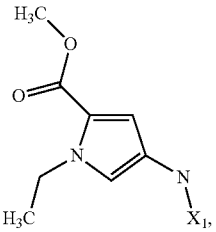
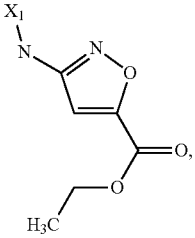
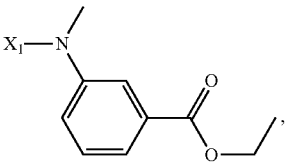
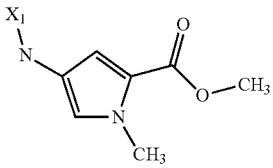
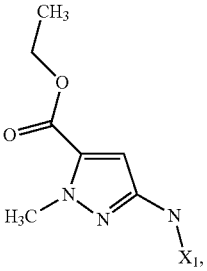
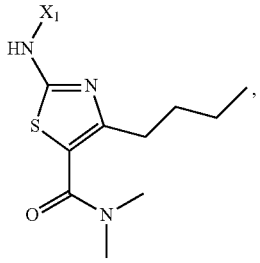
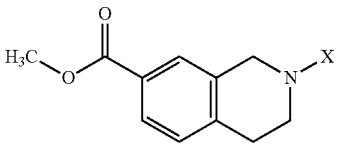
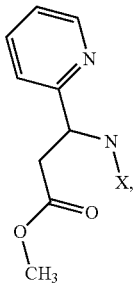
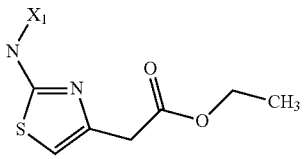
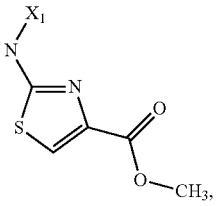

-continued
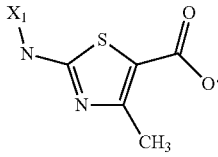
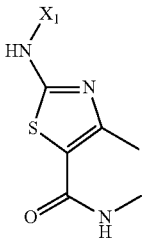
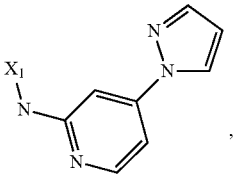
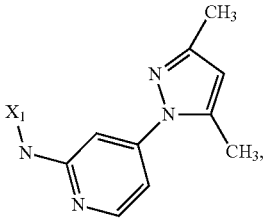
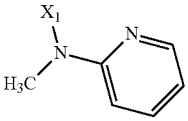
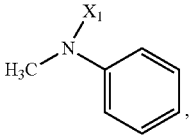
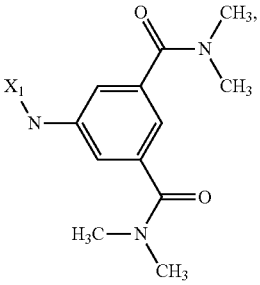
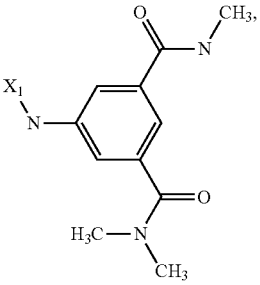
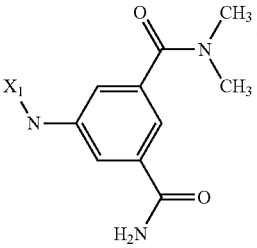
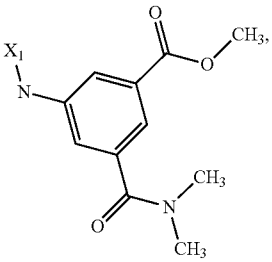
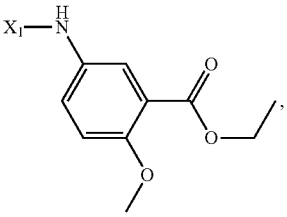
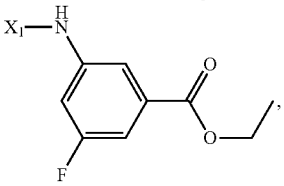
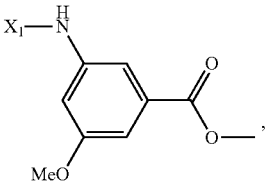
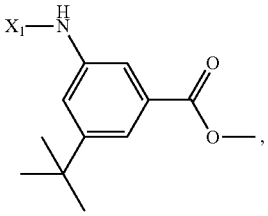
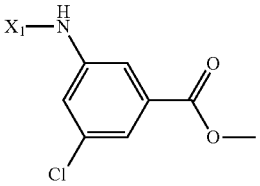
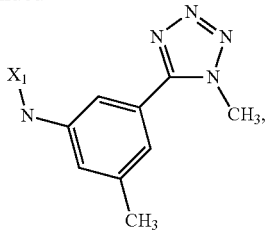
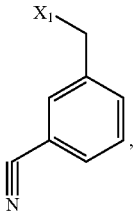
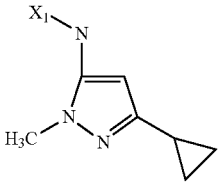
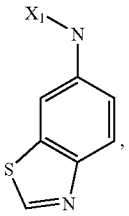
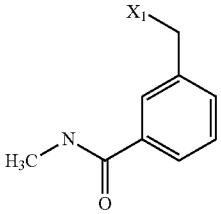
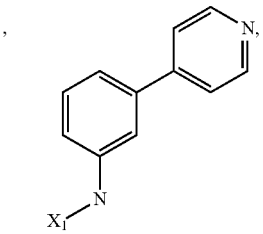
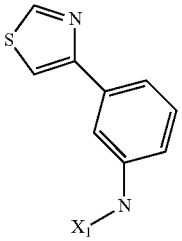
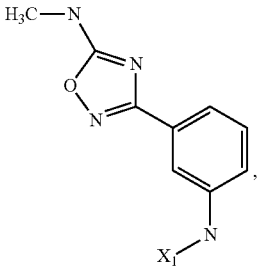
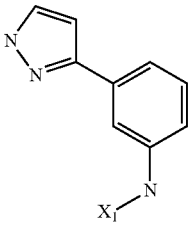
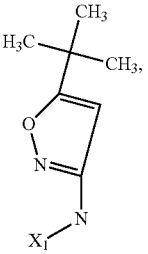
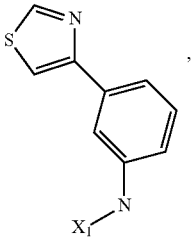
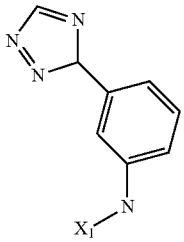
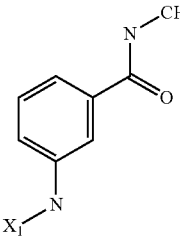
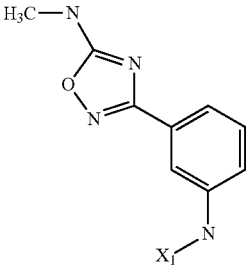
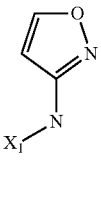
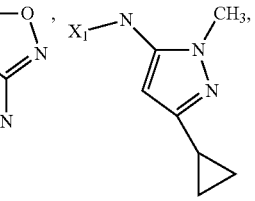

-continued
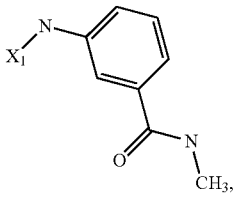
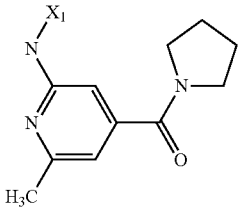
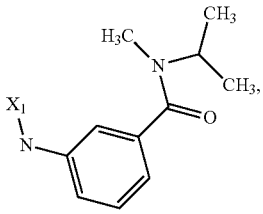
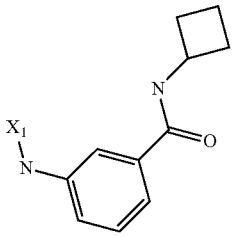
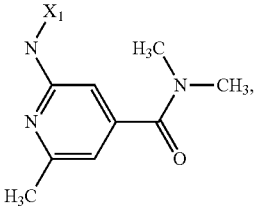
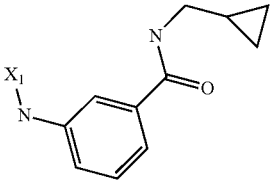
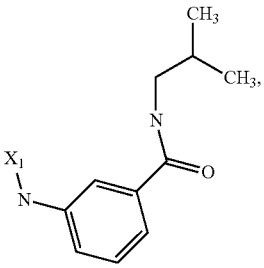
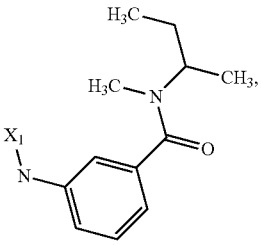
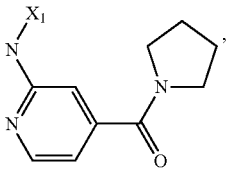
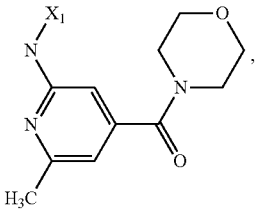
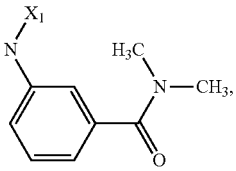
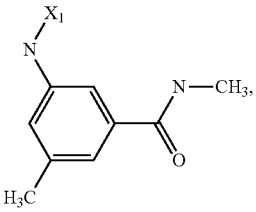
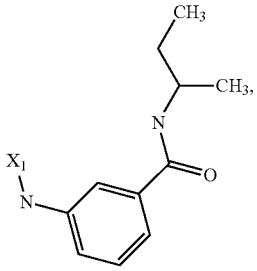
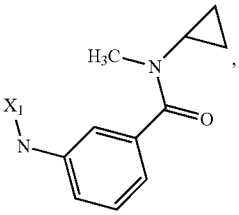
-continued
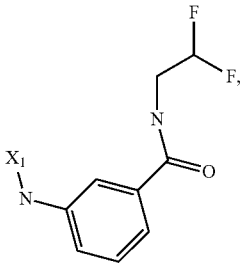
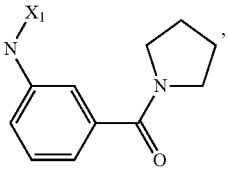
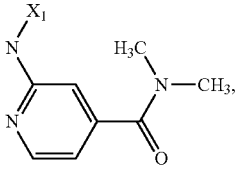
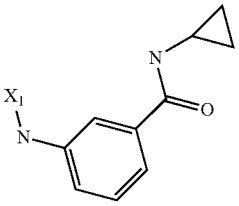
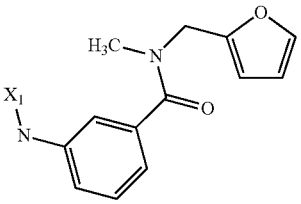
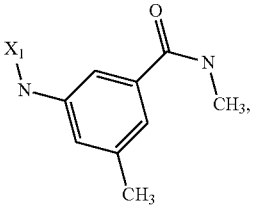
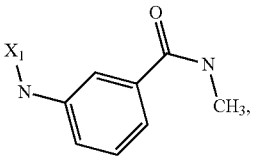
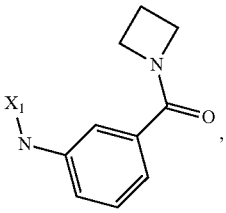
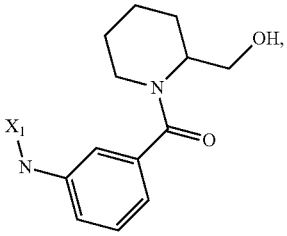
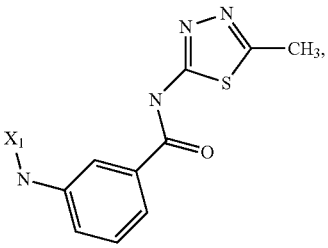
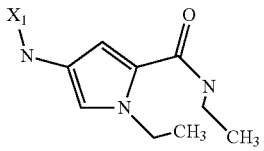
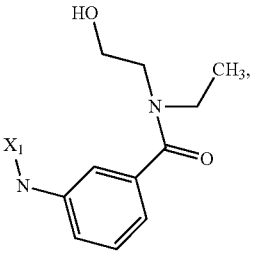

-continued
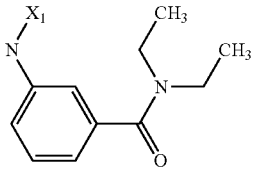
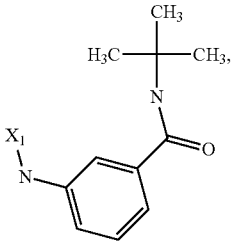
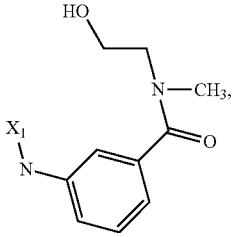
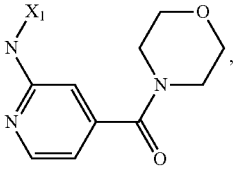
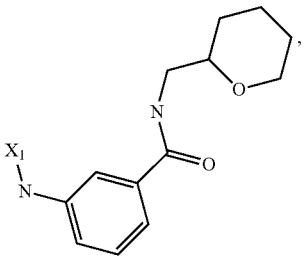
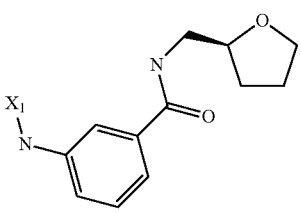
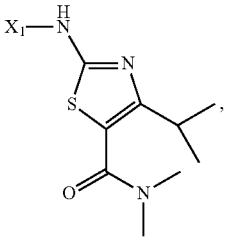
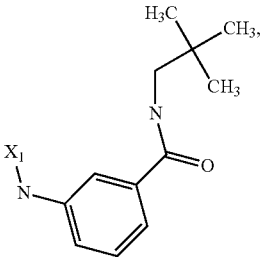
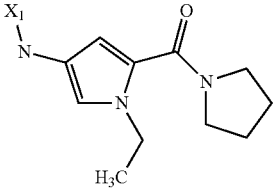
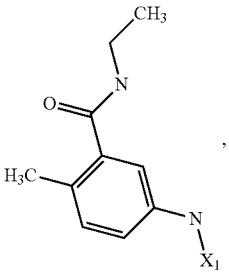
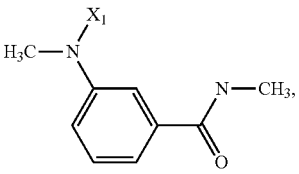
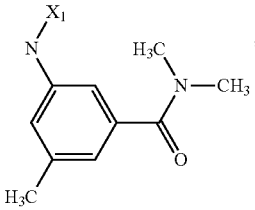
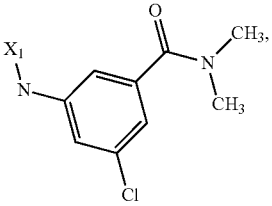
-continued
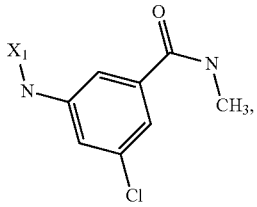
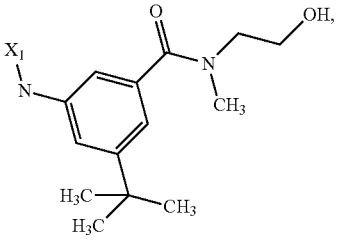
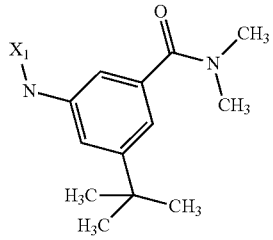
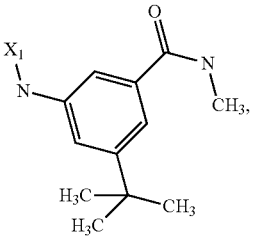
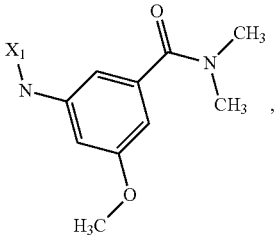
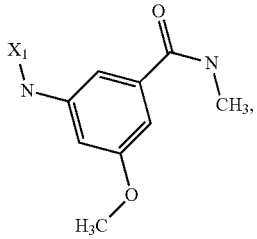
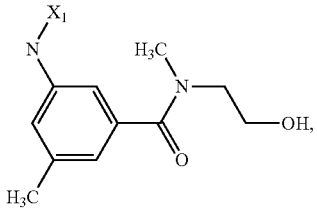
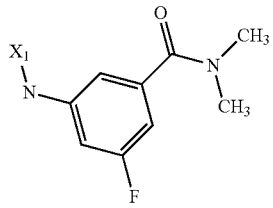
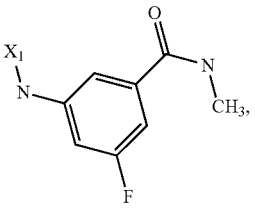
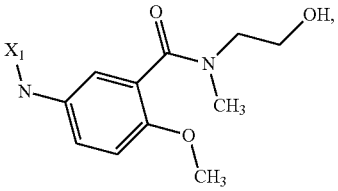
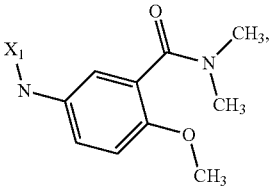
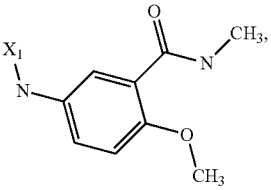

-continued
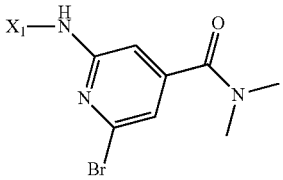
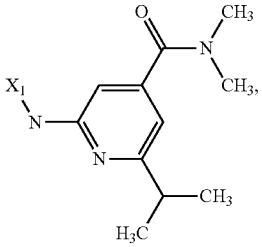
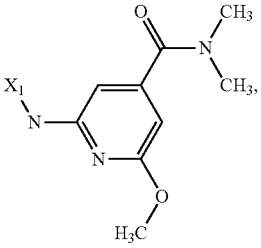
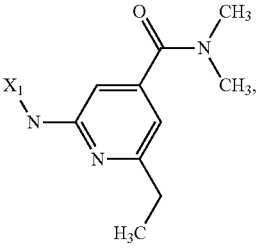
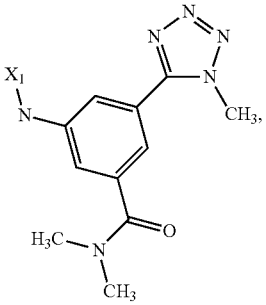
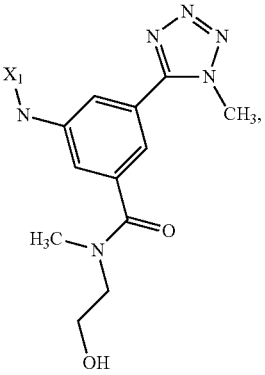
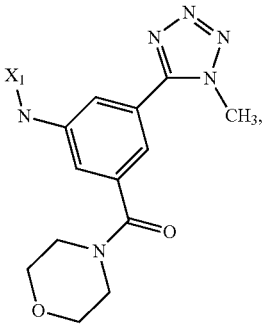
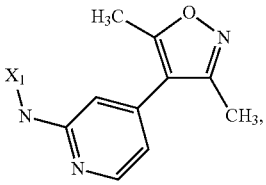
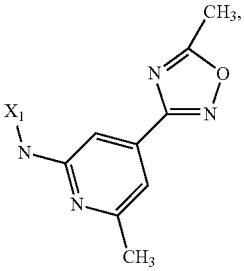
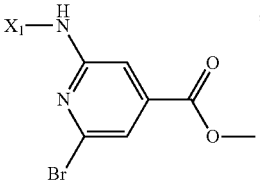
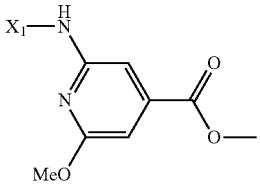
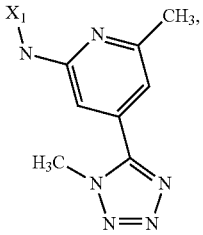
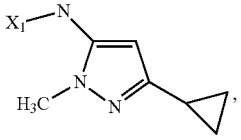
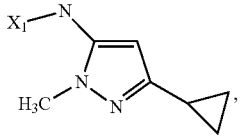
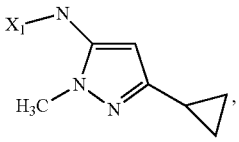
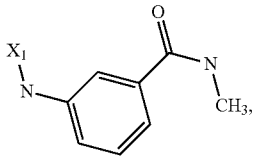
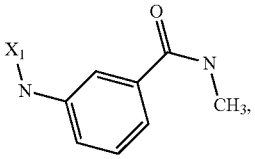
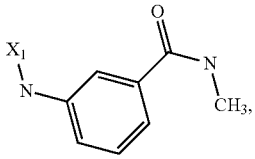
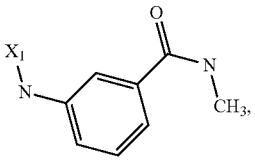
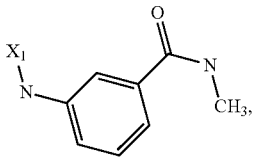
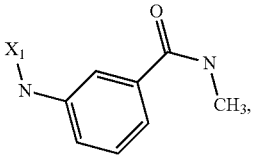
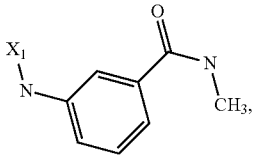
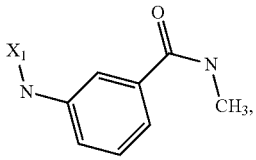
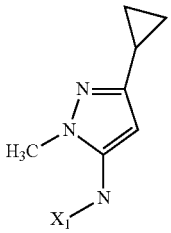
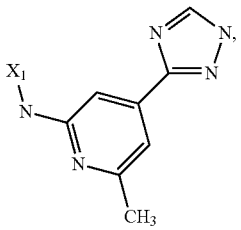
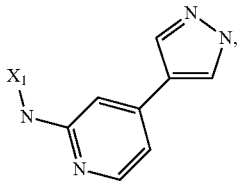
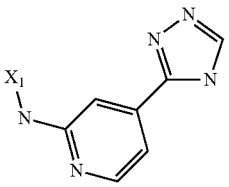
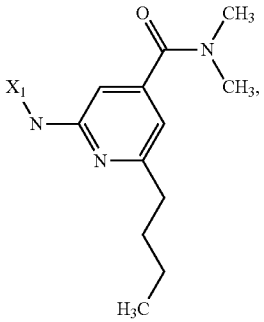

-continued
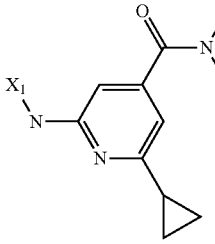
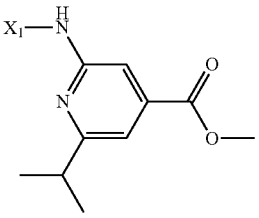
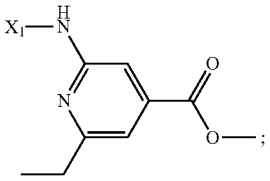
$R^2$ is selected from
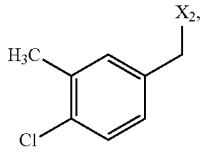
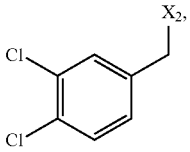
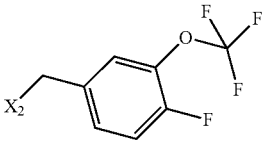
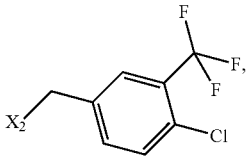
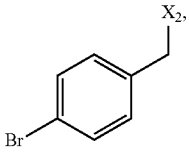
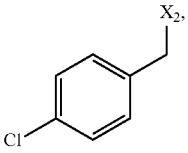
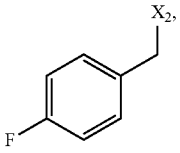
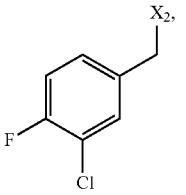
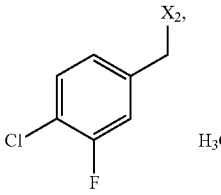
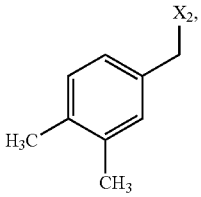
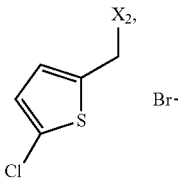
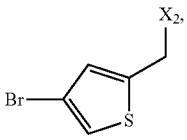
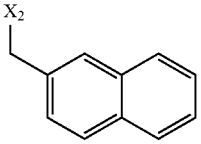
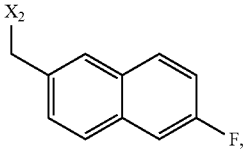
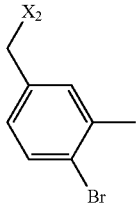
$R^3$ is H;
$R^4$ is H;
or $R^3$ and $R^4$ together are forming a $CH_2$—$CH_2$ group.
Another embodiment of the present invention are compounds of formula 1, wherein A is defined as above; $R^3$ is H; $R^4$ is H; and $R^2$ is defined as in table 1 shown below; and $R^1$ is selected from
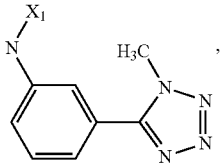
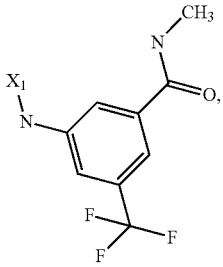
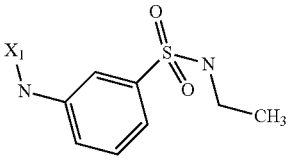
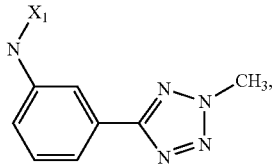
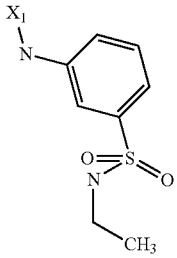
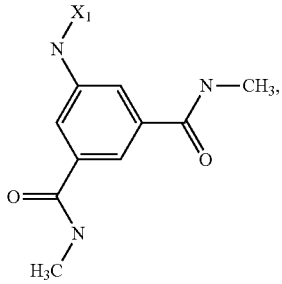
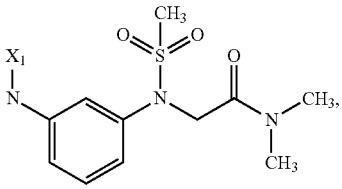
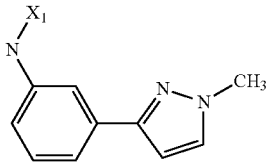
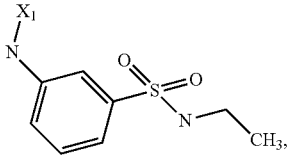
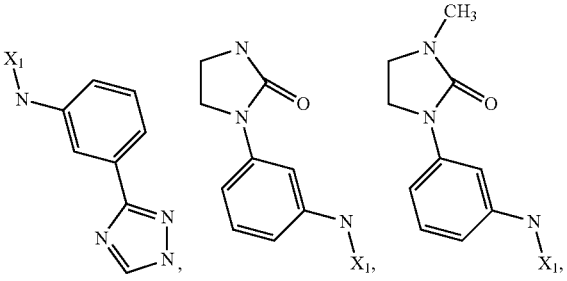
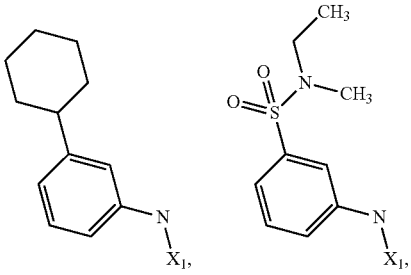

-continued
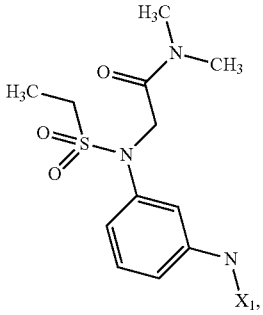
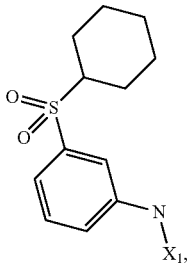
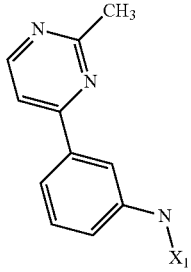
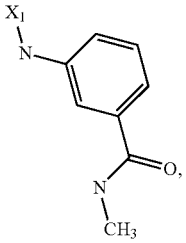
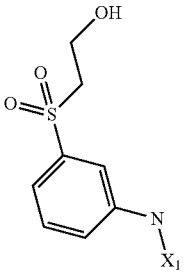
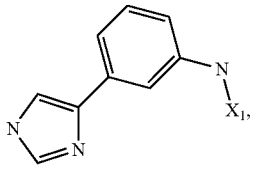
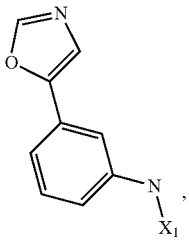
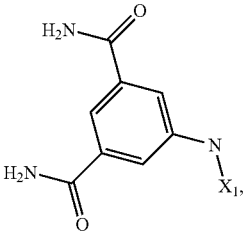
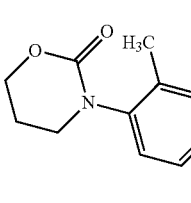
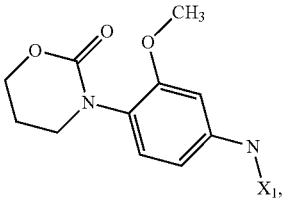
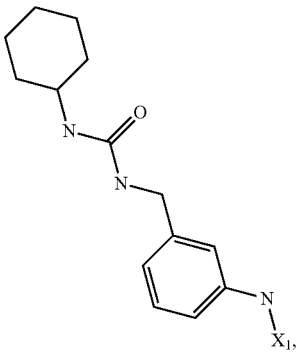
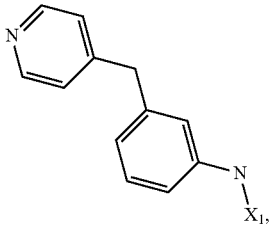
-continued
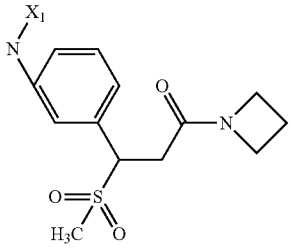
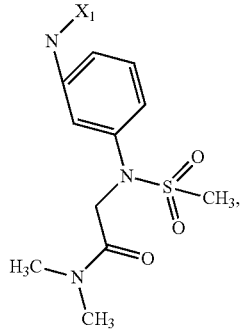
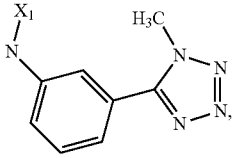
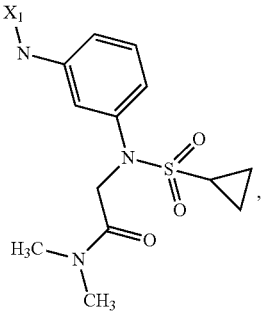
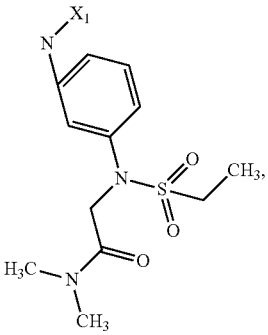
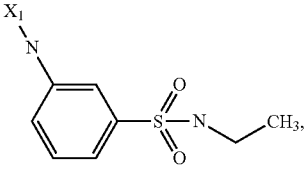
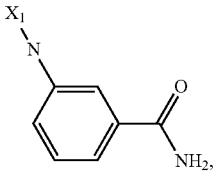
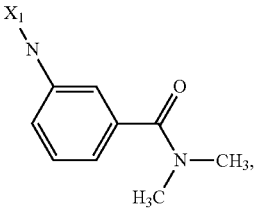
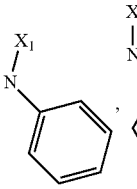
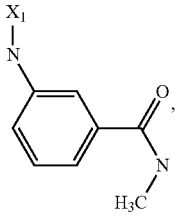
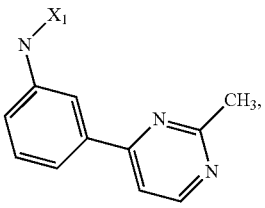
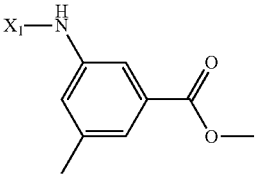
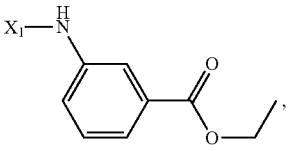

-continued
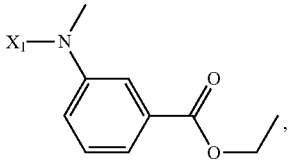
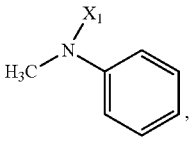
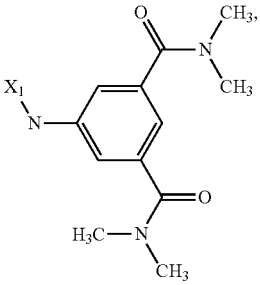
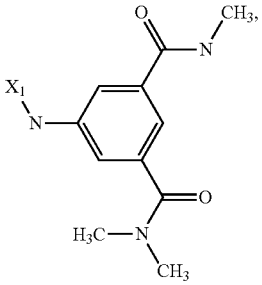
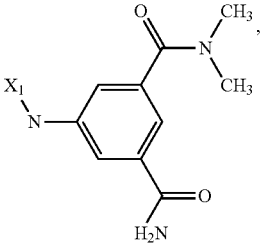
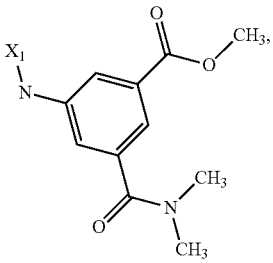
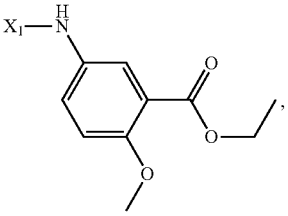
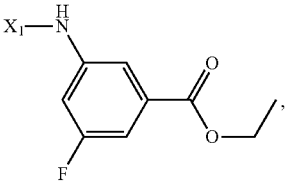
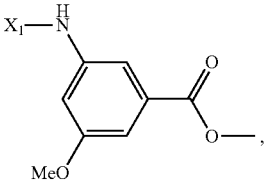
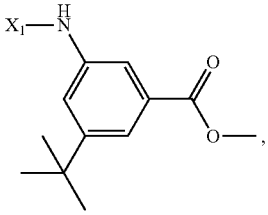
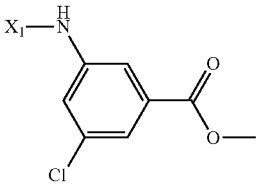
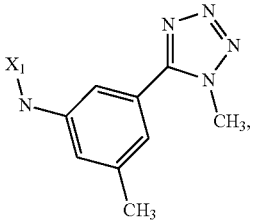
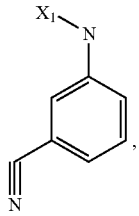
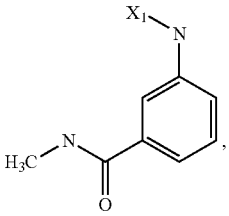
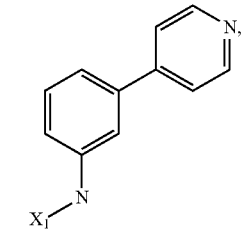
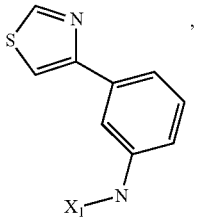
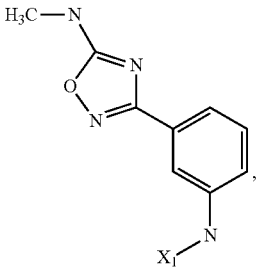
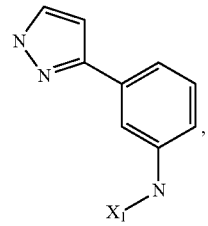
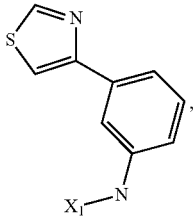
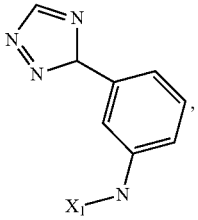
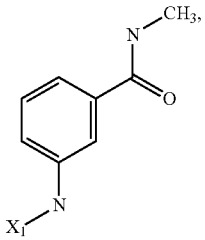
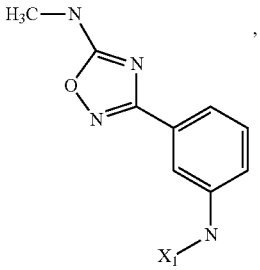
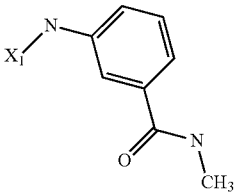
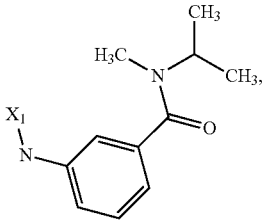
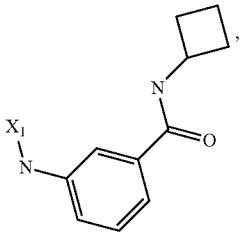
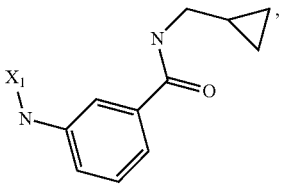
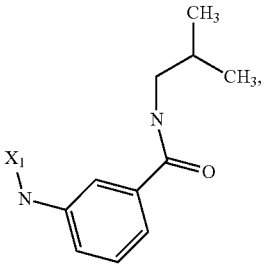
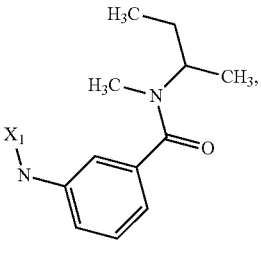

-continued
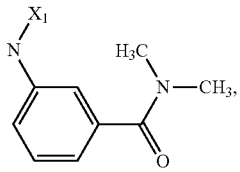
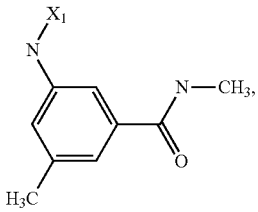
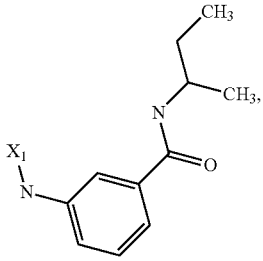
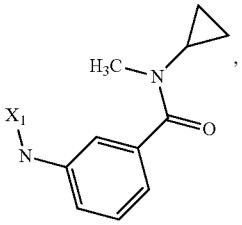
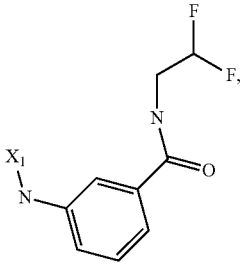
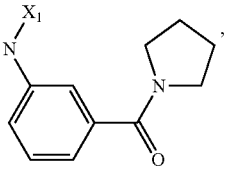
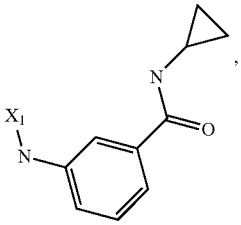
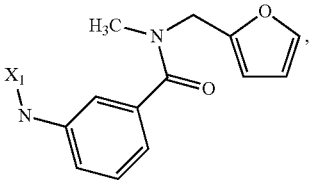
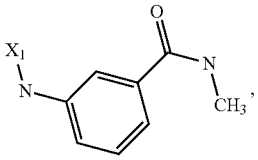
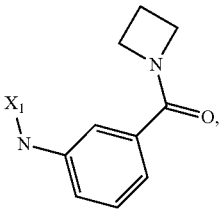
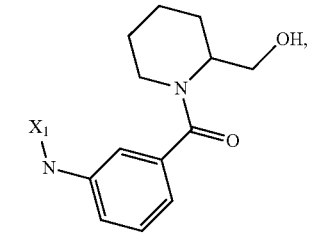
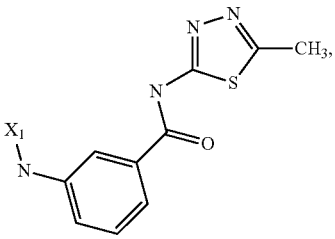
-continued
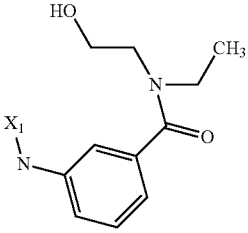
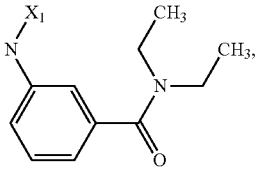
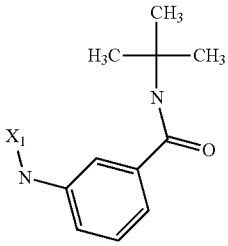
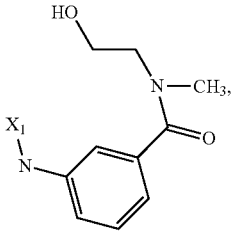
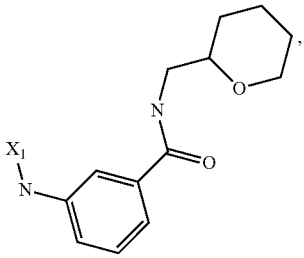
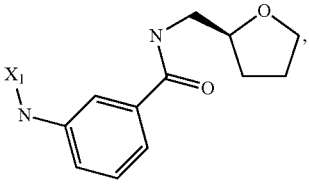
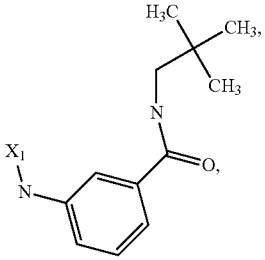
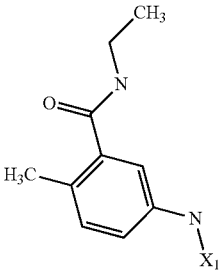
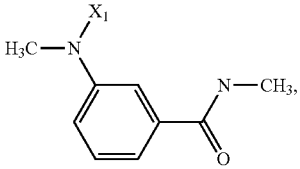
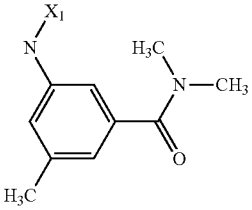
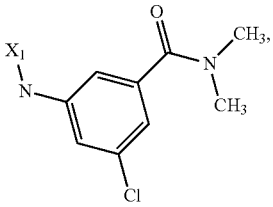
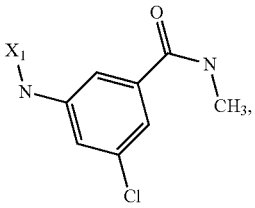

-continued
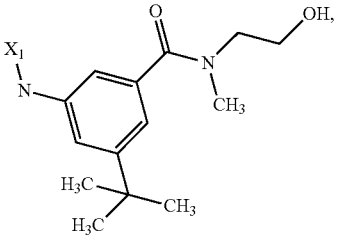
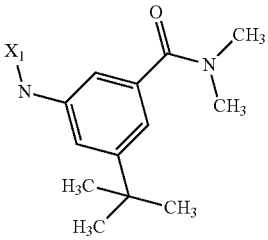
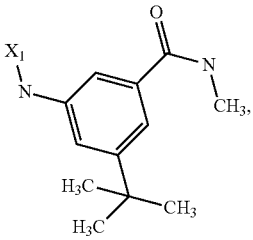
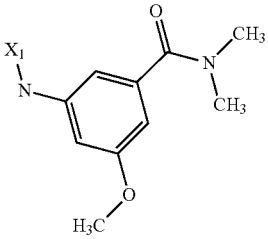
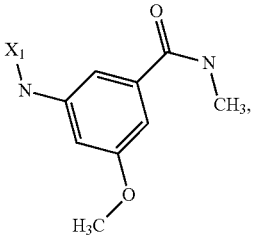
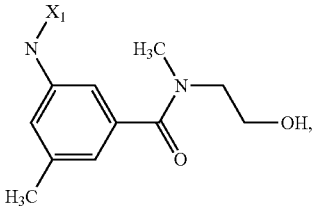
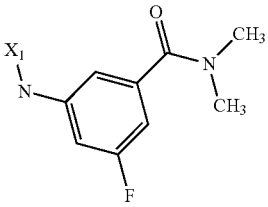
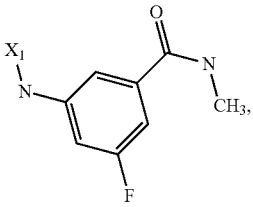
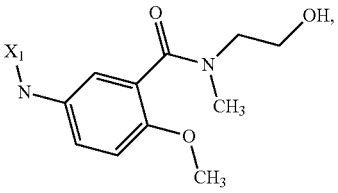
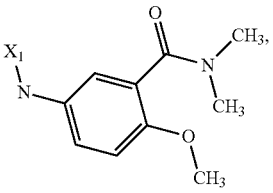
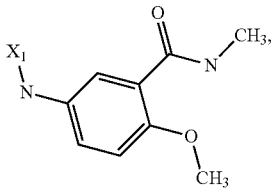
-continued
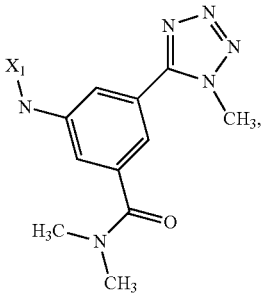
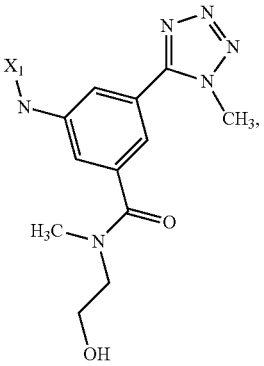
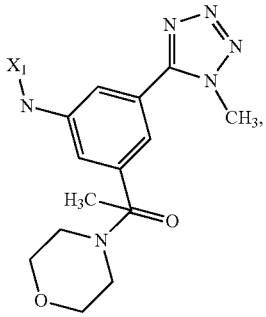
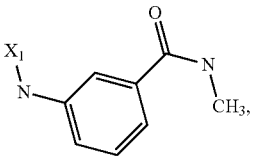
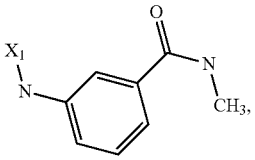
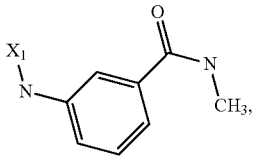
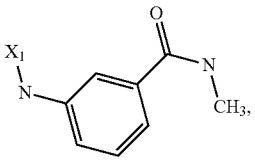
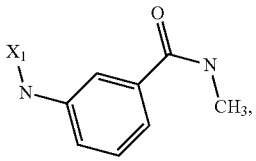
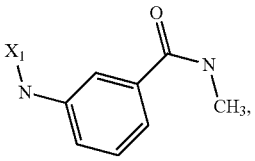
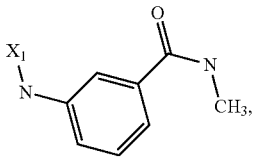
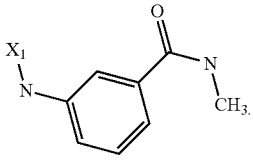
Another embodiment of the present invention are compounds of formula 1, wherein A is defined as above; $R^3$ is H; $R^4$ is H; and $R^2$ is defined as in table 1 shown below; and $R^1$ is selected from

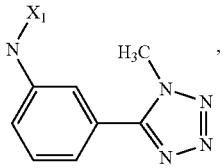
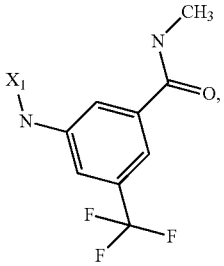
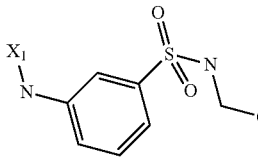
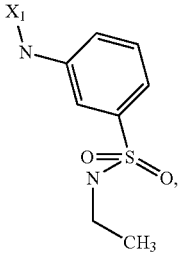
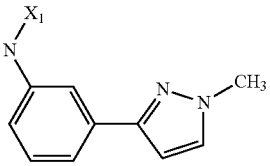
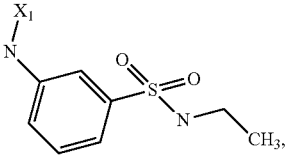
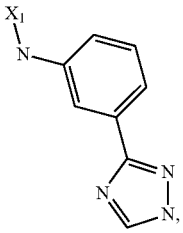
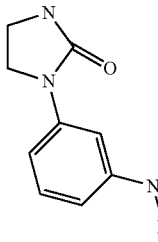
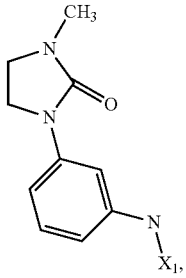
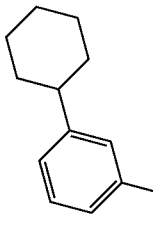
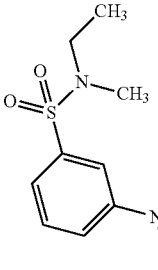
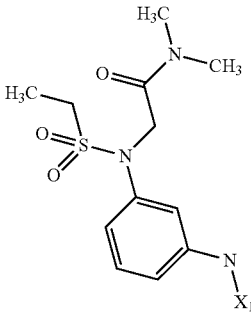
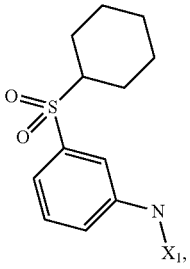
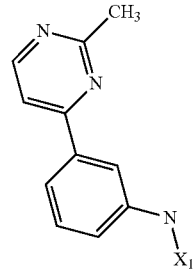
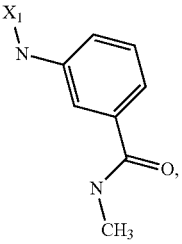
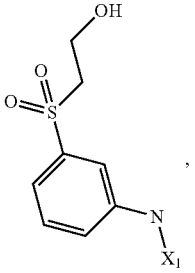
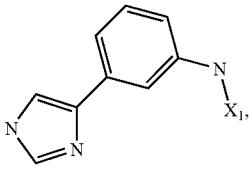
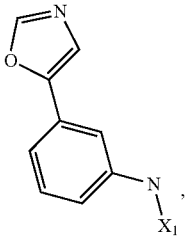
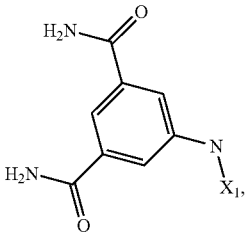
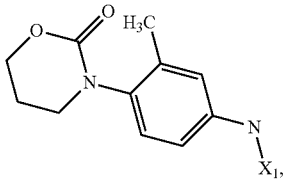
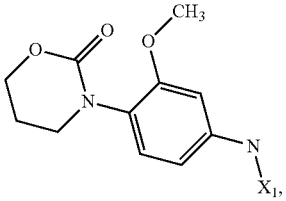
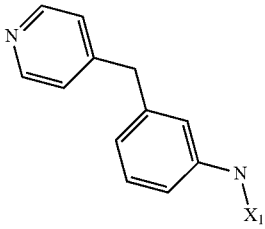
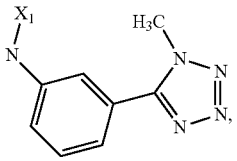
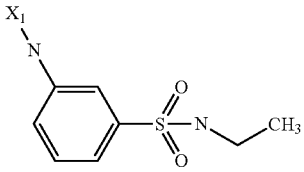
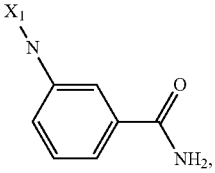
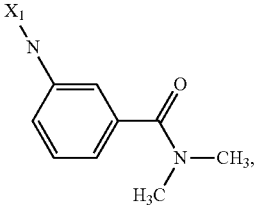
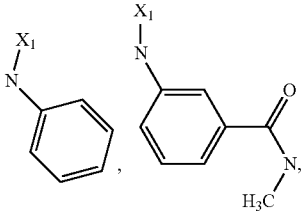

-continued
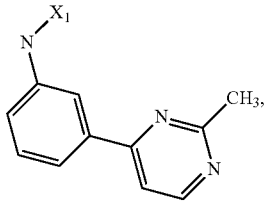
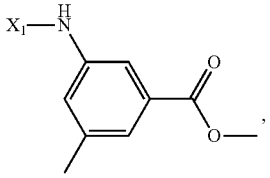
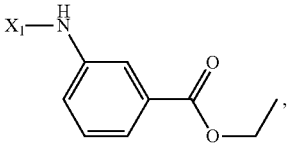
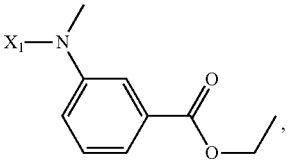
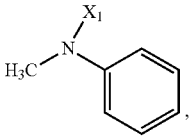
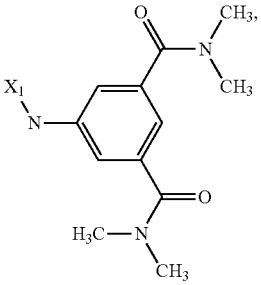
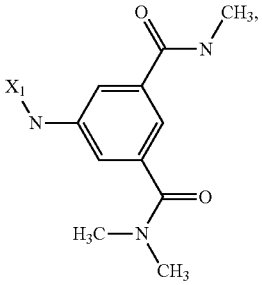
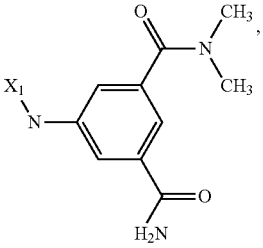
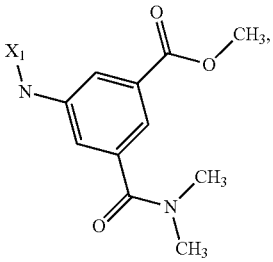
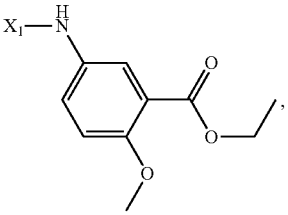
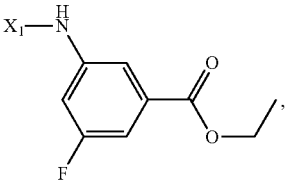
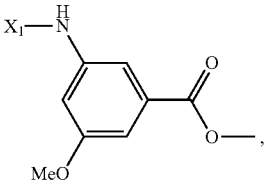
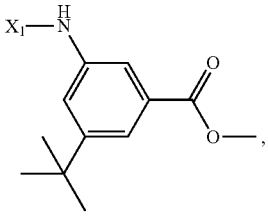
-continued
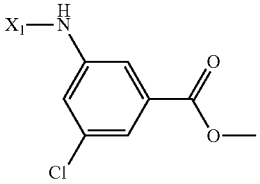
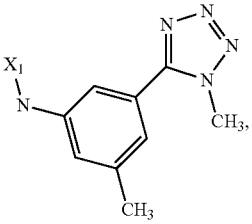
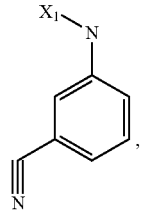
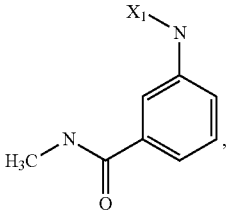
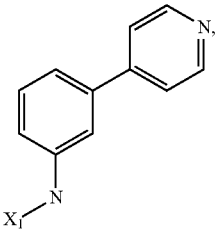
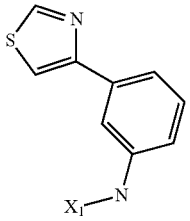
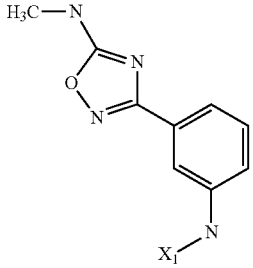
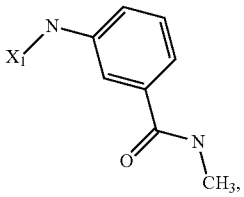
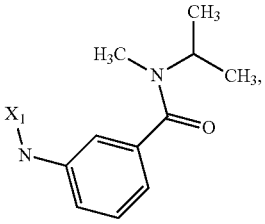
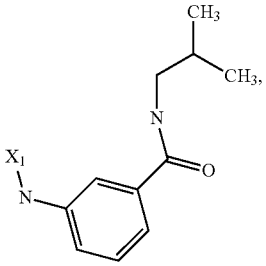
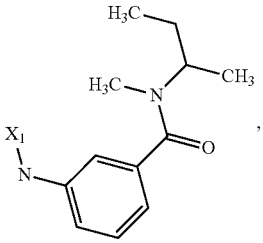
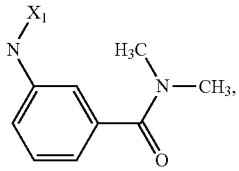
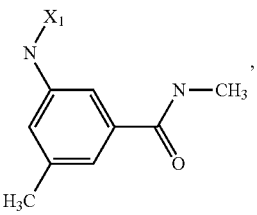
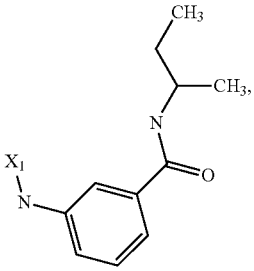

-continued
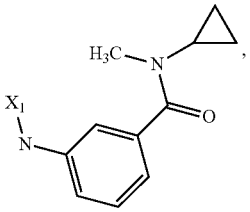
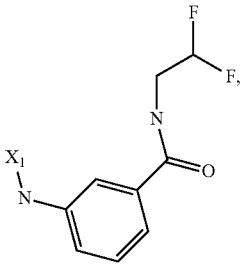
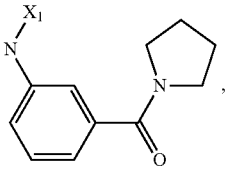
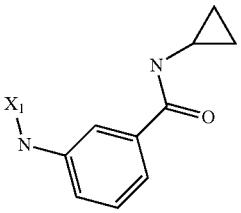
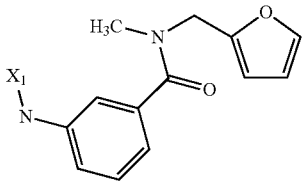
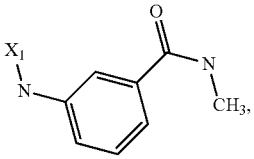
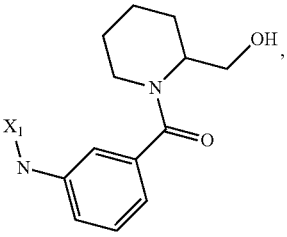
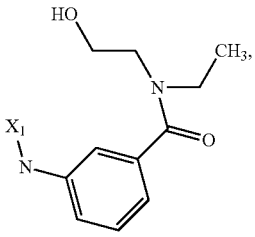
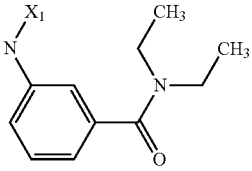
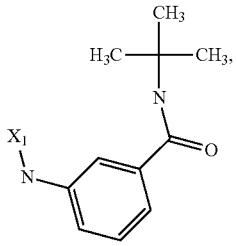
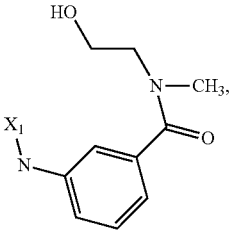
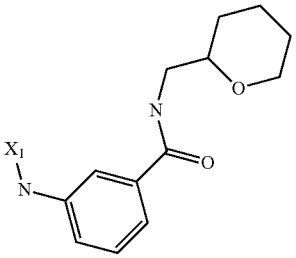
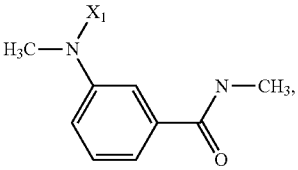
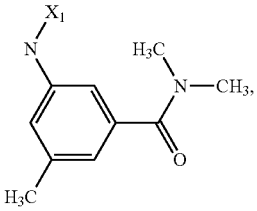
-continued
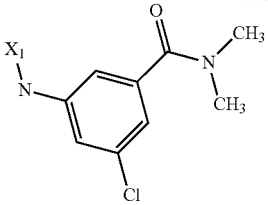
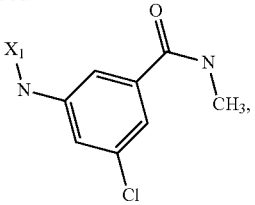
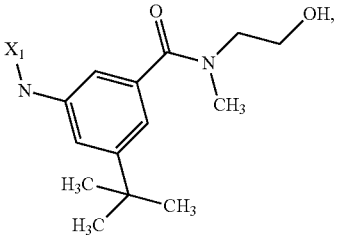
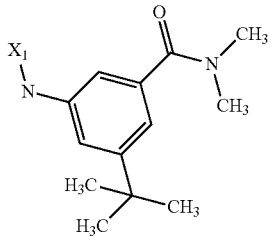
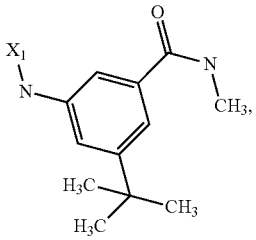
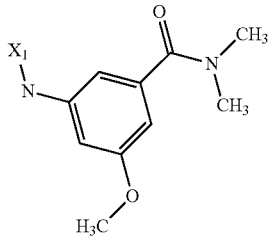
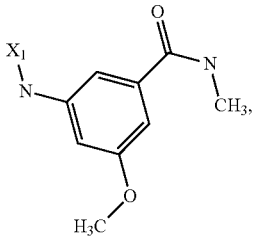
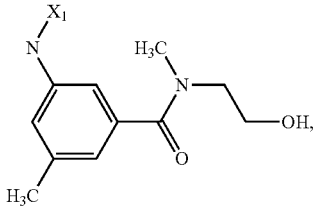
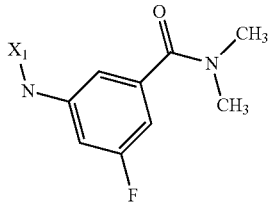
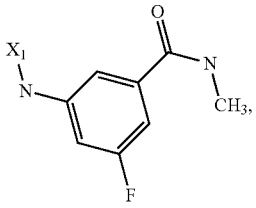
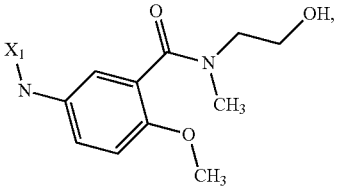
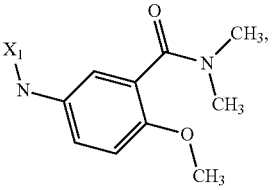
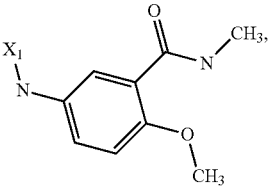

-continued
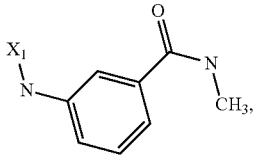
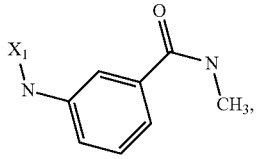
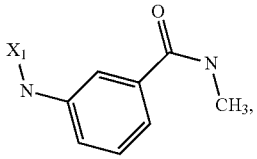
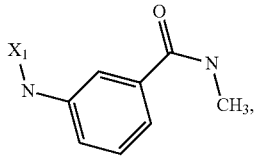
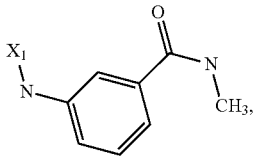
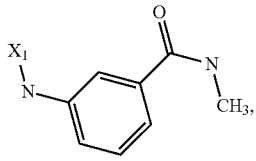
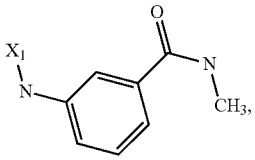
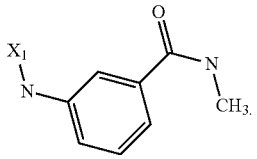
Another embodiment of the present invention are compounds of formula 1, wherein A is defined as above; $R^3$ is H; $R^4$ is H; and $R^2$ is defined as in table 1 shown below; $R^1$ is selected from
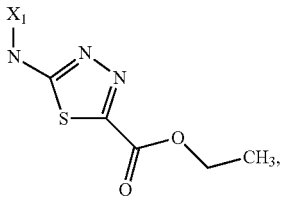
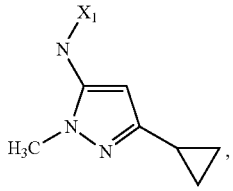
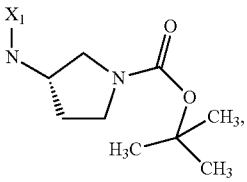
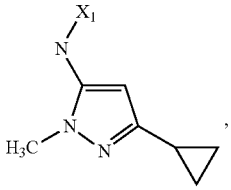
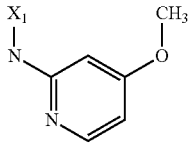
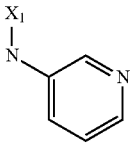
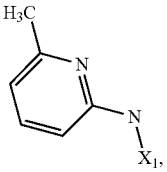
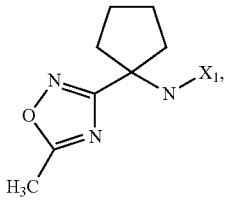
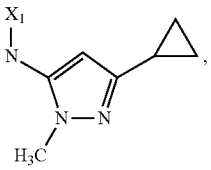
-continued
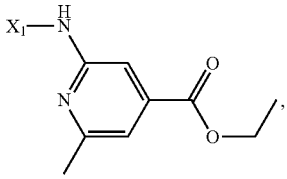
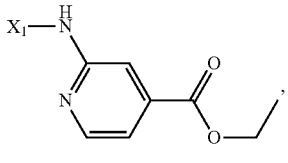
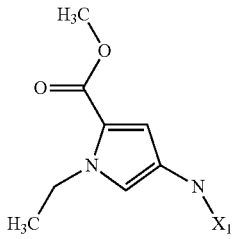
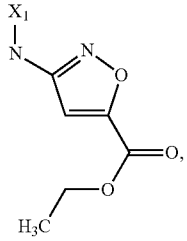
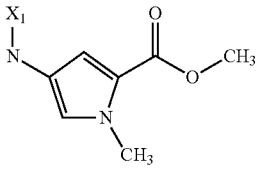
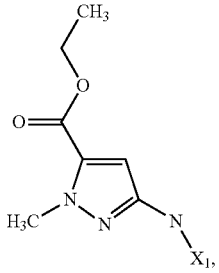
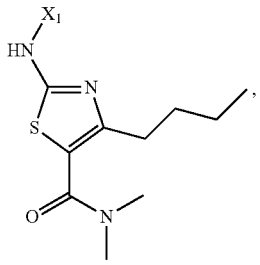
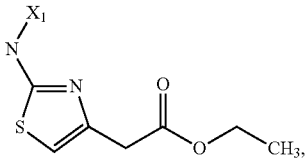
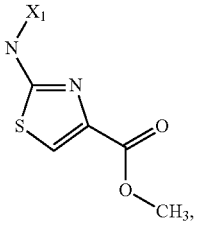
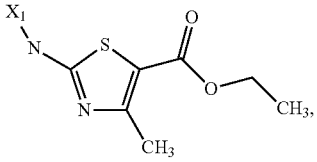
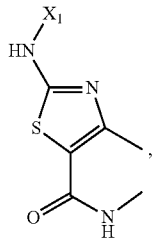
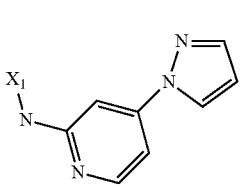
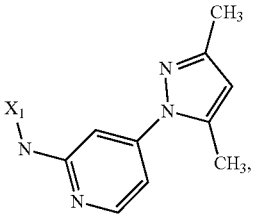

-continued
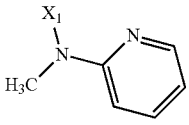
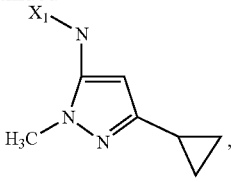
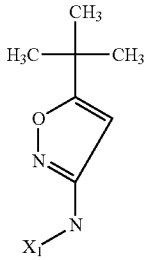
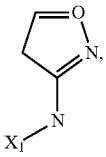
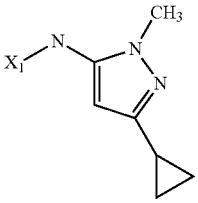
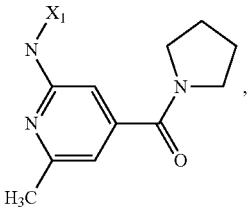
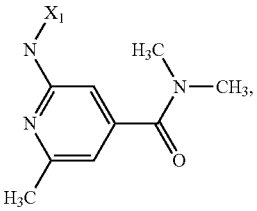
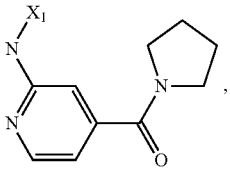
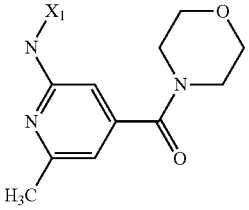
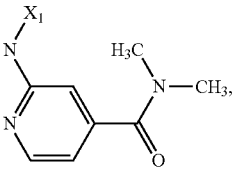
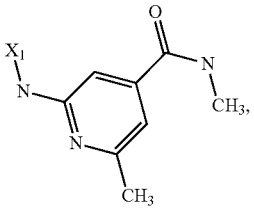
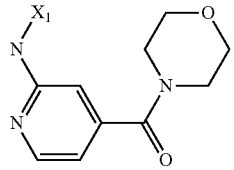
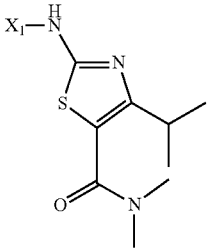
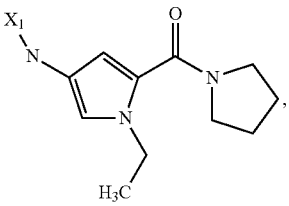
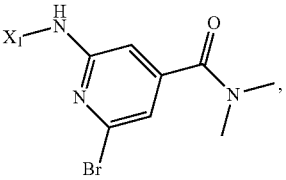
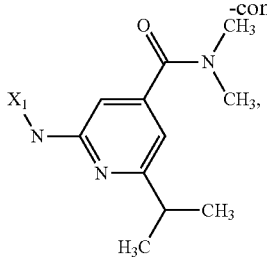
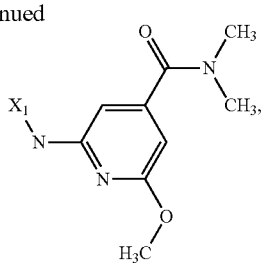
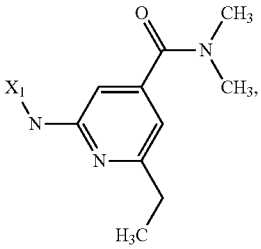
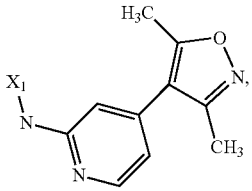
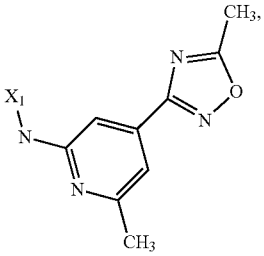
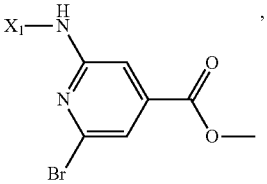
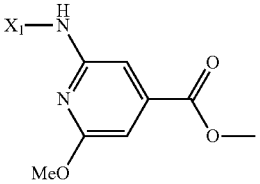
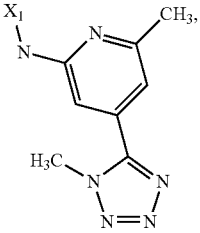
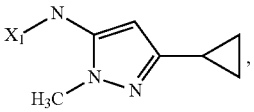
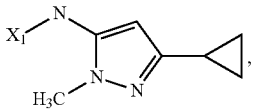
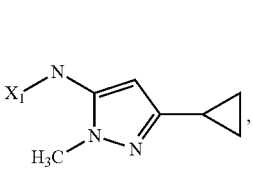
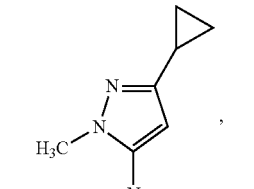
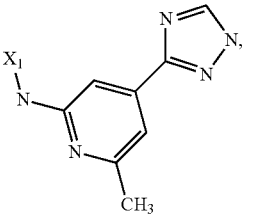

-continued
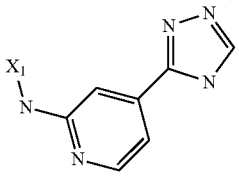
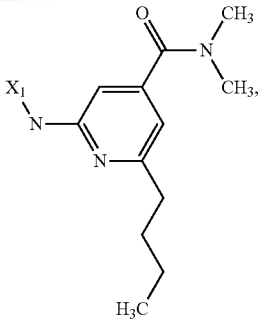
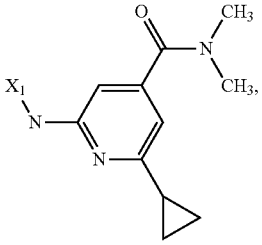
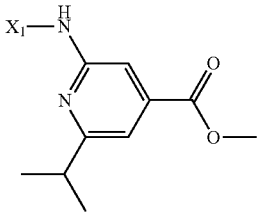
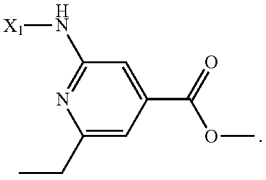
Another embodiment of the present invention are compounds of formula 1, wherein A is defined as above; $R^3$ is H; $R^4$ is H; and $R^2$ is defined as in table 1 shown below; $R^1$ is selected from
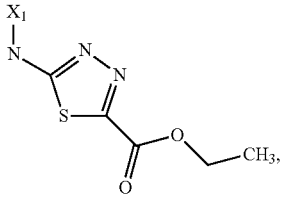
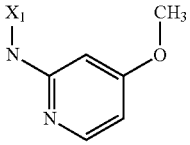
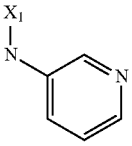
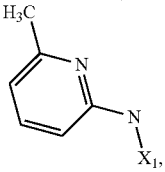
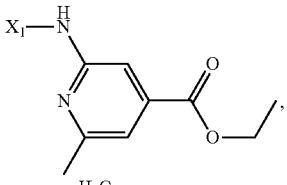
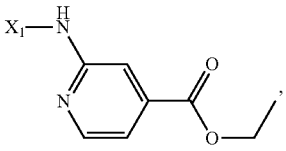
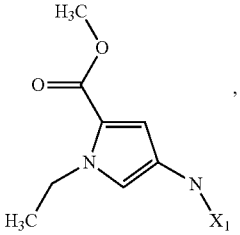
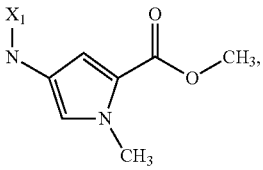
-continued
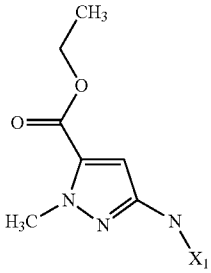
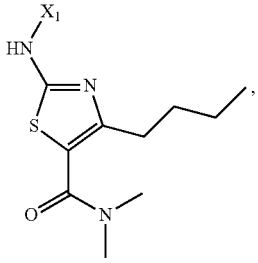
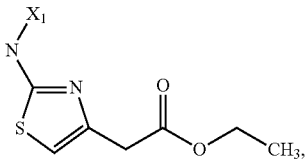
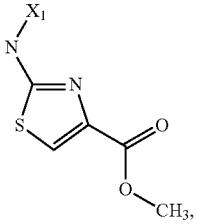
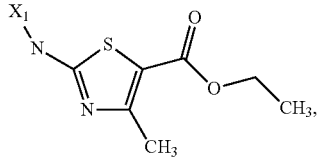
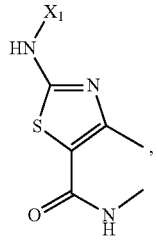
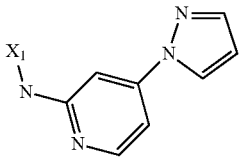
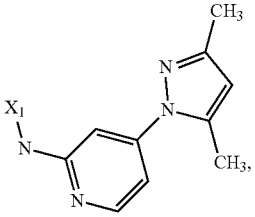
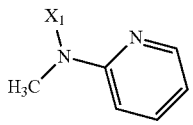
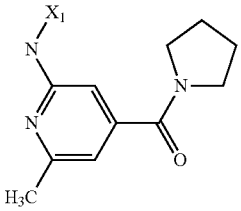
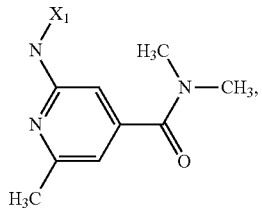
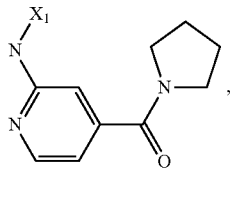
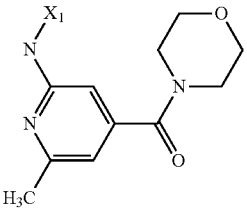
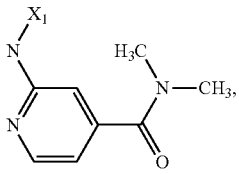

-continued
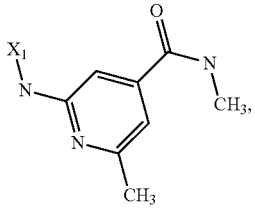
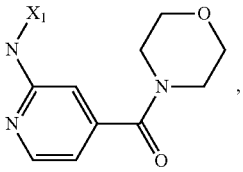
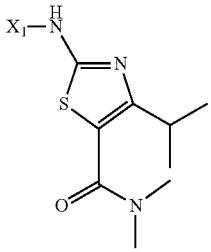
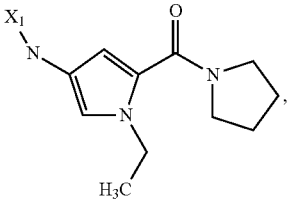
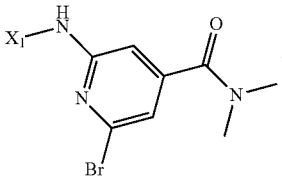
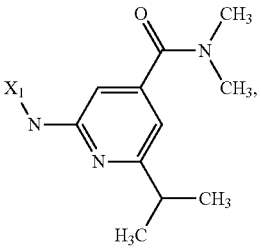
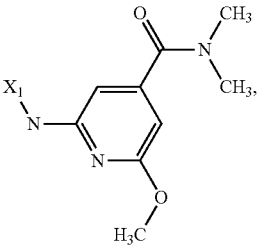
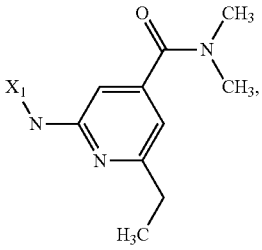
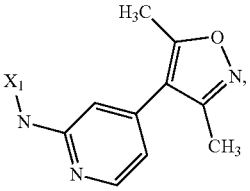
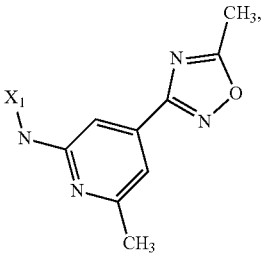
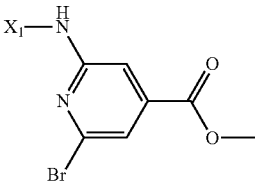
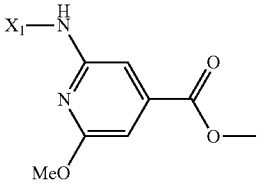
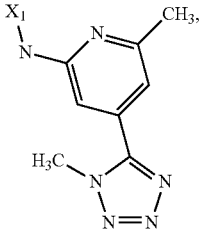
-continued
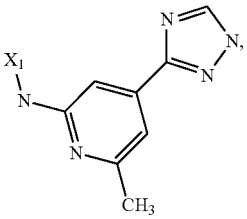
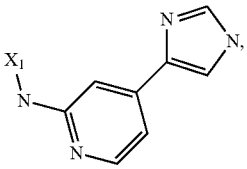
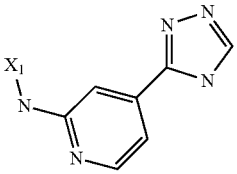
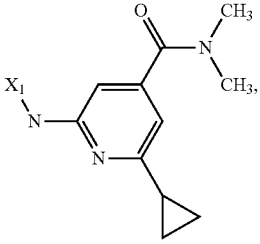
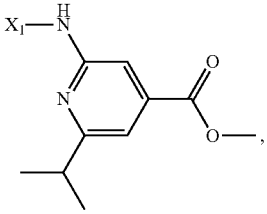
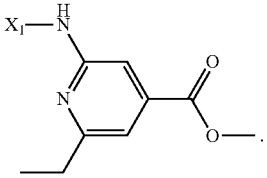
TABLE 1
| $R^2$ is defined as one of the groups shown below in the definitions 1 to 4: |
|---|
| Definition 1 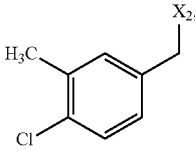 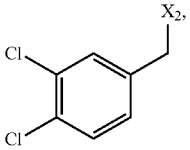 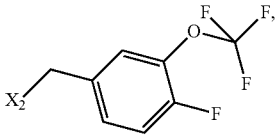 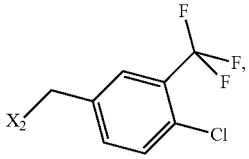 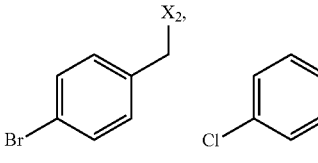   |

TABLE 1-continued $R^2$ is defined as one of the groups shown below in the definitions 1 to 4:

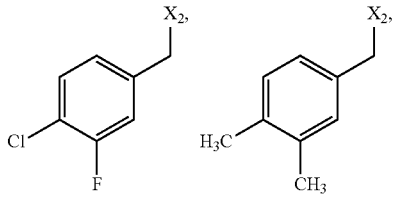

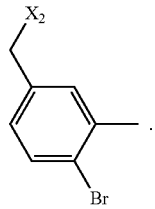

Definition 2

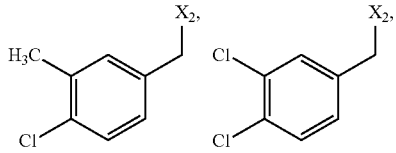

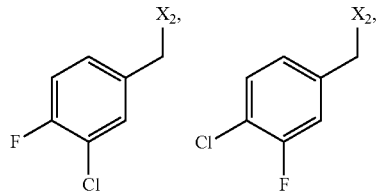

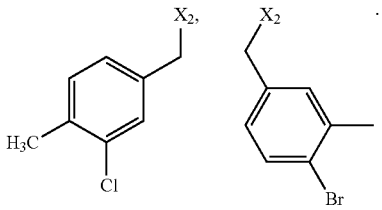

Definition 3

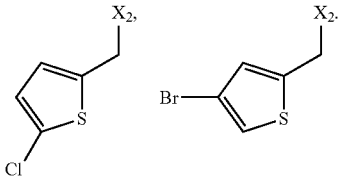

Definition 4

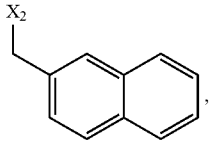

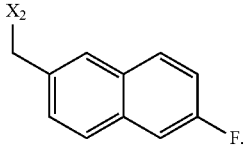

TABLE 1-continued $R^2$ is defined as one of the groups shown below in the definitions 1 to 4:

Definition 5

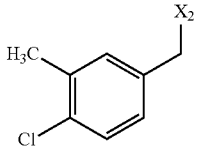

Definition 6

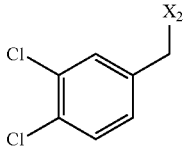

Definition 7

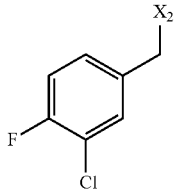

Definition 8

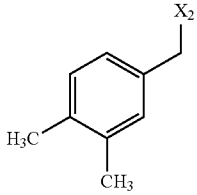

Definition 9

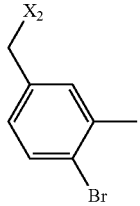

Definition 10

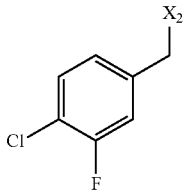

A further embodiment of the invention are compounds of formula 1, wherein the compounds of formula 1 are present in the form of the individual optical isomers, mixtures of the individual enantiomers or racemates, preferably in the form of the enantiomerically pure compounds. Especially preferred is the R-enantiomer of the compounds of formula 1 which is the following formula R-1

R-1

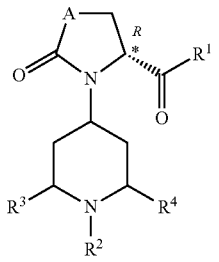

A further embodiment of the invention are compounds of formula 1, wherein the compounds of formula 1 are present in the form of the acid addition salts thereof with pharmacologically acceptable acids as well as optionally in the form of the solvates and/or hydrates.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —C1-6 alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

- Straight-chain or branched carbon chains, optionally interrupted by heteroatoms, optionally substituted by rings, heteroatoms or other common functional groups.
- Aromatic or non-aromatic ring systems consisting of carbon atoms and optionally heteroatoms, which may in turn be substituted by functional groups.
- A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, Succinate, Sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl Sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,P-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

By the term heterocyclic rings ("het") are meant five-, six- or seven-membered, saturated or unsaturated heterocyclic rings or 5-10 membered, bicyclic hetero rings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

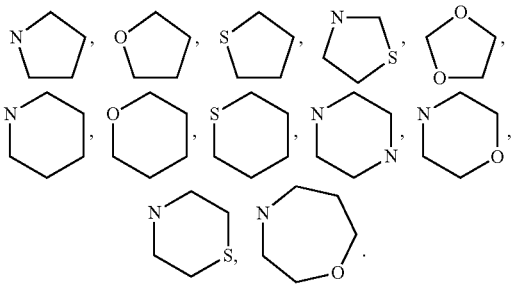

Unless stated otherwise, a heterocyclic ring may be provided with a keto group. Examples include:

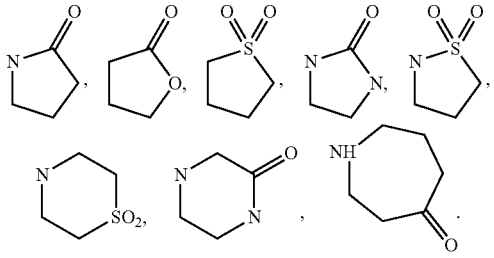

Examples of 5-10-membered bicyclic hetero rings are pyrrolizine, indole, indolizine, isoindole, indazole, purine, quinoline, isoquinoline, benzimidazole, benzofurane, benzopyrane, benzothiazole, benzoisothiazole, pyridopyrimidine, pteridine, pyrimidopyrimidine,

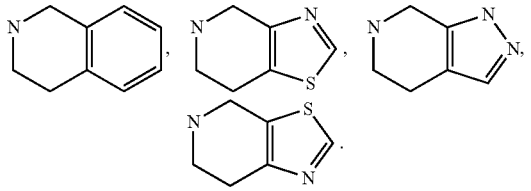

Although the term heterocyclic rings includes heterocyclic aromatic groups, the term heterocyclic aromatic groups ("hetaryl") denotes five- or six-membered heterocyclic aromatic groups or 5-10 membered, bicyclic hetaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

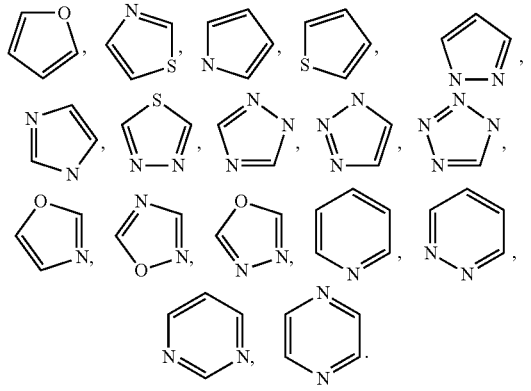

Examples of 5-10-membered bicyclic hetaryl rings include pyrrolizine, indole, indolizine, isoindole, indazole, purine, quinoline, isoquinoline, benzimidazole, benzofuran, benzopyrane, benzothiazole, benzoisothiazole, pyridopyrimidine, pteridine, pyrimidopyrimidine.

The term "halogen" as used herein means a halogen substituent selected from fluoro, chloro, bromo or iodo.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the respective groups with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are preferred. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the respective groups with the same number of carbons. Thus for example propynyl also includes 1-methylethynylene and butynylene includes 1-methylpropynylene, 1,1-dimethylethynylene, 1,2-dimethylethynylene.

The term "$C_{3-6}$cycloalkyl" (including those which are part of other groups) as used herein means cyclic alkyl groups with 3 to 8 carbon atoms, preferred are cyclic alkyl groups with 5 to 6 carbon atoms. Examples include: cyclopropyl, cyclobutyl, cyclopentyl or cyclohexyl.

By the term "$C_{1-6}$-haloalkyl" (including those which are part of other groups) are meant branched and unbranched alkyl groups with 1 to 6 carbon atoms wherein one or more hydrogen atoms are replaced by a halogen atom selected from among fluorine, chlorine or bromine, preferably fluorine and chlorine, particularly preferably fluorine. By the term "$C_{1-4}$-haloalkyl" are meant correspondingly branched and unbranched alkyl groups with 1 to 4 carbon atoms, wherein one or more hydrogen atoms are replaced analogously to what was stated above. $C_{1-4}$-haloalkyl is preferred. Examples include: $CH_2F$, $CHF_2$, $CF_3$,

EXAMPLES

S. General Synthesis Procedures for Examples

The examples of the present invention are synthesized according to the following general scheme:

General Synthesis Scheme:

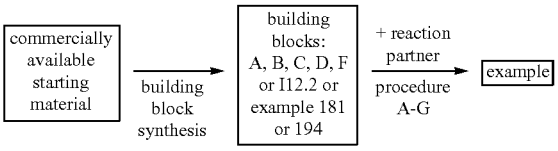

where "building block" and "reaction partner" are defined for the procedures A-G below in which A, $R^1$, $R^2$, $R^3$ and $R^4$ are defined as above. In case a building block or reaction partner is not commercially available, its synthesis is described below, commencing from a commercially available staring material, and where necessary, involving intermediate(s), "I".

The term "linker" is used to mean a chemical moiety whose definition is restricted to that of R1 and is able to bear the specific functional group as stated in order to undergo the reaction of the procedure. In procedure E, the synthesis starts from intermediate I12.2 which defines the "building block". In procedure G, the synthesis starts from example 181 or 194 which define the "building block"

S.1. Procedures A-G

Procedure A

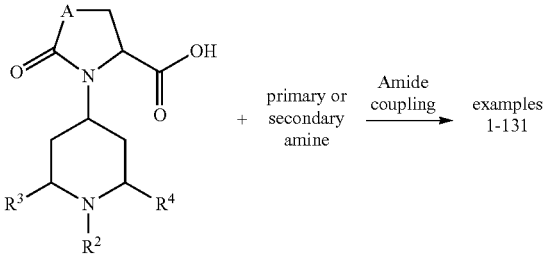

building block A1-A8

Procedure B
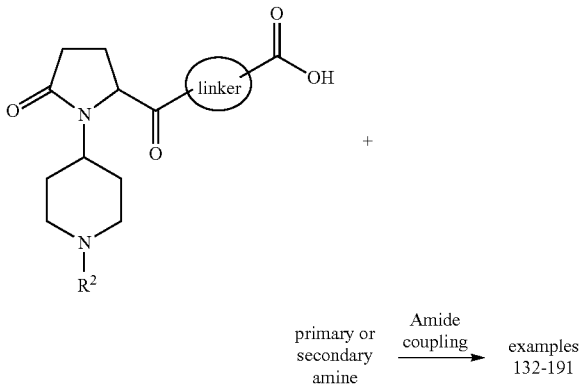
building block B1-B20
Procedure C
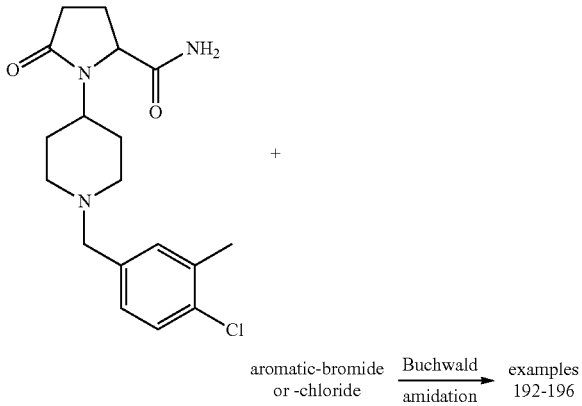
building block C1
Procedure D
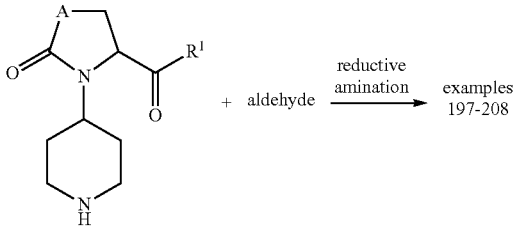
building block D1-D2
Procedure E
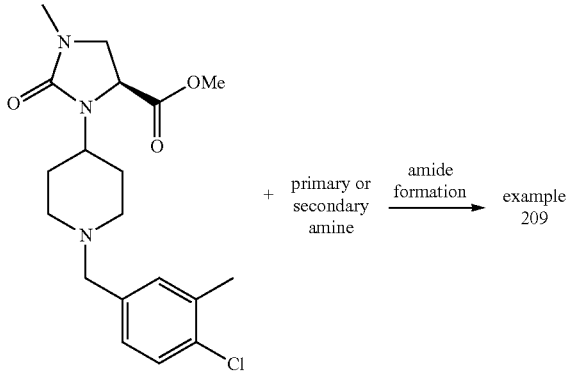
I12.2 (see synthesis of building block A7)
Procedure F
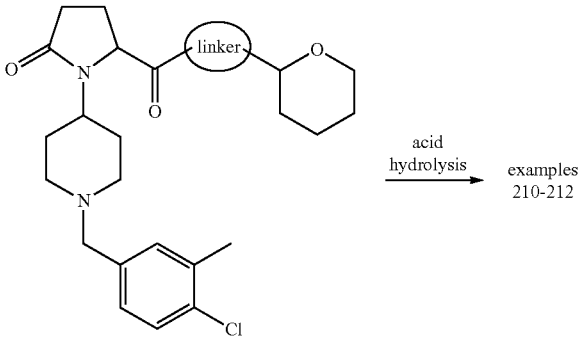
building block F1-F3
Procedure G
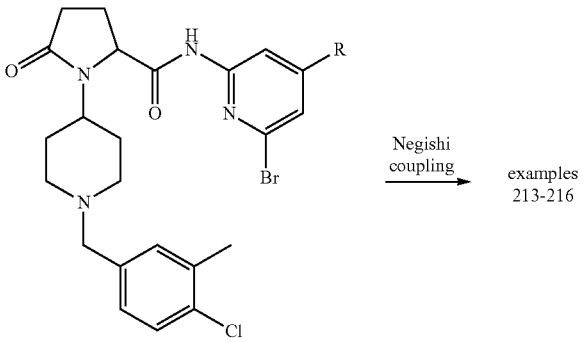
example 181 or 194

S.2. Building Block Syntheses

S.2.1 Synthesis of Building Blocks of Formula A

Synthesis of Building Blocks A1-A4

Synthesis of Building Block A1

Step 1

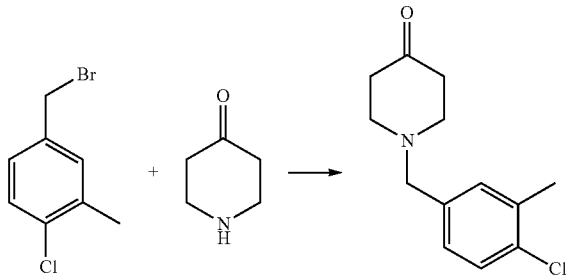

I1

4-Chloro-3-methyl benzylbromide (20 g) [synthesized according to literature: J. L. Kelley, J. A. Linn, J. W. T. Selway, J. Med. Chem. 1989, 32(8), 1757-1763], 4-Piperidone (22 g), $K_2CO_3$ (26 g) in acetonitrile (300 ml) was heated at 50° C. for 14 h. The suspension was filtered and the filtrate concentrated in vacuum. The residue was purified by flash chromatography (cyclohexane/EtOAc 1:1) to yield 17.4 g of intermediate I1.

Step 2

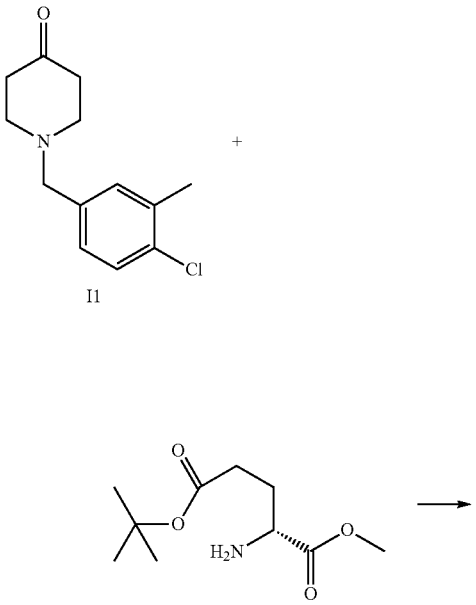

I1

-continued

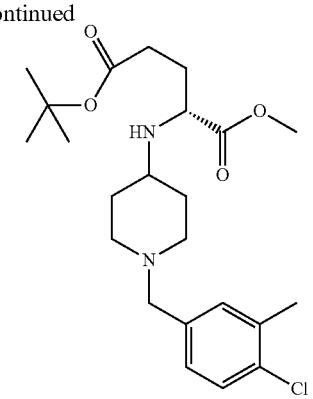

I2

Intermediate I1 (10 g) and D-H-Glu(O$^t$Bu)-OMe (10.8 g) was dissolved in DMF (200 ml) and HOAc (5 ml). Then molecular sieve (1.0 g, 4 Å, powder) was added and the suspension was stirred overnight. Sodium triacetoxyborohydride (37.5 g) was added and the suspension stirred until complete conversion of the intermediate formed imine was observed. A basic pH was achieved by slow addition (foam formation!) of aqueous $NaHCO_3$ solution before additional water and DCM (500 mL) was added. The organic phase was separated and the water phase extracted with DCM (500 ml). The organic phase was washed with brine, dried and concentrated in vacuum to yield 19.5 g (74% purity) of intermediate I2.

Step 3

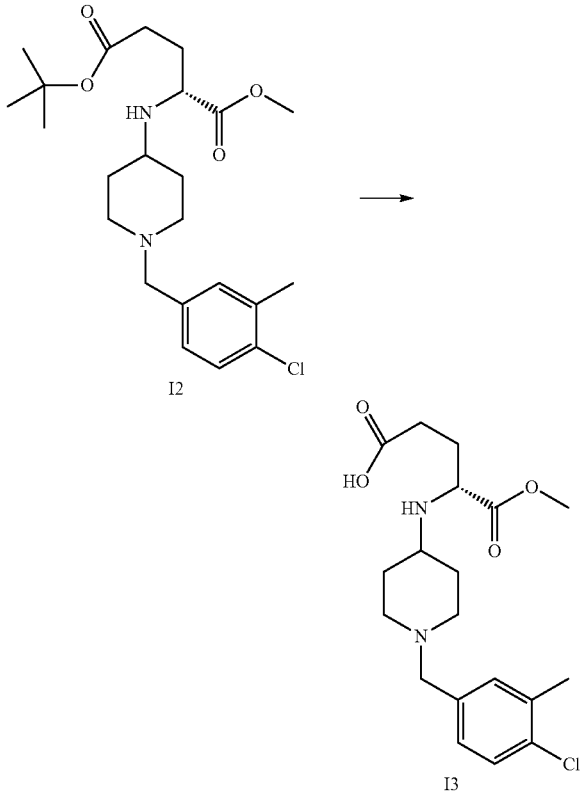

I2

I3

Intermediate I2 (19.5 g, 74% purity) was dissolved in DCM (40 ml) and trifluoroacetic acid (20 ml, TFA). The solution was stirred at 25° C. for 14 h before additional 40 ml TFA was added and the solution continued stirring for further 7 h. The reaction mixture was then concentrated in vacuum, dissolved in toluene and concentrated again to provide 29.5 g (purity 55%) of intermediate I3.

Step 4

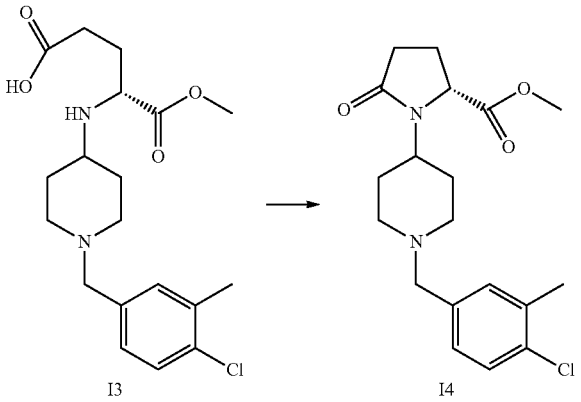

Intermediate I3 (29 g, purity 55%) was dissolved in DCM (100 ml) and DIPEA (22 ml). TBTU (15 g) was added and the solution was stirred for 30 min. Then DCM (150 ml), water (100 ml) and saturated $NaHCO_3$ solution (100 ml) was added, the organic phase was separated and the water phase extracted once with DCM (100 ml). The organic phase was dried and concentrated to provide an oil which was then fractionated via reversed phase HPLC. The fractions containing the building block D1 were concentrated in vacuum, then a basic pH was adjusted with addition of $NaHCO_3$ solution and the product was extracted with DCM to provide 8.1 g of intermediate I4.

Step 5

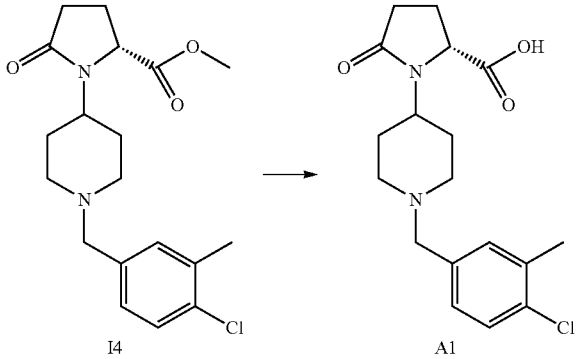

Intermediate I4 (7 g) was dissolved in dioxane (50 ml). 2.5 M LiOH solution (23 ml) and water (20 ml) was added and stirred at 25° C. overnight. The solution was acidified with aqueous 4N HCl and then concentrated in vacuum. The residue was dissolved in water, acetonitrile and a small amount of dioxane and lyophilised to provide 10.4 g solid (71% purity) of building block A1.

The building blocks were synthesized in analogy to acid A1:

A2

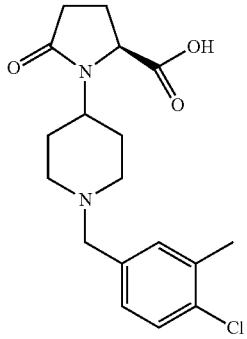

A3

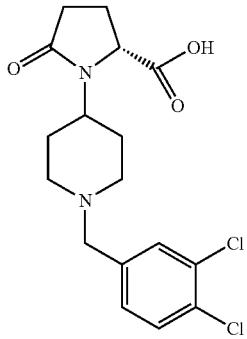

A4

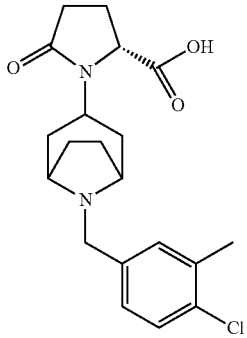

Synthesis of Building Block A5

Step 1

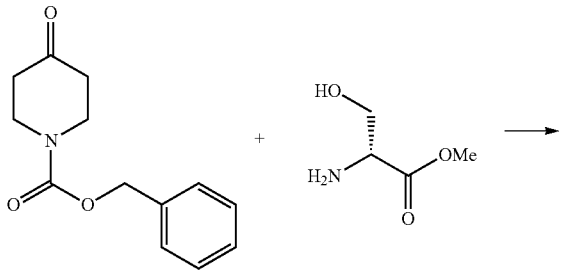

-continued

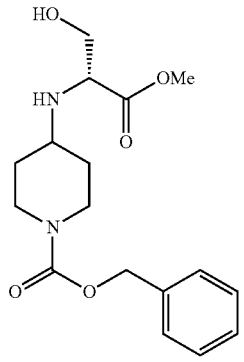

I5

Acetic acid (5.7 ml) was added to a stirred suspension of (R)-2-amino-3-hydroxy-propionic acid methyl ester hydrochloride (5.98 g) and 4-oxo-piperidine-1-carboxylic acid benzyl ester (9.86 g) in DCM (382 ml), and the conditions maintained for 70 min. To the resulting solution was then added sodium triacetoxyborohydride (28.51 g) in one portion, and the resulting suspension stirred overnight. The reaction mixture was then neutralized with a saturated aqueous solution of $NaHCO_3$, the organic phase concentrated under reduced pressure to 60 ml, basified (pH 8.5) with a saturated aqueous solution of $NaHCO_3$ and solid $Na_2CO_3$, MeOH (20 ml) was added and the phases separated, the aqueous one extracted twice with a DCM: MeOH 3:1 mixture, the combined organic layers dried over $Na_2SO_4$ and evaporated to dryness to afford the product. The crude I5 (17.58 g) was used in the next step without any further purification.

HPLC ($R_t$)=2.48 min (method L)

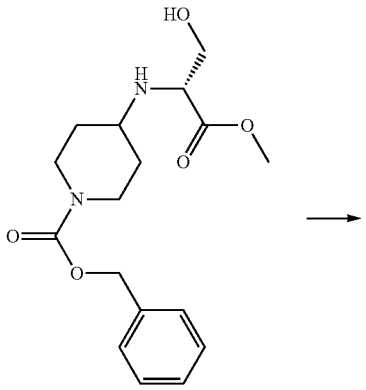

I5

-continued

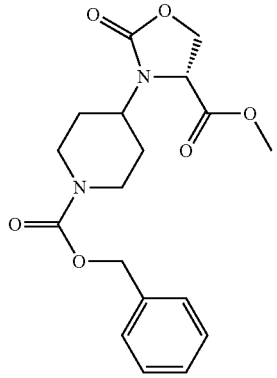

I6

Intermediate I5 (8 g, 35% content) was dissolved in THF (250 ml), then triethylamine (3.48 ml), 4-dimethylamino pyridine (100 mg) and 1,1' carbonyldiimidazole (5.40 g) were added in sequence and the whole mixture stirred and refluxed under a nitrogen atmosphere for 48 h. The solvent and the volatiles were removed under reduced pressure and the resulting residue was taken up in EtOAc (150 ml), washed with water (3×100 ml), 10% citric acid (100 ml) and brine (100 ml). The organic phase was dried over $Na_2SO_4$, filtered and evaporated to dryness to afford product (6.6 g). This was purified twice (50 g Isolute® silica gel cartridge, eluting in the first purification with EtOAc/n-hexane 80/20 and with 100% EtOAc in the second purification); the title compound (1.27 g).

HPLC ($R_t$)=3.16 min (method G)

Step 3

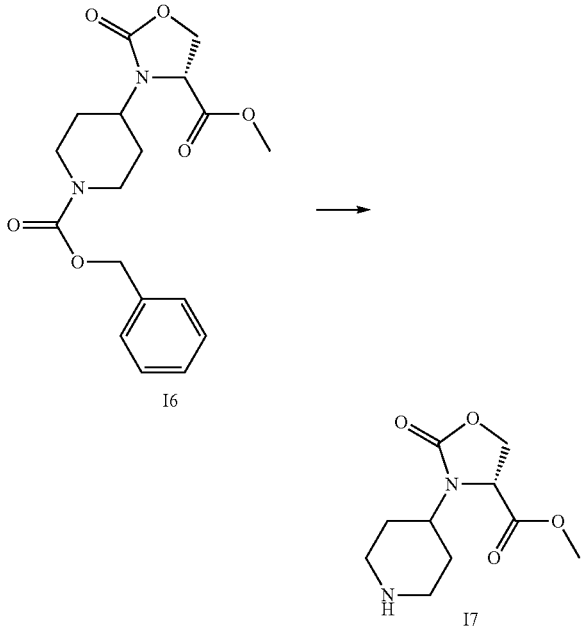

I6

I7

A suspension of 10% Pd/C (380 mg) in 50% aq. MeOH (4 ml) was added to a stirred solution of intermediate I6 (3.79 g) in MeOH (28 ml). The mixture was then stirred under a positive pressure of hydrogen 14 h. The reaction mixture was then filtered over Celite®, the cake washed with MeOH (4×10 ml) and the filtrate evaporated to dryness under reduced pressure to afford the desired free amine (2.2 g).

HPLC ($R_t$)=0.51 min (method L)

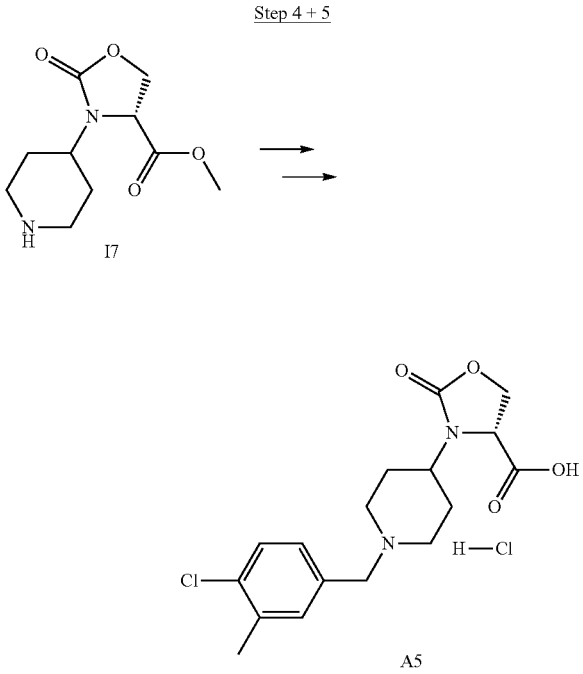

Intermediate I7 (1.01 g) was suspended in dry acetonitrile (17.8 ml) in a nitrogen atmosphere; 4-bromomethyl-1-chloro-2-methyl-benzene (1.46 g) and $K_2CO_3$ (1.22 g) were added in sequence and the whole stirred overnight. The solvent was removed under reduced pressure, the residue was taken up in EtOAc (50 ml), washed with water (1×30 ml), the layers separated, the aqueous extracted with EtOAc (1×50 mL) and a 3:1 DCM:MeOH mixture (50 ml). The combined organic layers were dried over $Na_2SO_4$, filtered and evaporated to dryness. The residue was taken up in DCM and loaded on a 10 g-SCX cartridge eluting with DCM (50 ml), MeOH (50 ml), then ammonia (50 ml of a 0.5 M MeOH solution). Evaporation under reduced pressure of the MeOH and methanolic ammonia fractions afforded the product (895 mg) under vacuum, as a mixture of the methyl and benzyl esters (4.5:1 by LC-MS).

The mixture of esters (895 mg) was suspended in THF (10 ml) and MeOH (2 ml) was then added; the solution was ice chilled, LiOH*H2O (155 mg) and water (10 ml) were added sequentially. The reaction was allowed to warm to room temperature and the resulting solution stirred for 70 min. The reaction mixture was diluted with diethyl ether (10 ml), the phases separated; the aqueous was then acidified to pH 4 by dropwise addition of 6N HCl and freeze-dried overnight to afford the carboxylic acid-hydrochloride salt. The residue was suspended in a 4:1 DCM:iPrOH mixture, stirred at room temperature for 10 min, then filtered on cotton, the solvent evaporated to dryness under reduced pressure to afford the product (844 mg).

HPLC (Rt)=2.12 min (method H)

The following building blocks were synthesized in analogy to acid A5:

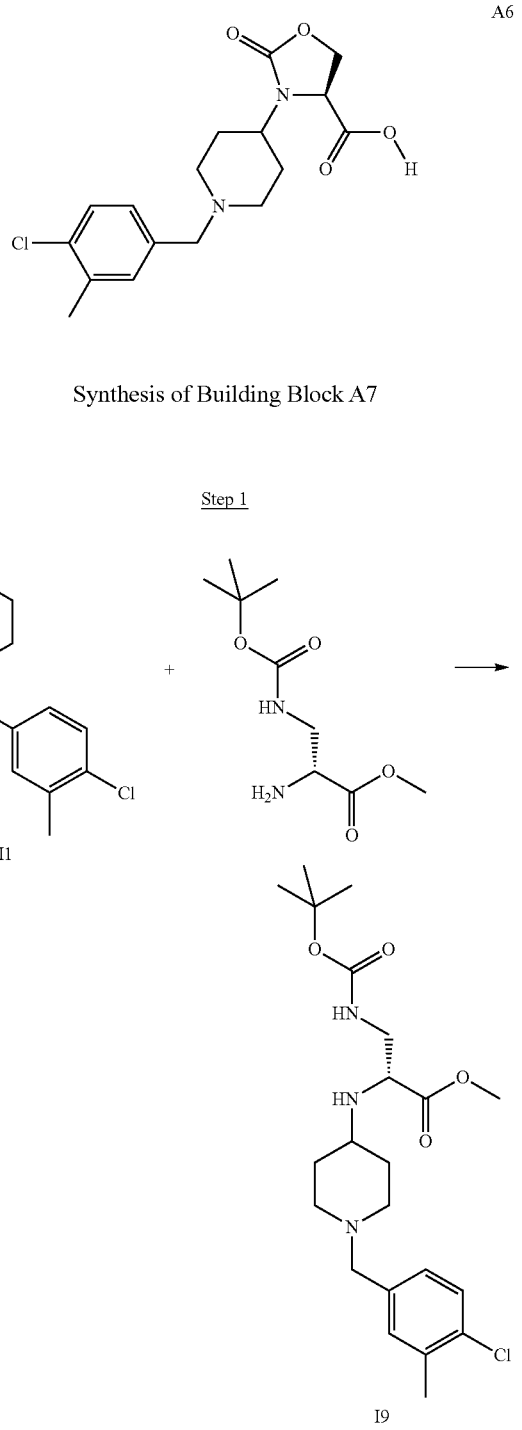

To a stirred suspension of (R)-2-amino-3-tert-butoxycarbonylamino-propionic acid methyl ester hydrochloride (5.0 g) and 1-(4-chloro-3-methyl-benzyl)-piperidin-4-one (5.13 g) in DCM (200 ml), was added acetic acid (2.81 ml). After 70 min sodium triacetoxyborohydride (14.56 g) was added in one portion, and the resulting suspension stirred for 48 h. The reaction mixture was then diluted with a saturated aqueous solution of $NaHCO_3$ (1×150 ml), the two layers separated, the aqueous extracted with DCM (1×200 ml), the combined organic layers dried over $Na_2SO_4$ and evaporated to dryness to afford the product. The crude was purified by flash chromatography (Biotage® SP1; 65M silica gel cartridge; gradient elution: DCM/MeOH/$NH_3$ from 98/2/0.2 to 80/20/2 in 12 column volumes) affording 19 (7.0 g).

HPLC ($R_t$)=10.03 min (method O)

Step 2

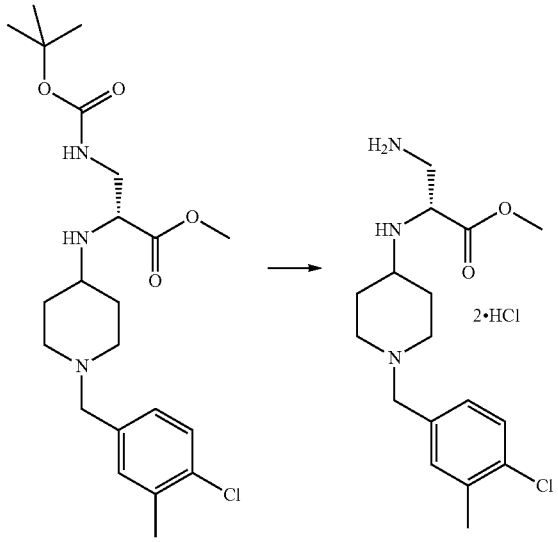

I9 I10

To a stirred solution of Intermediate I9 (7.00 g in dioxane (50 ml), at room temperature, was added HCl (39.78 ml of a 4N solution in 1,4-dioxane) dropwise. MeOH (20 ml) was then added, and the reaction mixture stirred overnight. The solvents and the volatiles were removed under reduced pressure, and the residue was triturated with diethyl ether affording product I10 (6.1 g). HPLC ($R_t$)=1.89 min (method H)

Step 3

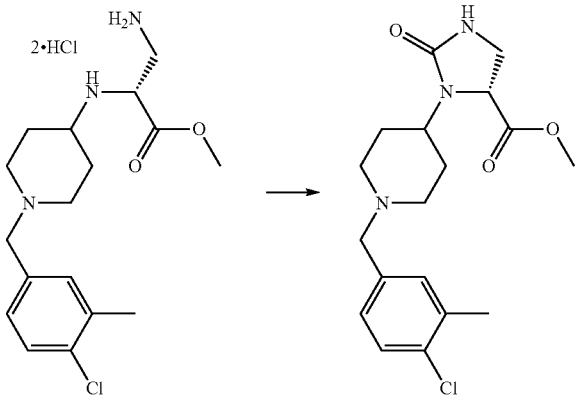

I10 I11

Intermediate I10 (6.1 g) was suspended in THF (300 ml), then triethylamine (12.41 ml), and 1,1' carbonyldiimidazole (5.99 g) were added sequentially and the reaction refluxed under a nitrogen atmosphere for 100 min. The reaction mixture was allowed to cool down, filtered and the filtrate evaporated under reduced pressure. and the residue was purified by flash column chromatography (Biotage® SP1; 65M silica gel cartridge; gradient elution: DCM/MeOH/$NH_3$ from 98/2/0.2 to 80/20/2 in 12 column volumes), affording a solid which was triturated with diethyl ether, to give I11 (1.85 g)

HPLC ($R_t$)=8.37 min (method O)

Step 4

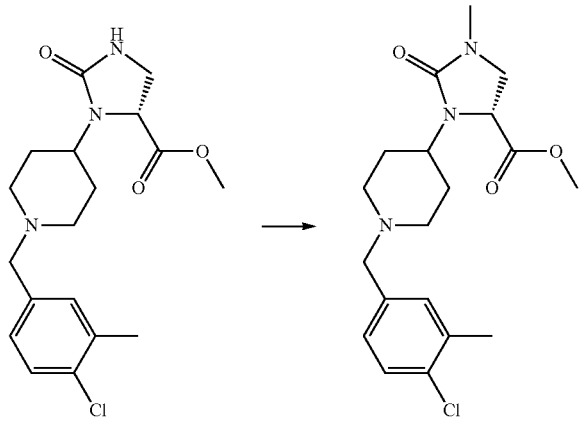

I11 I12

A stirred solution of potassium t-butoxide in THF (7.38 ml, 1 M) at −50° C. under a nitrogen atmosphere was added dropwise to a solution of intermediate I11 (1.80 g) in dry THF (45 ml). After 1 h, a solution of iodomethane (0.46 ml) in dry THF (5 ml) was added dropwise to the resulting suspension, and the temperature was allowed to warm to 0° C. over 1 h. After this time, excess iodomethane was removed under reduced pressure at room temperature, the reaction was quenched with saturated $NH_4Cl$(aq) (10 ml), the salts were filtered off and the filtrate diluted with EtOAc (30 mL) and brine (15 ml), the layers separated, the organic washed once more with brine (15 ml), dried over $Na_2SO_4$ and evaporated to dryness to afford a colourless oil, that was purified by flash column chromatography (Biotage® SP1; 65M silica gel cartridge; gradient elution: DCM/MeOH from 98/2 to 80/20 in 15 column volumes), affording product I12 (600 mg).

HPLC ($R_t$)=8.92 min (method O)

Step 5

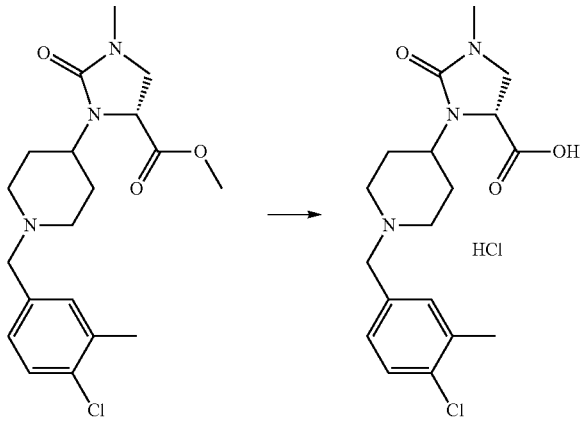

I12 A7

Intermediate I12 (0.9 g) was dissolved in 4N HCl (30 ml) and refluxed for 1 h. The solvent was evaporated to afford an oily residue that was taken up in acetone and evaporated to dryness to afford a white solid, which was triturated with diisopropyl ether to afford building block A7 (0.79 g).

HPLC ($R_t$)=5.48 min (method O)

Building block A8 was synthesized in analogy to A7:

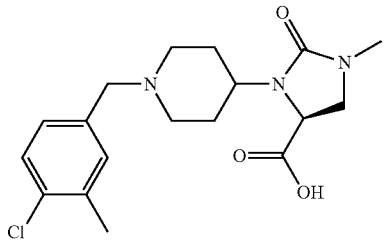

S.2.2. Synthesis of Building Blocks with Formula B

Synthesis of Building Block B1

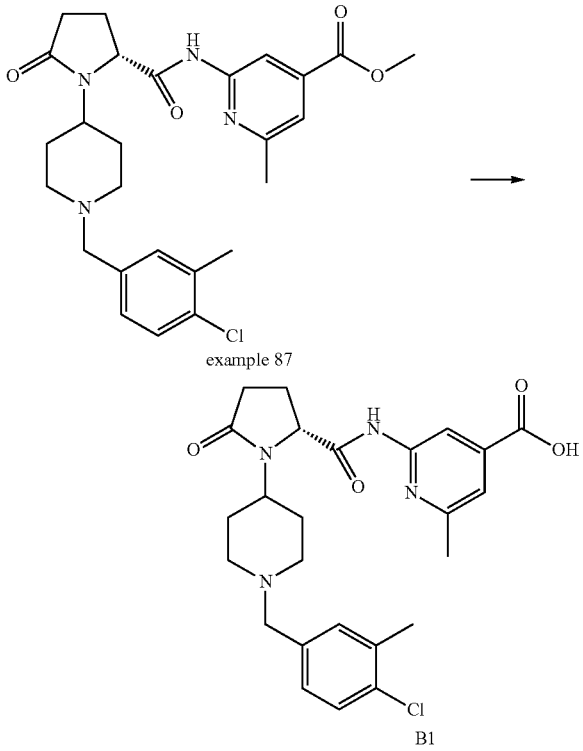

To a stirred solution of example 87 (350 mg) in dioxane (10 ml) at 25° C. was added LiOH(aq) (0.7 ml, 2.5 M) and water (2 ml). After 3 h, 4N HCl (aq) solution was added to adjust the pH to 1-2. The solution was concentrated in vacuum, and water and acetonitrile added and the mixture lyophilised giving building block B 1. HPLC: 1.25 min (method D). This was used without further purification in the next step.

Synthesis of Building Blocks B2-B15

The building blocks B2-B15 were synthesized in analogy to building block B1 from the examples 88-92 (B2-B6), 110 (B7), 113 (B8), 111 (B9), 112 (B10), 109 (B11), 216 (B12), 215 (B13), 195 (B14), 194 (B15)

B2

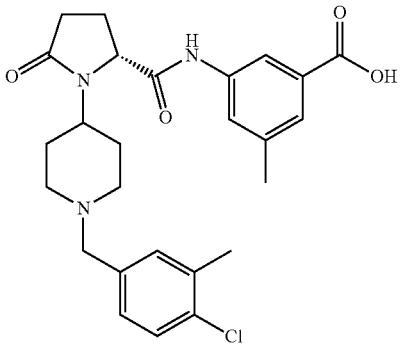

B3

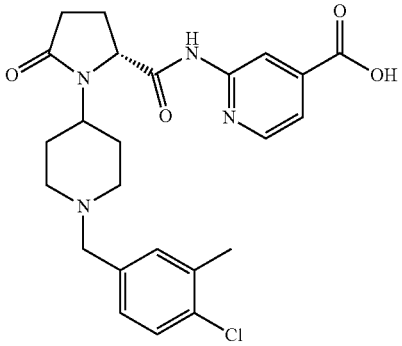

B4

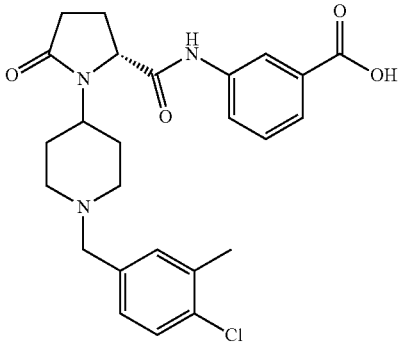

B5

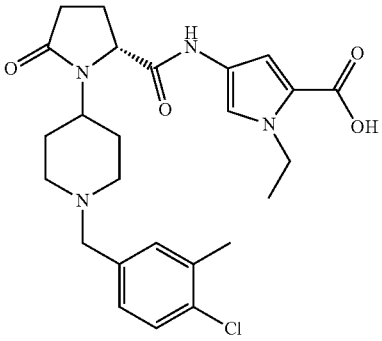

-continued
B6
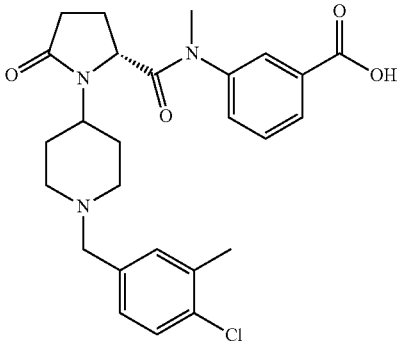
B7
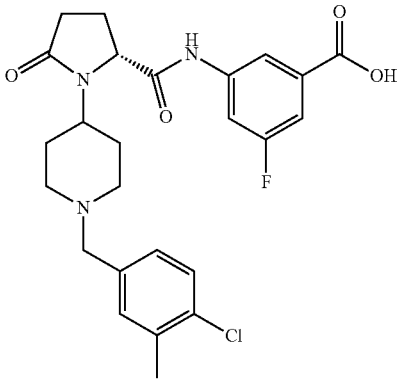
B8
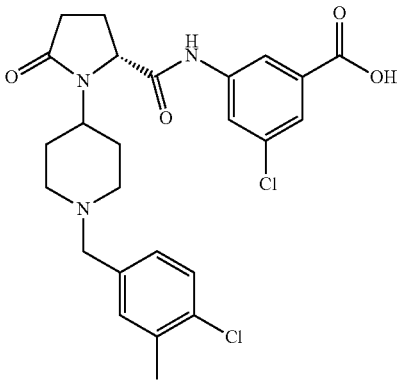
B9
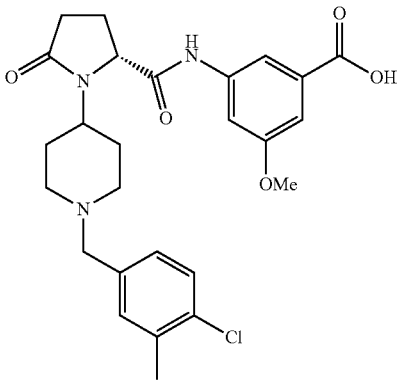
-continued
B10
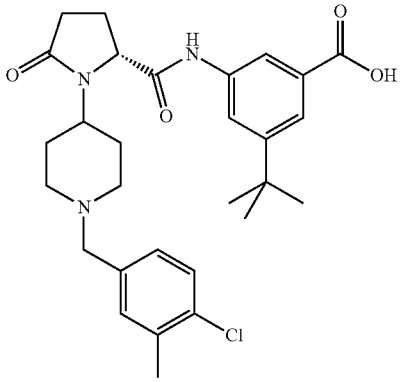
B11
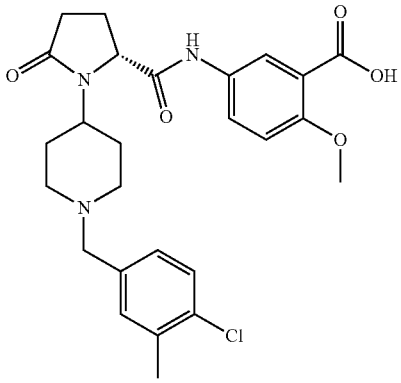
B12
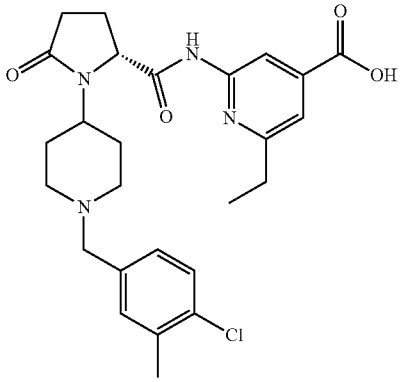
B13
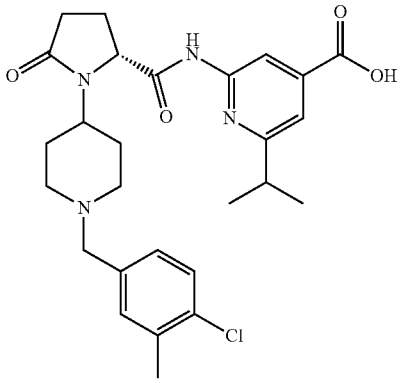

-continued

B14

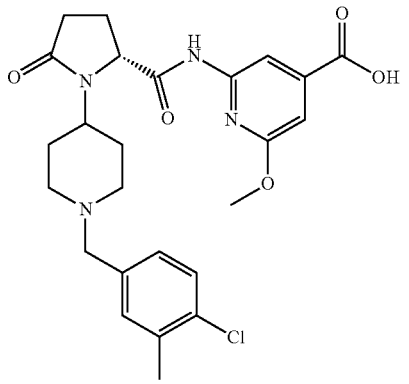

B15

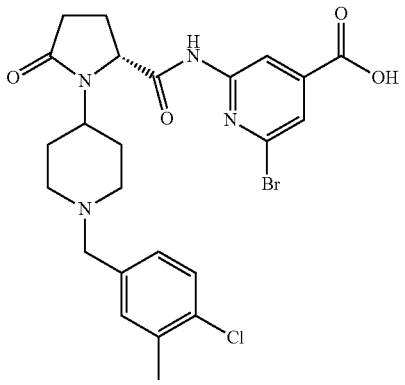

Synthesis of Building Block B16

B16

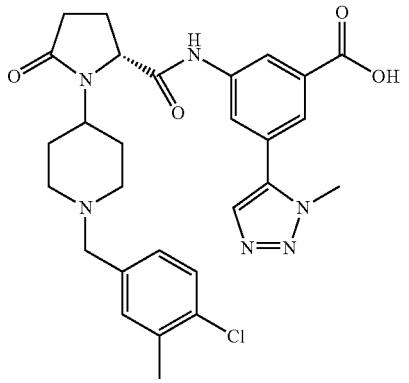

Step 1

3-Bromo-N-methyl-5-nitro-benzamide

To a solution of 3-bromo-5-nitro-benzoic acid (2.1 g) in DCM (50 ml) was added oxalylchloride (1.5 ml). 1 drop of DMF was added and the reaction stirred at room temperature for 2 h. The reaction was concentrated in vacuum. This was dissolved in THF and added dropwise to a pre-cooled 2M solution of methylamine in THF (22 ml) at 0° C. This was allowed to warm to room temperature and further stirred overnight. The reaction mixture was filtered and the filtrate concentrated in vacuum. The residue was dissolved in EtOAc and washed with water. The organic layer was separated, dried and concentrated in vacuum to leave the product (2.1 g). Rt 1.37 min (method D).

Step 2

5-(3-Bromo-5-nitro-phenyl)-1-methyl-1H-tetrazole

To a solution of 3-bromo-N-methyl-5-nitro-benzamide (0.6 g) in DCM (15 ml) at −15° C. was added triflic anhydride (0.6 ml) and the reaction stirred for 30 min. Sodium azide (226 mg) was added and the reaction allowed to warm to room temperature and stirred further overnight. $NaHCO_3$(aq) was added to neutralise the reaction and the mixture extracted into EtOAc. The organic layer was separated, dried and concentrated in vacuum and the residue purified by flash chromatography (9:1 to 2:8 cyclohexane:EtOAc) to give the title compound (290 mg). $R_f$=0.51 (3:2 cyclohexane:EtOAc).

Step 3

3-Bromo-5-(1-methyl-1H-tetrazol-5-yl)-phenylamine

A solution of 5-(3-Bromo-5-nitro-phenyl)-1-methyl-1H-tetrazole (2.1 g) in EtOAc (100 ml) was hydrogenated on a H-cube® apparatus at 20° C., room pressure with a flow rate of 1 ml/min using a Raney-Ni cartridge. After reaction completion, the mixture was concentrated in vacuum and triturated with MeOH. The solid was filtered and further triturated and air-dried to give the title compound (290 mg). Rt 1.25 min (method D).

Step 4

1-[1-(4-Chloro-3-methyl-benzyl)-piperidin-4-yl]-5-oxo-pyrrolidine-2-carboxylic acid [3-bromo-5-(1-methyl-1H-tetrazol-5-yl)-phenyl]-amide To a solution of 1-[1-(4-Chloro-3-methyl-benzyl)-piperidin-4-yl]-5-oxo-pyrrolidine-2-carboxylic acid as DIPEA salt (2.6 g) in DMF (100 ml) was added DIPEA (2.1 g), and HATU (4 g). 3-Bromo-5-(1-methyl-1H-tetrazol-5-yl)-phenylamine (1.4 g) was added and the reaction stirred overnight at rt. The reaction mixture was filtered and the filtrate partitioned between water and EtOAc. The organic layer was separated, dried and concentrated in vacuum and the residue purified by flash chromatography (DCM:MeOH 100:0 to 95:5 gradient) to give the title compound (400 mg). $R_f$=0.19 (95:5 DCM:MeOH).

Step 5

3-({1-[1-(4-Chloro-3-methyl-benzyl)-piperidin-4-yl]-5-oxo-pyrrolidine-2-carbonyl}-amino)-5-(1-methyl-1H-tetrazol-5-yl)-benzoic acid methyl ester To a solution of 1-[1-(4-Chloro-3-methyl-benzyl)-piperidin-4-yl]-5-oxo-pyrrolidine-2-carboxylic acid [3-bromo-5-(1-methyl-1H-tetrazol-5-yl)-phenyl]-amide (400 mg) in MeOH (20 ml) was added triethylamine (140 μl), DMF (5 ml), and [1,1'-bis(diphenylphosphino)-ferrocen]palladium (II) chloride (50 mg) and the reaction stirred for 2 d at 80° C. under a 3 bar CO atmosphere. The reaction mixture was filtered and the filtrate concentrated in vacuum. The residue was partitioned between water and EtOAc and the organic layer was then separated, dried and concentrated in vacuum. The residue was purified by flash chromatography (DCM:MeOH 100:0 to 95:5 gradient) to give the title compound (400 mg). $R_f$=0.37 (95:5 DCM:MeOH).

Step 6

3-({1-[1-(4-Chloro-3-methyl-benzyl)-piperidin-4-yl]-5-oxo-pyrrolidine-2-carbonyl}-amino)-5-(1-methyl-1H-tetrazol-5-yl)-benzoic acid To a solution of 3-({1-[1-(4-Chloro-3-methyl-benzyl)-piperidin-4-yl]-5-oxo-pyrrolidine-2-carbonyl}-amino)-5-(1-methyl-1H-tetrazol-5-yl)-benzoic acid methyl ester (270 mg) in MeOH (10 ml) at room temperature was added 4M NaOH (aq) (10 ml) and the reaction stirred overnight. The organic and aqueous layers were separated and the organic layer concentrated in vacuum. The residue was triturated in toluene and diethyl ether successively leaving the title compound (220 mg). $R_t$=0.96 min (method E).

Synthesis of Building Block B17

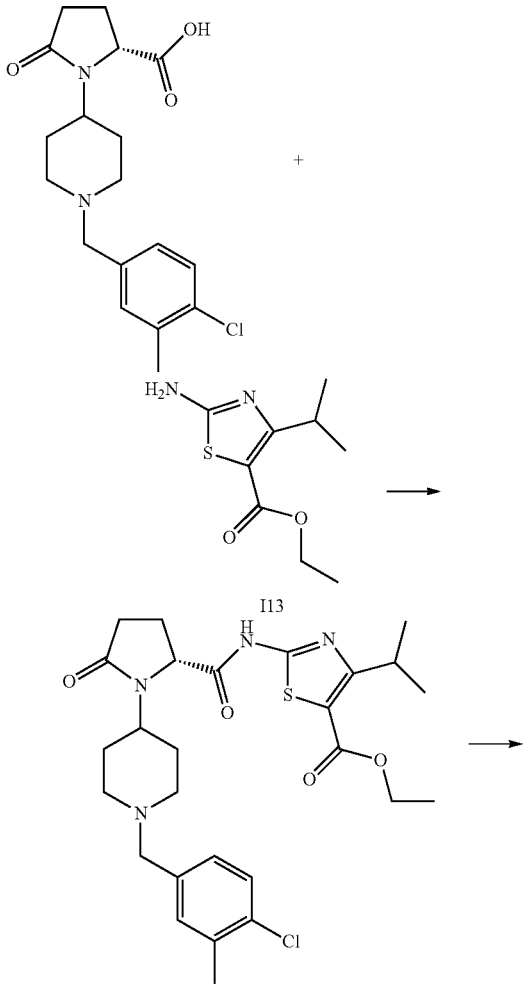

-continued

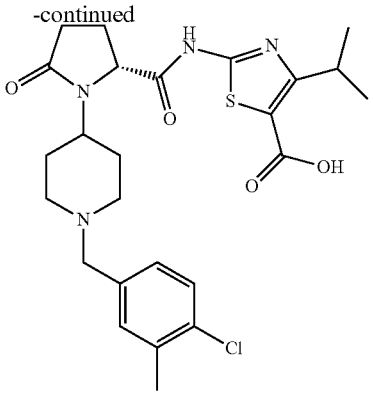

B17

Step 1

To a stirred solution of 1-[1-(4-Chloro-3-methyl-benzyl)-piperidin-4-yl]-5-oxo-pyrrolidine-2-carboxylic acid (500 mg) in DMF (5 ml) at room temperature was added DIPEA (1.1 ml) followed by HATU (1.1 g). After 45 min, intermediate I13 (0.34 g) was added and the reaction stirred overnight at rt. Saturated brine solution was added followed by EtOAc. The organic layer was separated, dried and concentrated in vacuum and the residue purified by HPLC to give the product (557 mg). ($R_t$ 1 50 min, method D)

Step 2

To a stirred solution of the product of step 1 (557 mg) in dioxane (5 ml) was added lithium hydroxide (195 mg) dissolved in a sufficient amount of water. After overnight stirring, the reaction was acidified with HCl(aq) (4M), then concentrated in vacuum. The residue was purified by HPLC to afford building block B17 (155 mg). ($R_t$ 1.34 min, method D).

Synthesis of I13 for Building Block B17

I13

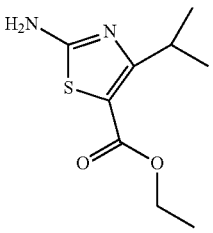

Step 1

Ethyl 2-bromo-4-methyl-3-oxopentanoate

To a suspension of sodium acetate (1.9 g) in glacial acetic acid (15 ml) was added 4-methyl-3-oxo-pentanoic acid ethyl ester (2 g) and the reaction mixture cooled to 10° C. Bromine (0.7 ml) was then added dropwise. The resulting solution was allowed to warm to room temperature and stirred for 1 h. The reaction was complete (by TLC) and was concentrated in vacuum affording 3.8 g crude ethyl product which was used directly in the next synthetic step.

Step 2

Ethyl 2-amino-4-isopropylthiazole-5-carboxylate (I13)

A solution of thiourea (1.1 g) in ethanol (10 mL) was brought to reflux. Ethyl 2-bromo-4-methyl-3-oxopentanoate (3.0 g) was then added and the reaction mixture refluxed further for 1 h. The reaction was complete (by TLC) and was concentrated in vacuum. Flash chromatography (100% DCM→90:10 DCM:MeOH) afforded the product (1.1 g).

Synthesis of Building Block B18

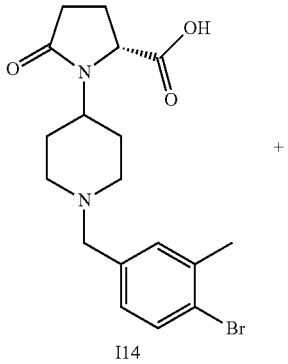

I14

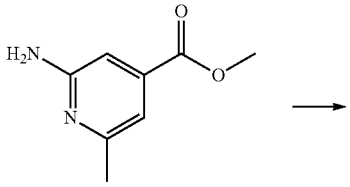

I16

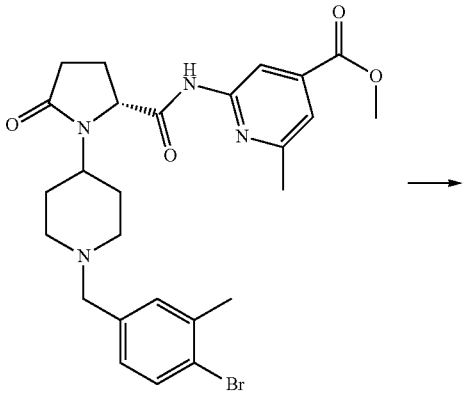

-continued

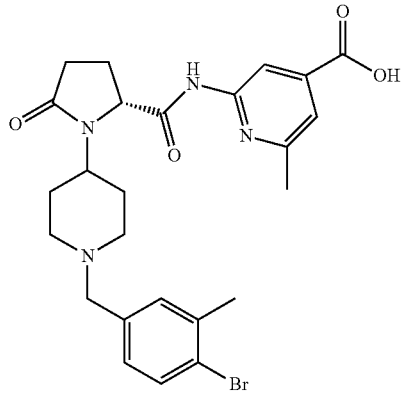

B18

Intermediate I14 was synthesized according to procedure D with subsequent saponification.

Synthesis of Intermediate I16

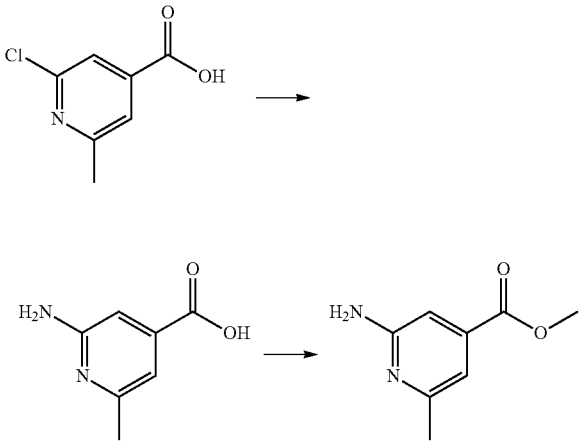

I15 I16

2-chloro-6-methylnicotinic acid (9 g), of aq ammonia (44 ml), of Cu(II)$SO_4$ (0.9 g) and of sodium sulphide (0.32 g) were added to an autoclave and heated to 155° C. overnight. The crude product was suspended in water to yield product 115 (3.6 g). The filtrate was concentrated and again suspended in water to yield a further 1.9 g of product 115. HPLC: $R_t$=0.37 min (method D)

Step 2

To 50 ml of MeOH was added dropwise acetylchloride (3 ml) at rt. After 15 min, intermediate I15 (2.3 g) was added and the mixture was stirred overnight at 50° C. After concentrating the solution, the resulting residue was suspended in acetone and then filtered and dried at 50° C. in vacuum, to yield product 116 (4.1 g).

HPLC: $R_t$=0.91 min (method D)

Synthesis of Building Block B19

B19

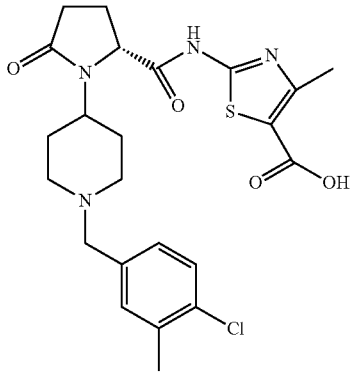

B19 was synthesized in analogy to B17. Synthesis of I13a for building block B19 was analogous to that for I13.

I13a

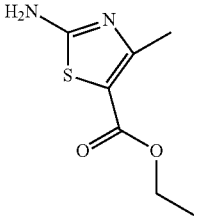

Synthesis of Building Block B20

B20

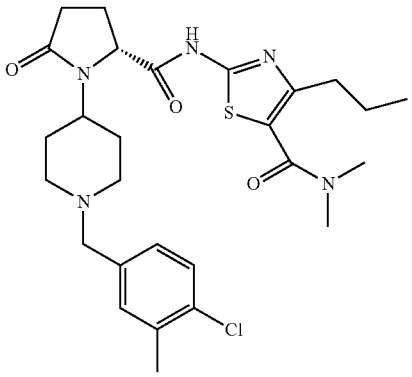

B20 was synthesized in analogy to B17. Synthesis of I13b for building block B20 was analogous to that for I13.

I13b

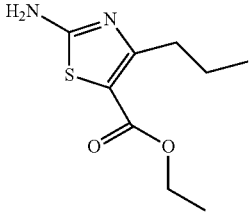

S.2.3. Synthesis of Building Blocks with Formula C

Synthesis of Building Block C1

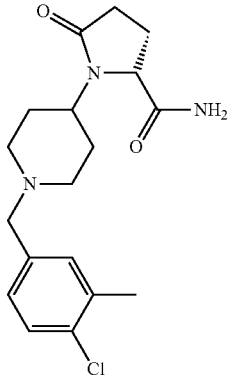

Building block A1, as its N,N-diisopropylethylamine salt (500 mg), was suspended in dry DMF (7 ml) under inert atmosphere and TBTU (836 mg) was added, followed by N,N-diisopropylethylamine (0.53 ml). After stirring for 1 h at room temperature, hexamethyldisilazane (0.44 ml) was added and the mixture was stirred for 6 h. Further portions of TBTU (334 mg) and hexamethyldisilazane (0.22 ml) were added and the reaction was stirred for further 18 h. The solvent was evaporated under reduced pressure and residue partitioned between saturated aqueous solution of $NaHCO_3$ and EtOAc. The layers were separated and the aqueous phase extracted with EtOAc. The combined organic extracts were washed with brine, dried under $Na_2SO_4$, filtered and the solvent was evaporated under reduced pressure. The crude was purified by flash chromatography (20 g Isolute® silica gel cartridge; eluent: DCM/MeOH/$NH_4OH$ 95/5/0.5) affording the title compound. (295 mg). HPLC ($R_t$)=1.24 min (method M)

S.2.4. Synthesis of Building Blocks with Formula D

Synthesis of Building Block D1

Step 1

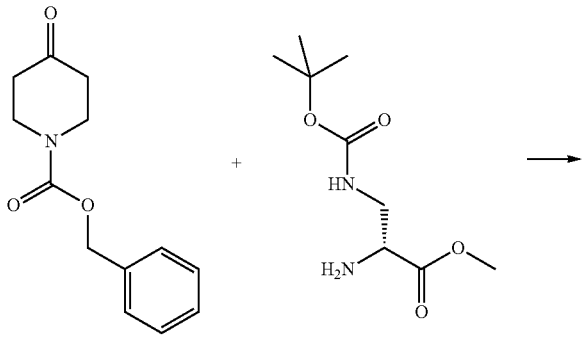

-continued

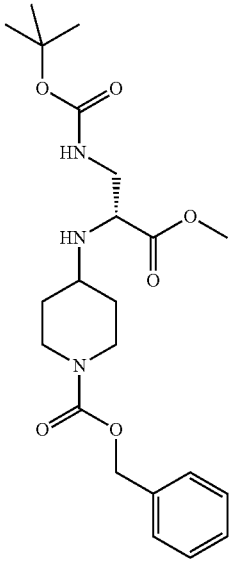

I17

Intermediate I17 was prepared starting from (R)-2-amino-3-tert-butoxycarbonylamino-propionic acid methyl ester hydrochloride (10.00 g) and 4-oxo-piperidine-1-carboxylic acid phenyl ester (12.07 g), following the procedures described for the synthesis of I9. Product obtained 19.50 g (content 70%). HPLC ($R_t$)=3.20 min (method Q)

Step 2

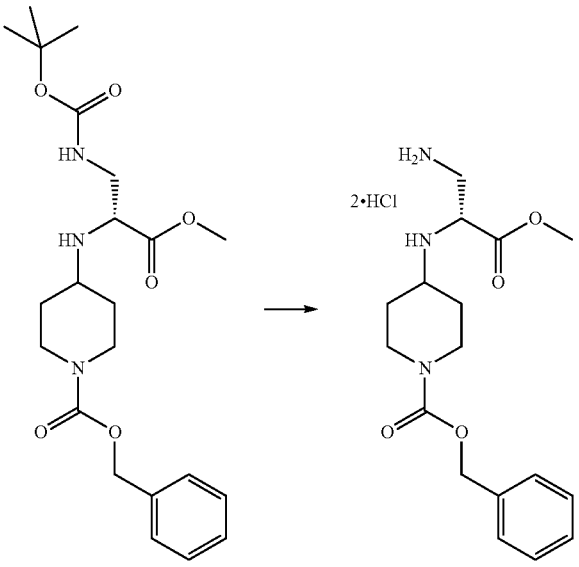

I17 I18

Intermediate I18 was prepared starting from I17 (19.5 g, content 70%) and following the procedures described for the synthesis of I10. Product obtained 12.50 g (content 75%).

HPLC ($R_t$)=1.96 min (method H)

Step 3

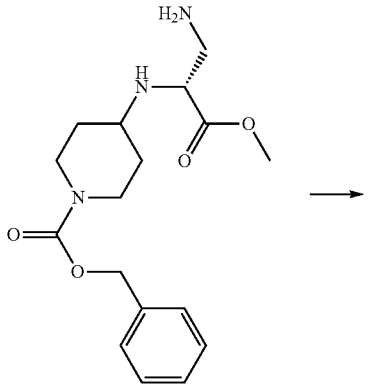

I18

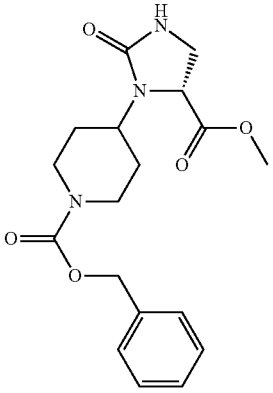

I19

Intermediate I19 was prepared starting from I18 12.50 g (content 75%) and following the procedures described for the synthesis of I11. Product obtained=2.90 g. HPLC ($R_t$)=2.79 min (method H)

Step 4

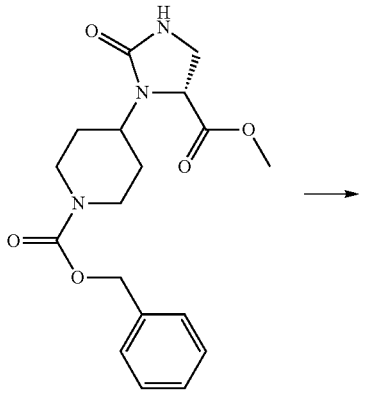

I19

-continued

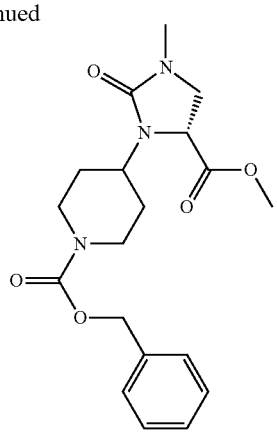

I20

Intermediate I20 was prepared starting from I19 (2.70 g) and following the procedures described for the synthesis of I12. Product obtained=2.45 g (content 85%) used in the next step without any further purification. HPLC (Rt)=3.00 min (method H)

Step 5

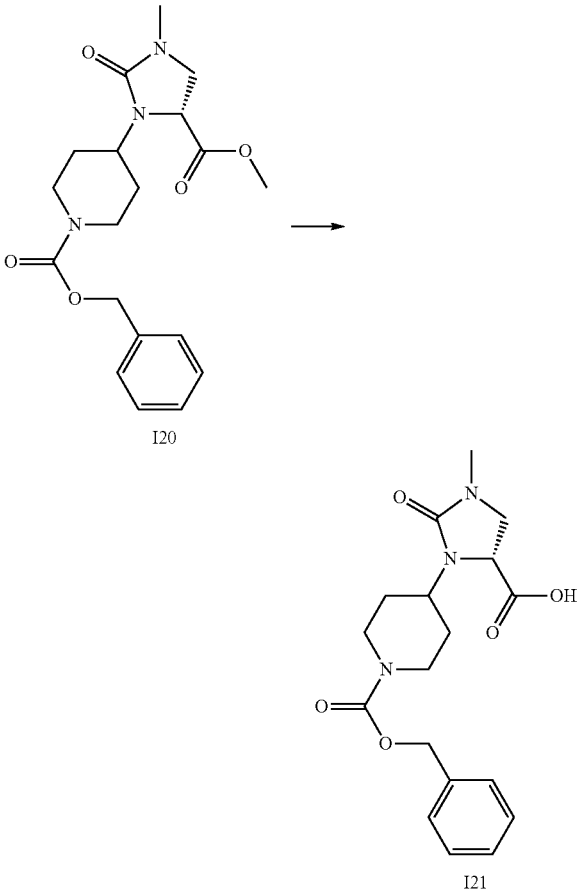

I20

I21

To an ice-chilled solution of intermediate I20 (2.40 g, content 85%) in THF (60 ml) and water (10 ml) was added lithium hydroxide monohydrate (0.68 g, 16.30 mmol). The temperature was allowed to warm to 25° C. and the resulting solution stirred until complete disappearance of the starting material (3 h). The organic solvent was evaporated under reduced pressure, the aqueous residue diluted with water 10 ml), acidified to pH 2.5 with 4N HCl. EtOAc (50 ml) was added, the phases separated, the organic layer washed with brine (20 ml), dried over $Na_2SO_4$ and evaporated to dryness. The residue was triturated with a 1/1 n-hexane/$Et_2O$ mixture, the solid dried at 40° C. under vacuum to afford I21 (1.90 g). HPLC ($R_t$)=2.65 min (method H)

Step 6

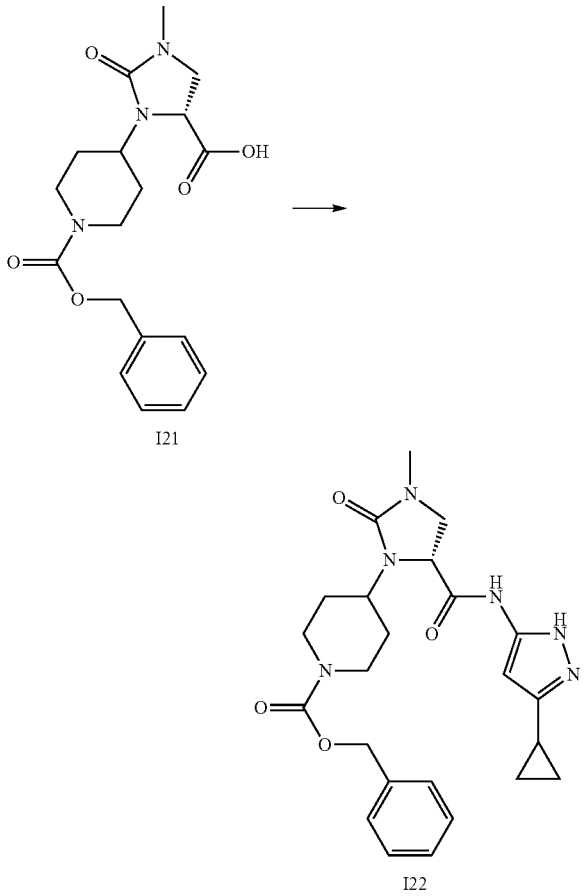

I21

I22

Intermediate I21 (1.80 g) was dissolved in dry DMF (15 ml), and the resulting solution stirred in a nitrogen atmosphere. HATU (2.46 g) and DIPEA (3.22 ml) were added sequentially and the whole stirred at room temperature for 30 min. 3-cyclopropyl-1-methyl-1H-pyrazole-5-amine (1.02 g) was then added in one portion and the reaction mixture heated at 40° C. overnight. Extra HATU (2.27 g) and 3-cyclopropyl-1-methyl-1H-pyrazole-5-amine (0.68 g) were then added, and the heating maintained for 8 h. The reaction mixture was concentrated under reduced pressure, the resulting residue diluted with water (40 ml) and EtOAc (50 ml). The layers were separated and the organic phase washed with 1M HCl (3×20 ml), 10% aq. $Na_2CO_3$ (2×20 ml), water (1×20 ml) and brine (1×25 ml), dried over $Na_2SO_4$ and evaporated to dryness, affording a solid. The residue was triturated with diisopropyl ether, affording product I22 (1.70 g). HPLC ($R_t$)=2.85 min (method H)

Step 7

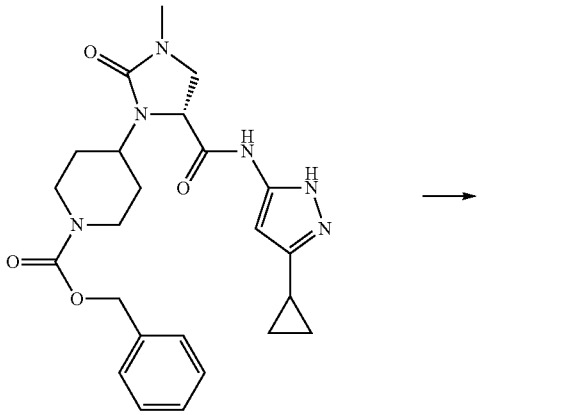

I22

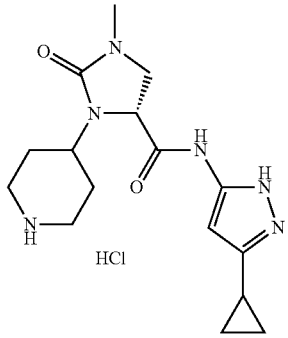

D1

A suspension of 10% Pd/C (211 mg) in 80% aq. ethanol (5 ml) was added to a stirred solution of intermediate I22 (1.7 g, content 90%) in EtOH (30 ml). The whole was then stirred under a positive pressure of hydrogen. After 4 h extra catalyst (100 mg) was added and the conditions maintained overnight. The reaction mixture was then filtered over Celite®, the cake carefully washed with EtOH (3×10 ml) and the filtrate evaporated to dryness under reduced pressure. The residue was dissolved in an 8/2 EtOAc/MeOH mixture (30 ml) and treated with HCl (6 ml of a 4N solution in 1,4 dioxane) to form the corresponding hydrochloride salt. The solvent was evaporated to dryness and the residue triturated with MTBE, the solid filtrated and dried at 40° C. under vacuum to afford the building block D1 (1.20 g). HPLC ($R_t$)=1.60 min (method H)

Synthesis of Building Block D2

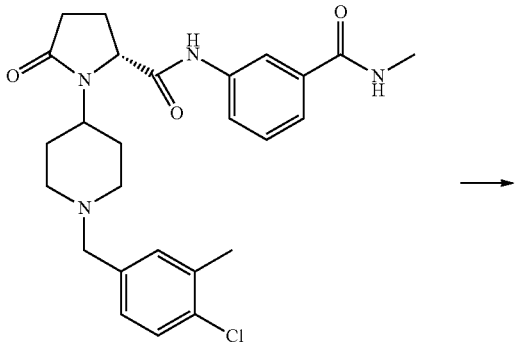

example 35

-continued

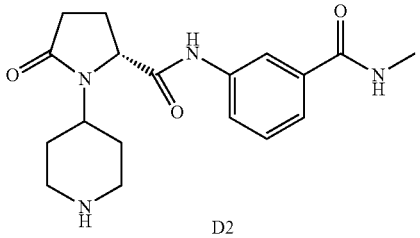

D2

Example 35 (1.0 g) was dissolved in MeOH (20 ml), and Pd/C was added and the mixture was hydrogenated at 50° C. and 50 psi for 12 h. After this period, further Pd/C was added and the mixture was again hydrogenated at 50° C. and 50 psi for 7 h. The solution was then filtered and concentrated in vacuum to give 0.62 g of building block D2 which was used without further purification. HPLC: 0.98 min (method D)

Synthesis of Building Block D3

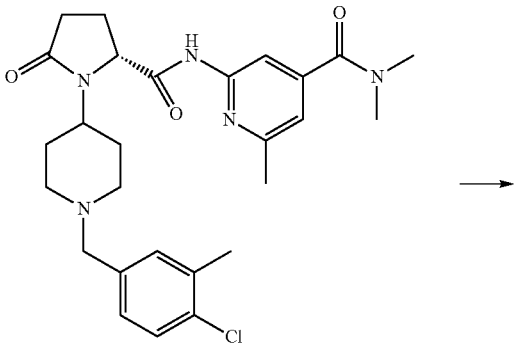

example 135

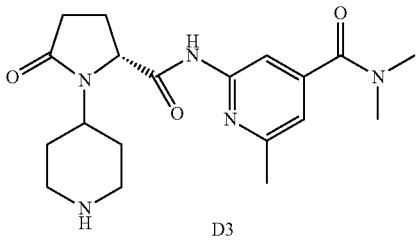

D3

Building block D3 was prepared in analogy to building block D2 starting from example 135.

S.2.5 Synthesis of Intermediate I12.2 (Building Block for Procedure E)

see synthesis of building block A6, step 4.

S.2.6. Synthesis of Building Blocks with Formula F

Synthesis of Building Block F1

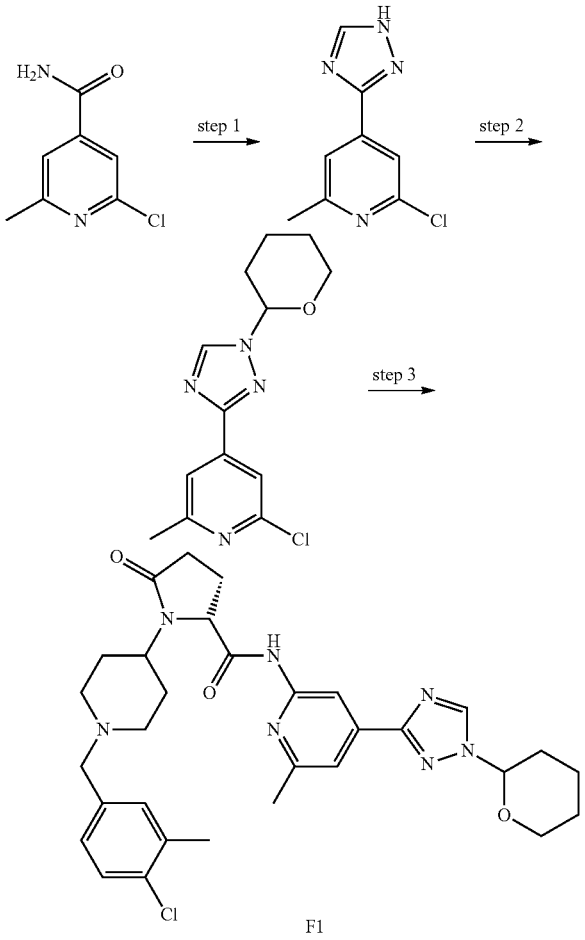

F1

2-Chloro-6-methyl-isonicotinamide (1.23 g) and N,N-dimethylformamide dimethyl acetal (1.05 ml) were dissolved in dry DMF (4 ml) under inert atmosphere and the resulting solution was heated to 90° C. and stirred for 1 h. The reaction mixture was cooled to room temperature and a solution of hydrazine acetate (3.32 g) in acetic acid (8 ml) was dropwise added. The mixture was heated to 90° C. and stirred for 1 h. The solvent was removed under reduced pressure and the residue partitioned between saturated aqueous solution of $NaHCO_3$ and EtOAc. The organic phase was separated, washed with brine, dried under $Na_2SO_4$, filtered and the solvent was evaporated under reduced pressure. The crude was purified by flash column chromatography (10 g Isolute® silica gel cartridge; gradient elution: hexane/EtOAc from 1/1 to 3/7) affording 2-Chloro-6-methyl-4-(1H-[1,2,4]triazol-3-yl)-pyridine (0.92 g). GC ($R_t$)=13.21 min (method=3A)

Step 2

2-Chloro-6-methyl-4-(1H-[1,2,4]triazol-3-yl)-pyridine (120 mg) and 3,4-dihydro-2H-pyran (84 μL) were suspended in dry DCM (3.5 mL) under inert atmosphere and pyridinium p-toluenesulfonate (15.5 mg) was added. The reaction mixture was stirred at room temperature for 18 h. The solution was diluted with DCM, washed with water and brine, dried under $Na_2SO_4$, filtered and the solvent was evaporated under reduced pressure. The crude was purified by flash column chromatography (10 g Isolute® silica gel cartridge; eluent: hexane/EtOAc 3/7) affording product (155 mg). HPLC ($R_t$) =1.51 min (method M)

Step 3

2-Chloro-6-methyl-4-[1-(tetrahydro-pyran-2-yl)-1H-[1,2,4]triazol-3-yl]-pyridine (33.0 mg, 0.12 mmol) and building block C1 were dissolved in dry dioxane (1.2 mL) under inert atmosphere and palladium(II)acetate (2.12 mg), 4,5-bis (diphenylphosphino)-9,9-dimethylxanthene (10.9 mg) and caesium carbonate (81.0 mg) were added subsequently. The mixture was heated to 100° C. and stirred for 18 h. After cooling to room temperature the reaction mixture was diluted with DCM, washed with water and brine, dried under $Na_2SO_4$, filtered and the solvent was evaporated under reduced pressure. The crude was purified by flash column chromatography (10 g Isolute® silica gel cartridge; gradient elution: DCM/MeOH from 97/3 to 95/5) affording building block F1 (70 mg). HPLC ($R_t$)=1.75 min (method M)

Syntheses of Building Blocks F2 and F3

Building blocks F2 and F3 were prepared in analogy to building block F1

F2

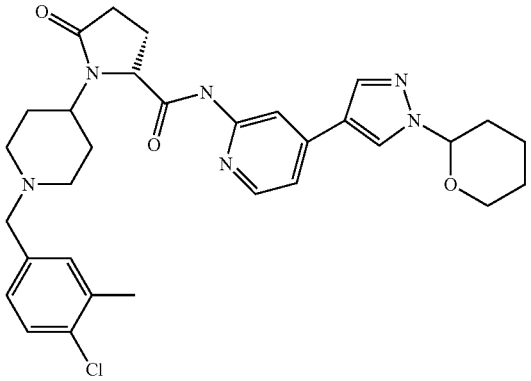

UPLC ($R_t$) = 1.69 min
method M

F3

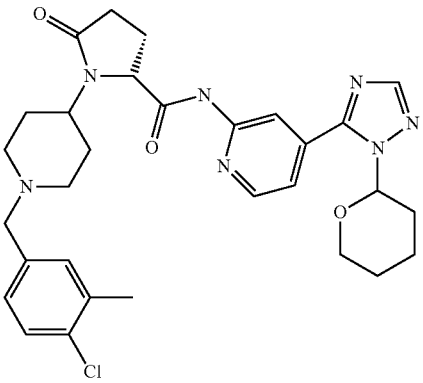

UPLC (Rt) = 3.10 min
method M

The chloropyridines were prepared as follows:

2-Chloro-4-[4-(tetrahydro-pyran-2-yl)-1H-[1,2,4] triazol-3-yl]-pyridine

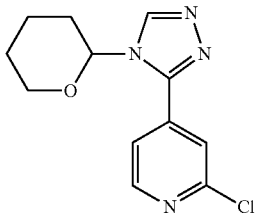

2-Chloro-4-[4-(tetrahydro-pyran-2-yl)-1H-[1,2,4]triazol-3-yl]-pyridine was prepared in analogy to 2-Chloro-6-methyl-4-[1-(tetrahydro-pyran-2-yl)-1H-[1,2,4]triazol-3-yl]-pyridine. HPLC ($R_t$)=1.68 min (method M)

2-Chloro-4-[1-(tetrahydro-pyran-2-yl)-1H-pyrazol-4-yl]-pyridine

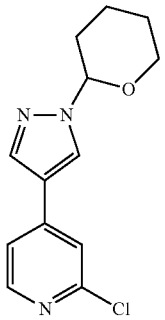

4-Bromo-1-(tetrahydro-pyran-2-yl)-1H-pyrazole (0.73 g) and 2-chloropyridine-4-boronic acid (0.20 g) were dissolved in dry DMF (2 mL) under inert atmosphere and 1,1'-bis (diphenylphosphino)ferrocenedichloro palladium(II)(102 mg) was added followed by caesium carbonate (0.84 g). The mixture was heated to 80° C. and stirred for 2 h. After cooling to room temperature the reaction mixture was diluted with DCM and the inorganic salts filtered off. The filtrate was washed with water and brine, dried under $Na_2SO_4$, filtered and the solvent was evaporated under reduced pressure. The crude was purified by flash chromatography (20 g Isolute® silica gel cartridge; gradient elution: hexane/EtOAc from 10/0 to 8.5/1.5) affording the title compound (144 mg). HPLC ($R_t$)=1.39 min (method M)

S.3 Synthesis of Reaction Partners for Procedures A-F

S.3.1. Synthesis of Primary or Secondary Amines for Procedures A and B

Synthesis of (I25) for Example 7

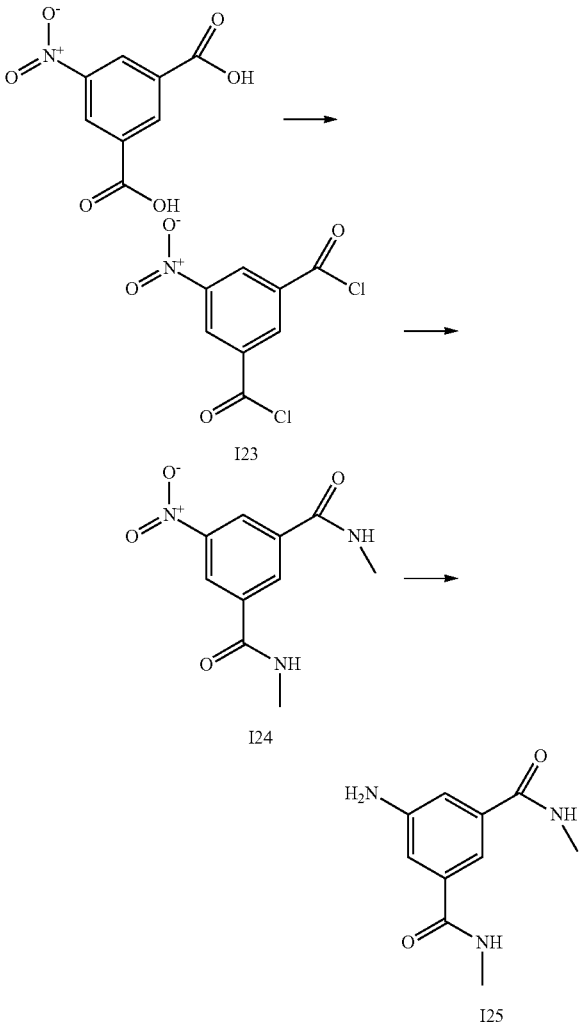

To a stirred mixture of 5-nitroisophthalic acid (20.0 g) in DCM was added oxalyl chloride (36 ml, 2M in DCM), followed by DMF (0.5 ml). The mixture was stirred for 2 h at room temperature, before volatiles were removed in vacuum. The residue was suspended in dry toluene and concentrated again to yield crude I23 (10 g), which was used without further purification in the next step.

Step 2

I23 (10 g) was dissolved in THF (20 ml) and added dropwise to a solution of methylamine (40 ml, 2M in THF) in THF (80 ml) under stirring at −20° C. After 20 min, the mixture was filtered, and the filtrate concentrated in vacuum. The residue was triturated with diethylether to form a solid that was filtered off and dried to yield intermediate I24 (3.53 g)

Step 3

A solution of intermediate I24 (0.52 g) in MeOH (30 ml) was treated with hydrogen (50 psi) in the presence of Raney-Nickel (90 mg) at room temperature for 14 h. The mixture was then filtered and concentrated in vacuum to afford I25. The compound was used without further purification in the next step.

HPLC ($R_t$)=0.33 min (method D)

Synthesis of N-(8-amino-4,5-dihydronaphtho[2,1-d] thiazol-2-yl)acetamide for Example 10

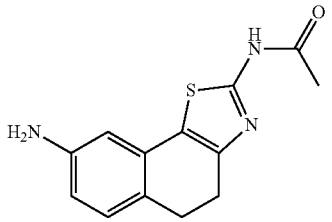

This intermediate was synthesized according to WO2006040279.

Synthesis of N-(4-Amino-cyclohexyl)-benzenesulfonamide for Example 29

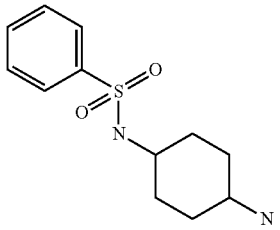

This intermediate was synthesized analog to WO2001096295.

Synthesis of 3-(4-Amino-2-methyl-phenyl)-[1,3]oxazinan-2-one for Example 30

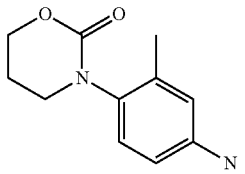

This intermediate was synthesized analog to WO2005111029.

Synthesis of 5-Amino-2,3-dihydro-indole-1-carboxylic acid methylamide for Example 37

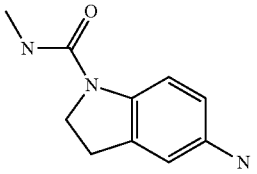

This intermediate was synthesized analog to WO2008113760.

Synthesis of 1-(3-Amino-benzyl)-3-cyclohexyl-urea for Example 39

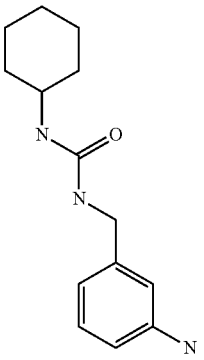

Step 1: 1-Cyclohexyl-3-(3-nitro-benzyl)-urea

3-Nitro-benzyl-amine (5 g) was suspended in THF (130 ml) and cyclohexyl isocyanate (7 ml) was added dropwise at 25° C. After stirring for 2 h the resulting precipitate was filtered off, washed with diethyl ether and treated with 5% aqueous $NH_4OH$. After filtering and drying the title compound was isolated (4.5 g, FP 168-169° C.)

Step 2: 1-(3-Amino-benzyl)-3-cyclohexyl-urea

1-Cyclohexyl-3-(3-nitro-benzyl)-urea (4 g) was suspended in ethanol (70 ml) and Raney nickel (2 g) was added. Under stirring aqueous hydrazine solution (2.5 ml, 80%) was added. DMF was added (50 ml) and the reaction mixture was stirred for additional 2 h and filtered. The solution was evaporated i.v. affording the title compound (3 g, $R_f$=0.43 DCM/ethanol 19:1).

Synthesis of
trans-1-(4-Amino-cyclohexyl)-3-phenyl-urea for
Example 44

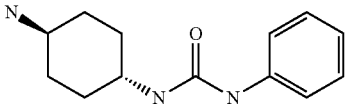

This intermediate was synthesized analog to WO2005095339.

Synthesis of
1-Methanesulfonyl-pyrrolidin-3-ylamine for
Example 53

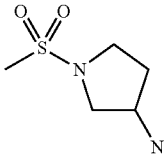

This intermediate was synthesized analog to WO2006118256.

Synthesis of 3-Pyridin-4-ylmethyl-phenylamine for
Example 66

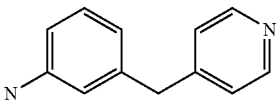

This intermediate was synthesized analog to WO2004009546.

Synthesis of 1-(5-Chloro-1H-benzoimidazol-2-yl)-2-methoxy-ethylamine for Example 67

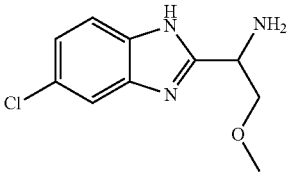

This intermediate was synthesized analog to WO2004056784.

Synthesis of
C-(6-Chloro-2-methyl-pyridin-3-yl)-methylamine for
Example 70

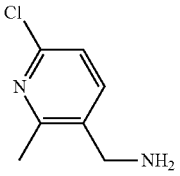

Step 1

2-Methyl-6-oxo-1,6-dihydro-pyridine-3-carbonitrile

A solution of (E)-3-amino-but-2-enenitrile (100 g) and propynoic acid methyl ester in DMF (200 ml) was stirred at 25° C. for 2 h and refluxed for additional 1 h. Dowtherm (100 ml) was added and the temperature was rised to 230° C. DMF and MeOH were distilled off. The reaction mixture was cooled down, EtOAc (200 ml) was added and the resulting crystals were filtered off and washed with EtOAc and ether affording the title compound (44.8 g, FP>250° C.).

Step 2

6-Chloro-2-methyl-nicotinonitrile

A mixture of 2-Methyl-6-oxo-1,6-dihydro-pyridine-3-carbonitrile (44 g) and POCl3 (250 ml) was refluxed for 3 h. The reaction mixture was dried down in vacuum and ice followed by conc. aqueous ammonia (300 ml) was added. The aqueous layer was extracted with EtOAc. The organic layer was separated, dried and concentrated in vacuum affording the title compound (23.5 g, BP (18 mbar) 119-120° C.).

Step 3

C-(6-Chloro-2-methyl-pyridin-3-yl)-methylamine

To a solution of 6-Chloro-2-methyl-nicotinonitrile (6 g) in THF (120 ml) at 25° C. was added $NaBH_4$ (3 g) followed by the dropwise addition of $BF_3$ etherate (6 ml). The reaction mixture was stirred for 3 h. MeOH (100 ml) and 2N HCl (100 ml) was added and refluxed for 1 h. The organic solvent was removed in vacuum and conc. NaOH (40 ml) was added followed by extraction with diethyl ether. The organic layer was separated, dried and concentrated in vacuum followed by filtration over silica gel (EtOAc/MeOH 80:20). The title compound was crystallized from MeOH/HCl (5.5 g)

Synthesis of N-(3-aminophenyl)-N-(2-(azetidin-1-yl)-2-oxoethyl)methanesulfonamide for Example 75

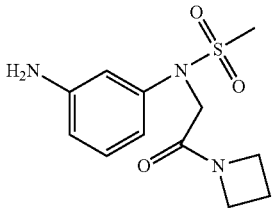

This intermediate was synthesized analog according to WO2006114371.

Synthesis of N-(3-aminophenyl)-methylsulfonamido)-N,N-dimethylacetamide for Example 76

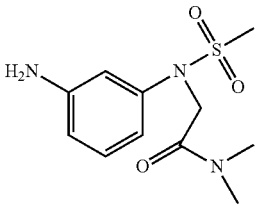

This intermediate was synthesized analog to WO2006114371.

Synthesis of N-(3-aminophenyl)-cyclopropane-sulfonamido)-N,N-dimethylacetamide for Example 78

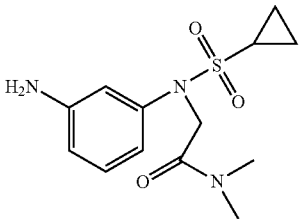

This intermediate was synthesized analog according to WO2006114371.

Synthesis of 2-[(3-Amino-phenyl)-ethanesulfony-lamino]-N,N-dimethyl-acetamide for Example 79

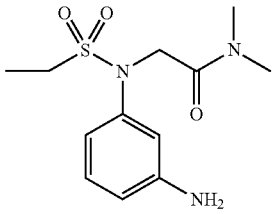

This intermediate was synthesized analog to WO2006114371.

Synthesis of ethyl 5-amino-3-methylbenzoate for example 88

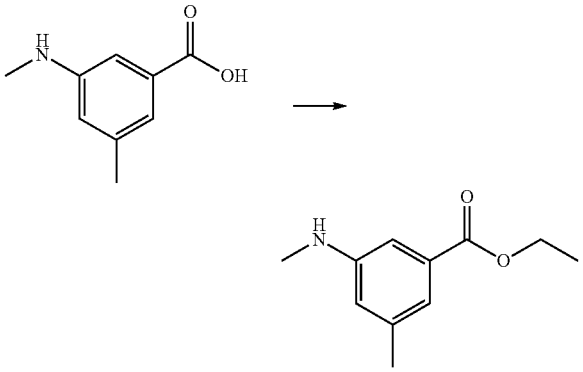

2 g acid was dissolved in 22 mL ethanolic HCl and stirred at 60° C. for 2 days. The mixture was then concentrated and used without further purification.

Synthesis of ethyl 3-methylaminobenzoate for Example 92

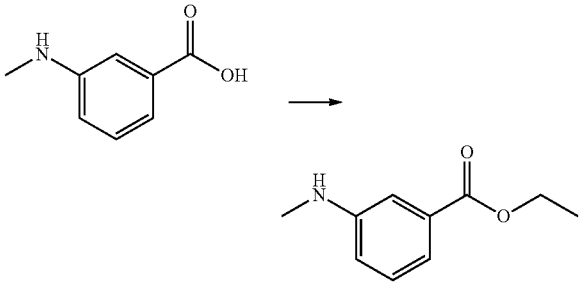

2 g acid was dissolved in 22 mL ethanolic HCl and stirred at 60° C. for 2 days. The mixture was then concentrated and used without further purification.

Synthesis of 4-(3,5-Dimethyl-pyrazol-1-yl)-pyridin-2-ylamine for Example 102

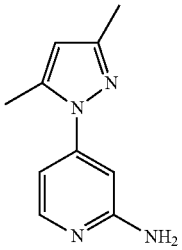

A 10 ml microwave reaction vessel was charged with 4-Chloro-pyridinamine (0.5 g) and 3,5-dimethylpyrazole (1.12 g); hydrochloric acid (37%, 0.5 ml) and dioxane were then added. The reaction mixture was irradiated in a Microwave oven with the following parameters: potency: 150 W; temperature: 120° C.; time: 180 min.

The reaction mixture was cooled at room temperature and treated with diethyl ether (2 ml) and ethanol (1 ml) and sonicated during 30 min. At end of treatment the mixture was cooled during 14 h at 4° C. A solid was filtered off and washed with diethyl ether and n-hexane to furnish the product as the hydrochloride salt (450 mg).

Synthesis of 5-amino-tetramethylisophthalamide (I29) for Example 105

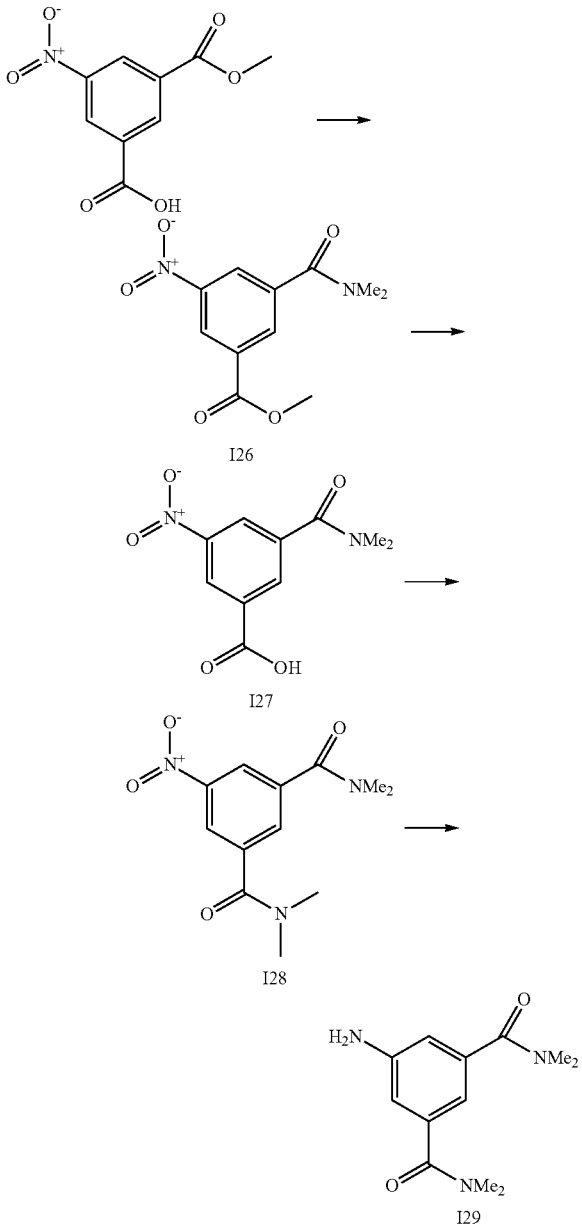

To a stirred solution of mono methyl 5-nitroisophthalate (1.0 g) and DIPEA (1.43 ml) in DCM (30 ml) and DMF (3 ml) was added HATU (1.69 g) at rt. After 10 min, dimethylamine (4.4 ml, 2M solution in THF) was added and stirring was continued for 12 h. Water and sodium bicarbonate were added to the reaction mixture and extracted with DCM. The organic layer was separated and concentrated in vacuum. The reside was further purified by normal phase MPLC (cyclohexane: EtOAc=80:20 to 30:70) to afford intermediate I26 (0.91 g)

HPLC ($R_t$)=1.29 min (method D)

Step 2

A mixture of I26(2.5 g), MeOH (20 ml) and LiOH(aq) (8 wt. %, 5.9 ml) was stirred at 50° C. for 1 h. Volatiles were then removed in vacuum and the residue was acidified by treatment with 2 M HCl (aq). The mixture was lyophilized, the remaining solid suspended in water and warmed to 50° C. The resulting suspension was filtered, the solid was washed with water and petrolether and dried in vacuum at 50° C. to yield 127 (1.56 g) that was used without further purification.

HPLC ($R_t$)=0.27 min (method E)

Step 3

HATU (707 mg) was added in two portions to a mixture of 127 (400 mg), DCM (5 ml), DMF (2 ml), diisopropylamine (0.68 ml), and HOBt (227 mg) under stirring at rt. Dimethylamine (2.1 ml, 2M in THF) was added and stirring continued for 48 h. Water and sodium bicarbonate were then added and the resulting mixture was extracted with DCM. The organic layer was separated, dried ($Na_2SO_4$) and concentrated in vacuum. The residue was further purified by reversed phase HPLC the product containing fractions were combined volatiles removed in vacuum and the remaining aqueous mixture extracted with DCM. The organic layer was concentrated to afford I28 (71 mg).

Step 4

A solution of intermediate I28 (71 mg) in MeOH (10 ml) was treated with hydrogen in the presence of Raney-Nickel (10 mg) at rt. The mixture was then filtered and concentrated in vacuum to afford the title compound I29 (40 mg). The compound was used without further purification in the next step.

HPLC ($R_t$)=0.70 min (method D)

The reaction partners for example 107 and 106 were synthesized analogously as for example 105.

| Intermediate for the synthesis of example | Structure | HPLC method | $R_t$ [min] |
|---|---|---|---|
| 107 | 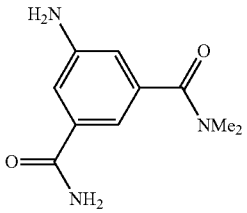 | D | 1.26 |

-continued

| Intermediate for the synthesis of example | Structure | HPLC method | $R_t$ [min] |
|---|---|---|---|
| 106 | 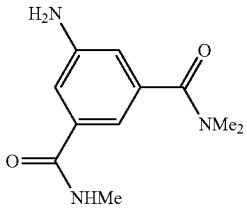 | D | 1.26 |

Synthesis of methyl 3-amino-5-(dimethylcarbamoyl)benzoate for Example 108

A solution of intermediate I26 (0.91 g) in MeOH (40 ml) was treated with hydrogen in the presence of Raney-Nickel (90 mg) at rt. The mixture was then filtered and concentrated in vacuum to afford the title compound (810 mg). The compound was used without further purification in the next step.

HPLC ($R_t$)=0.98 min (method D)

Synthesis of methyl 3-amino-5-methoxy benzoate for the Synthesis of Example 111

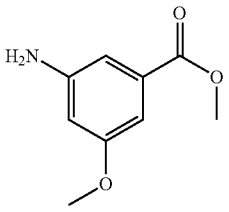

To a stirred suspension of 3-amino-5-methoxy benzoic acid (500 mg) in a mixture of DCM (4.0 ml) and MeOH (2.0 ml) at 0° C. was added a solution of trimethylsilyldiazomethan in hexane (3.39 ml, 2M) dropwise. After 15 min, the reaction was concentrated in vacuum. The remaining crude product was purified by reversed phase HPLC to yield the trifluoroacetate salt of title compound (280 mg).

HPLC ($R_t$)=1.02 min (method D)

Synthesis of ethyl 3-amino-5-chloro benzoate for the Synthesis of Example 112

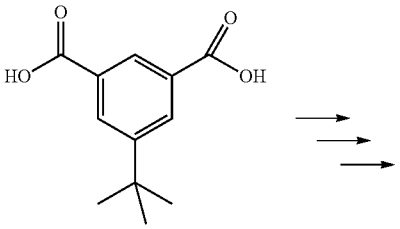

-continued

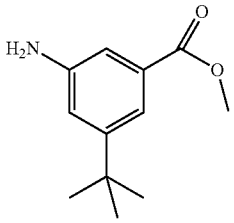

5-tert-butylisophthalic acid (1.3 g) was dissolved in MeOH (20 ml). The resulting solution was cooled to 0° C. and thionylchloride (0.45 ml) was added dropwise under stirring. After complete addition, the mixture was allowed to warm to room temperature and was stirred for additional 7 h. The mixture was then poured on an ice cold sodium bicarbonate solution and extracted repeatedly with EtOAc. The aqueous phase was acidified with HCl and again extracted with EtOAc. The combined organic layers were washed with brine and concentrated in vacuum. The residue was worked up by flash column chromatography on silica gel (DCM:MeOH=20:1) to yield methyl 5-tert-butylisophthalate (1.3 g).

Step 2

Under an atmosphere of argon, 5-tert-butylisophthalate (0.5 g) was dissolved in tert.-butanol (20 ml). To the resulting solution, triethylamine (0.35 ml) and diphenyl phosphoreazidate (0.56 ml) were added subsequently. The mixture was then heated to reflux for 12 h, cooled to room temperature and concentrated in vacuum. The residue was taken up in EtOAc, and subsequently washed with dilute aqueous citric acid, saturated sodium bicarbonate solution and brine. The organic layer was concentrated in vacuum and the residue was worked up by flash chromatography (petrol ether:EtOAc=3:1) to yield methyl 3-(tert.-butoxycarbonylamino)-5-tert-butylbenzoate (0.61 g).

Step 3

Methyl 3-(tert.-butoxycarbonylamino)-5-tert-butylbenzoate (0.42 g) was dissolved in DCM (5 ml). To the resulting solution, TFA (1 ml) was added, the mixture was stirred for 30 min at room temperature and then concentrated in vacuum. The residue was dissolved in DCM and extracted with aqueous sodium bicarbonate solution. The organic layer was separated, dried over sodium sulphate and concentrated in vacuum to yield ethyl 3-amino-5-tert-butylbenzoate (0.28 g), which was used for the synthesis of example 112 without further purification.

Synthesis of methyl 3-amino-5-chloro benzoate for the Synthesis of Example 113

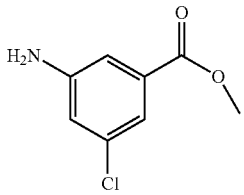

A solution of methyl 3-chloro-5-nitrobenzoate (300 mg) in THF (50 ml) was treated with hydrogen (3 bar) in the presence of Raney-Nickel (10 mg) at rt. The mixture was then filtered and concentrated in vacuum to afford the title compound (204 mg). The compound was used without further purification in the next step.

HPLC ($R_t$)=1.36 min (method D)

Synthesis of 3-Methyl-5-(1-methyl-1H-tetrazol-5-yl)-phenylamine for Example 114

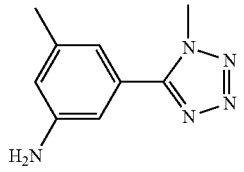

Step 1

3-Chlorocarbonyl-5-nitro-benzoic acid ethyl ester

To a solution of 5-nitroisophtalic acid monoethyl ester (80 g) in DCM (700 ml) at 25° C. was added 2M oxalyl chloride solution in DCM (63 ml), and DMF (5 ml). The reaction was stirred for 2 h and then concentrated in vacuum. The residue was triturated with toluene and again concentrated in vacuum leaving the title compound (60 g). $R_t$=1.40 min for derivatised methylester (method D).

Step 2

N-Methyl-5-nitro-isophthalamic acid ethyl ester

To a 2M solution of methylamine in THF (256 ml) at −20° C. was added a pre-cooled solution of 3-chlorocarbonyl-5-nitro-benzoic acid ethyl ester (60 g) in THF (500 ml) dropwise. This was stirred for 20 min and then filtered. The filtrate was concentrated in vacuum and the solid recrystallised from diethyl ether to give the title compound (22.5 g) as a solid. An oxalyl chloride solution in DCM (63 ml, 2M), was added with DMF (5 ml). The reaction was stirred for 2 h and then concentrated in vacuum. The residue was triturated with toluene and again concentrated in vacuum leaving the title compound (60 g). $R_t$=1.53 min (method D).

Step 3

3-(1-Methyl-1H-tetrazol-5-yl)-5-nitro-benzoic acid ethyl ester

To a 2M solution of N-methyl-5-nitro-isophthalamic acid ethyl ester (10 g) in dichloroethane (200 ml) at −20° C. was added pre-cooled triflic anhydride (10 ml) dropwise. This was stirred for 30 min and then sodium azide (4.6 g) was added. This was allowed to warm to room temperature and stirred overnight. The reaction was neutralised with 5% $NaHCO_3$ (aq) solution and the organic and aqueous layers were separated and the organic layer dried and concentrated in vacuum. Flash chromatography (100:0 to 50:50 gradient cyclohexane: EtOAc) afforded the title compound (6.5 g). $R_t$=1.52 min (method D).

Step 4

3-Amino-5-(1-methyl-1H-tetrazol-5-yl)-benzoic acid ethyl ester

A solution of 3-(1-Methyl-1H-tetrazol-5-yl)-5-nitro-benzoic acid ethyl ester (6.5 g) in EtOAc:ethanol (1:1, 320 ml) was hydrogenated at 20° C. and 50 psi with 10% Pd/C (750 mg). After reaction completion, the mixture was filtered and the filtrate concentrated in vacuum to give the title compound (4.2 g). $R_t$=1.21 min (method D).

Step 5

[3-Amino-5-(1-methyl-1H-tetrazol-5-yl)-phenyl]-methanol

To a solution of 3-Amino-5-(1-methyl-1H-tetrazol-5-yl)-benzoic acid ethyl ester (250 mg) in THF (5 ml) at 0° C. was added pre-cooled 1M $LiAlH_4$ solution in THF (2 ml) dropwise. This was stirred for 3 h. The reaction mixture was poured onto ice-water and extracted into EtOAc. The organic layer was separated, dried and concentrated in vacuum. Flash chromatography (100:0 to 95:5 gradient DCM:MeOH) afforded the title compound (70 mg).

$R_f$=0.19 (DCM:MeOH 95:5).

Step 6

3-Methyl-5-(1-methyl-1H-tetrazol-5-yl)-phenylamine

A solution of [3-Amino-5-(1-methyl-1H-tetrazol-5-yl)-phenyl]-methanol (450 mg) in MeOH (20 ml) with a few drops of conc. HCl (aq) was hydrogenated on a H-cube apparatus at 30° C., and 10 bar with a flow rate of 1 mL/min using a Pd/C cartridge. After reaction completion, the mixture was concentrated in vacuum and the residue basified with a dilute $K_2CO_3$(aq). This was extracted with EtOAc and the organic layer was separated, dried and concentrated in vacuum. The residue was purified by flash chromatography (98:2 DCM: MeOH) to give the title compound (320 mg).

$R_f$=0.46 (95:5 DCM:MeOH)

S3.2 Synthesis of aromatic-chlorides or -bromides for Procedure C

Synthesis of 2-Chloro-4-(3,5-dimethyl-isoxazol-4-yl)-pyridine for Example 187

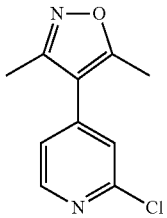

The title compound was prepared from 4-bromo-3,5-dimethylisoxazole generally according to the synthetic procedure described for 2-Chloro-4-[1-(tetrahydro-pyran-2-yl)-1H-pyrazol-4-yl]-pyridine. HPLC ($R_t$)=0.81 min (method N)

Synthesis of 2-Chloro-6-methyl-4-(5-methyl-[1,2,4] oxadiazol-3-yl)-pyridine for Example 188

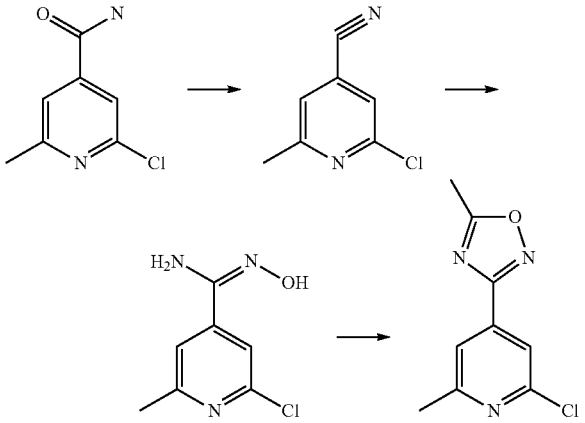

To a suspension of 2-chloro-6-methyl-isonicotinamide (0.50 g, 2.93 mmol) in dry DCM (10 ml), dry pyridine (0.26 ml) was added and the mixture was cooled to 0° C. under inert atmosphere. Trifluoroacetic anhydride (0.45 ml) was added dropwise under stirring, the cooling bath was removed and the reaction mixture was stirred for 4 h. After this period other portions of pyridine (0.074 ml) and trifluoroacetic anhydride (0.12 ml) were added and the mixture stirred at room temperature for further 3 h.

The reaction was quenched with aqueous solution of $NaHCO_3$, the phases were separated and the aqueous layer extracted with DCM. The combined organic extracts were washed with brine, dried under $Na_2SO_4$, filtered and the solvent was evaporated under reduced pressure. The crude product was obtained (0.378 g) and used in next step without further purification. HPLC ($R_t$)=1.65 min (method M)

2-Chloro-6-methyl-isonicotinonitrile (378 mg) was dissolved in ethanol (4 ml) and hydroxylamine hydrochloride (379 mg) was added followed by a solution of sodium carbonate (577 mg) in water (8 ml). The reaction mixture is heated to 75° C. and stirred for 18 h. Ethanol was evaporated under reduced pressure and the aqueous residue extracted with EtOAc. The combined extracts were washed with water and brine, dried under $Na_2SO_4$, filtered and the solvent was evaporated under reduced pressure. The crude product was obtained (401 mg) and used in next step without further purification. HPLC ($R_t$)=0.67 min (method M)

2-Chloro-N-hydroxy-6-methyl-isonicotinamidine (120 mg) was suspended in trimethylorthoacetate (3 ml) under inert atmosphere and acetic acid (0.3 ml) was added. The mixture was heated to 100° C. and stirred for 2 h. After cooling to room temperature the solvent was evaporated under reduced pressure and the residue partitioned between EtOAc and aqueous solution of $NaHCO_3$. The organic layer was separated, washed with water and brine, dried under $Na_2SO_4$, filtered and the solvent was evaporated under reduced pressure. The crude was purified by flash column chromatography (10 g Isolute® silica gel cartridge; gradient elution: hexane/EtOAc from 10/0 to 9/1) affording the title compound (107 mg).

HPLC ($R_t$)=3.17 min (method L).

Synthesis of methyl 2,6 dibromo-isonicotinate for the Synthesis of Example 194

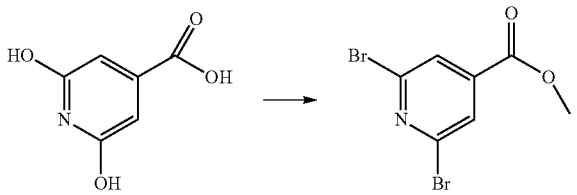

In a three necked round bottom flask equipped with a mechanic stirrer and gas outlet solid cirtrazinic acid (15 g) and phosphorous oxybromide (45 g) were thoroughly mixed and heated to 140° C. for 12 to 14 h. The resulting mixture was cooled to 0° C. before MeOH (100 ml) was added carefully under vigorous stirring. The resulting mixture was then poured into a cooled (0° C.) aqueous sodium carbonate solution (1M, 500 ml), before Chloroform (500 ml) was added. The biphasic mixture was filtered through a paper filter, before the organic layer was separated. After filtering through charcoal, the solution was concentrated in vacuum. The residue was purified by MPLC (DCM:MeOH=100:3 to 100:6) to yield methyl 2,6 dibromo-isonicotinate (13.7 g).

HPLC ($R_t$)=1.62 (method D)

Synthesis of methyl 2-bromo-6-methoxyisonicotinate for Example 195

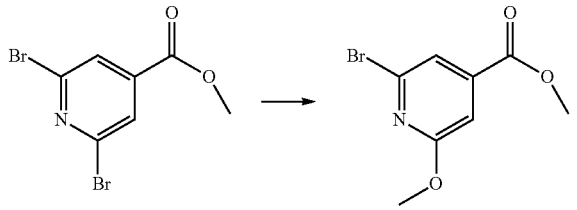

A solution of sodium methoxide (375 mg) and methyl 2,6 dibromo-isonicotinate (1.0 g) in MeOH (20 ml) was heated in a microwave oven at 130° C. for 30 min. Then additional sodium methoxide (281 mg) was added and heating continued for additional 15 min at 130° C. Concentrated sulfuric acid (1.86 ml) was then added to the reaction mixture and the resulting suspension was heated for 4 h at 80-85° C.

After cooling to room temperature, the mixture was poured in an ice cold aqueous sodium carbonate solution (100 mL) and extracted with DCM (100 ml). The organic layer was separated, dried over $Na_2SO_4$ and concentrated in vacuum. The residue was purified by MPLC (DCM:MeOH=100:3 to 100:5) to yield 710 mg of a 70:30 mixture of desired product (497 mg) and the corresponding trimethyl cirtrazinic acid (213 mg). The mixture was used for subsequent transformations without further purification.

HPLC ($R_t$)=1.66 min (method D)

Synthesis of 2-Chloro-6-methyl-4-(1-methyl-1H-tetrazol-5-yl)-pyridine for Example 191

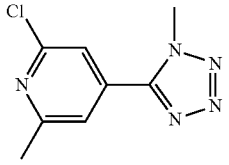

Step 1

2-Chloro-6,N,N-trimethyl-isonicotinamide

To a solution of 2-Chloro-6-methyl-isonicotinic acid (1 g) in DMF (200 ml) at 25° C. was added DIPEA (2.9 mL) and TBTU (1.8 ml). After 5 min, dimethylamine (0.75 g) was added dropwise. This was stirred overnight. The reaction was added to water and extracted with EtOAc. The organic layer was separated, dried and concentrated in vacuum. Flash:chromatography (9:1 to 2:8 gradient cyclohexane:EtOAc) afforded the title compound (320 mg). $R_f$=0.56 (1:1 cyclohexane:EtOAc)

Step 2

2-Chloro-6-methyl-4-(1-methyl-1H-tetrazol-5-yl)-pyridine

To a solution of 2-Chloro-6,N,N-trimethyl-isonicotinamide (2.3 g) in acetonitrile (30 ml) at −15° C. was added DCM (20 ml) pre-cooled triflic anhydride (3 mL) dropwise. This was stirred for 10 min at −10° C. and then sodium azide (4.6 g) was added. This was allowed to warm to room temperature and after 2 h, the reaction was neutralised with a cold 5% $NaHCO_3$(aq) solution and extracted with EtOAc. The organic layer was separated, dried and concentrated in vacuum. Flash chromatography (100:0 to 40:60 gradient cyclohexane:EtOAc) afforded the title compound (260 mg). $R_t$=1.21 min (method D).

S.4. Synthesis of Examples According to Procedure A to G

S.4.1. Synthesis of Examples According to Procedure A

Examples 1-131

Amide Formation Method A

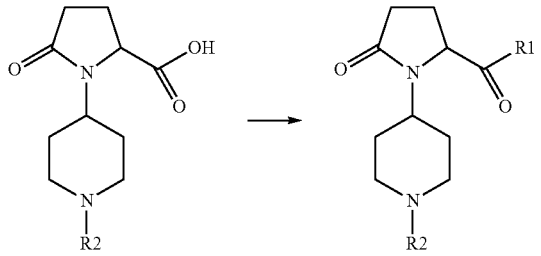

To a stirred solution of building block A (1 eq) in DMF, NMP, DCM or chloroform at room temperature is added DIPEA or TEA (2-8 eq), HATU or TBTU (1-4 eq) and HOBt (0-2 eq). After 20-45 min, amine reaction partner (1.2-2 eq) is added and the mixture stirred for an additional 40-120 min. Water and TFA is then added and the mixture is separated via reversed phase HPLC to provide the desired amides. The reaction mixture can be filtered over basic ALOX or extracted with DCM after addition of aqueous $NaHCO_3$ solution followed by concentrating the organic fractions in vacuum before the HPLC purification.

Synthesis of Example 1

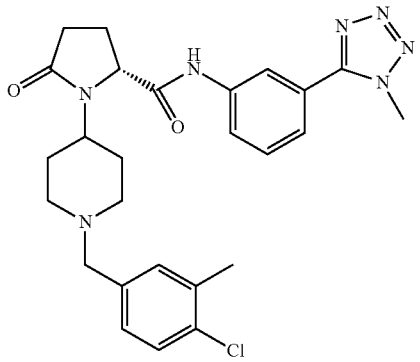

Building block A1 (60 mg) was dissolved in NMP (0.5 ml) and DIPEA (0.15 ml). HATU (120 mg) was added and the solution was stirred for 45 min at rt. 3-(1-methyl-1H-tetrazol-5-yl)aniline (34 mg) was added and the mixture was stirred for a further 1 h. A few drops of water and TFA were added and the mixture was separated via reversed phase HPLC. The desired fractions were collected, combined and lyophilised to yield example 1 (18 mg) as the TFA salt. HPLC: 1.3 min (method D)

Amide Formation Method B

To a stirred solution of building block A (1 eq) in DCM at room temperature is added oxalylchloride (2-5 eq, neat or 2M solution in DCM) and the mixture stirred for 0.5-2 h and then concentrated in vacuum. Pyridine, DMAP (0-0.1 eq) and amine reaction partner (2-3 eq) is added and the mixture stirred for 1-2 h, then concentrated, dissolved in ACN, water and TFA and separated via reversed phase HPLC to give the desired amides.

Synthesis of Example 2

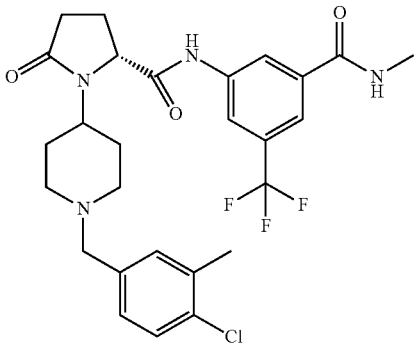

Building block A1 (80 mg) was dissolved in DCM (2 ml), and a solution of oxalylchloride in DCM (0.2 ml, 2M) was added and the mixture was stirred at 25° C. for 2 h and then concentrated in vacuum. Pyridine (1 ml) and 3-amino-N-methyl-5-(trifluoromethyl)benzamide hydrochloride (88 mg) is added and the mixture was further stirred for 2 h, then concentrated, dissolved in acetonitrile, water and TFA and separated via reversed phase HPLC to give of example 2 (45 mg) as the TFA salt. HPLC: 1.37 min (method D)

Synthesis of Example 3

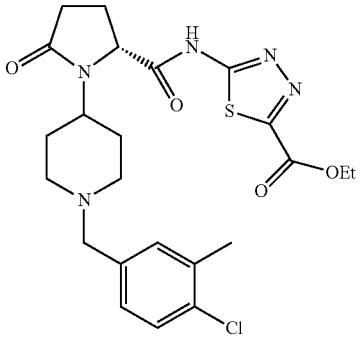

Building block A1 (80 mg) was dissolved in DCM (2 ml), oxalylchloride (0.07 ml) was added and the mixture was stirred at room temperature for 0.75 h and then concentrated in vacuum. Pyridine (1 ml), 4-dimethylaminopyridine (2 mg) and 5-Amino-1,3,4-thiadiazole-2-carboxylic acid ethyl ester (60 mg) were added and the mixture was further stirred for 1 h, then concentrated, dissolved in acetonitrile and separated via reversed phase HPLC to give example 3 (17 mg). HPLC: 1.34 min (method D)

The following examples 4-115 were synthesized in analogy to example 1-3 from building blocks A1 to A4.

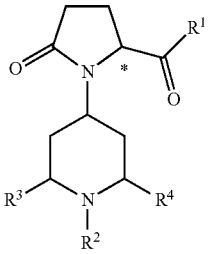

| # | $R^2$ | $R^1$ | $R^3$, $R^4$ | * | $R_t$ [min] (method) | Amide formation Method | Building block |
|---|---|---|---|---|---|---|---|
| 4 | 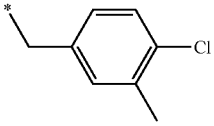 | 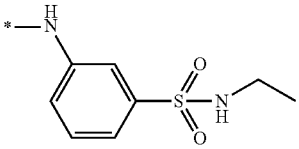 | H, H | R | 1.26 (D) | A | A1 |
| 5 | 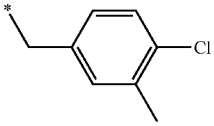 | 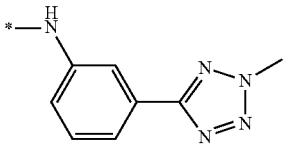 | H, H | R | 1.36 (D) | A | A1 |
| 6 | 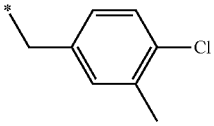 | 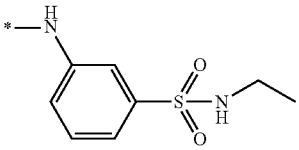 | H, H | R | 1.35 (D) | A | A3 |

-continued
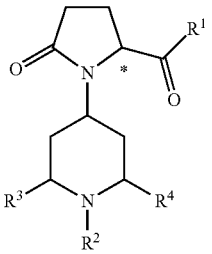
| # | $R^2$ | $R^1$ | $R^3$, $R^4$ | * | $R_t$ [min] (method) | Amide formation Method | Building block |
|---|---|---|---|---|---|---|---|
| 7 | 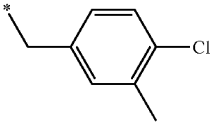 | 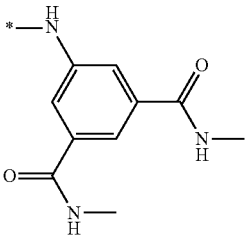 | H, H | R | 1.21 (D) | A | A1 |
| 8 | 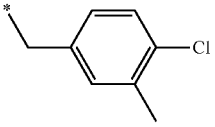 | 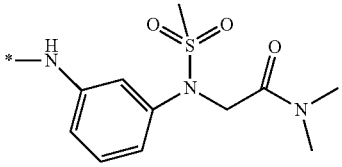 | H, H | R | 1.29 (D) | A | A1 |
| 9 | 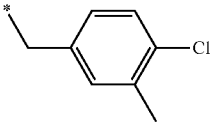 | 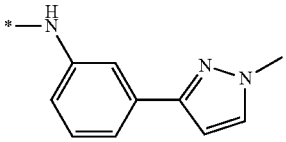 | H, H | R | 1.35 (D) | A | A1 |
| 10 | 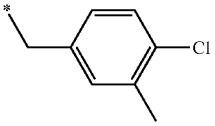 | 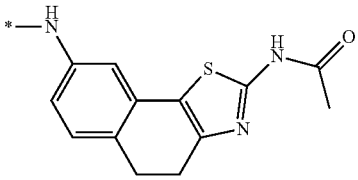 | H, H | R | 1.34 (D) | A | A1 |
| 11 | 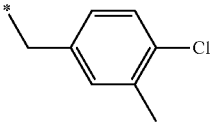 | 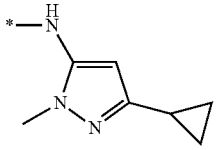 | H, H | R | 1.30 (D) | A | A1 |
| 12 | 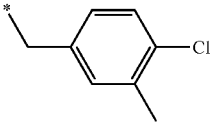 | 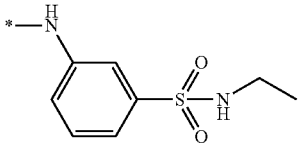 | H, H | S | 1.20 (C) | A | A1 |
| 13 | 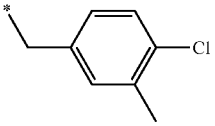 | 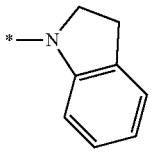 | H, H | R | 1.39 (D) | A | A1 |

-continued
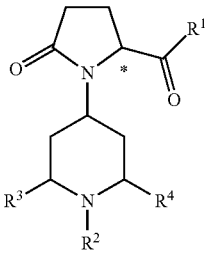
| # | $R^2$ | $R^1$ | $R^3$, $R^4$ | * | $R_t$ [min] (method) | Amide formation Method | Building block |
|---|---|---|---|---|---|---|---|
| 14 | 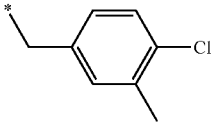 | 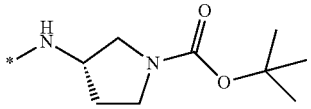 | H, H | R | 1.36 (D) | A | A1 |
| 15 | 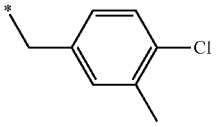 | 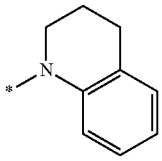 | H, H | R | 1.39 (D) | A | A1 |
| 16 | 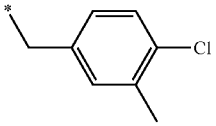 | 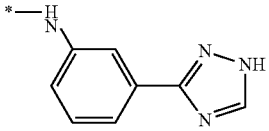 | H, H | R | 1.26 (D) | B | A1 |
| 17 | 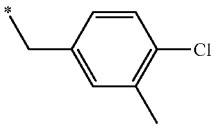 | 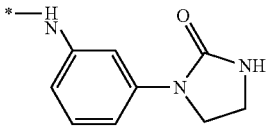 | H, H | R | 1.55 (B) | A | A1 |
| 18 | 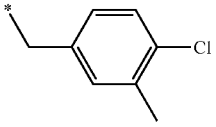 | 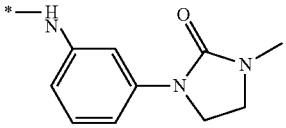 | H, H | R | 1.61 (B) | A | A1 |
| 19 | 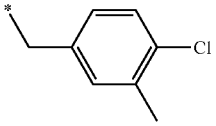 | 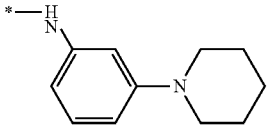 | H, H | R | 1.46 (B) | A | A1 |
| 20 | 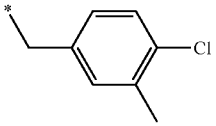 | 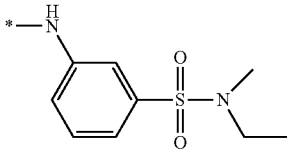 | H, H | R | 1.74 (B) | A | A1 |
| 21 | 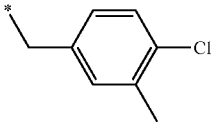 | 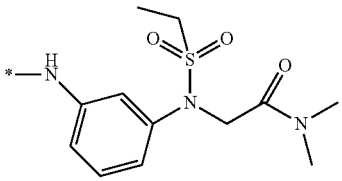 | H, H | R | 1.61 (B) | A | A1 |

-continued
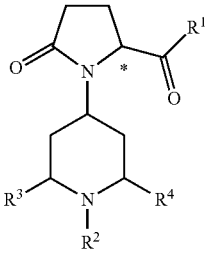
| # | $R^2$ | $R^1$ | $R^3$, $R^4$ | * | $R_t$ [min] (method) | Amide formation Method | Building block |
|---|---|---|---|---|---|---|---|
| 22 | 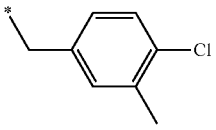 | 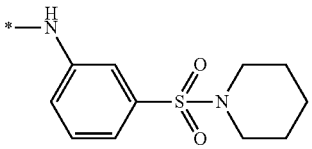 | H, H | R | 1.80 (B) | A | A1 |
| 23 | 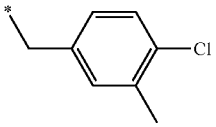 | 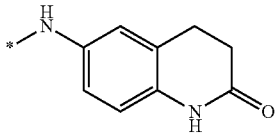 | H, H | S | 1.51 (B) | A | A1 |
| 24 | 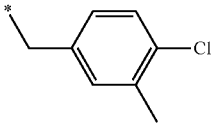 | 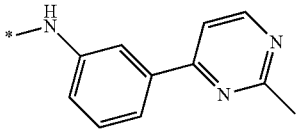 | H, H | R | 1.53 (B) | A | A1 |
| 25 | 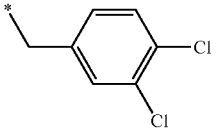 | 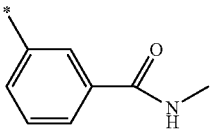 | H, H | R | 1.25 | A | A3 |
| 26 | 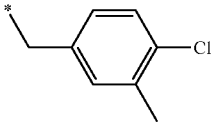 | 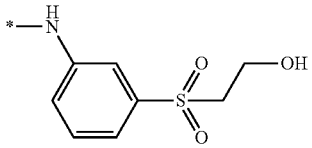 | H, H | R | 1.59 (B) | A | A1 |
| 27 | 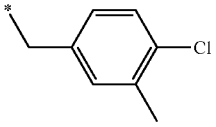 | 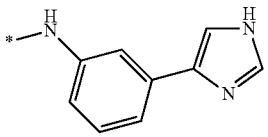 | H, H | R | 1.42 (B) | A | A1 |
| 28 | 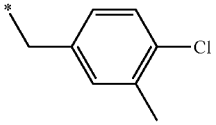 | 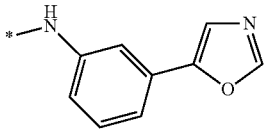 | H, H | R | 1.62 (B) | A | A1 |
| 29 | 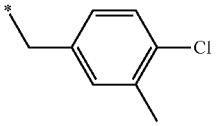 | 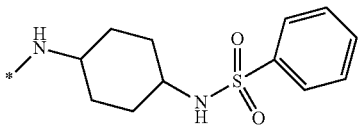 | H, H | R | 1.58 (B) | A | A1 |

-continued
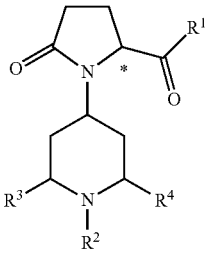
| # | $R^2$ | $R^1$ | $R^3$, $R^4$ | * | $R_t$ [min] (method) | Amide formation Method | Building block |
|---|---|---|---|---|---|---|---|
| 30 | 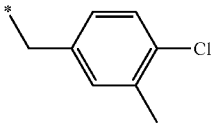 | 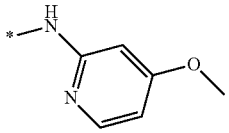 | H, H | R | 1.36 (B) | A | A1 |
| 31 | 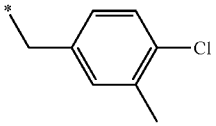 | 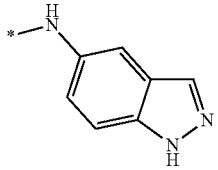 | H, H | R | 1.50 (B) | A | A1 |
| 32 | 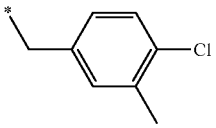 | 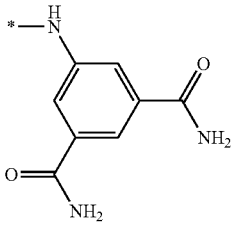 | H, H | R | 1.43 (B) | A | A1 |
| 33 | 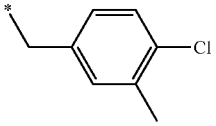 | 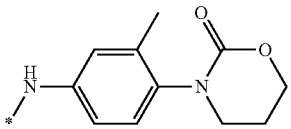 | H, H | R | 1.54 (B) | A | A1 |
| 34 | 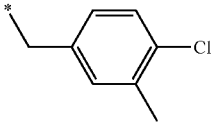 | 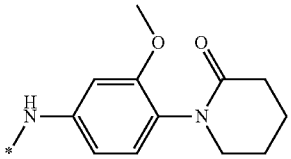 | H, H | R | 1.58 (B) | A | A1 |
| 35 | 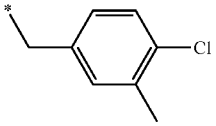 | 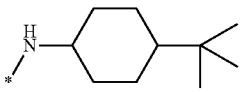 | H, H | S | 1.90 (B) | A | A2 |
| 36 | 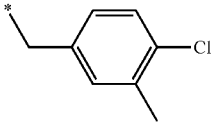 | 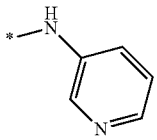 | H, H | R | 1.30 (B) | A | A1 |
| 37 | 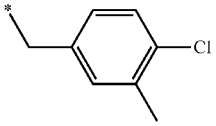 | 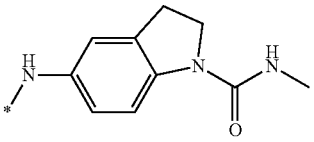 | H, H | R | 1.52 (B) | A | A1 |

-continued
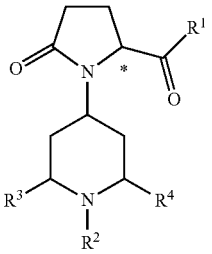
| # | $R^2$ | $R^1$ | $R^3$, $R^4$ | * | $R_t$ [min] (method) | Amide formation Method | Building block |
|---|---|---|---|---|---|---|---|
| 38 | 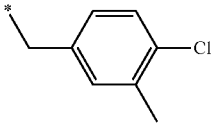 | 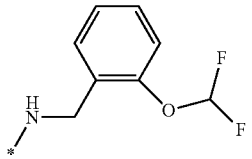 | H, H | S | 1.71 (B) | A | A1 |
| 39 | 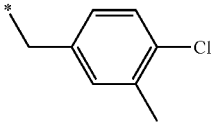 | 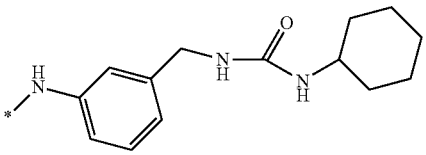 | H, H | R | 1.72 (B) | A | A1 |
| 40 | 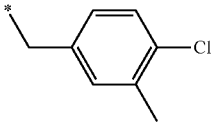 | 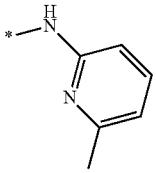 | H, H | S | 1.49 (B) | A | A2 |
| 41 | 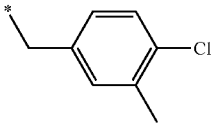 | 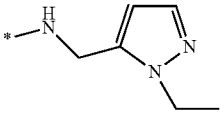 | H, H | R | 1.43 (B) | A | A1 |
| 42 | 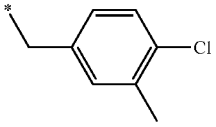 | 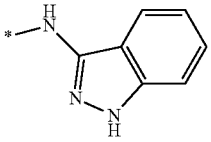 | H, H | S | 1.64 (B) | A | A1 |
| 43 | 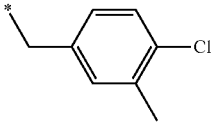 | 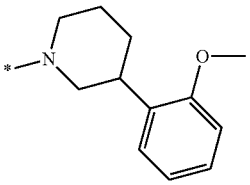 | H, H | R | 1.72 (B) | A | A1 |
| 44 | 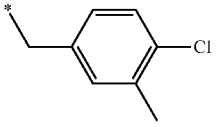 | 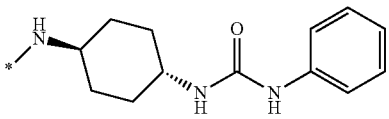 | H, H | R | 1.59 (B) | A | A1 |
| 45 | 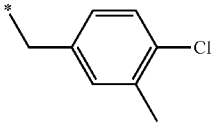 | 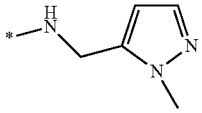 | H, H | S | 1.50 (B) | A | A2 |

-continued
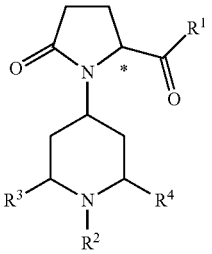
| # | $R^2$ | $R^1$ | $R^3$, $R^4$ | * | $R_t$ [min] (method) | Amide formation Method | Building block |
|---|---|---|---|---|---|---|---|
| 46 | 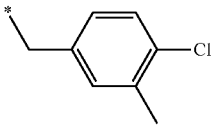 | 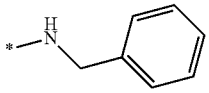 | H, H | S | 1.63 (B) | A | A2 |
| 47 | 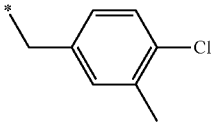 | 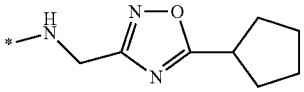 | H, H | S | 1.68 (B) | A | A2 |
| 48 | 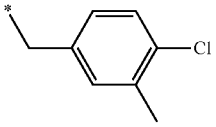 | 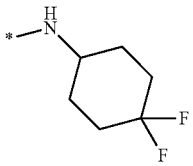 | H, H | S | 1.66 (B) | A | A2 |
| 49 | 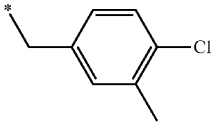 | 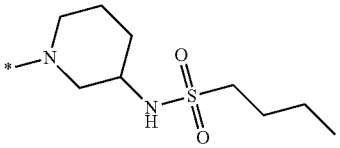 | H, H | S | 1.68 (B) | A | A2 |
| 50 | 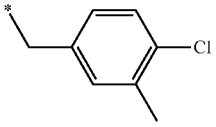 | 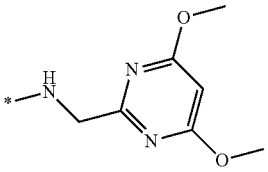 | H, H | S | 1.59 (B) | A | A2 |
| 51 | 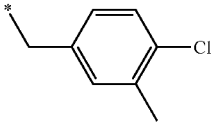 | 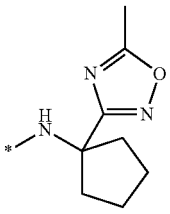 | H, H | S | 1.63 (B) | A | A2 |
| 52 | 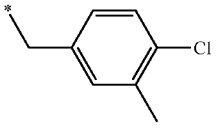 | 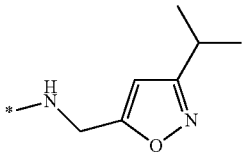 | H, H | S | 1.65 (B) | A | A2 |

-continued
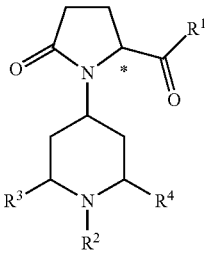
| # | $R^2$ | $R^1$ | $R^3$, $R^4$ | * | $R_t$ [min] (method) | Amide formation Method | Building block |
|---|---|---|---|---|---|---|---|
| 53 | 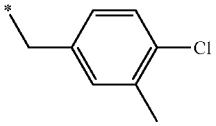 | 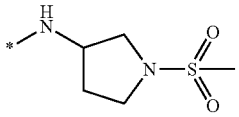 | H, H | S | 1.51 (B) | A | A2 |
| 54 | 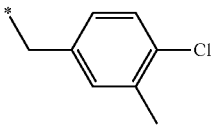 | 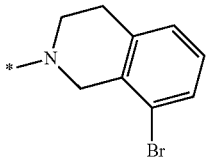 | H, H | R | 1.75 (B) | A | A2 |
| 55 | 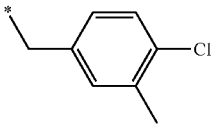 | 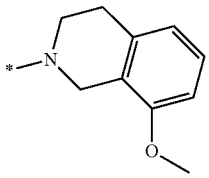 | H, H | S | 1.74 (B) | A | A2 |
| 56 | 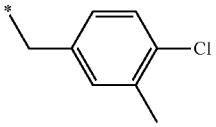 | 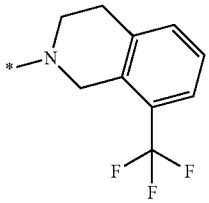 | H, H | S | 1.78 (B) | A | A2 |
| 57 | 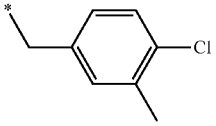 | 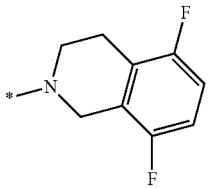 | H, H | S | 1.74 (B) | A | A2 |
| 58 | 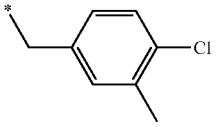 | 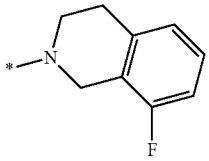 | H, H | S | 1.72 (B) | A | A2 |
| 59 | 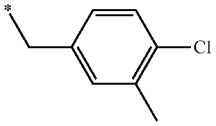 | 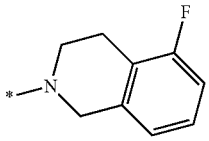 | H, H | R | 1.72 (B) | A | A2 |

-continued
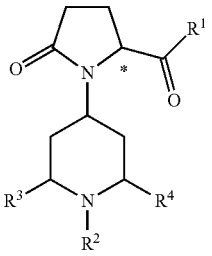
| # | $R^2$ | $R^1$ | $R^3$, $R^4$ | * | $R_t$ [min] (method) | Amide formation Method | Building block |
|---|---|---|---|---|---|---|---|
| 60 | 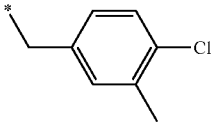 | 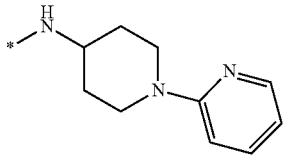 | H, H | S | 1.39 (B) | A | A2 |
| 61 | 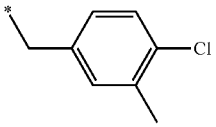 | 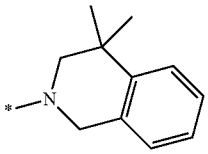 | H, H | S | 1.78 (B) | A | A2 |
| 62 | 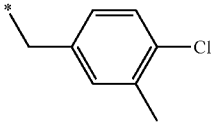 | 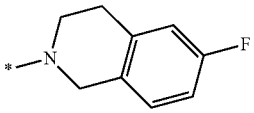 | H, H | S | 1.72 (B) | A | A2 |
| 63 | 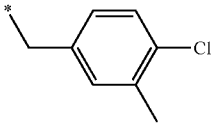 | 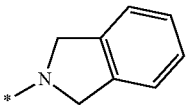 | H, H | R | 1.64 (B) | A | A2 |
| 64 | 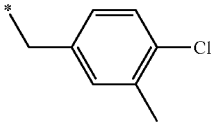 | 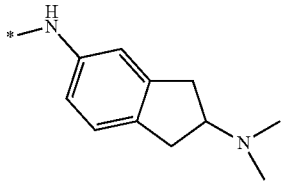 | H, H | R | 1.40 (B) | A | A2 |
| 65 | 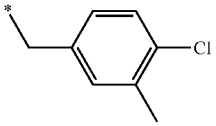 | 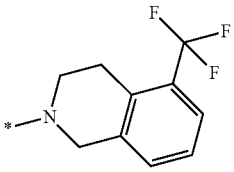 | H, H | R | 1.40 (B) | A | A2 |
| 66 | 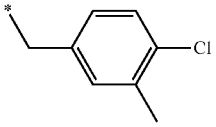 | 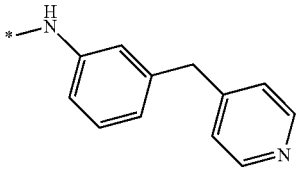 | H, H | S | 1.42 (B) | A | A2 |

-continued
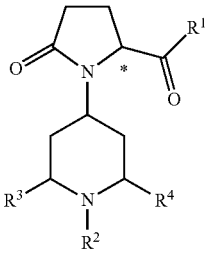
| # | $R^2$ | $R^1$ | $R^3$, $R^4$ | * | $R_t$ [min] (method) | Amide formation Method | Building block |
|---|---|---|---|---|---|---|---|
| 67 | 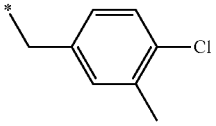 | 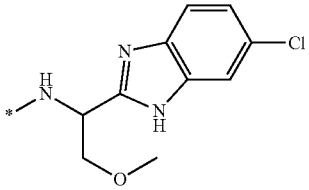 | H, H | S | 1.56; 1.64 (B) | A | A2 |
| 68 | 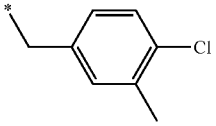 | 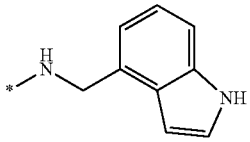 | H, H | R | 1.61 (B) | A | A2 |
| 69 | 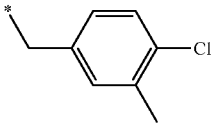 | 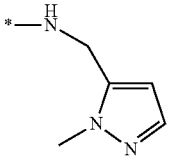 | H, H | S | 1.44 (B) | A | A2 |
| 70 | 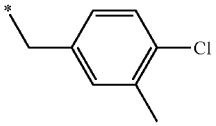 | 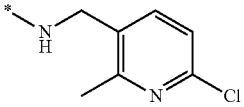 | H, H | S | 1.62 (B) | A | A2 |
| 71 | 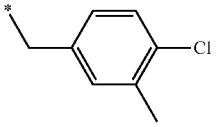 | 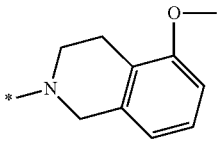 | H, H | S | 1.72 (B) | A | A2 |
| 72 | 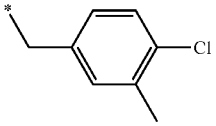 | 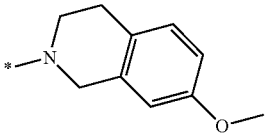 | H, H | S | 1.68 (B) | A | A2 |
| 73 | 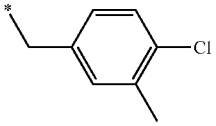 | 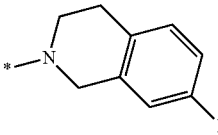 | H, H | S | 1.70 (B) | A | A2 |
| 74 | 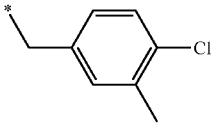 | 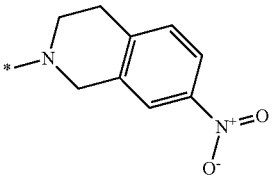 | H, H | R | 1.68 (B) | A | A2 |

-continued
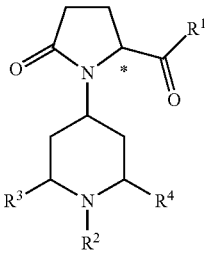
| # | $R^2$ | $R^1$ | $R^3$, $R^4$ | * | $R_t$ [min] (method) | Amide formation Method | Building block |
|---|---|---|---|---|---|---|---|
| 75 | 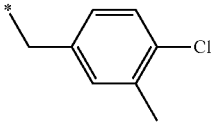 | 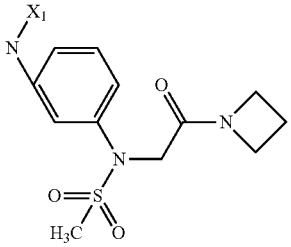 | 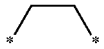 | R | 1.31 (E) | A | A4 |
| 76 | 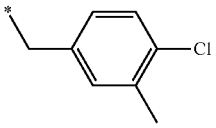 | 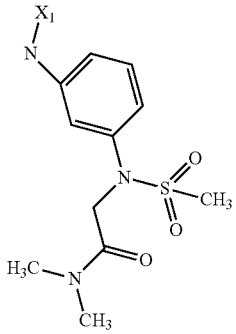 | 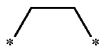 | R | 1.31 (E) | A | A4 |
| 77 | 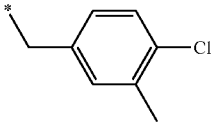 | 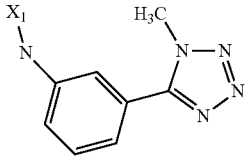 | 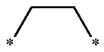 | R | 1.31 (E) | A | A4 |
| 78 | 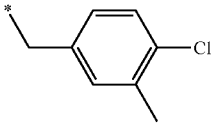 | 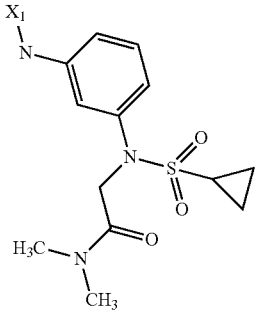 | 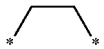 | R | 1.33 (E) | A | A4 |

-continued
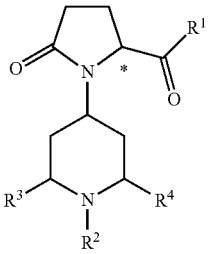
| # | $R^2$ | $R^1$ | $R^3$, $R^4$ | * | $R_t$ [min] (method) | Amide formation Method | Building block |
|---|---|---|---|---|---|---|---|
| 79 | 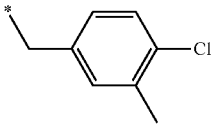 | 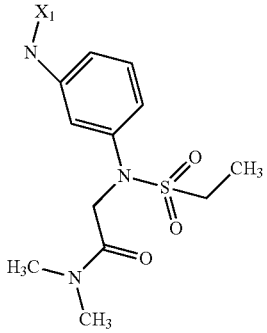 | 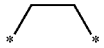 | R | 1.34 (E) | A | A4 |
| 80 | 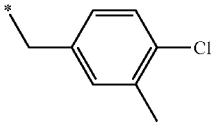 | 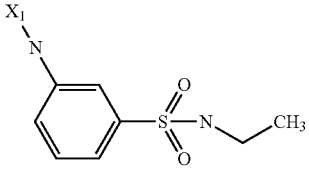 | 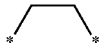 | R | 1.38 (E) | A | A4 |
| 81 | 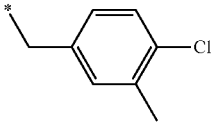 | 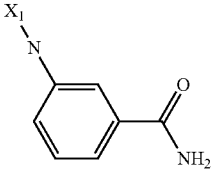 | 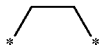 | R | 1.22 (E) | A | A4 |
| 82 | 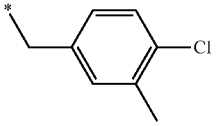 | 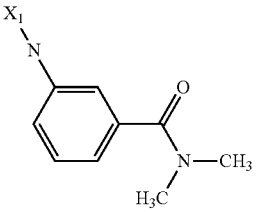 | 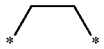 | R | 1.24; 1.29 (E) | A | A4 |
| 83 | 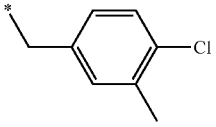 | 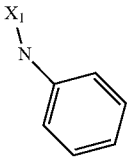 | 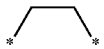 | R | 1.45 (E) | A | A4 |
| 84 | 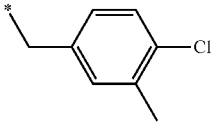 | 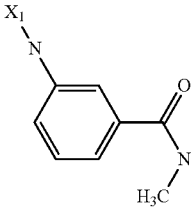 | 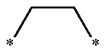 | R | 1.23 (E) | A | A4 |

-continued
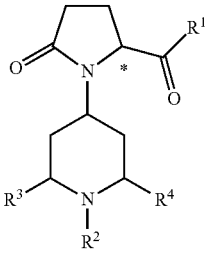
| # | $R^2$ | $R^1$ | $R^3$, $R^4$ | * | $R_t$ [min] (method) | Amide formation Method | Building block |
|---|---|---|---|---|---|---|---|
| 85 | 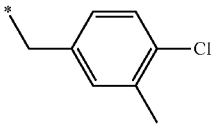 | 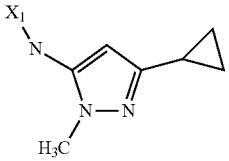 | 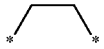 | R | 1.33 (E) | A | A4 |
| 86 | 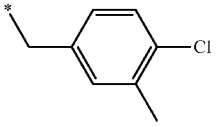 | 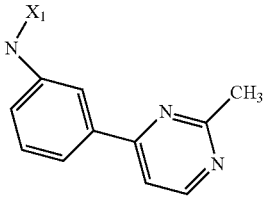 | 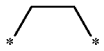 | R | 1.37 (E) | A | A4 |
| 87 | 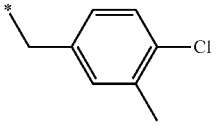 | 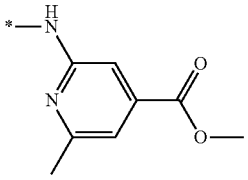 | H, H | R | 1.35 (D) | A | A1 |
| 88 | 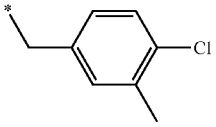 | 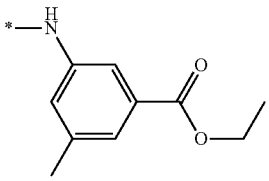 | H, H | R | 1.48 (D) | A | A1 |
| 89 | 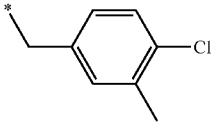 | 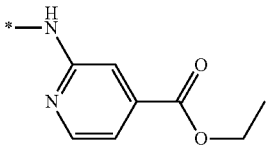 | H, H | R | 1.37 (D) | A | A1 |
| 90 | 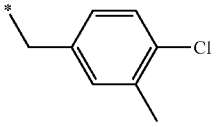 | 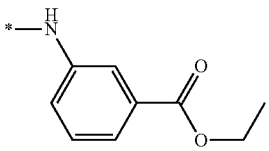 | H, H | R | 1.40 (D) | A | A1 |
| 91 | 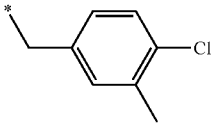 | 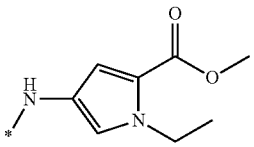 | H, H | R | 1.67 (B) | A | A1 |

-continued
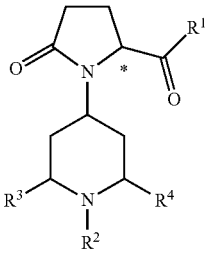
| # | $R^2$ | $R^1$ | $R^3$, $R^4$ | * | $R_t$ [min] (method) | Amide formation Method | Building block |
|---|---|---|---|---|---|---|---|
| 92 | 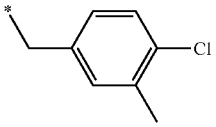 | 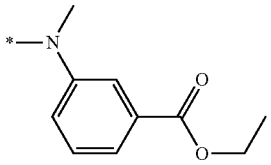 | H, H | R | 1.39 (D) | A | A1 |
| 93 | 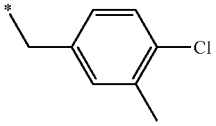 | 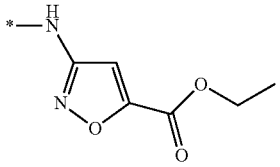 | H, H | R | 1.26 (D) | A | A1 |
| 94 | 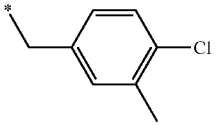 | 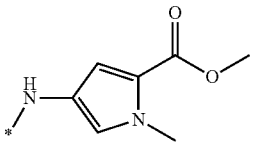 | H, H | R | 1.87 (A) | A | A1 |
| 95 | 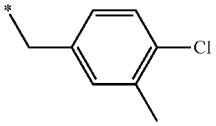 | 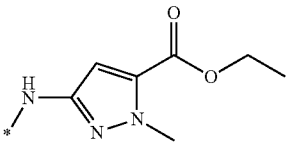 | H, H | R | 1.91 (A) | A | A1 |
| 96 | 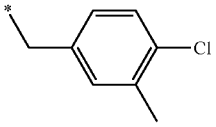 | 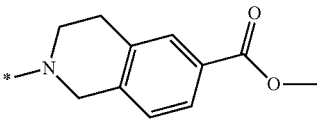 | H, H | R | 1.66 (B) | A | A2 |
| 97 | 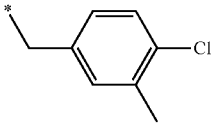 | 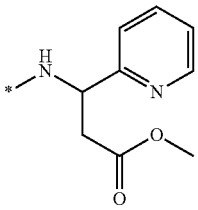 | H, H | S | 1.37 (B) | A | A2 |
| 98 | 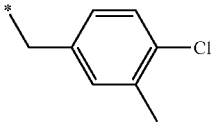 | 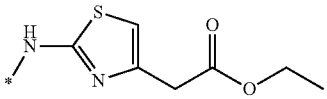 | H, H | R | 1.36 (D) | B | A2 |
| 99 | 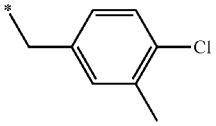 | 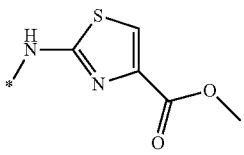 | H, H | R | 1.31 (D) | B | A1 |

-continued
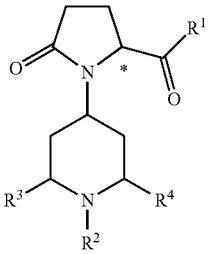
| # | $R^2$ | $R^1$ | $R^3$, $R^4$ | * | $R_t$ [min] (method) | Amide formation Method | Building block |
|---|---|---|---|---|---|---|---|
| 100 | 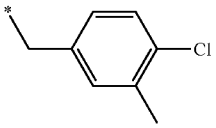 | 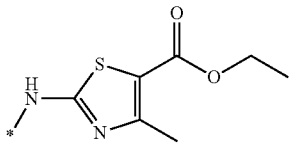 | H, H | R | 2.07 (A) | A | A1 |
| 101 | 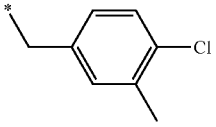 | 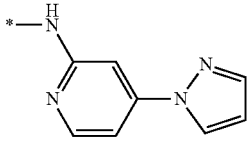 | H, H | R | 9.22 (O) | A | A1 |
| 102 | 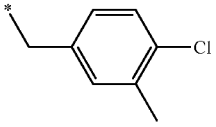 | 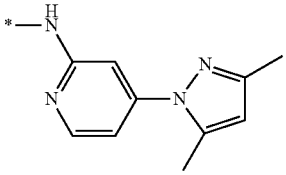 | H, H | R | 9.75 (O) | A | A1 |
| 103 | 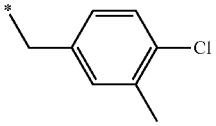 | 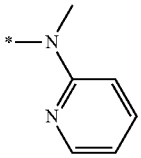 | H, H | R | 1.26 (D) | B | A1 |
| 104 | 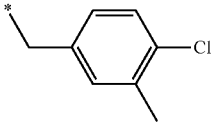 | 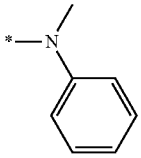 | H, H | R | 1.35 (D) | A | A1 |
| 105 | 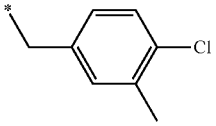 | 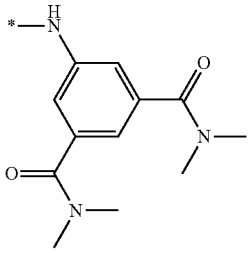 | H, H | R | 1.23 (D) | B | A1 |

-continued
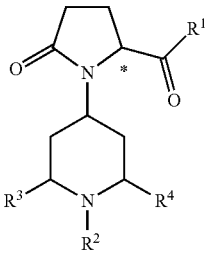
| # | $R^2$ | $R^1$ | $R^3$, $R^4$ | * | $R_t$ [min] (method) | Amide formation Method | Building block |
|---|---|---|---|---|---|---|---|
| 106 | 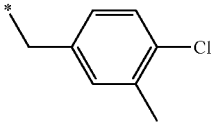 | 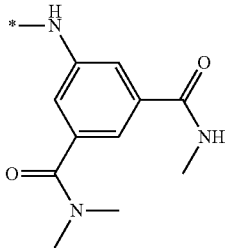 | H, H | R | 1.23 (D) | A | A1 |
| 107 | 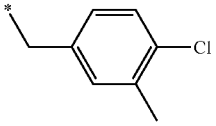 | 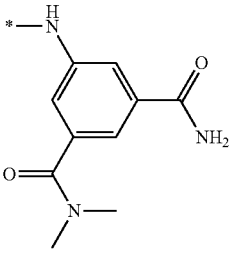 | H, H | R | 1.20 (D) | A | A1 |
| 108 | 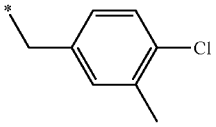 | 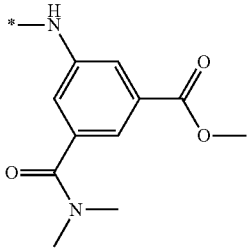 | H, H | R | 1.21 (D) | B | A1 |
| 109 | 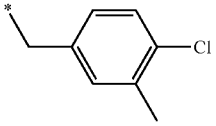 | 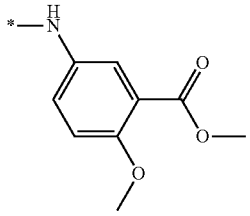 | H, H | R | 1.33 (D) | A | A1 |
| 110 | 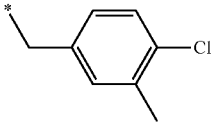 | 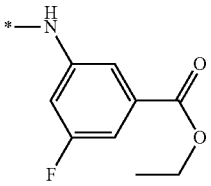 | H, H | R | 1.47 (D) | B | A1 |

-continued
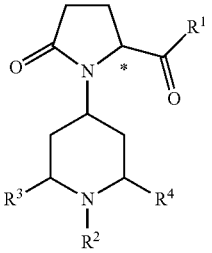
| # | $R^2$ | $R^1$ | $R^3$, $R^4$ | * | $R_t$ [min] (method) | Amide formation Method | Building block |
|---|---|---|---|---|---|---|---|
| 111 | 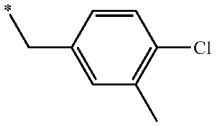 | 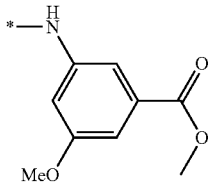 | H, H | R | 1.40 (D) | A | A1 |
| 112 | 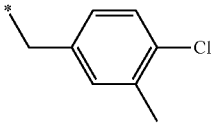 | 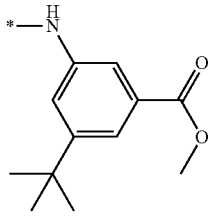 | H, H | R | 1.53 (D) | A | A1 |
| 113 | 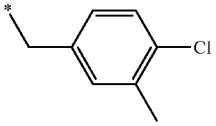 | 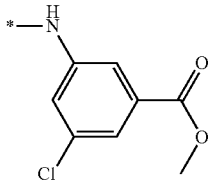 | H, H | R | 1.48 (D) | A | A1 |
| 114 | 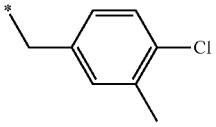 | 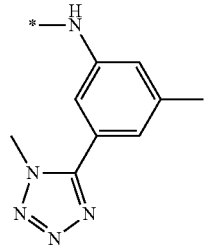 | H, H | R | 1.26 (E) | A | A1 |
| 115 | 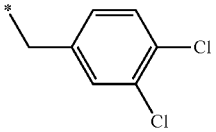 | 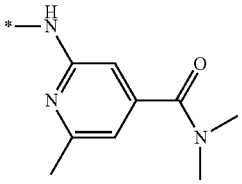 | H, H | R | 1.26 (D) | A | A3 |

Example 116

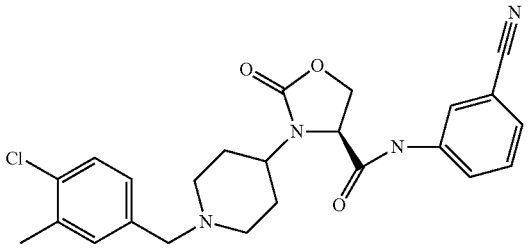

To an ice-chilled stirred solution of building block A5 (0.11 g), 3-amino-benzonitrile (0.08 g), DIPEA (0.26 ml) and DMAP (0.01 g) in dry DMF (1 ml), was added tetramethyl fluoroformamidinium hexafluorophosphate (0.1 mg). After 5 min the cooling bath was removed and the reaction mixture stirred at room temperature until complete disappearance of the starting acid.

The solvent and the volatiles were removed under reduced pressure, the thick oily residue was purified by preparative LC-MS, affording example 116 (as TFA salt) (0.02 mg). HPLC (Rt)=8.38 min (method O)

The following examples are synthesized in analogy to the Preparation of example 116:

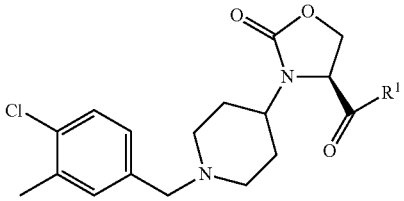

| Example | $R^1$ | $R_t$ [min] (method) | Building block |
|---|---|---|---|
| 117 | 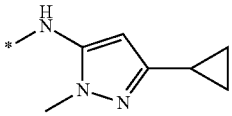 | 8.27 (P) | A5 |
| 118 | 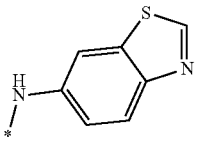 | 6.90 (P) | A5 |
| 119 | 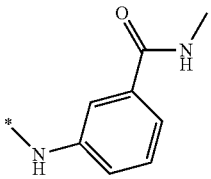 | 8.38 (O) | A5 |

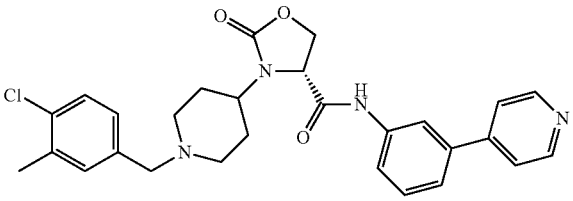

Building block A7 (0.07 g) was dissolved in dry DMF (2 ml); HATU (0.09 g) and DIPEA (0.15 mL) were added in sequence and the whole stirred at room temperature for 15 min. Then 3-pyridin-4-yl-phenylamine was added (0.04 g) and the resulting yellow solution stirred at 40° C. until complete disappearance of the starting acid. The solvent and the volatiles were removed under reduced pressure; the oily residue was purified by preparative LC-MS, affording the title compound (as TFA salt) (62 mg). HPLC ($R_t$)=10.02 min, Method=F The following examples are synthesized in analogy to the preparation of example 120

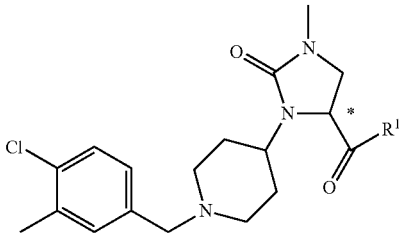

| # | $R^1$ | * | $R_t$ [min] (method) | Building block |
|---|---|---|---|---|
| 121 | 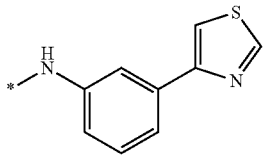 | R | 7.33 (P) | A7 |
| 122 | 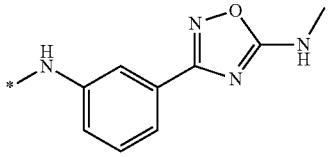 | R | 6.90 (P) | A7 |
| 123 | 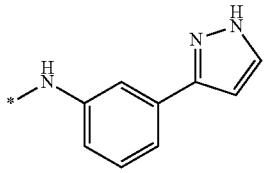 | R | 7.08 (P) | A7 |
| 124 | 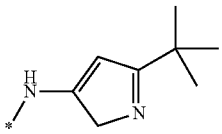 | S | 3.05 (G) | A8 |

-continued

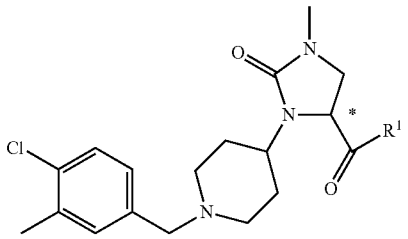

| # | $R^1$ | * | $R_t$ [min] (method) | Building block |
|---|---|---|---|---|
| 125 | 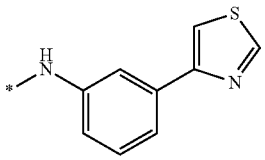 | S | 2.88 (G) | A8 |
| 126 | 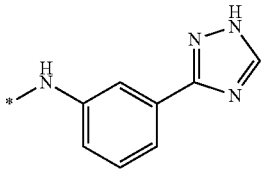 | S | 2.43 (G) | A8 |
| 127 | 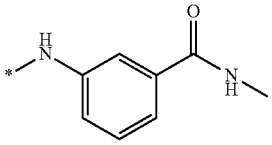 | S | 8.27 (F) | A8 |
| 128 | 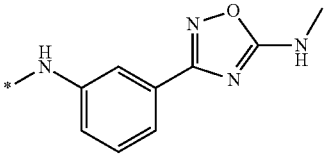 | S | 2.72 (G) | A8 |
| 129 | 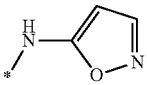 | S | 2.49 (G) | A8 |
| 130 | 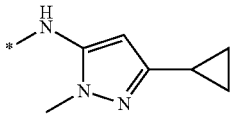 | R | 2.67 (G) | A6 |

-continued

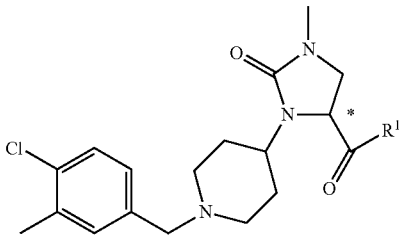

| # | $R^1$ | * | $R_t$ [min] (method) | Building block |
|---|---|---|---|---|
| 131 | 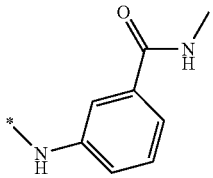 | R | 2.49 (G) | A6 |

S.4.2. Synthesis of Examples According to Procedure B

Examples 132-191

Synthesis of Example 132

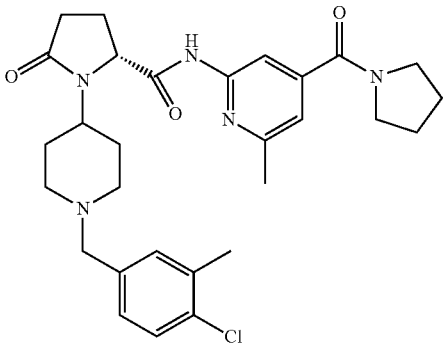

To a stirred solution of Building block B1 (120 mg) in DMF (2 ml) at room temperature, was added DIPEA (0.2 ml), HATU (175 mg). After 20 min, pyrrolidine (49 mg) was added and the mixture stirred for a further 1.5 h. A few drops of water and TFA were added and the mixture was separated via reversed phase HPLC. The desired fractions were collected, combined and lyophilised to yield example 132 (30 mg) as the TFA salt. HPLC: $R_t$=1.29 min (method D)

The following examples have been synthesized from building block B1 to B18 in analogy to example 132.

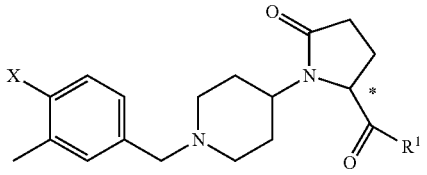
| # | $R^1$ | X | * | $R_t$ [min] (method) | Building block |
|---|---|---|---|---|---|
| 133 | 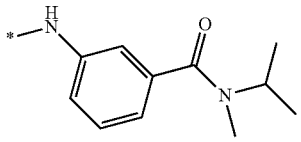 | Cl | R | 1.34 (D) | B4 |
| 134 | 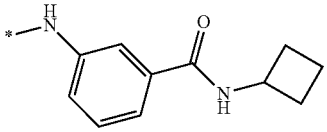 | Cl | R | 1.34 (D) | B4 |
| 135 | 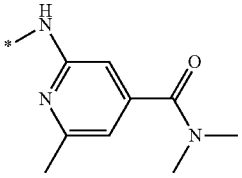 | Cl | R | 1.26 (D) | B1 |
| 136 | 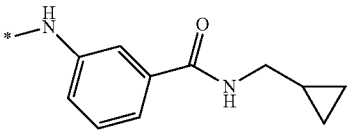 | Cl | R | 1.35 (D) | B4 |
| 137 | 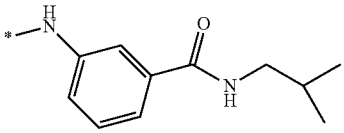 | Cl | R | 1.34 (D) | B4 |
| 138 | 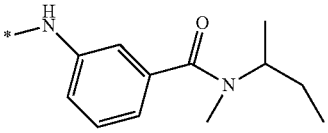 | Cl | R | 1.37 (D) | B4 |
| 139 | 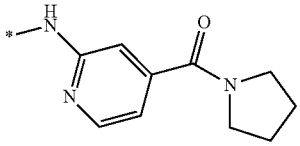 | Cl | R | 1.32 (D) | B3 |
| 140 | 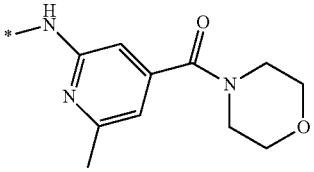 | Cl | R | 1.26 (D) | B1 |
| 141 | 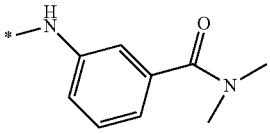 | Cl | R | 1.28 (D) | B4 |

-continued
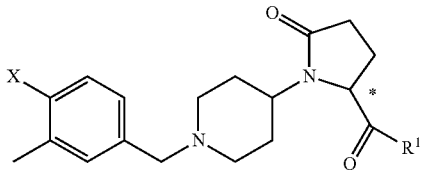
| # | $R^1$ | X | * | $R_t$ [min] (method) | Building block |
|---|---|---|---|---|---|
| 142 | 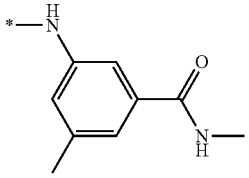 | Cl | R | 1.29 (D) | B2 |
| 143 | 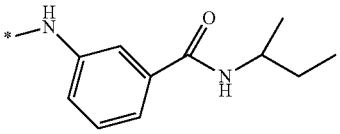 | Cl | R | 1.36 (D) | B4 |
| 144 | 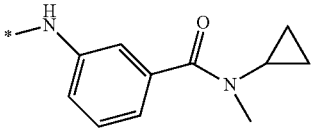 | Cl | R | 1.32 (D) | B4 |
| 145 | 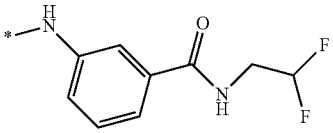 | Cl | R | 1.32 (D) | B4 |
| 146 | 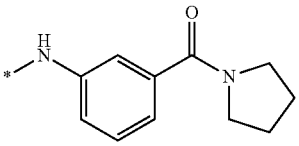 | Cl | R | 1.31 (D) | B4 |
| 147 | 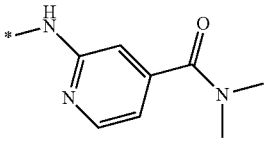 | Cl | R | 1.24 (D) | B3 |
| 148 | 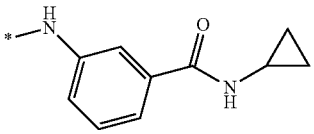 | Cl | R | 1.29 (D) | B4 |
| 149 | 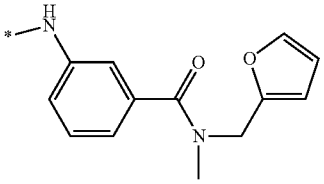 | Cl | R | 1.38 (D) | B4 |

-continued
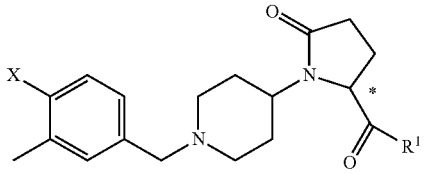
| # | $R^1$ | X | * | $R_t$ [min] (method) | Building block |
|---|---|---|---|---|---|
| 150 | 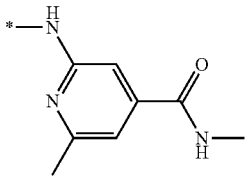 | Cl | R | 1.26 (D) | B1 |
| 151 | 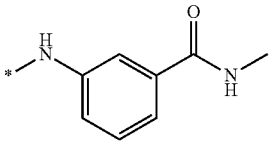 | Cl | R | 1.25 (D) | B4 |
| 152 | 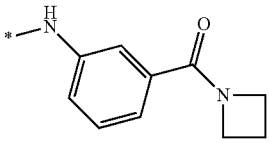 | Cl | R | 1.30 (D) | B4 |
| 153 | 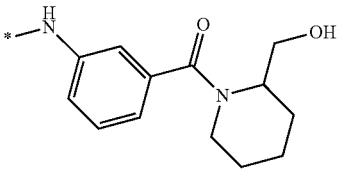 | Cl | R | 1.29 (D) | B4 |
| 154 | 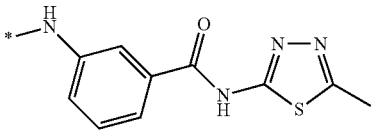 | Cl | R | 1.34 (D) | B4 |
| 155 | 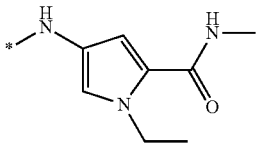 | Cl | R | 1.53 (B) | B5 |
| 156 | 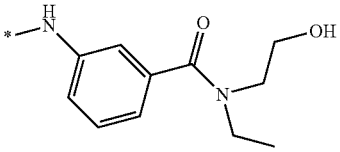 | Cl | R | 1.25 (D) | B4 |
| 157 | 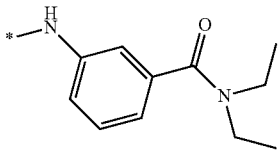 | Cl | R | 1.35 (D) | B4 |

-continued
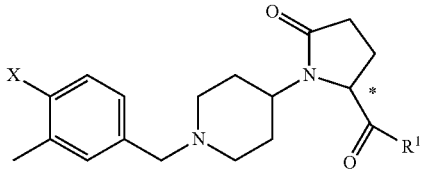
| # | $R^1$ | X | * | $R_t$ [min] (method) | Building block |
|---|---|---|---|---|---|
| 158 | 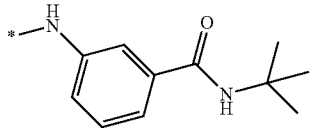 | Cl | R | 1.39 (D) | B4 |
| 159 | 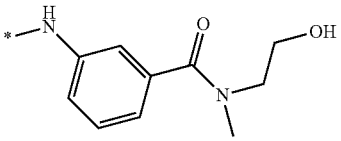 | Cl | R | 1.22 (D) | B4 |
| 160 | 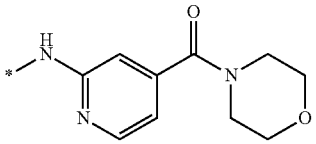 | Cl | R | 1.24 (D) | B3 |
| 161 | 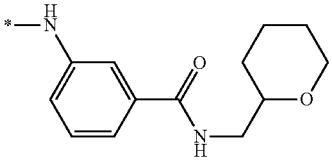 | Cl | R | 1.29 (D) | B4 |
| 162 | 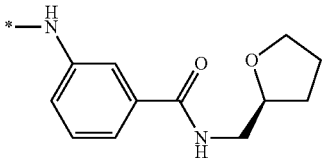 | Cl | R | 1.28 (D) | B4 |
| 163 | 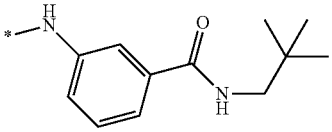 | Cl | R | 1.41 (D) | B4 |
| 164 | 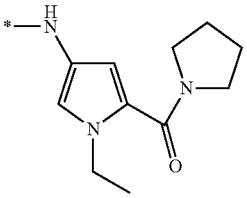 | Cl | R | 1.53 (B) | B5 |
| 165 | 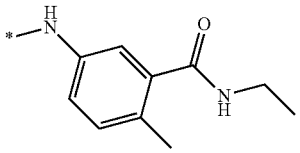 | Cl | R | 1.59 (B) | B1 |

-continued
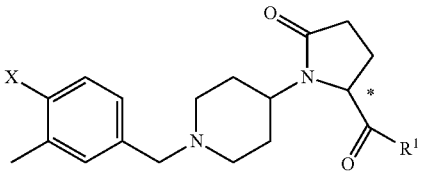
| # | $R^1$ | X | * | $R_t$ [min] (method) | Building block |
|---|---|---|---|---|---|
| 166 | 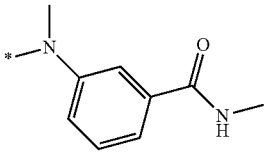 | Cl | R | 1.26 (D) | B6 |
| 167 | 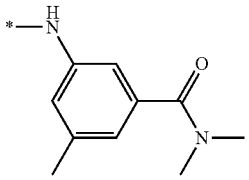 | Cl | R | 1.22 (E) | B2 |
| 168 | 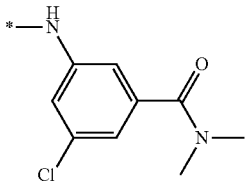 | Cl | R | 1.26 (E) | B8 |
| 169 | 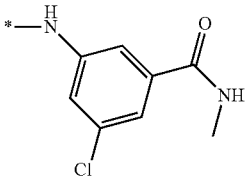 | Cl | R | 1.24 (E) | B8 |
| 170 | 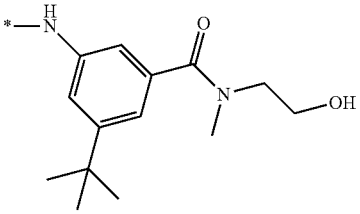 | Cl | R | 1.25 (E) | B10 |
| 171 | 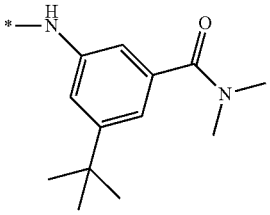 | Cl | R | 1.35 (E) | B10 |
| 172 | 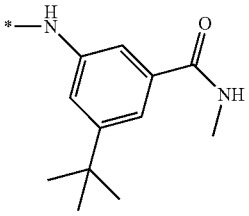 | Cl | R | 1.30 (E) | B10 |

-continued
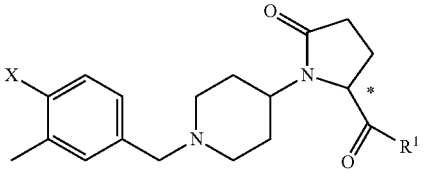
| # | $R^1$ | X | * | $R_t$ [min] (method) | Building block |
|---|---|---|---|---|---|
| 173 | 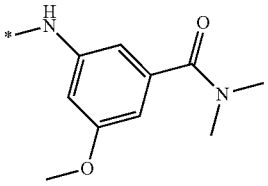 | Cl | R | 1.22 (E) | B9 |
| 174 | 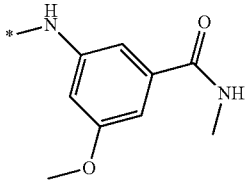 | Cl | R | 1.19 (E) | B9 |
| 175 | 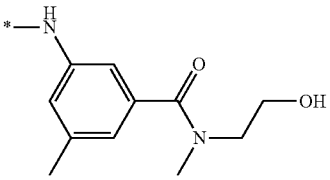 | Cl | R | 1.14 (E) | B2 |
| 176 | 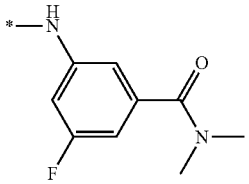 | Cl | R | 1.24 (E) | B7 |
| 177 | 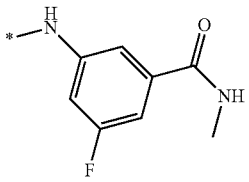 | Cl | R | 1.20 (E) | B7 |
| 178 | 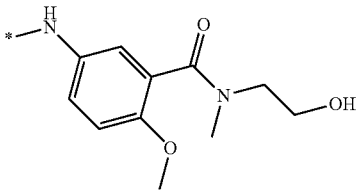 | Cl | R | 1.12 (E) | B11 |
| 179 | 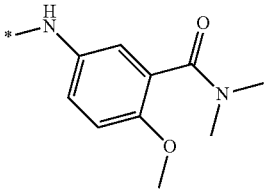 | Cl | R | 1.18 (E) | B11 |

-continued
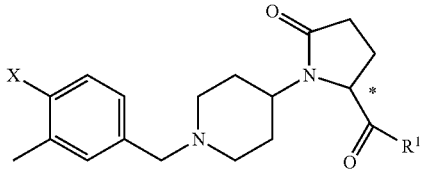
| # | $R^1$ | X | * | $R_t$ [min] (method) | Building block |
|---|---|---|---|---|---|
| 180 | 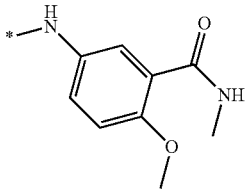 | Cl | R | 1.18 (E) | B11 |
| 181 | 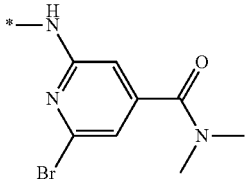 | Cl | R | 1.34 (D) | B15 |
| 182 | 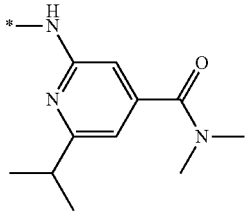 | Cl | R | 1.36 (D) | B13 |
| 183 | 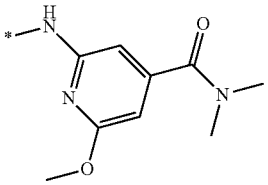 | Cl | R | 1.29 (D) | B14 |
| 184 | 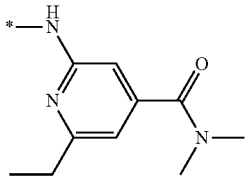 | Cl | R | 1.31 (D) | B12 |
| 185 | 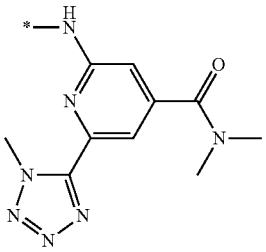 | Cl | R | 1.17 (E) | B16 |

-continued
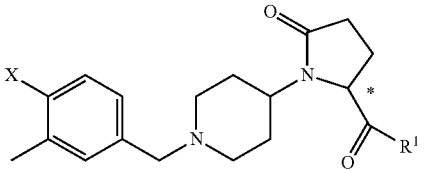
| # | $R^1$ | X | * | $R_t$ [min] (method) | Building block |
|---|---|---|---|---|---|
| 186 | 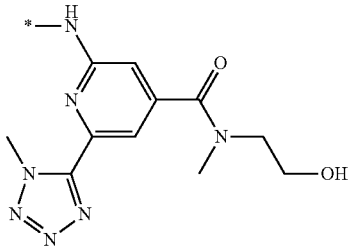 | Cl | R | 1.24 (D) | B16 |
| 187 | 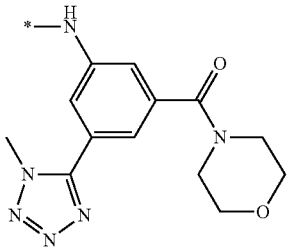 | Cl | R | 1.26 (D) | B16 |
| 188 | 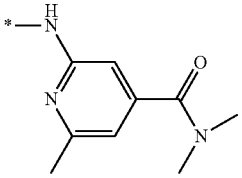 | Br | R | 1.28 (D) | B18 |
| 189 | 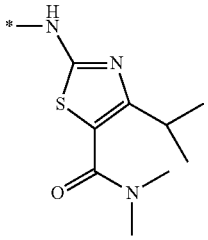 | Cl | R | 1.34 (D) | B17 |
| 190 | 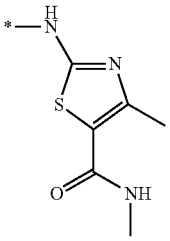 | Cl | R | 1.50 (B) | B19 |

-continued

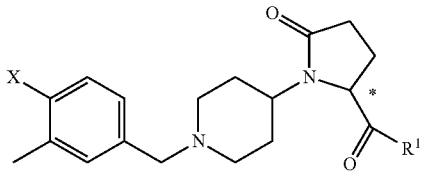

| # | $R^1$ | X | * | $R_t$ [min] (method) | Building block |
|---|---|---|---|---|---|
| 191 | 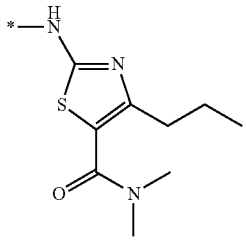 | Cl | R | 1.34 (D) | B20 |

S.4.3. Synthesis of Examples According to Procedure C

Examples 192-196

Example 192

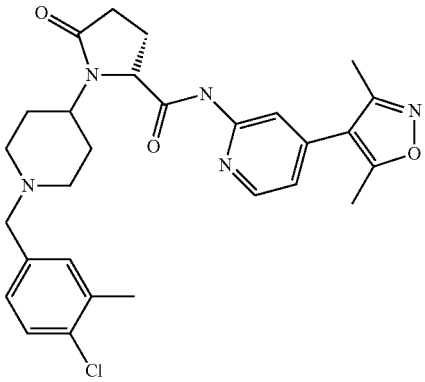

2-Chloro-4-(3,5-dimethyl-isoxazol-4-yl)-pyridine (25 mg) and building block C1 (25 mg) were dissolved in dry dioxane (1.2 ml) under inert atmosphere and palladium(II) acetate (2 mg), 4,5-bis(diphenylphosphino)-9,9-dimethylxanthene (11 mg) and caesium carbonate (81 mg) were added subsequently. The mixture was heated to 100° C. and stirred for 18 h. After cooling to room temperature the reaction mixture was diluted with DCM, washed with water and brine, dried under $Na_2SO_4$, filtered and the solvent was evaporated under reduced pressure. The crude was purified by flash column chromatography (10 g Isolute® silica gel cartridge; gradient elution: DCM/MeOH from 97/3 to 95/5) affording the title compound (49 mg). HPLC(Rt)=9.47 min (method O)

The following examples are synthesized in analogy to the preparation of example 192

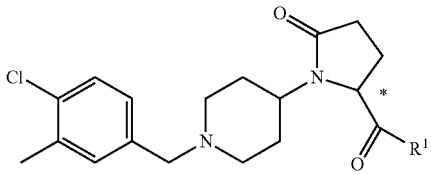

| # | $R^1$ | * | $R_t$ [min] (method) | Building block |
|---|---|---|---|---|
| 193 | 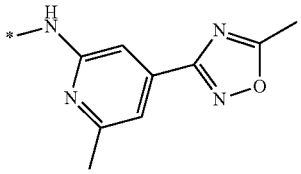 | R | 3.37 (L) | C1 |
| 194 | 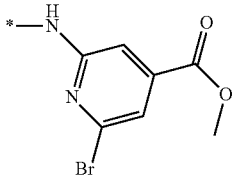 | R | 1.45 (D) | C1 |
| 195 | 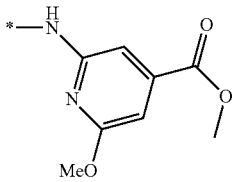 | R | 1.46 (D) | C1 |
| 196 | 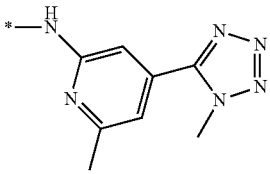 | R | 1.23 (E) | C1 |

S.4.4. Synthesis of Examples According to Procedure D

Examples 197-208

Example 197

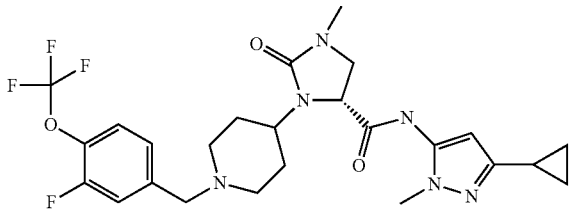

Building block D1 (0.08 g) and 3-fluoro-4-trifluoromethoxy benzaldehyde (0.05 g) were dissolved in 25% MeOH in DCM (4 ml) and the resulting solution stirred at room temperature for 30 min. Sodium cyanoborohydride (0.02 g) was then added in one portion and the whole allowed to react overnight. The solvent was evaporated under reduced pressure, 10% aq. $K_2CO_3$ (3 ml) and DCM (5 ml) were added, the layers separated, the organic phase dried over $Na_2SO_4$ and evaporated to dryness. The resulting crude was then purified by preparative LC-MS to afford the target compound as a TFA salt (0.03 g). HPLC ($R_t$)=7.01 min (method P)

The following examples are synthesized in analogy to the preparation of example 197

Synthesis of Example 200

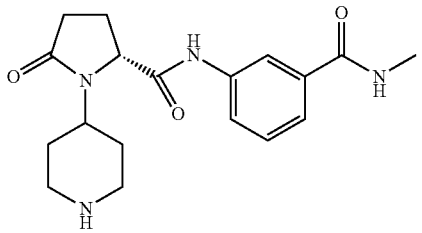

D2

+

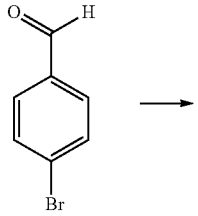

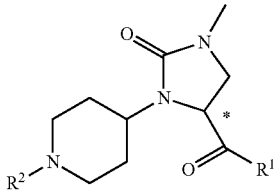

| # | $R^1$ | $R^2$ | * | $R_t$ [min] (method) | Building block |
|---|---|---|---|---|---|
| 198 | 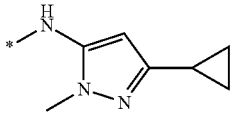 | 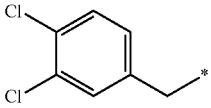 | R | 2.60 (G) | D1 |
| 199 | 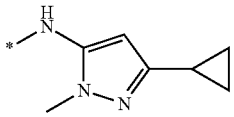 | 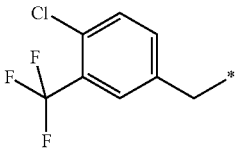 | R | 9.30 (O) | D1 |

-continued

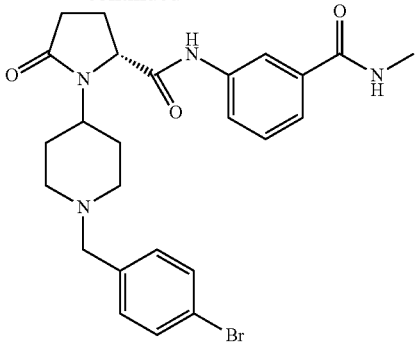

200

D2 (0.05 g) was dissolved in EtOH (1 ml) and of 4-bromobenzaldehyde (0.081 g), HOAc (0.026 g) and a small amount of molecular sieve 4 Å was added and the suspension stirred at 25° C. overnight. Sodium triacetoxyborhydride (0.154 g) was added and again the mixture stirred for 1 h, concentrated and suspended in MeOH, water and TFA. After filtration the mixture was separated via reversed phase HPLC and fractions containing the product collected and lyophilised to provide example 200 (0.049 g). HPLC: 1.21 min (method D)

The following examples 201-208 were synthesized in analogy to example 200 from building block D2 or D3.

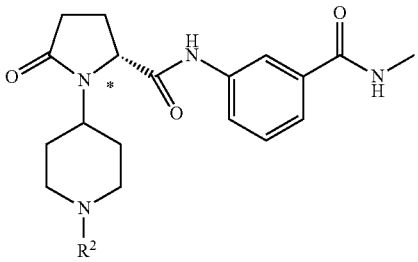

| # | $R^2$ | * | $R_t$ [min] (method) | Building block |
|---|---|---|---|---|
| 201 | 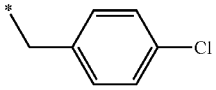 | R | 1.20 (D) | D2 |
| 202 | 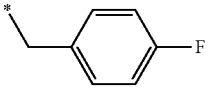 | R | 1.14 (D) | D2 |
| 203 | 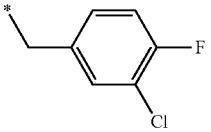 | R | 1.21 (D) | D2 |
| 204 | 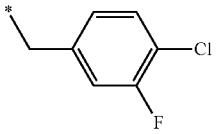 | R | 1.23 (D) | D2 |

-continued

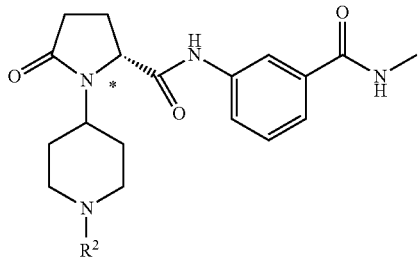

| # | $R^2$ | * | $R_t$ [min] (method) | Building block |
|---|---|---|---|---|
| 205 | 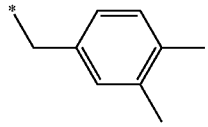 | R | 1.23 (D) | D2 |
| 206 | 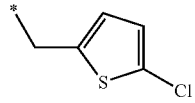 | R | 1.18 (D) | D2 |
| 207 | 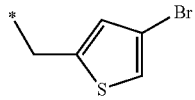 | R | 1.18 (D) | D2 |
| 208 | 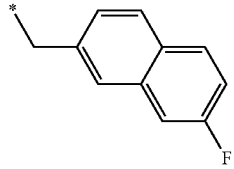 | R | 1.29 (D) | D3 |

S.4.5. Synthesis of Examples According to Procedure E

Example 209

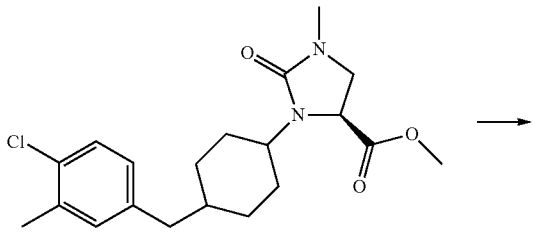

I12.2

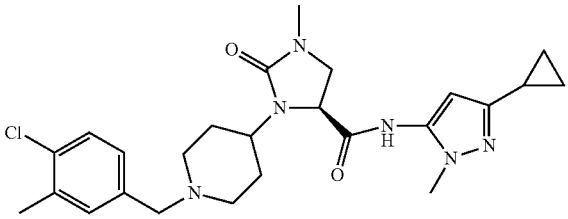

Intermediate I12.2, (0.20 g), 3-cyclopropyl-1-methyl-1H-pyrazole-5-amine (0.14 g), potassium t-butoxide (0.10 ml of a 1M THF solution) and dioxane (2 ml) were transferred to a microwave vial and heated under microwave irradiation under the following conditions: max power 150 W, T 150° C., 15 min; after the first cycle 0.05 mL of base were added and two more cycles of irradiation performed under the same conditions. The reaction mixture was evaporated to dryness, and the oily residue was purified by preparative LC-MS affording example 208 (as TFA salt) (0.09 g). HPLC ($R_t$)= 7.12 min (method P)

S.4.6. Synthesis of Examples According to Procedure F

Examples 210-212

Example 210

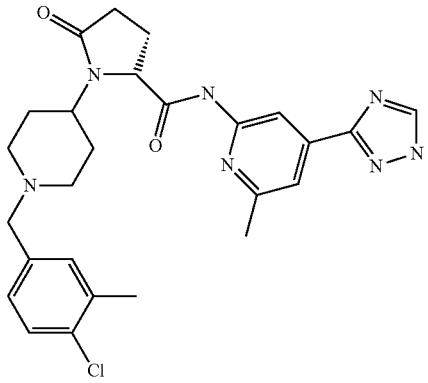

Building block F1 (70 mg) was dissolved in ethanol (5 ml) and conc. hydrochloric acid (1.5 ml) was added. The solution was stirred at room temperature for 4 h. Ethanol was removed under reduced pressure and the residue partitioned between saturated aqueous solution of $NaHCO_3$ and EtOAc. The layers were separated and the aqueous phase extracted with EtOAc. The combined organic extracts were washed with brine, dried under $Na_2SO_4$, filtered and the solvent was evaporated under reduced pressure. The crude was purified by flash column chromatography (5 g Isolute® silica gel cartridge; gradient elution: DCM/MeOH from 97/3 to 95/5) affording the title compound (55 mg). HPLC ($R_t$)=8.08 min (method O)

Example 211-212 was synthesized in analogy to example 210.

| # | $R^1$ | * | $R_t$ [min] (method) | Building block |
|---|---|---|---|---|
| 210 | 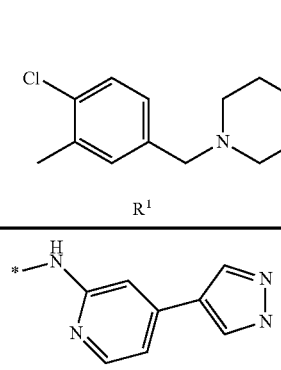 | R | 8.50 (O) | F2 |

-continued

| # | $R^1$ | * | $R_t$ [min] (method) | Building block |
|---|---|---|---|---|
| 211 | 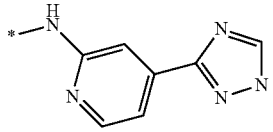 | R | 2.37 (M) | F3 |

S.4.7. Synthesis of Examples According to Procedure G

Examples 213-216

Example 213

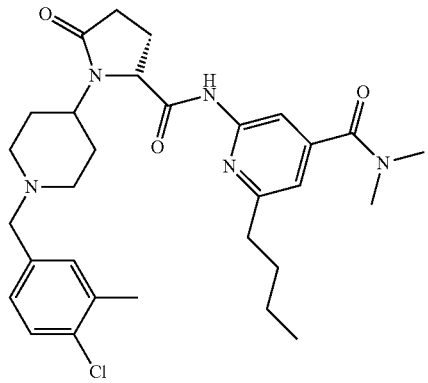

To a solution of example 181 (36 mg) in dioxane (3 ml) was added $dppfPdCl_2$ (2.3 mg) and butylzinc bromide (0.137 ml of a 0.5 M solution in THF) under an atmosphere of argon. The solution was stirred for 45 min at room temperature before additional $dppfPdCl_2$ (2 mg) and butylzinc bromide (0.07 ml of a 0.5 M solution in THF) was added and the solution was stirred for additional 20 min at rt. The reaction was quenched with a few drops of water, the resulting mixture was diluted with dioxane and filtered. The filtrate was concentrated and the crude product purified by reversed phase HPLC affording the title compound (19 mg). HPLC: 1.41 min (method D).

The following examples were synthesized in analogy to example 213

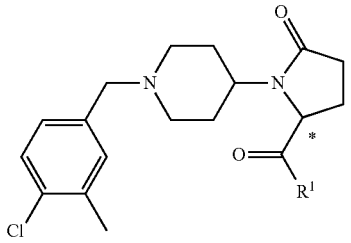

| # | $R^1$ | * | $R_t$ [min] (method) | Building block |
|---|---|---|---|---|
| 214 | 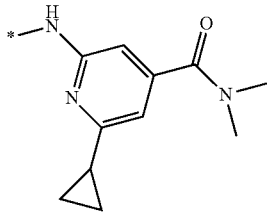 | R | 1.34 (D) | example 181 |
| 215 | 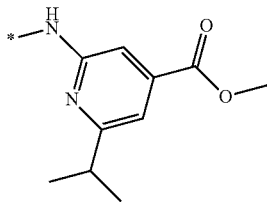 | R | 1.48 (D) | example 194 |
| 216 | 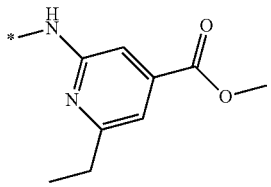 | R | 1.42 (D) | example 194 |

S.5.1 Chromatographic Methods (HPLC and HPLC Methods)

Method A

Waters ZQ2000 MS, Alliance 2790 HPLC, Waters 2996 DAD (210-500 nm), Waters 2700 Autosampler
Mobile Phases:
A: Water with 0.10% TFA
B: Acetonitrile with 0.10% TFA

| Time in min | % A | % B | Flowrate in ml/min |
|---|---|---|---|
| 0.00 | 95 | 5 | 1.00 |
| 0.10 | 95 | 5 | 1.00 |
| 3.60 | 2 | 98 | 1.00 |
| 6.50 | 2 | 98 | 1.00 |
| 7.00 | 95 | 5 | 1.00 |

Stationary phase: Waters, Sunfire C18, 3.5 μm, 4,6×50 mm.
Column temp: constant at 40° C.
Method B
Waters ZQ2000 MS, HP1100 HPLC+DAD (210-500 nm), Gilson 215 Autosampler.
Mobile Phases:
A: Water with 0.10% TFA
B: Acetonitrile with 0.10% TFA

| Time in min | % A | % B | Flowrate in ml/min |
|---|---|---|---|
| 0.00 | 95 | 5 | 1.50 |
| 2.00 | 0 | 100 | 1.50 |
| 2.50 | 0 | 100 | 1.5 |
| 2.60 | 95 | 5 | 1.50 |

Stationary phase: Waters, Sunfire C18, 3.5 μm, 4.6×50 mm.
Column temp: constant at 40° C.
Method C
Alliance 2690/2695 HPLC, waters 996/2996 DAD (210-400 nm)
mobile phases:
A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

Stationary phase Merck Chromolith™ Flash RP-18e, 4.6 Mm×25 mm (at 25° C.).
Method D
Alliance 2690/2695 HPLC, waters 996/2996 DAD (210-400 nm) mobile phases:
A: water with 0.10% TFA
B: acetonitrile with 0.10% TFA

| time in min | % A | % B | flow rate in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

Stationary phase Merck Chromolith™ Flash RP-18e, 3 Mm×100 mm (at 25° C.).
Method E
Waters ZQ MS, Alliance 2690/2695 HPLC, Waters 996/2996 Diode array detector
Mobile Phases:
A: Water with 0.10% NH3
B: Acetonitrile with 0.10% NH3

| Time in min | % A | % B | Flowrate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

Stationary phase: Waters, X-Bridge, C18, 3.5 μm, 4.6×20 mm.
Column temp: constant at 25° C.
Die Diode array detection is at the wavelength range of 210-500 nm.
Method F
Instrument: LC/MS ThermoFinnigan. HPLC Surveyor DAD, MSQ Quadrupole; column: Symmetry C8, 5 um, 3×150 mm;

eluent A: 90% water+10% acetonitrile+ammonium formate 10 mM; eluent B=ACN 90%+10% $H_2O$+$NH_4COOH$ 10 mM; gradient: A (100) for 1.5 min, then to B (100) in 10 min for 1.5 min; flow rate: 1.2 mL/min; UV Detection: 254 nm; Ion source: APCI Method G Instrument: LC/MS Waters. HPLC Alliance 2695 DAD, ZQ Quadrupole; column: Sunfire MS-C18, 3.5 um, 4.6×50 mm; eluent A: water+0.1% TFA+10% acetonitrile; eluent B: acetonitrile; gradient: A/B (80:20), then to A/B (10:90) in 3.25 min for 0.75 min; flow rate:1.3 ml/min; UV Detection: 254 nm; Ion source: ESI.

Method H

Instrument: LC/MS Waters. HPLC Alliance 2695 DAD, ZQ Quadrupole; column: Xterra MS-C18, 3.5 um, 4.6×50 mm; eluent A: water+0.1% TFA+10% acetonitrile; eluent B: acetonitrile; gradient: A (100), then to A/B (10:90) in 3.25 min for 0.75 min; flow rate:1.3 ml/min; UV Detection: 254 nm; Ion source: ESI.

Method L

Instrument: LC/MS Waters. HPLC Alliance 2695 DAD, ZQ Quadrupole. Column: Xterra MS-C8, 3.5 um, 4.6×50 mm; eluent A:water+ammonium formate 5 mM+10% acetonitrile; eluent B:acetonitrile; gradient: A 100, then to A/B (10:90) in 3.25 min for 0.75 min; flow rate: 1.3 ml/min; UV Detection: 254 nm; Ion source: ESI.

Method M

Instrument: HPLC/MS Waters. Acquity HPLC® system, ZQ Quadrupole. Column: HSS C18, 1.8 um, 2.1×50 mm; eluent A: water+ammonium formate 5 mM+10% acetonitrile; eluent B:acetonitrile; gradient: A/B (90:10), then to A/B (10:90) in 1.70 min for 0.64 min; flow rate: 0.56 ml/min; UV Detection: 254 nm; Ion source: ESI.

Method N

Instrument: HPLC/MS Waters. Acquity HPLC® system, ZQ Quadrupole. Column: BEH C18, 1.7 um, 2.1×50 mm; eluent A: water+0.1% TFA+10% acetonitrile; eluent B: acetonitrile; gradient: A/B (50:50), then to A/B (10:90) in 1.99 min for 0.77 min; flow rate: 0.48 ml/min; UV Detection: 254 nm; Ion source: ESI.

Method O

Instrument: LC/MS ThermoFinnigan. HPLC Surveyor DAD, MSQ Quadrupole; 1c) column: SynergyHydro-RP80A, 4 um, 4.60×100 mm; eluent A: 90% water+10% acetonitrile+ammonium formate 10 mM; eluent B=ACN 90%+10% $H_2O$+$NH_4COOH$ 10 mM; gradient: A (100) for 1 5 min, then to B (100) in 10 min for 1.5 min; flow rate: 1.2 mL/min; UV Detection: 254 nm; Ion source: APCI Method P Instrument: LC/MS ThermoFinnigan. HPLC Surveyor DAD, Finnigan LCQduo Ion trap; column: Symmetry—C18, 5 um, 3×150 mm; eluent A: 95% water+5% acetonitrile+formic acid 0.1%; eluent B=Acetonitrile 95%+5% water+formic acid 0.1%; gradient: A/B (95/5) for 1 5 min, then to A/B (5/95) in 10 min for 1.5 min; flow rate: 1 mL/min; UV Detection: 254 nm; Ion source: ESI Method Q Instrument: LC/MS Waters. HPLC Alliance 2695 DAD, ZQ Quadrupole. Column: Zorbax Eclipse Plus C18, 3.5 um, 4.6×50 mm; eluent A:water+ammonium formate 5 mM+10% acetonitrile; eluent B:acetonitrile; gradient: A 100, then to A/B (10:90) in 3.5 min for 1 min; flow rate: 1.3 ml/min; UV Detection: 254 nm; Ion source: ESI.

S.5.2 Chromatographic Methods: GC Methods

Method 3A

Instrument: GC/MS Finnigan TRACE GC, TRACE MS Quadrupole; column: Agilent DB-5MS, 25 m×0.25 mm×0.25 um; carriage gas: Helium; flow rate: 1 ml/min constant flow; oven program: 50° C. (hold 1 min), to 100° C. in 10° C./min , to 200° C. in 20° C./min., to 300° C. in 30° C./min.; Detection: TRACE MS quadrupole; Ion source: EI.

Microwave Heating

Microwave apparatus type: Discover® CEM instruments, equipped with 10 and 35 mL vessels;

Pharmacological Part

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The CCR3 receptor binding test is based on a K562 cell line (leukemia myelogenic blast cells) transfected with the human chemokine receptor CCR3 (hCCR3-C1 cells). The cell membranes were prepared by disrupting the hCCR3-C1 cells by nitrogen decomposition. The preparation was centrifuged at 400 g 4° C. for 30 min. The supernatant was transferred into fresh tubes followed by a second centrifugation at 48000 g, 4° C. for 1 h. The membranes were re-suspended in the SPA incubation buffer (25 mM HEPES, 25 mM $MgCl_2$ 6×$H_2O$, 1 mM $CaCl_2$ 2×$H_2O$) without bovine serum albumin and homogenized by passing through a single use needle (Terumo, 23G×1"). The membranes were stored in aliquots at −80° C.

The CCR3 receptor binding assay was performed in a Scintillation Proximity Assay (SPA) design with the radioligand recombinant human $^{125}$Iodine-eotaxin-1. Cell membranes of hCCR3 C1 cells were again homogenized by passing through a single use needle (Terumo, 23G×1") and diluted in SPA incubation buffer in suitable concentrations (0.5-10 μg protein/well) in 96 well microtiter plates (1450-514, Perkin Elmer). The SPA assay was set up in the SPA incubation buffer with a final volume of 200 μl and final concentration of 25 mM HEPES, 25 mM $MgCl_2$ 6×$H_2O$, 1 mM $CaCl_2$ 2×$H_2O$ and 0.1% bovine serum albumin. The SPA assay mixture contained 60 μl of the membrane suspension, 80 μl of Wheat Germ Agglutinin coated PVT beads (organic scintillator, GE Healthcare, RPNQ-0001) 0.2 mg/well), 40 μl of recombinant human $^{125}$Jodine-eotaxin-1 (Biotrend), diluted in SPA buffer to a final concentration of 30.000 dpm per well, and 20 μl of the test compound (dissolved in DMSO dilutions). The SPA assay mixture was incubated for 2 h at room temperature. Bound radioactivity was determined with a scintillation counter (Micro Beta "Trilux", Wallac). Included were controls for total binding (no displacer added, Bo) and non-specific binding (NSB) by adding unlabelled recombinant human Eotaxin-1 (Biotrend, Cat #300-21) or a reference compound.

Determination of the affinity of a test compound was calculated by subtraction of the non-specific binding (NSB) from the total binding (Bo) or the binding in the presence of the test compound (B) at a given compound concentration. The NSB value was set to 100% inhibition. The Bo-NSB value was set to 0% inhibition.

% inhibition values were obtained at a defined compound concentration, e.g. at 1 μM, % inhibition of the test compound was calculated by the formula 100−((B−NSB)*100/(Bo−NSB)). % inhibition values above 100% are founded by assay variance.

The dissociation constant $K_i$ was calculated by iterative fitting of experimental data obtained at several compound concentrations over a dose range from 0.1 to 10000 nM using the law of mass action based program "easy sys" (Schittkowski, Num Math 68, 129-142 (1994)).

The utility of the compounds in accordance with the present invention as inhibitors of chemokine receptor activity may be demonstrated by methodology known in the art, such as the assays for CCR3 ligand binding, as disclosed by Ponath et al., J. Exp. Med., 183, 2437-2448 (1996) and Uguccioni et al., J. Clin. Invest., 100, 11371143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as L1.2, K562, CHO or HEK-293 cells. Finally, blood or tissue cells, for example human peripheral blood eosinophils, isolated using methods as described by Hansel et al., J. Immunol. Methods, 145, 105-110 (1991), can be utilized in such assays. In particular, the compounds of the present invention have activity in binding to the CCR3 receptor in the aforementioned assays and inhibit the activation of CCR3 by CCR3 ligands, including eotaxin-1, eotaxin-2, eotaxin-3, MCP-2, MCP-3, MCP-4 or RANTES.

As used herein, "activity" is intended to mean a compound demonstrating an inhibition of 50% at 1 μM or higher in inhibition when measured in the aforementioned assays. Such a result is indicative of the intrinsic activity of the compounds as inhibitor of CCR3 receptor activity.

% inhibition and Ki values are (human Eotaxin-1 at human CCR3-Rezeptor):

| # | CCR3 % inh @ 1 μM | CCR3 Ki (nM) |
|---|---|---|
| 1 | 101 | 4 |
| 2 | 98 | 4 |
| 3 | 75 | 240 |
| 4 | 99 | 5 |
| 5 | 98 | 6 |
| 6 | 100 | 7 |
| 7 | 97 | 7 |
| 8 | 99 | 9 |

-continued

| # | CCR3 % inh @ 1 μM | CCR3 Ki (nM) |
|---|---|---|
| 9 | 95 | 12 |
| 10 | 98 | 16 |
| 11 | 92 | 27 |
| 12 | 84 | 88 |
| 13 | 71 | 373 |
| 14 | 60 | 540 |
| 15 | 38 | 1111 |
| 16 | 98 | 20 |
| 17 | 100 | 5 |
| 18 | 96 | 7 |
| 19 | 98 | 7 |
| 20 | 97 | 9 |
| 21 | 96 | 11 |
| 22 | 84 | 13 |
| 23 | 95 | 18 |
| 24 | 99 | 22 |
| 25 | 91 | 21 |
| 26 | 97 | 27 |
| 27 | 96 | 28 |
| 28 | 97 | 29 |
| 29 | 94 | 31 |
| 30 | 95 | 47 |
| 31 | 93 | 50 |
| 32 | 82 | 145 |
| 33 | 83 | 150 |
| 34 | 80 | 152 |
| 35 | 83 | 152 |
| 36 | 80 | 159 |
| 37 | 80 | 175 |
| 38 | 78 | 211 |
| 39 | 80 | 227 |
| 40 | 75 | 229 |
| 41 | 66 | 395 |
| 42 | 63 | 482 |
| 43 | 59 | 523 |
| 44 | 63 | 552 |
| 45 | 50 | 713 |
| 46 | 44 | 873 |
| 47 | 31 | 1188 |
| 48 | 40 | 965 |
| 49 | 41 | 1184 |
| 50 | 41 | 1287 |
| 51 | 30 | 1615 |
| 52 | 28 | 1752 |
| 53 | 33 | 2010 |
| 54 | 90 | 89 |
| 55 | 78 | 235 |
| 56 | 76 | 254 |
| 57 | 74 | 302 |
| 58 | 76 | 221 |
| 59 | 66 | 402 |
| 60 | 65 | 430 |
| 61 | 57 | 492 |
| 62 | 63 | 507 |
| 63 | 60 | 518 |
| 64 | 60 | 545 |
| 65 | 57 | 602 |
| 66 | 81 | 658 |
| 67 | 52 | 700 |
| 68 | 48 | 715 |
| 69 | 55 | 749 |
| 70 | 46 | 791 |
| 71 | 49 | 810 |
| 72 | 48 | 875 |
| 73 | 48 | 922 |
| 74 | 46 | 927 |
| 75 | 97 | 30 |
| 76 | 97 | 37 |
| 77 | 96 | 38 |
| 78 | 94 | 50 |
| 79 | 91 | 52 |
| 80 | 95 | 55 |
| 81 | 89 | 111 |
| 82 | 87 | 153 |
| 83 | 81 | 223 |
| 84 | 77 | 232 |

-continued

| # | CCR3 % inh @ 1 μM | CCR3 Ki (nM) |
|---|---|---|
| 85 | 68 | 350 |
| 86 | 65 | 419 |
| 91 | 98 | 18 |
| 93 | 95 | 29 |
| 94 | 94 | 52 |
| 95 | 94 | 40 |
| 96 | 51 | 670 |
| 97 | 50 | 669 |
| 98 | 75 | 202 |
| 99 | 91 | 67 |
| 100 | 100 | 7 |
| 101 | 95 | 45 |
| 102 | 100 | 19 |
| 103 | 54 | 1402 |
| 104 | 24 | 2399 |
| 105 | 99 | 5 |
| 106 | 100 | 3 |
| 107 | 99 | 13 |
| 108 | 98 | 4 |
| 114 | 99 | 4 |
| 115 | 80 | 18 |
| 116 | 93 | 47 |
| 117 | 98 | 17 |
| 118 | 94 | 40 |
| 119 | 87 | 81 |
| 120 | 95 | 35 |
| 121 | 98 | 21 |
| 122 | 95 | 30 |
| 123 | 95 | 34 |
| 124 | 93 | 41 |
| 125 | 97 | 58 |
| 126 | 89 | 71 |
| 127 | 90 | 81 |
| 128 | 87 | 96 |
| 129 | 70 | 334 |
| 130 | 91 | 77 |
| 131 | 89 | 85 |
| 132 | 102 | 1 |
| 133 | 100 | 3 |
| 134 | 101 | 3 |
| 135 | 101 | 3 |
| 136 | 100 | 4 |
| 137 | 101 | 4 |
| 138 | 101 | 4 |
| 139 | 101 | 5 |
| 140 | 98 | 6 |
| 141 | 94 | 6 |
| 142 | 100 | 17 |
| 143 | 99 | 7 |
| 144 | 100 | 7 |
| 145 | 99 | 8 |
| 146 | 100 | 8 |
| 147 | 99 | 8 |
| 148 | 99 | 10 |
| 149 | 99 | 10 |
| 150 | 97 | 10 |
| 151 | 95 | 18 |
| 152 | 100 | 12 |
| 153 | 99 | 12 |
| 154 | 98 | 14 |
| 155 | 98 | 15 |
| 156 | 98 | 15 |
| 157 | 99 | 15 |
| 158 | 100 | 16 |
| 159 | 96 | 19 |
| 160 | 97 | 19 |
| 161 | 97 | 20 |
| 162 | 97 | 20 |
| 163 | 99 | 23 |
| 164 | 96 | 24 |
| 165 | 90 | 62 |
| 166 | 60 | 905 |
| 167 | 98 | 6 |
| 168 | 99 | 4 |
| 169 | 99 | 19 |
| 170 | 100 | 6 |

-continued

| # | CCR3 % inh @ 1 μM | CCR3 Ki (nM) |
|---|---|---|
| 171 | 99 | 5 |
| 172 | 95 | 7 |
| 173 | 99 | 13 |
| 174 | 99 | 13 |
| 175 | 99 | 6 |
| 176 | 100 | 11 |
| 177 | 97 | 24 |
| 178 | 86 | 108 |
| 179 | 95 | 34 |
| 180 | 97 | 16 |
| 182 | 99 | 4 |
| 183 | 75 | 232 |
| 184 | 100 | 8 |
| 185 | 98 | 1 |
| 186 | 99 | 1 |
| 187 | 99 | 4 |
| 188 | 99 | 6 |
| 189 | 100 | 4 |
| 190 | 100 | 6 |
| 191 | 100 | 5 |
| 192 | 96 | 6 |
| 193 | 99 | 19 |
| 196 | 89 | 95 |
| 197 | 44 | 1251 |
| 198 | 91 | 67 |
| 199 | 66 | 453 |
| 200 | 86 | 114 |
| 201 | 86 | 119 |
| 202 | 69 | 390 |
| 203 | 75 | 237 |
| 204 | 80 | 299 |
| 205 | 76 | 247 |
| 206 | 77 | 357 |
| 207 | 75 | 442 |
| 208 | 94 | 43 |
| 209 | 95 | 33 |
| 210 | 96 | 13 |
| 211 | 93 | 48 |
| 212 | 97 | 26 |
| 213 | 66 | 414 |
| 214 | 101 | 2 |

Indications

The compounds of the instant application are useful for manufacturing a medicament for the prevention and/or treatment of diseases wherein the activity of a CCR3-receptor is involved.

Preferred is the manufacturing of a medicament for the prevention and/or treatment of a wide variety of inflammatory, infectious, and immunoregulatory disorders and diseases of the respiratory or gastrointestinal complaints, inflammatory diseases of the joints and allergic diseases of the nasopharynx, eyes, and skin, including asthma and allergic diseases, eosinophilic diseases, infection by pathogenic microbes (which, by definition, includes viruses), as well as autoimmune pathologies such as the rheumatoid arthritis and atherosclerosis, as well as diseases associated with abnormal enhanced neovascularization such as age-related macular degeneration (AMD), diabetic retinopathy and diabetic macular edema Age-related macular degeneration is a leading cause of blindness world wide. Most blindness in AMD results from invasion of the retina by choroidal neovascularization. CCR3 is specifically expressed in choroidal neovascular endothelial cells of AMD patients. In an often used mouse animal model for AMD laser injury-induced choroidal neovascularization was dimished by genetic depletion of CCR3 or CCR3 ligands as well as by treatment of the mice with an anti-CCR3 antibody or an CCR3 antagonist (Takeda et al, Nature 2009, 460(7252):225-30)

Most preferred is the manufacturing of a medicament for the prevention and/or treatment of e.g. inflammatory or allergic diseases and conditions, including respiratory allergic diseases such as asthma, perennial and seasonal allergic rhinitis, allergic conjunctivitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); non-allergic asthma; Exercise induced bronchoconstriction; systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, immune thrombocytopenia (adult ITP, neonatal thrombocytopenia, paediatric ITP), immune haemolytic anaemia (auto-immune and drug induced), Evans syndrome (platelet and red cell immune cytopaenias), Rh disease of the newborn, Goodpasture's syndrome (anti-GBM disease), Celiac, Auto-immune cardio-myopathy juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); erythema nodosum; eosinophilic myositis, eosinophilic fasciitis; cancers with leukocyte infiltration of the skin or organs; chronic obstructive pulmonary disease, age-related macular degeneration (AMD), diabetic retinopathy and diabetic macular edema.

Method of Treatment

Accordingly, the present invention is directed to compounds which are useful in the prevention and/or treatment of a wide variety of inflammatory, infectious, and immunoregulatory disorders and diseases, including asthma and allergic diseases, chronic obstructive pulmonary disease, infection by pathogenic microbes (which, by definition, includes viruses), autoimmune pathologies such as the rheumatoid arthritis and atherosclerosis as well as age-related macular degeneration (AMD), diabetic retinopathy and diabetic macular edema.

For example, an instant compound which inhibits one or more functions of a mammalian chemokine receptor (e.g., a human chemokine receptor) may be administered to inhibit (i.e., reduce or prevent) inflammation, infectious diseases or abnormal enhanced neovascularization. As a result, one or more inflammatory process, such as leukocyte emigration, adhesion, chemotaxis, exocytosis (e.g., of enzymes, growth factors, histamine) or inflammatory mediator release, survival or proliferation of CCR3 expressing cells is inhibited. For example, eosinophilic infiltration to inflammatory sites (e.g., in asthma or allergic rhinitis) can be inhibited according to the present method. In particular, the compound of the following examples has activity in blocking the activation and migration of cells expressing the CCR3 receptor using the appropriate chemokines in the aforementioned assays. In another instance, endothelial proliferation and neovascularization may be inhibited (i.e., reduced or prevented). As a result abnormal enhanced neovascularization, i.e. of the retina, is inhibited.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom inhibition of chemokine receptor activity is desired.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); chronic obstructive pulmonary disease (including rhinovirus-induced exacerbations); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Also diseases associated with abnormal enhanced neovascularization such as age-related macular degeneration (AMD), diabetic retinopathy and diabetic macular edema can be treated.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commerical kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidale anti-inflammatory agents (NSAIDs), CRTH2 antagonists, DP1-receptor modulators, Thromboxane receptor antagonists, CCR3 antagonists, $CCR^4$ antagonists, $CCR^1$ antagonists, CCR5 antagonists, CCR6 antagonists, CCR7 antagonists, CCR8 antagonists, CCR9 antagonists, $CCR^{30}$ antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, but also combinations of two or three active substances, i.e.:

- Betamimetics with corticosteroids, PDE4-inhibitors, CRTH2-inhibitors or LTD4-antagonists,
- Anticholinergics with betamimetics, corticosteroids, PDE4-inhibitors, CRTH2-inhibitors or LTD4-antagonists,
- Corticosteroids with PDE4-inhibitors, CRTH2-inhibitors or LTD4-antagonists
- PDE4-inhibitors with CRTH2-inhibitors or LTD4-antagonists
- CRTH2-inhibitors with LTD4-antagonists.

Pharmaceutical Forms

Suitable preparations for administering the compounds of formula 1 include for example tablets, capsules, suppositories, solutions and powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the above-mentioned excipients.

For administering the compounds of formula 1 it is particularly preferred according to the invention to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also include concentrates or sterile inhalable solutions ready for use. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with 40 physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 μm, more preferably from 1 to 5 μm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols-particularly isopropyl alcohol, glycols-particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the μg range. The compounds of formula 1 may also be used effectively above the μg range. The dosage may then be in the gram range, for example.

In another aspect the present invention relates to the above-mentioned pharmaceutical formulations as such which are characterised in that they contain a compound of formula 1, particularly the above-mentioned pharmaceutical formulations which can be administered by inhalation.

The following examples of formulations illustrate the present invention without restricting its scope:

Examples of Pharmaceutical Formulations

| A) Tablets | per tablet |
|---|---|
| active substance 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) Tablets | per tablet |
|---|---|
| active substance 1 | 80 mg |
| lactose | 55 mg |
| maize starch | 190 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance 1 | 50 mg |
| sodium chloride | 50 mg |
| water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) Metering aerosol | |
|---|---|
| active substance 1 | 0.005 |
| sorbitan trioleate | 0.1 |
| monofluorotrichloromethane and TG134a:TG227 2:1 | ad 100 |

The suspension is transferred into a conventional aerosol container with metering valve. Preferably 50 μl suspension are released on each actuation. The active substance may also be released in higher doses if desired (e.g. 0.02 wt.-%).

| E) Solutions (in mg/100 ml) | |
|---|---|
| active substance 1 | 333.3 mg |
| benzalkonium chloride | 10.0 mg |
| EDTA | 50.0 mg |
| HCl (1N) | ad pH 2.4 |

This solution can be prepared in the usual way.

| F) Inhalable powder | |
|---|---|
| active substance 1 | 12 μg |
| lactose monohydrate | ad 25 mg |

The inhalable powder is prepared in the usual way by mixing the individual ingredients.

What is claimed is:

1. A compound of formula 1,

1

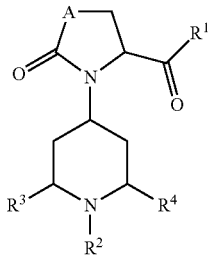

wherein

A is $CH_2$, O or N—$C_{1-6}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, methoxyphenyl;

a group selected from NHCH(pyridinyl)$CH_2$COO—$C_{1-6}$-alkyl, NHCH($CH_2$O—$C_{1-6}$-alkyl)-benzoimidazolyl, optionally substituted with halogen or CN;

or 1-aminocyclopentyl, optionally substituted with methyl-oxadiazole;

$R^{1.1}$ is phenyl, optionally substituted with one or two residues selected from the group consisting of $C_{1-6}$-alkyl, $C_{2-6}$-alkenyl, $C_{2-6}$-alkynyl, $C_{1-6}$-haloalkyl, $C_{1-6}$-alkylene-OH, $C_{2-6}$-alkenylene-OH, $C_{2-6}$-alkynylene-OH, $CH_2CON(C_{1-6}\text{-alkyl})_2$, $CH_2NHCONH$—$C_{3-6}$-cycloalkyl, CN, CO-pyridinyl, $CONR^{1.1.1}R^{1.1.2}$, COO—$C_{1-6}$-alkyl, N($SO_2$—$C_{1-6}$-alkyl)($CH_2CON(C_{1-4}\text{-alkyl})_2$) O—$C_{1-6}$-alkyl, O-pyridinyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl and =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2$CO-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one N or O, replacing a carbon atom of the ring, optionally substituted with one or two residues selected from the group consisting of $C_{1-6}$-alkyl, $C_{1-4}$-alkylene-OH, OH, =O;

or $R^{1.1}$ is phenyl, wherein two adjacent residues are together forming a five- or six-membered carbocyclic aromatic or non-aromatic ring, optionally containing independently from each other one or two N, S, or $SO_2$, replacing a carbon atom of the ring, wherein the ring is optionally substituted with $C_{1-4}$-alkyl or =O;

$R^{1.2}$ is selected from heteroaryl, optionally substituted with one or two residues selected from the group consisting of $C_{1-6}$-alkyl, $C_{2-6}$-alkenyl, $C_{2-6}$-alkynyl, $C_{3-6}$-cycloalkyl, $CH_2COO$—$C_{1-6}$-alkyl, $CONR^{1.2.1}R^{1.2.2}$, $COR^{1.2.3}$, COO—$C_{1-6}$-alkyl, $CONH_2$, O—$C_{1-6}$-alkyl, halogen, CN, $SO_2N(C_{1-6}\text{-alkyl})_2$ or heteroaryl optionally substituted with one or two residues selected from the group consisting of $C_{1-6}$-alkyl;

heteroaryl, optionally substituted with a five- or six-membered carbocyclic non-aromatic ring containing independently from each other two N, O, S, or $SO_2$, replacing a carbon atom of the ring;

an aromatic or non-aromatic $C_{9\ or\ 10}$-bicyclic-ring, whereas one or two carbon atoms are replaced by N, O or S each optionally substituted with one or two residues selected from the group consisting of $N(C_{1-6}\text{-alkyl})_2$, CONH—$C_{1-6}$-alkyl, =O;

a heterocyclic non-aromatic ring, optionally substituted with pyridinyl;

4,5-dihydro-naphtho[2,1-d]thiazole, optionally substituted with NHCO—$C_{1-6}$-alkyl, R1.2.1 H, $C_{1-6}$-alkyl, $C_{1-6}$-alkylene-$C_{3-6}$-cycloalkyl, $C_{1-4}$-alkylene-phenyl, $C_{1-4}$-alkylene-furanyl, $C_{3-6}$-cycloalkyl, $C_{1-4}$-alkylene-O—$C_{1-4}$-alkyl, $C_{1-6}$-haloalkyl or a five- or six-membered carbocyclic non-aromatic ring, optionally containing independently from each other one or two N, O, S, or $SO_2$, replacing a carbon atom of the ring, optionally substituted with 4-cyclopropylmethyl-piperazinyl $R^{1.2.2}$ H, $C_{1-6}$-alkyl;

$R^{1.2.3}$ a five- or six-membered carbocyclic non-aromatic ring, optionally containing independently from each other one or two N, O, S, or $SO_2$, replacing a carbon atom of the ring;

$R^{1.3}$ is selected from phenyl, heteroaryl or indolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl, phenyl, heteroaryl;

$R^2$ is selected from the group consisting of $C_{1-6}$-alkylene-phenyl, $C_{1-6}$-alkylene-naphthyl, and $C_{1-6}$-alkylene-heteroaryl; each optionally substituted with one, two or three residues selected from the group consisting of $C_{1-6}$-alkyl, $C_{1-6}$-haloalkyl, O—$C_{1-6}$-alkyl, O—$C_{1-6}$-haloalkyl, halogen;

$R^3$ is H, $C_{1-6}$-alkyl;

$R^4$ is H, $C_{1-6}$-alkyl;

or $R^3$ and $R^4$ together are forming a $CH_2$—$CH_2$ group.

2. The compound of formula 1 according to claim 1, wherein

A is $CH_2$, O or N—$C_{1-4}$-alkyl;

$R^1$ is selected from $NHR^{1.1}$, $NMeR^{1.1}$;

$NHR^{1.2}$, $NMeR^{1.2}$;

$NHCH_2$—$R^{1.3}$;

NH—$C_{3-6}$-cycloalkyl, whereas optionally one carbon atom is replaced by a nitrogen atom, whereas the ring is optionally substituted with one or two residues selected from the group consisting of $C_{1-6}$-alkyl, O—$C_{1-6}$-alkyl, $NHSO_2$-phenyl, NHCONH-phenyl, halogen, CN, $SO_2$—$C_{1-6}$-alkyl, COO—$C_{1-6}$-alkyl;

a $C_{9\ or\ 10}$-bicyclic-ring, whereas one or two carbon atoms are replaced by nitrogen atoms and the ring system is bound via a nitrogen atom to the basic structure of formula 1 and whereas the ring system is optionally substituted with one or two residues selected from the group consisting of $C_{1-6}$-alkyl, COO—$C_{1-6}$-alkyl, $C_{1-6}$-haloalkyl, O—$C_{1-6}$-alkyl, $NO_2$, halogen, CN, $NHSO_2$—$C_{1-6}$-alkyl, m-methoxyphenyl;

a group selected from NHCH(pyridinyl)$CH_2$COO—$C_{1-6}$-alkyl, NHCH($CH_2$O—$C_{1-6}$-alkyl)-benzoimidazolyl, optionally substituted with Cl;

or 1-aminocyclopentyl, optionally substituted with methyl-oxadiazolyl;

R1.1 is phenyl, optionally substituted with one or two residues selected from the group consisting of $C_{1-6}$-alkyl, $C_{1-6}$-haloalkyl, $CH_2CON(C_{1-6}\text{-alkyl})_2$, $CH_2NHCONH$—$C_{3-6}$-cycloalkyl, CN, $CONR^{1.1.1}R^{1.1.2}$, COO—$C_{1-6}$-alkyl, O—$C_{1-6}$-alkyl, $SO_2$—$C_{1-6}$-alkyl, $SO_2$—$C_{1-6}$-alkylen-OH, $SO_2$—$C_{3-6}$-cycloalkyl, $SO_2$-piperidinyl, $SO_2NH$—$C_{1-6}$-alkyl, $SO_2N(C_{1-6}\text{-alkyl})_2$, halogen, CN, CO-morpholinyl, $CH_2$-pyridinyl or a heterocyclic ring optionally substituted with one or two residues selected from the group consisting of $C_{1-6}$-alkyl, $NHC_{1-6}$-alkyl, =O;

$R^{1.1.1}$ H, $C_{1-6}$-alkyl, $C_{3-6}$-cycloalkyl, $C_{1-6}$-haloalkyl, $CH_2CON(C_{1-6}\text{-alkyl})_2$, $CH_2$CO-azetindinyl, $C_{1-6}$-alkylen-$C_{3-6}$-cycloalkyl, $CH_2$-pyranyl, $CH_2$-tetrahydrofuranyl, $CH_2$-furanyl, $C_{1-6}$-alkylen-OH or thiadiazolyl, optionally substituted with $C_{1-6}$-alkyl;

$R^{1.1.2}$ H, $C_{1-6}$-alkyl, $SO_2C_{1-6}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from heteroaryl, optionally substituted with one or two residues selected from the group consisting of $C_{1-6}$-alkyl, $C_{3-6}$-cycloalkyl, $CH_2COO$—$C_{1-6}$-alkyl, $CONR^{1.2.1}R^{1.2.2}$, COO—$C_{1-6}$-alkyl, $CONH_2$, O—$C_{1-6}$-alkyl, halogen, CN, CO-pyrrolidinyl, CO-morpholinyl or heteroaryl optionally substituted with one or two residues selected from the group consisting of $C_{1-6}$-alkyl;

benzothiazolyl, indazolyl, dihydro-indolyl, indanyl, tetrahydro-quinolinyl, each optionally substituted with one or two residues selected from the group consisting of $N(C_{1-6}\text{-alkyl})_2$, CONH—$C_{1-6}$alkyl, =O;

piperidinyl, optionally substituted with pyridinyl;

4,5-dihydro-naphtho[2,1-d]thiazole, optionally substituted with NHCO—$C_{1-6}$alkyl, $R^{1.2.1}$ H, $C_{1-6}$-alkyl;

$R^{1.2.2}$ H, $C_{1-6}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-6}$-alkyl, $C_{3-6}$-cycloalkyl, O—$C_{1-6}$-alkyl, O—$C_{1-6}$-haloalkyl;

$R^2$ is selected from $CH_2$-phenyl or $CH_2$-naphthyl, both optionally substituted with one or two residues selected from the group consisting of $C_{1-6}$-alkyl, $C_{1-6}$-haloalkyl, O—$C_{1-6}$-alkyl, O—$C_{1-6}$-haloalkyl, halogen; or $CH_2$-thiophenyl, optionally substituted with one or two residues selected from the group consisting of halogen;

$R^3$ is H, $C_{1-4}$-alkyl;

$R^4$ is H, $C_{1-4}$-alkyl;

or $R^3$ and $R^4$ together are forming a $CH_2$—$CH_2$ group.

3. The compound of formula 1 according to claim 1, wherein

A is $CH_2$, O or NMe;

$R^1$ is selected from $NHR^{1.1}$, $NMeR^{1.1}$;

$NHR^{1.2}$, $NMeR^{1.2}$;

$NHCH_2$—$R^{1.3}$;

NH-cyclohexyl, optionally substituted with one or two residues selected from the group consisting of $C_{1-4}$-alkyl, $NHSO_2$-phenyl, NHCONH-phenyl, halogen;

NH-pyrrolidinyl, optionally substituted with one or two residues selected from the group consisting of $SO_2$—$C_{1-4}$-alkyl, COO—$C_{1-4}$-alkyl;

piperidinyl, optionally substituted with one or two residues selected from the group consisting of $NHSO_2$—$C_{1-4}$-alkyl, m-methoxyphenyl;

dihydro-indolyl, dihydro-isoindolyl, tetrahydro-quinolinyl or tetrahydro-isoquinolinyl, optionally substituted with one or two residues selected from the group consisting of $C_{1-4}$-alkyl, COO—$C_{1-4}$-alkyl, $C_{1-4}$-haloalkyl, O—$C_{1-4}$-alkyl, $NO_2$, halogen;

a group selected from NHCH(pyridinyl)$CH_2$COO—$C_{1-4}$-alkyl, NHCH($CH_2$O—$C_{1-4}$-alkyl)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of $C_{1-4}$-alkyl, $C_{1-4}$-haloalkyl, $CH_2CON(C_{1-4}\text{-alkyl})_2$, $CH_2NHCONH$—$C_{3-6}$-cycloalkyl, CN, $CONR^{1.1.1}R^{1.1.2}$, COO—$C_{1-4}$-alkyl, O—$C_{1-4}$-alkyl, $SO_2$—$C_{1-4}$-alkyl, $SO_2$—$C_{1-4}$-alkylen-OH, $SO_2$—$C_{3-6}$-cycloalkyl, $SO_2$-piperidinyl, $SO_2NH$—$C_{1-4}$-alkyl, $SO_2N(C_{1-4}\text{-alkyl})_2$, halogen, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of $C_{1-4}$-alkyl, $NHC_{1-4}$-alkyl, =O;

$R^{1.1.1}$ H, $C_{1-6}$-alkyl, $C_{3-6}$-cycloalkyl, $C_{1-4}$-haloalkyl, $CH_2CON(C_{1-4}\text{-alkyl})_2$, $CH_2$CO-azetindinyl, $C_{1-4}$alkylen-$C_{3-6}$-cycloalkyl, $CH_2$-pyranyl, $CH_2$-tetrahydrofuranyl, $CH_2$-furanyl, $C_{1-4}$-alkylen-OH or thiadiazolyl, optionally substituted with $C_{1-4}$-alkyl;

$R^{1.1.2}$ H, $C_{1-4}$-alkyl, $SO_2C_{1-4}$-alkyl;

or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyridazinyl, pyrrolyl, pyrazolyl, isoxazolyl, thiazolyl, thiadiazolyl, optionally substituted with one or two residues selected from the group consisting of $C_{1-4}$-alkyl, $C_{3-6}$-cycloalkyl, $CH_2COO$—$C_{1-4}$-alkyl, $CONR^{1.2.1}R^{1.2.2}$, COO—$C_{1-4}$-alkyl, $CONH_2$, O—$C_{1-4}$-alkyl, halogen, CO-pyrrolidinyl, CO-morpholinyl or pyrazolyl, triazolyl, tetrazolyl, isoxazolyl, oxadiazolyl, each optionally substituted with one or two residues selected from the group consisting of $C_{1-4}$-alkyl;

benzothiazolyl, indazolyl, dihydro-indolyl, indanyl, tetrahydro-quinolinyl, each optionally substituted with one or two residues selected from the group consisting of $N(C_{1-4}\text{-alkyl})_2$, CONH—$C_{1-4}$-alkyl, =O;

piperidinyl, optionally substituted with pyridinyl;

4,5-dihydro-naphtho[2,1-d]thiazole, optionally substituted with NHCO—$C_{1-4}$-alkyl, $R^{1.2.1}$ H, $C_{1-4}$-alkyl;

$R^{1.2.2}$ H, $C_{1-4}$-alkyl;

$R^{1.3}$ is selected from phenyl, pyrazolyl, isoxazolyl, pyrimidinyl, indolyl or oxadiazolyl, each optionally substituted with one or two residues selected from the group consisting of $C_{1-4}$-alkyl, $C_{3-6}$-cycloalkyl, O—$C_{1-4}$-alkyl, O—$C_{1-4}$-haloalkyl;

$R^2$ is selected from $CH_2$-phenyl or $CH_2$-naphthyl, both optionally substituted with one or two residues selected from the group consisting of $C_{1-4}$-alkyl, $C_{1-4}$-haloalkyl, O—$C_{1-4}$-haloalkyl, halogen; or $CH_2$-thiophenyl, optionally substituted with one or two residues selected from the group consisting of halogen;

$R^3$ is H;

$R^4$ is H;

or $R^3$ and $R^4$ together are forming a $CH_2$—$CH_2$ group.

4. The compound of formula 1 according to claim 1, wherein

A is $CH_2$, O or NMe;

$R^1$ is selected from $NHR^{1.1}$, $NMeR^{1.1}$;

$NHR^{1.2}$, $NMeR^{1.2}$;

$NHCH_2$—$R^{1.3}$;

NH-piperidinyl, optionally substituted with pyridinyl;

NH-cyclohexyl, optionally substituted with one or two residues selected from the group consisting of t-Bu, $NHSO_2$-phenyl, NHCONH-phenyl, F;

NH-pyrrolidinyl, optionally substituted with one or two residues selected from the group consisting of $SO_2Me$, COO-t-Bu;

piperidinyl, optionally substituted with one or two residues selected from the group consisting of $NHSO_2$-n-Bu, m-methoxyphenyl;

dihydro-indolyl, dihydro-isoindolyl, tetrahydro-quinolinyl or tetrahydro-isoquinolinyl, optionally substituted with one or two residues selected from the group consisting of Me, COOMe, $CF_3$, OMe, $NO_2$, F, Br;

a group selected from NHCH(pyridinyl)$CH_2$COOMe, NHCH($CH_2$OMe)-benzoimidazolyl, optionally substituted with Cl;

or 1-aminocyclopentyl, optionally substituted with methyl-oxadiazolyl;

$R^{1.1}$ is phenyl, optionally substituted with one or two residues selected from the group consisting of Me, Et, t-Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, t-Bu, i-Pr, cyclopropyl, $CH_2$-i-Pr, $CH_2$-t-Bu, $CH(CH_3)CH_2CH_3$, $CH_2CHF_2$, $CH_2CONMe_2$, $CH_2$CO-azetindinyl, $CH_2$-cyclopropyl, $CH_2$-cyclobutyl, $CH_2$-pyranyl, $CH_2$-tetrahydro-furanyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho[2,1-d]thiazole, optionally substituted with NHCOMe, $R^{1.2.1}$ H, Me;

$R^{1.2.2}$ H, Me;

$R^{1.3}$ is selected from phenyl, pyrazolyl, isoxazolyl, pyrimidinyl, indolyl or oxadiazolyl, each optionally substituted with one or two residues selected from the group consisting of Me, Et, Pr, cyclopentyl, OMe, $OCHF_2$;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et; or $CH_2$-thiophenyl, optionally substituted with one or two residues selected from the group consisting of Cl, Br;

$R^3$ is H;

$R^4$ is H;

or $R^3$ and $R^4$ together are forming a $CH_2$—$CH_2$ group.

5. The compound of formula 1 according to claim 1, wherein

A is $CH_2$, O or NMe;

$R^1$ is selected from $NHR^{1.1}$ $NHR^{1.2}$, $R^{1.1}$ is phenyl, optionally substituted with one or two residues selected from the group consisting of Me, Et, Bu, $CF_3$, $CH_2CONMe_2$, $CH_2NHCONH$-cyclohexyl, CN, $CONR^{1.1.1}R^{1.1.2}$, COOMe, COOEt, OMe, $SO_2Me$, $SO_2CH_2CH_2OH$, $SO_2Et$, $SO_2$-cyclopropyl, $SO_2$-piperidinyl, $SO_2NHEt$, $SO_2NMeEt$, F, Cl, CO-morpholinyl, $CH_2$-pyridinyl, or imidazolidinyl, piperidinyl, oxazinanyl, pyrazolyl, triazolyl, tetrazolyl, oxazolyl, oxadiazolyl, thiazolyl, pyridinyl, pyrimidinyl, each optionally substituted with one or two residues selected from the group consisting of Me, NHMe, =O;

$R^{1.1.1}$ H, Me, Et, t-Bu, i-Pr, cyclopropyl, $CH_2$-i-Pr, $CH_2$-t-Bu, $CH(CH_3)CH_2CH_3$, $CH_2CHF_2$, $CH_2CONMe_2$, $CH_2CO$-azetindinyl, $CH_2$-cyclopropyl, $CH_2$-cyclobutyl, $CH_2$-pyranyl, $CH_2$-tetrahydro-furanyl, $CH_2$-furanyl, $CH_2CH_2OH$ or thiadiazolyl, optionally substituted with Me;

$R^{1.1.2}$ H, Me, Et, $SO_2Me$, $SO_2Et$ or $R^{1.1.1}$ and $R^{1.1.2}$ together are forming a four-, five- or six-membered carbocyclic ring, optionally containing one O, replacing a carbon atom of the ring, optionally substituted with one or two residues selected from the group consisting of $CH_2OH$ $R^{1.2}$ is selected from pyridinyl, pyrrolyl, pyrazolyl, isoxazolyl, thiazolyl, thiadiazolyl, optionally substituted with one or two residues selected from the group consisting of Me, Et, Pr, Bu, cyclopropyl, $CH_2COOEt$, $CONR^{1.2.1}R^{1.2.2}$, COOMe, COOEt, $CONH_2$, OMe, Cl, Br CO-pyrrolidinyl, CO-morpholinyl or pyrazolyl, triazolyl, tetrazolyl, isoxazolyl, oxadiazolyl, each optionally substituted Me;

benzothiazolyl, indazolyl, dihydro-indolyl, indanyl, tetrahydro-quinolinyl, each optionally substituted with one or two residues selected from the group consisting of $NMe_2$, CONHMe, =O;

4,5-dihydro-naphtho [2,1-d]thiazole, optionally substituted with NHCOMe, $R^{1.2.1}$ H, Me;

$R^{1.2.2}$ H, Me;

$R^2$ is selected from $CH_2$-phenyl or $CH_2$-naphthyl, both optionally substituted with one or two residues selected from the group consisting of $CH_3$, $CF_3$, $OCF_3$, F, Cl, Br, Et $R^3$ is H;

$R^4$ is H.

6. The compound of formula 1 according to claim 1, wherein

A is $CH_2$, O or NMe;

$R^1$ is selected from the group consisting of

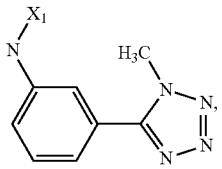

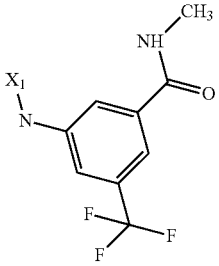

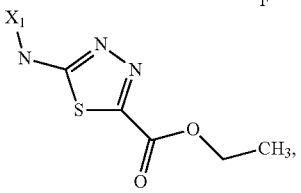

-continued

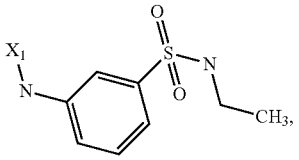

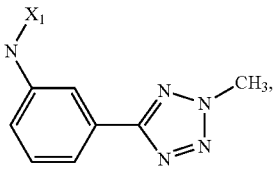

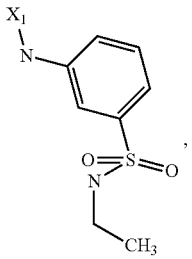

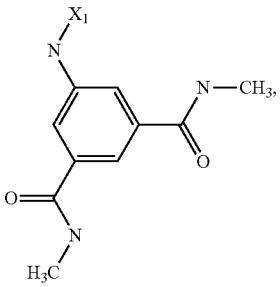

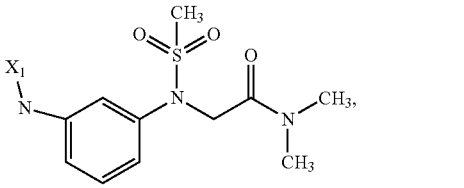

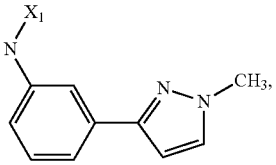

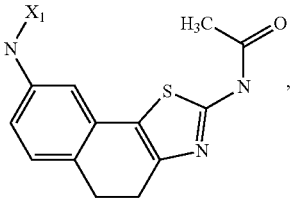

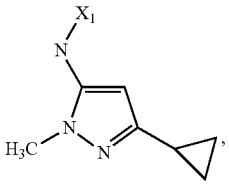

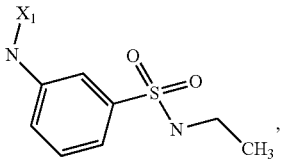

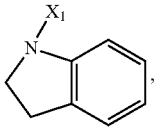

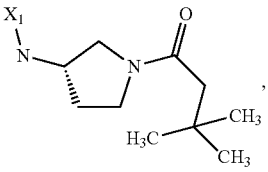

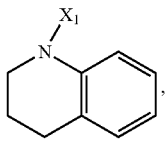

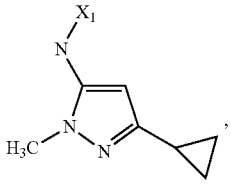

-continued
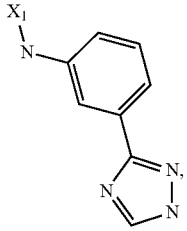
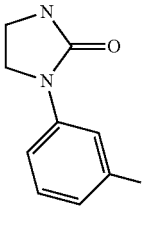
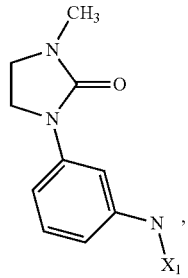
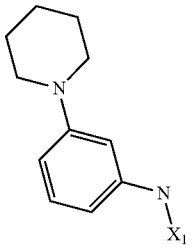
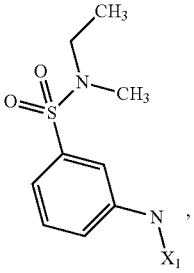
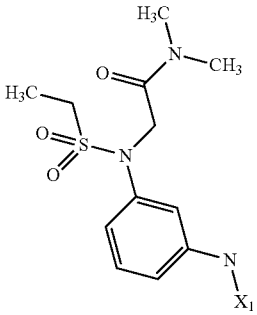
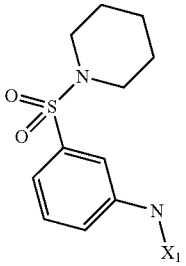
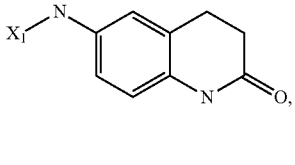
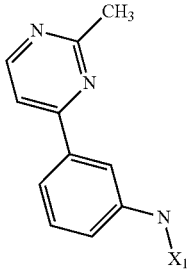
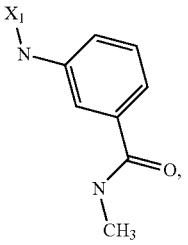
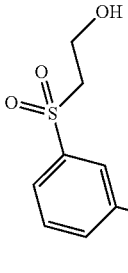
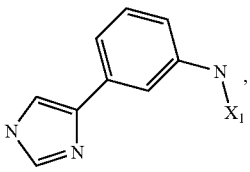
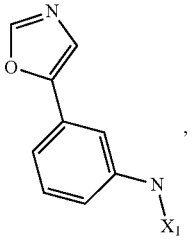
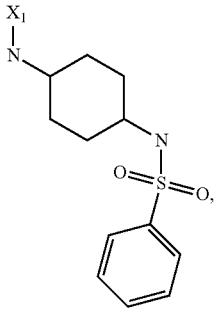
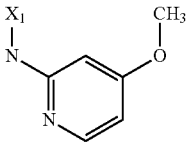
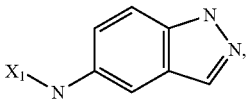
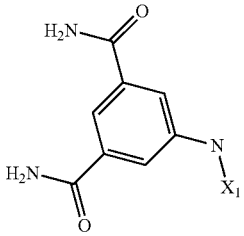
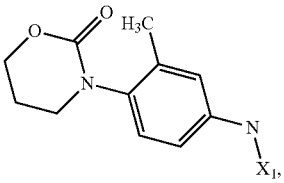
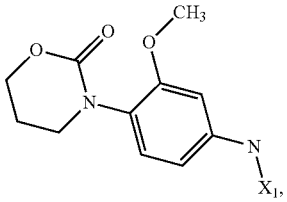
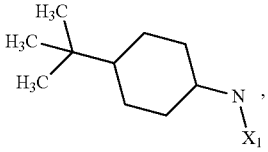
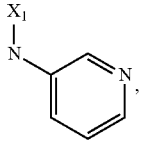
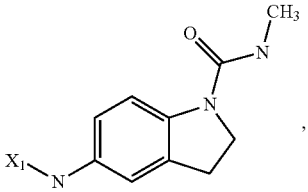
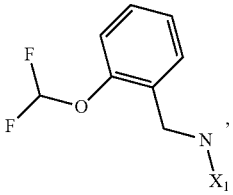
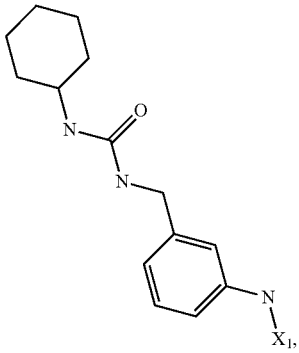
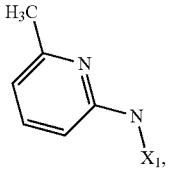
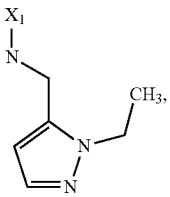
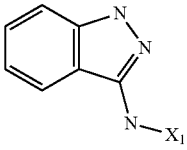
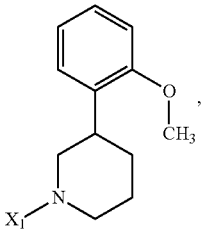

-continued
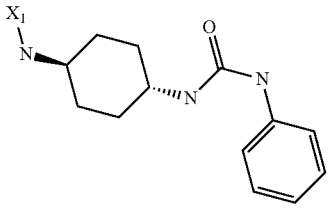
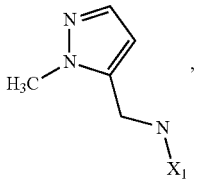
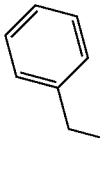
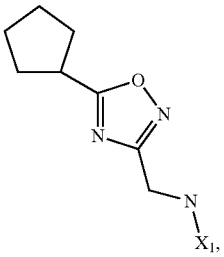
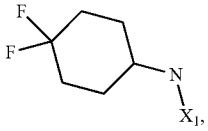
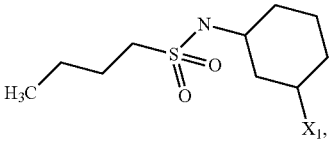
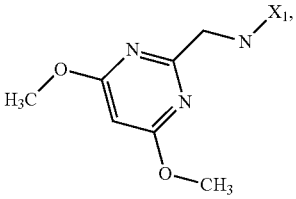
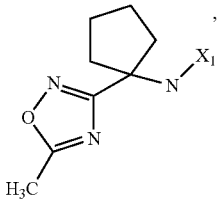
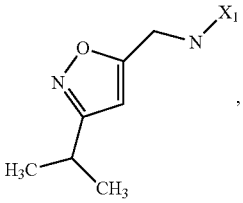
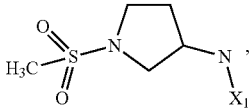
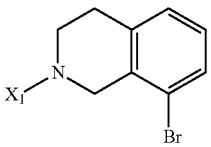
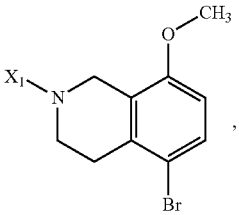
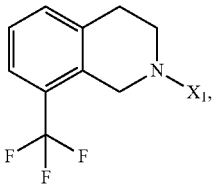
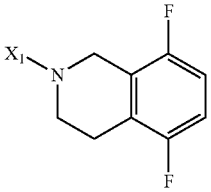
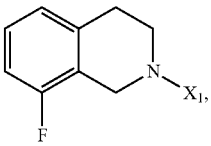
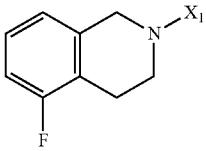
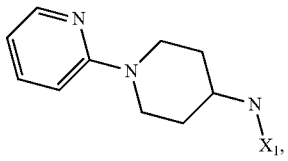
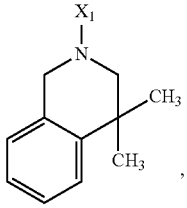
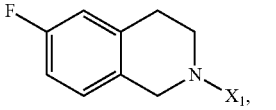
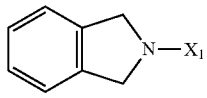
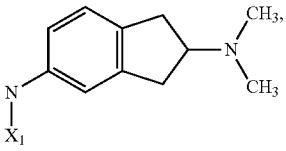
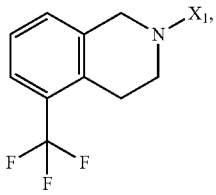
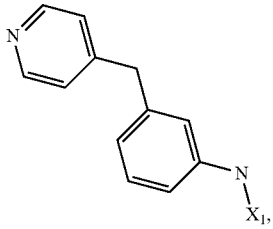
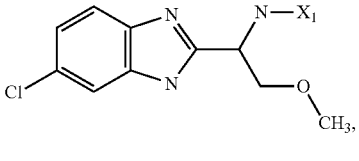
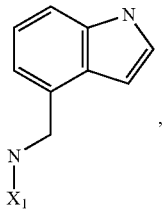
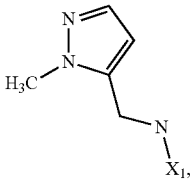
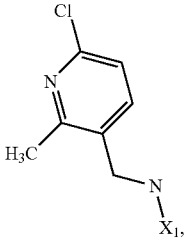
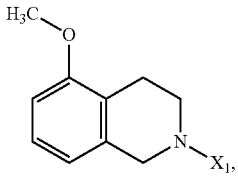
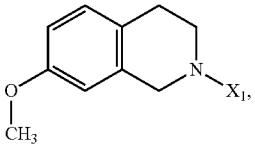
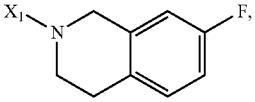
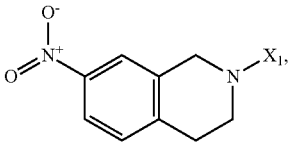

-continued
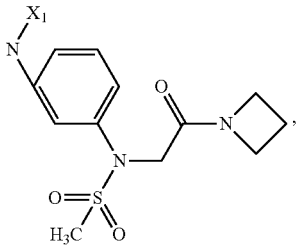
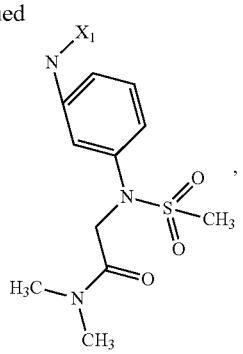
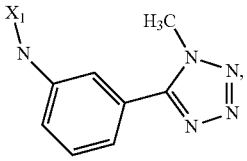
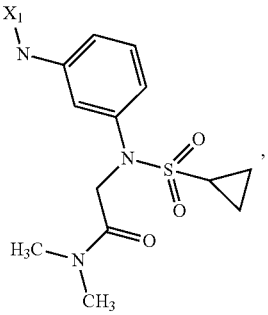
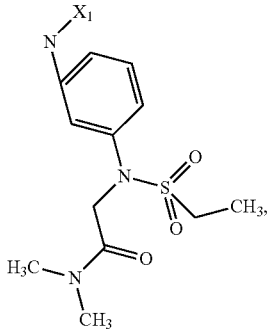
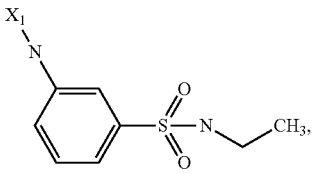
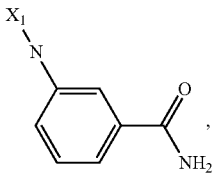
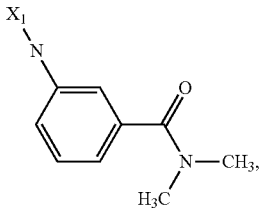
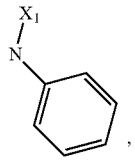
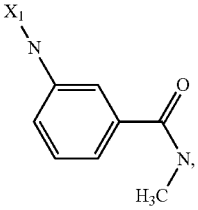
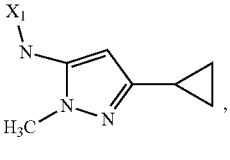
-continued
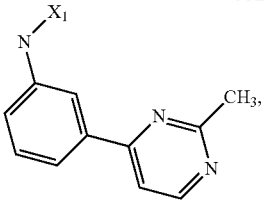
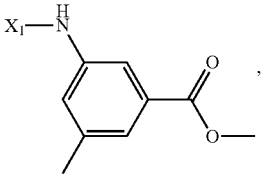
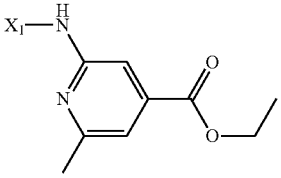
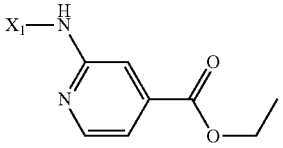
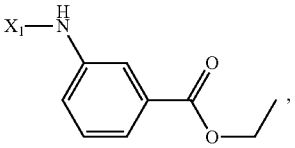
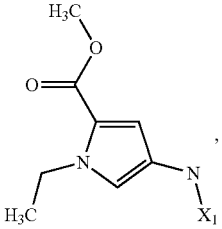
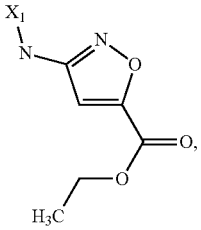
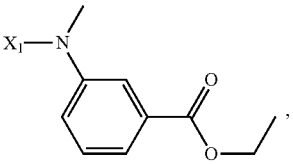
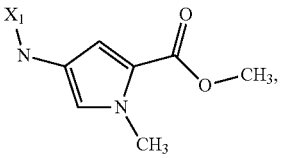
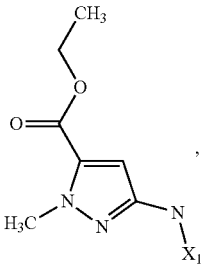
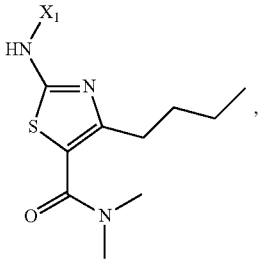

-continued
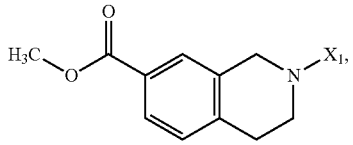
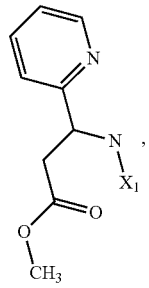
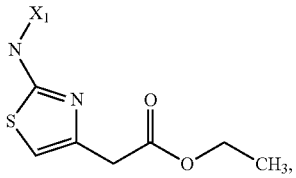
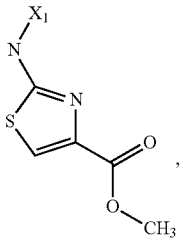
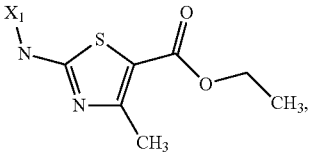
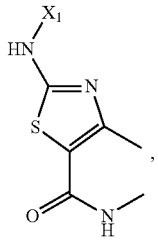
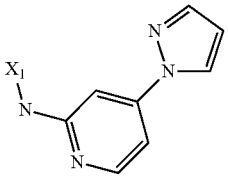
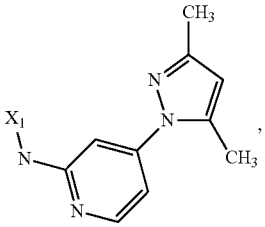
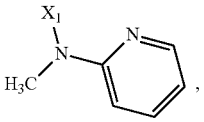
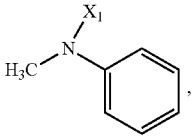
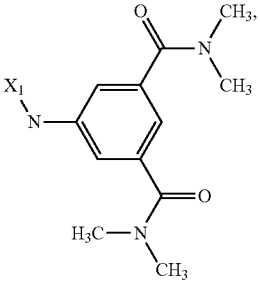
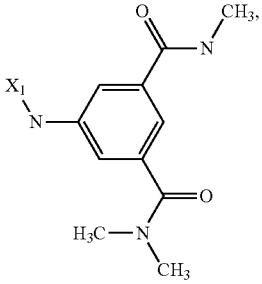
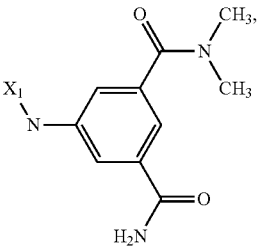
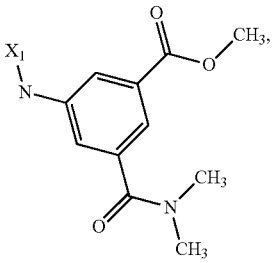
-continued
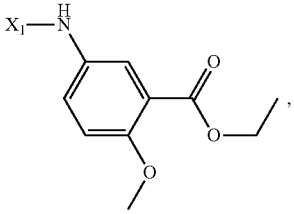
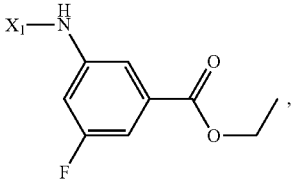
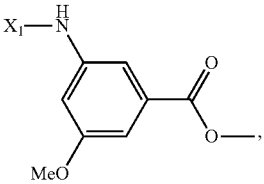
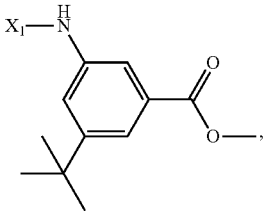
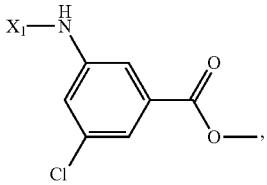
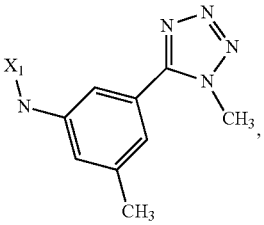
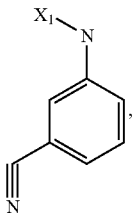
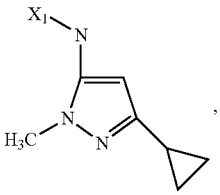
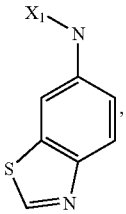
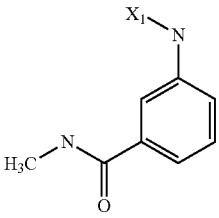
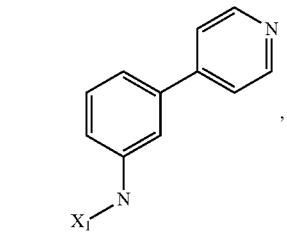
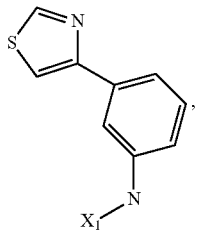
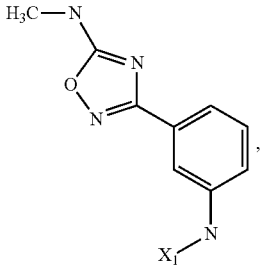

-continued
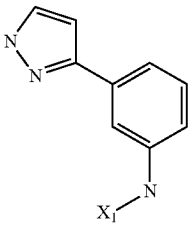
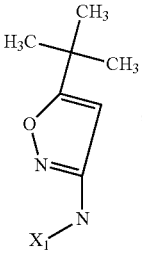
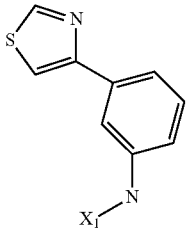
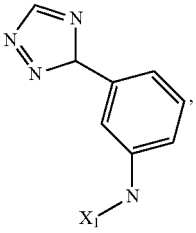
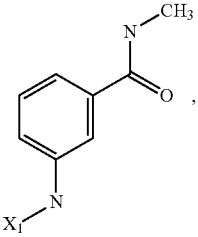
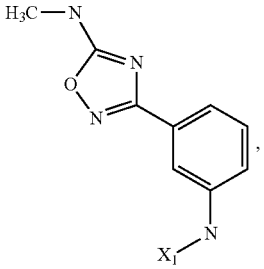
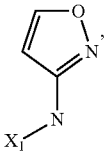
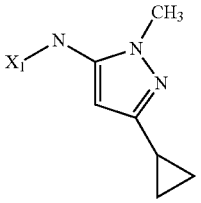
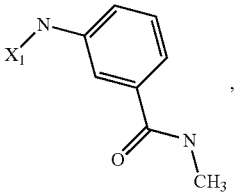
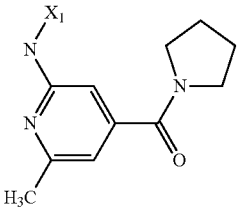
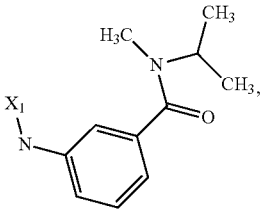
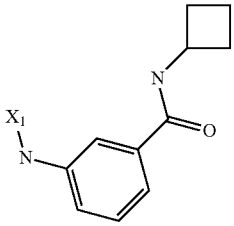
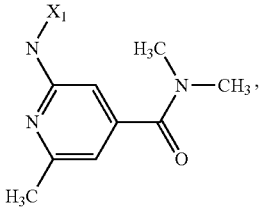
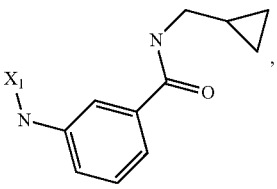
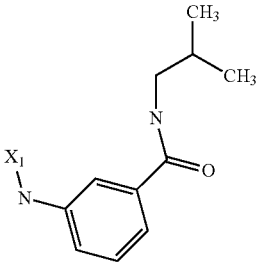
-continued
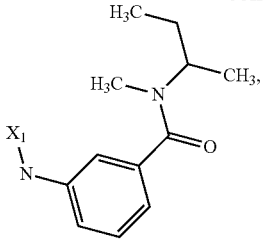
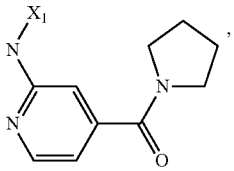
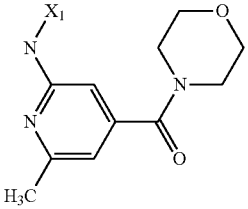
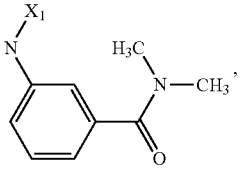
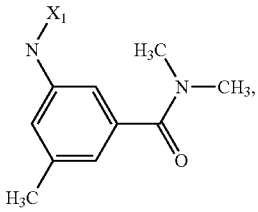
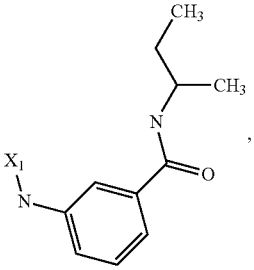
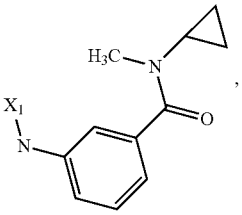
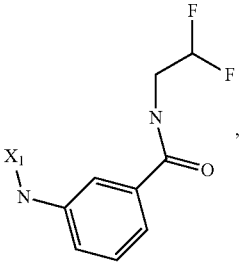
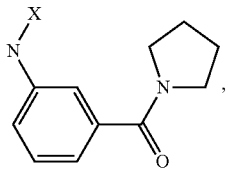
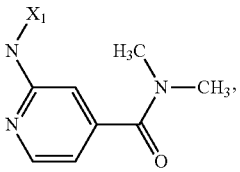
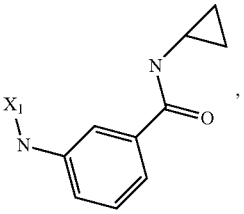
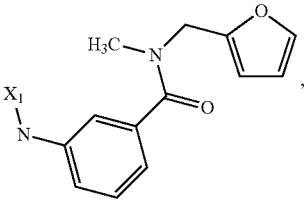
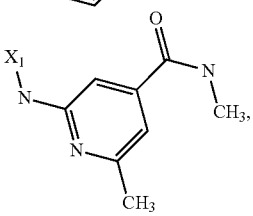
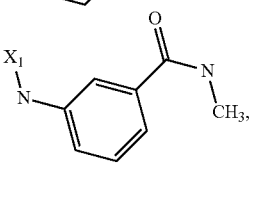

-continued
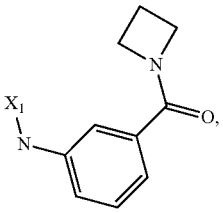
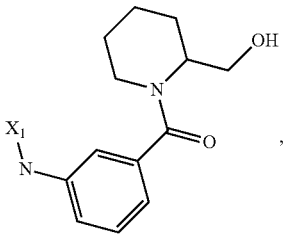
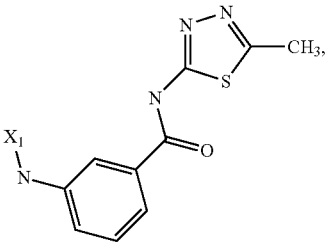
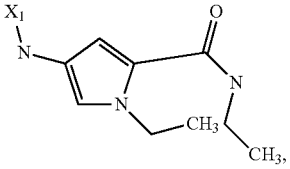
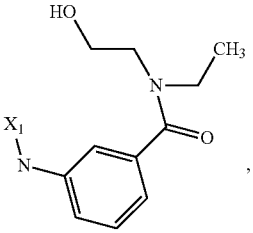
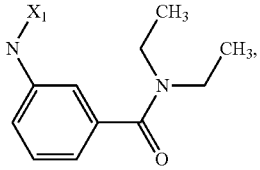
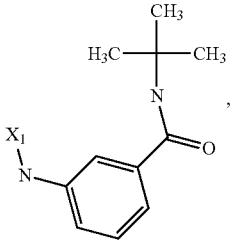
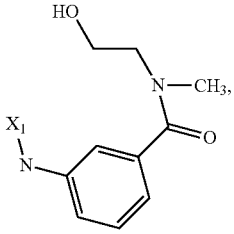
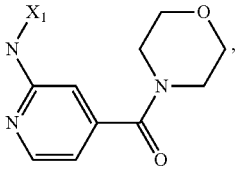
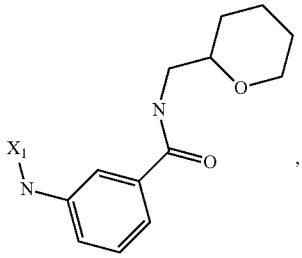
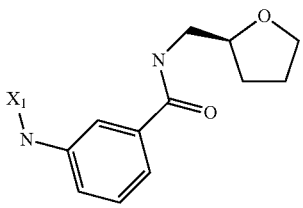
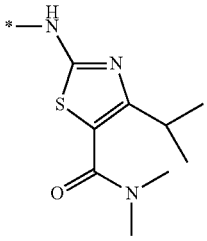
-continued
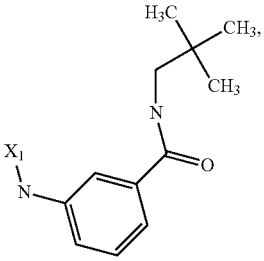
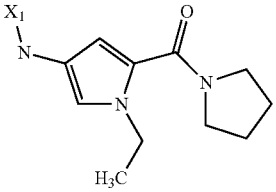
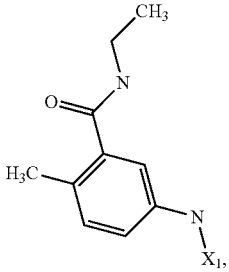
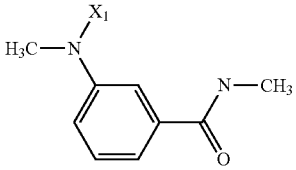
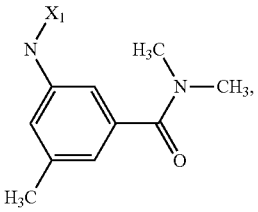
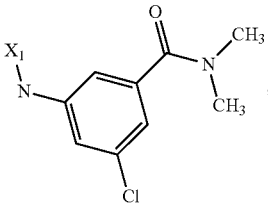
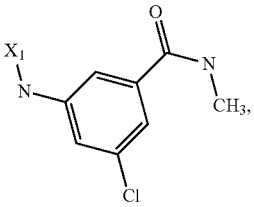
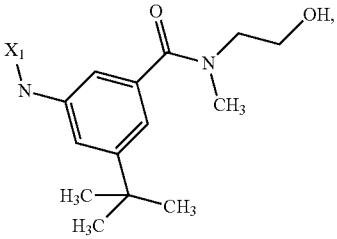
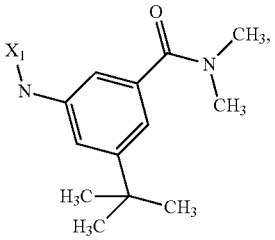
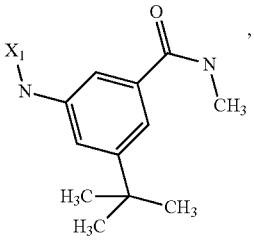
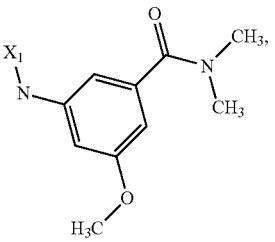
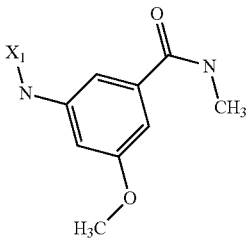

-continued
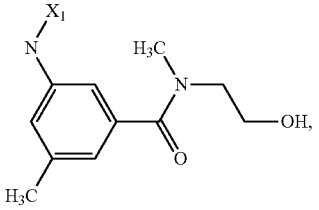
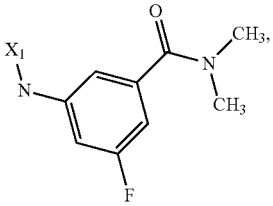
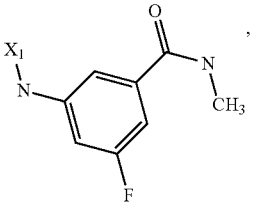
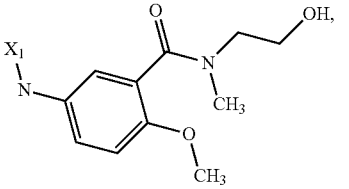
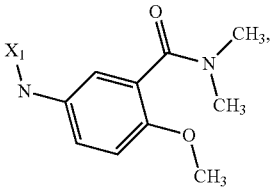
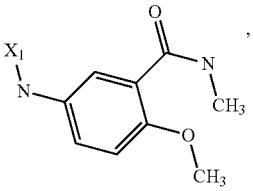
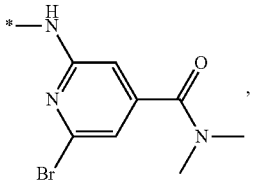
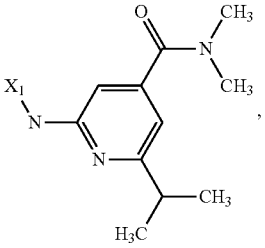
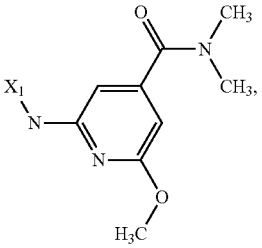
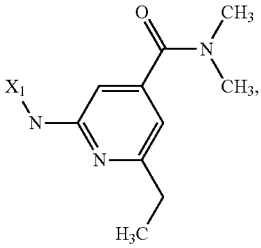
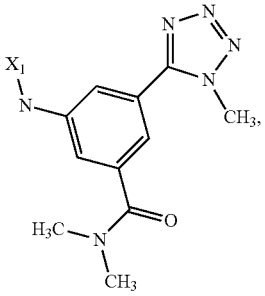
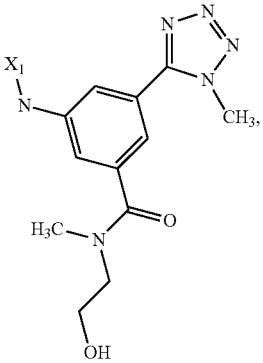
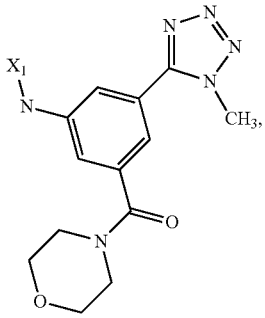
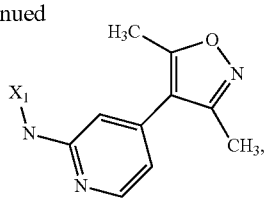
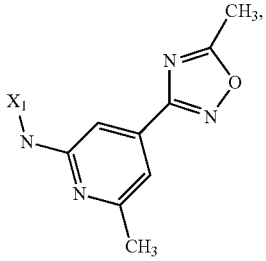
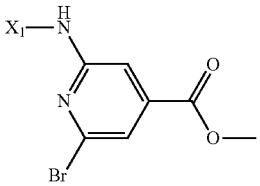
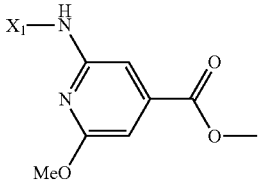
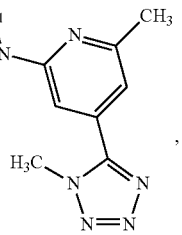
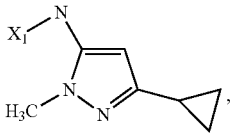
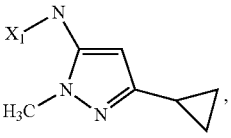
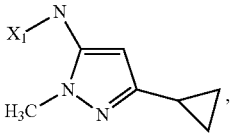
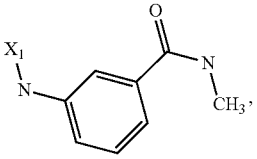
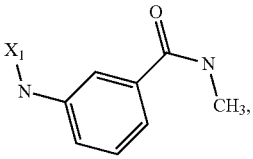
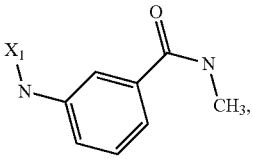
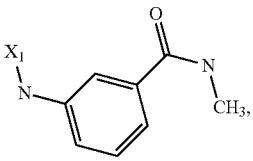
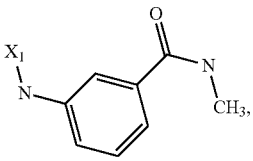
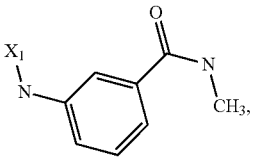
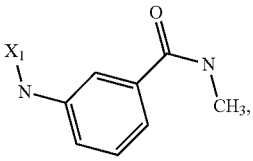

-continued

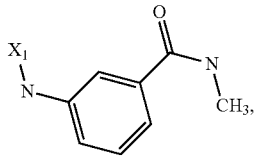

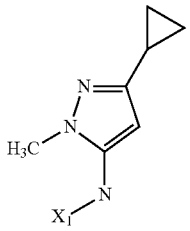

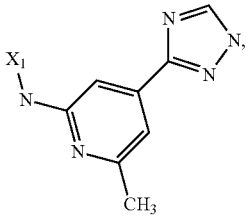

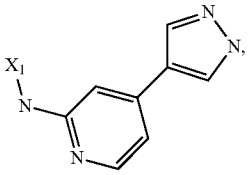

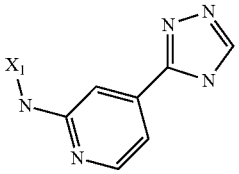

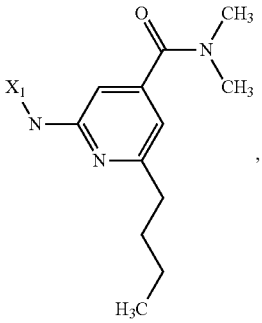

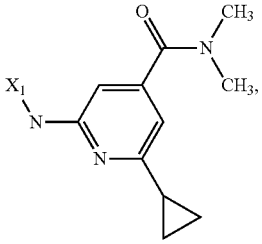

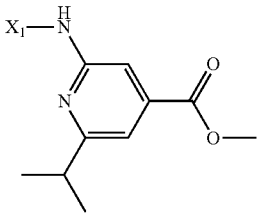

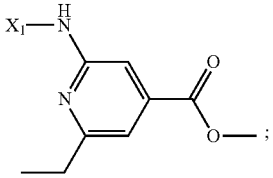

$R^2$ is selected from the group consisting of

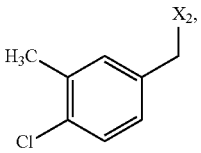

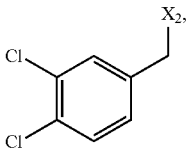

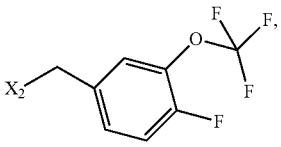

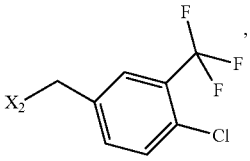

-continued

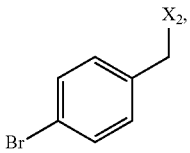

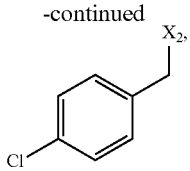

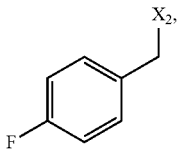

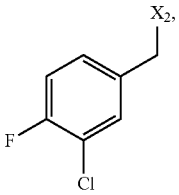

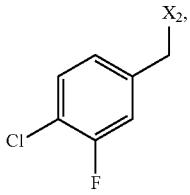

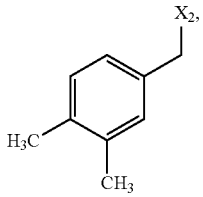

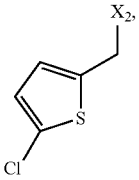

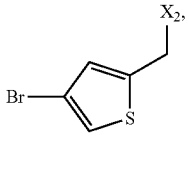

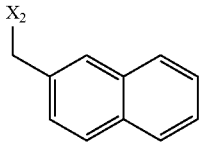

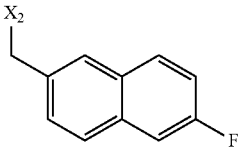

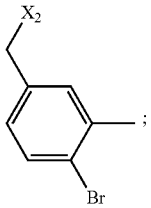

$R^3$ is H;

$R^4$ is H;

or $R^3$ and $R^4$ together are forming a $CH_2$—$CH_2$ group.

7. The compound of formula 1 according to claim 1, wherein the compound is present in the form of the individual optical isomers, a mixture of the individual enantiomers, a racemate or in the form of the enantiomerically pure compounds.

8. The compound of formula 1 according to claim 1, wherein the compound is present in the form of the R-enantiomer R-1

R-1

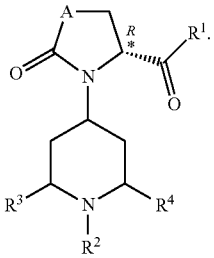

9. A pharmaceutical composition of matter comprising one or more compounds of formula 1 according to claim 1 and a pharmaceutically acceptable carrier or excipient.

10. A pharmaceutical composition of matter according to claim 9 further comprising a substance selected from the group consisting of betamimetics, anticholinergics, corticosteroids, PDE4 inhibitors, LTD4-antagonists, EGFR-inhibitors, CRTH2 inhibitors, 5-LO-inhibitors, Histamine receptor antagonists, CCR9 antagonists, SYK-inhibitors and combinations of any of such substances.

[11. The compound of formula 1 according to claim 1, wherein the compound is

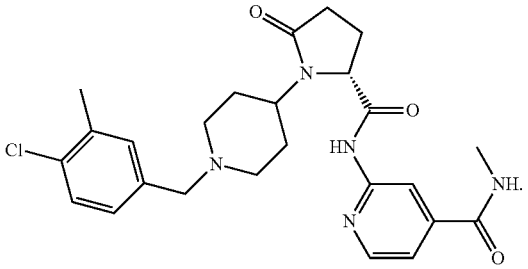

]

[12. The compound of formula 1 according to claim 1, wherein the compound is

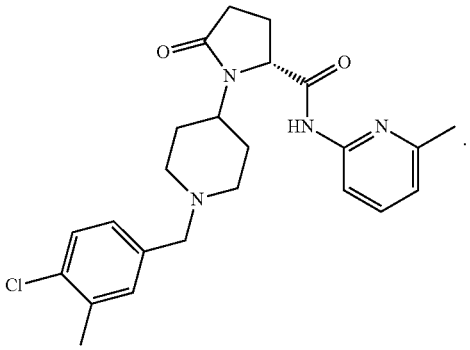

]

13. The compound of formula 1 according to claim 1, wherein the compound is

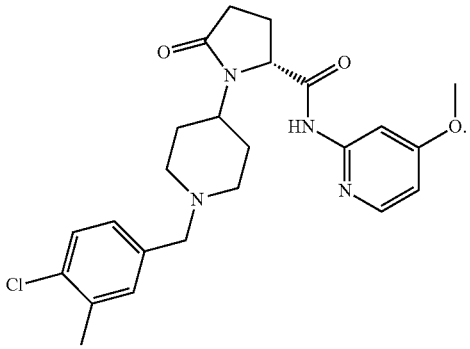

[14. The compound of formula 1 according to claim 1, wherein the compound is

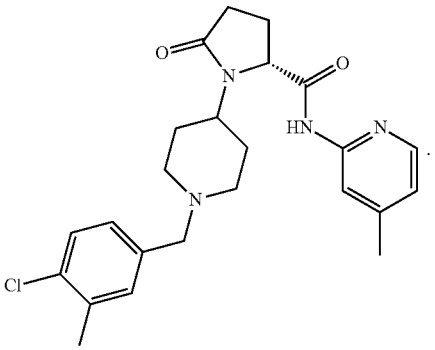

]

[15. The compound of formula 1 according to claim 1, wherein the compound is

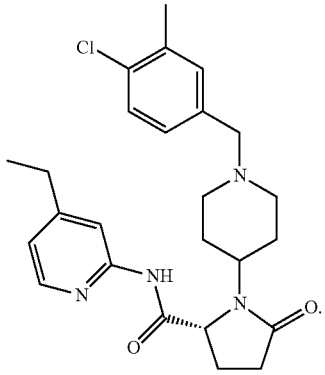

]

[16. The compound of formula 1 according to claim 1, wherein the compound is

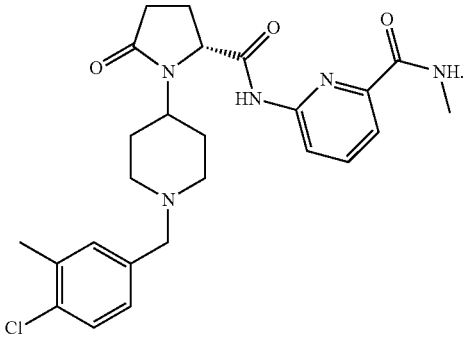

]

17. The compound of formula 1 according to claim 1, wherein the compound is

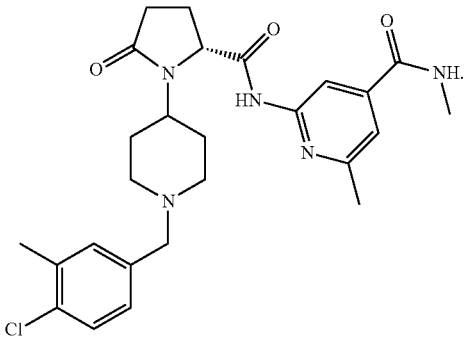

18. The compound of formula 1 according to claim 1, wherein the compound is

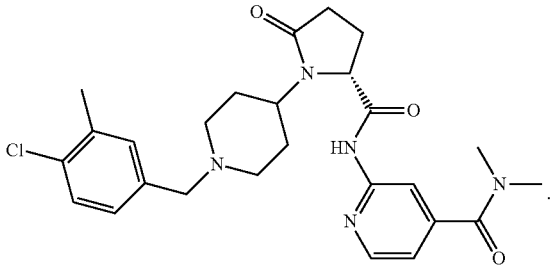

]

19. The compound of formula 1 according to claim 1, wherein the compound is

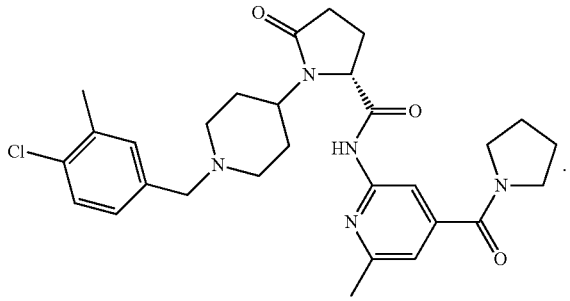

20. The compound of formula 1 according to claim 1, wherein

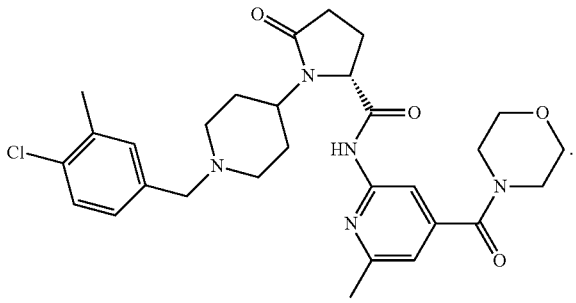

21. The compound of formula 1 according to claim 1, wherein the compound is

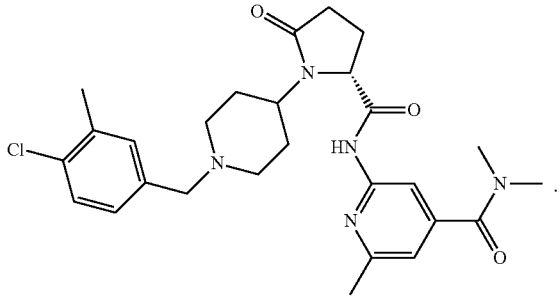

22. The compound of formula 1 according to claim 1, wherein the compound is

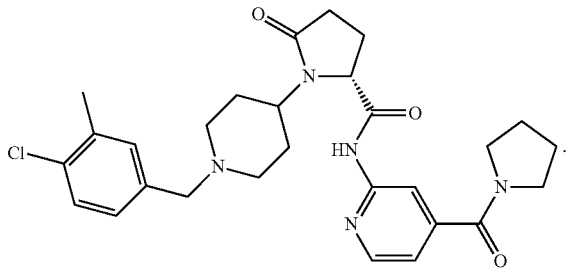

23. The compound of formula 1 according to claim 1, wherein the compound is

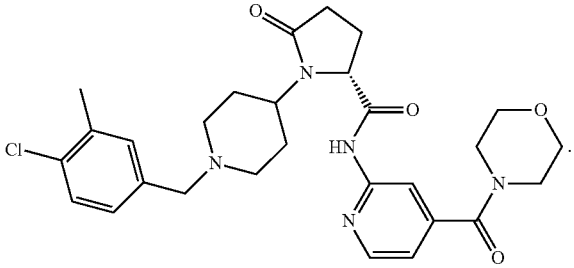

24. The compound of formula 1 according to claim 1, wherein the compound is

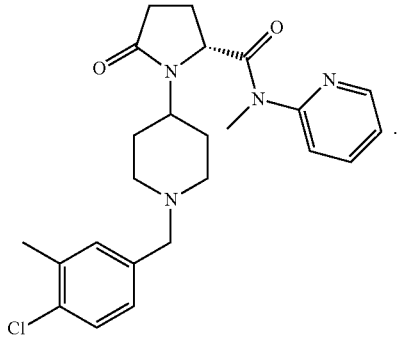

[25. The compound of formula 1 according to claim 1, wherein the compound is

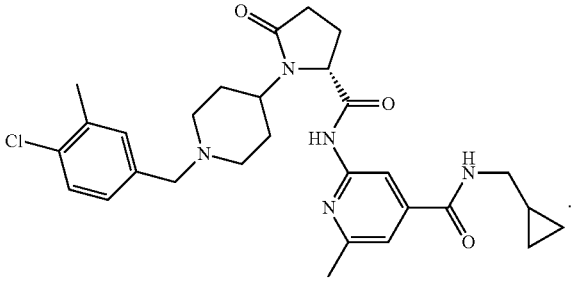

]

[26. The compound of formula 1 according to claim 1, wherein the compound is

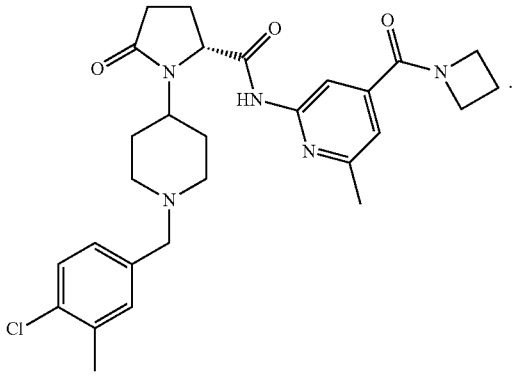

[27. The compound of formula 1 according to claim 1, wherein the compound is

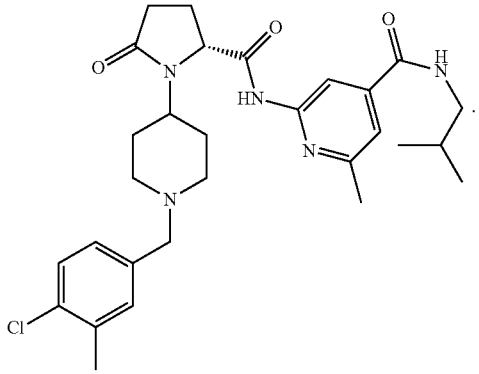

]

[28. The compound of formula 1 according to claim 1, wherein the compound is

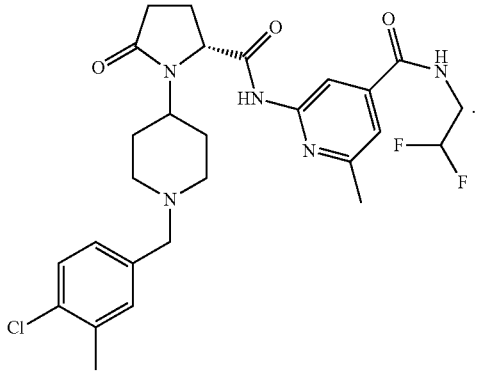

]

[29. The compound of formula 1 according to claim 1, wherein the compound is

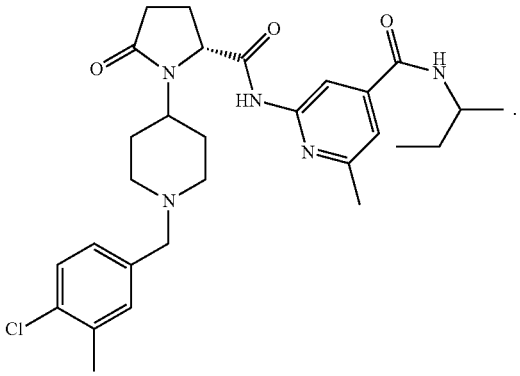

[30. The compound of formula 1 according to claim 1, wherein the compound is

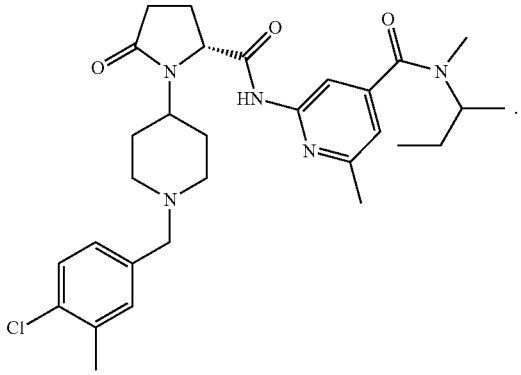

]

[31. The compound of formula 1 according to claim 1, wherein the compound is

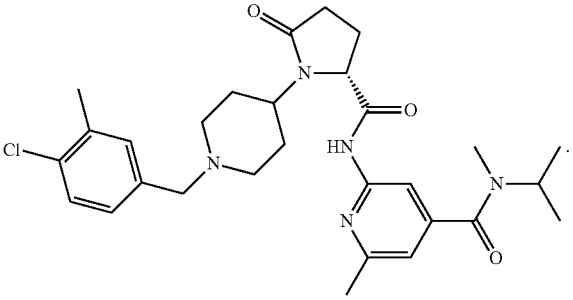

]

[32. The compound of formula 1 according to claim 1, wherein the compound is

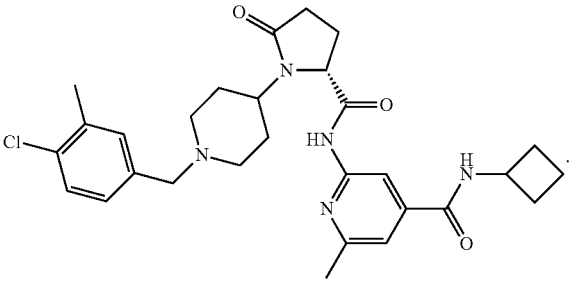

]

33. The compound of formula 1 according to claim 1, wherein the compound is

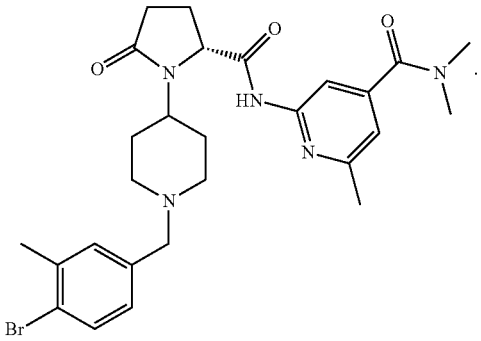

34. The compound of formula 1 according to claim 1, wherein the compound is

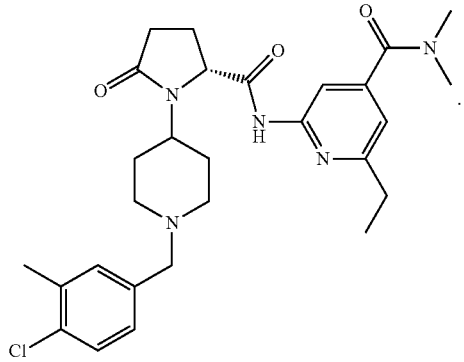

35. The compound of formula 1 according to claim 1, wherein the compound is

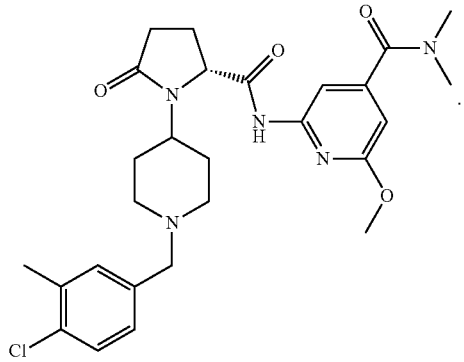

36. The compound of formula 1 according to claim 1, wherein the compound is

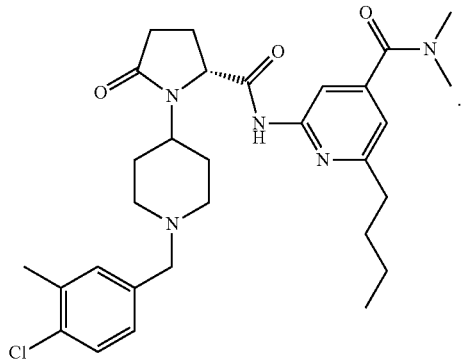

37. The compound of formula 1 according to claim 1, wherein the compound is

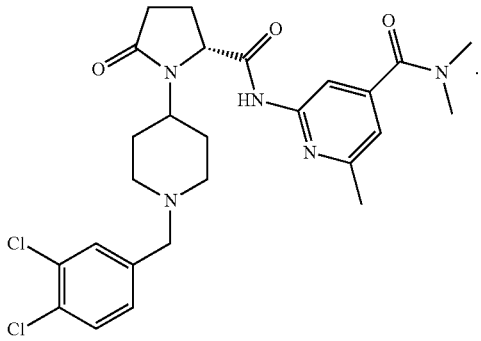

38. The compound of formula 1 according to claim 1, wherein the compound is

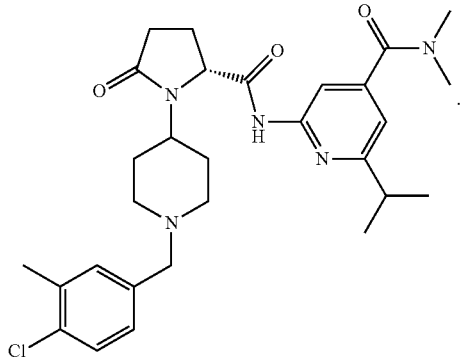

[39. The compound of formula 1 according to claim 1, wherein the compound is

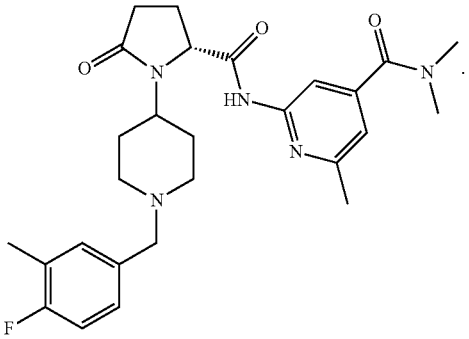

] [40. The compound of formula 1 according to claim 1, wherein the compound is

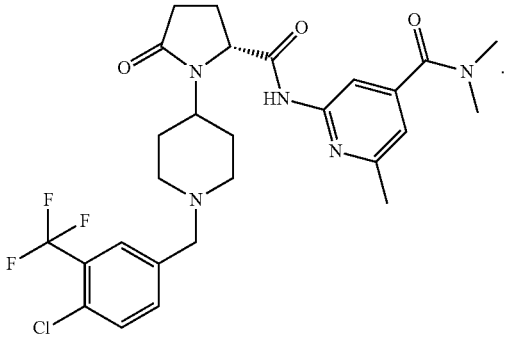

]

41. The compound of formula 1 according to claim 1, wherein the compound is

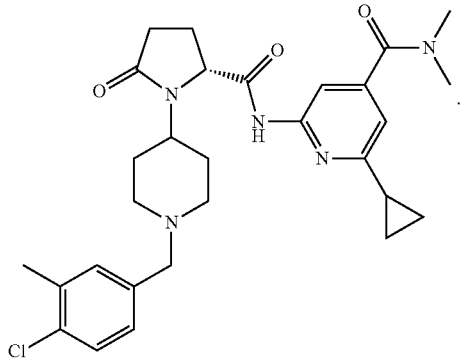

[42. The compound of formula 1 according to claim 1, wherein the compound is
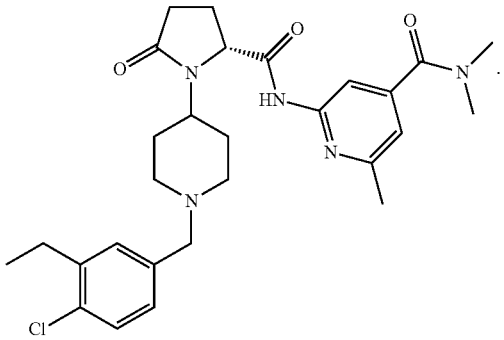
]
[43. The compound of formula 1 according to claim 1, wherein the compound is
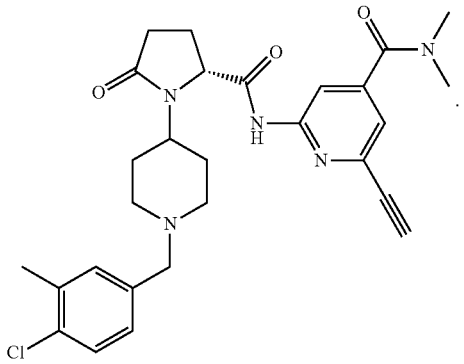
]
[44. The compound of formula 1 according to claim 1, wherein the compound is
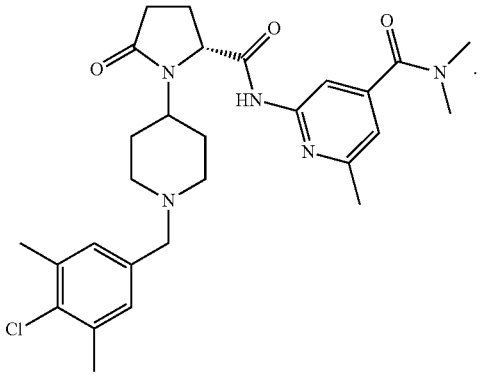
]
[45. The compound of formula 1 according to claim 1, wherein the compound is
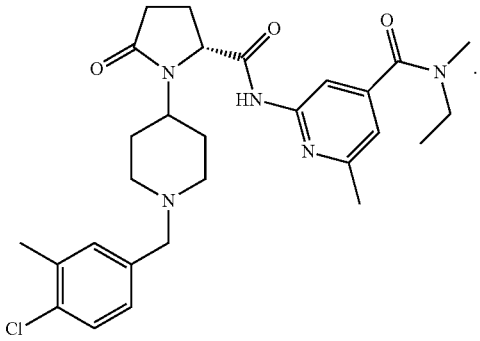
]
* * * * *